US009982272B2

(12) United States Patent
Bailey et al.

(10) Patent No.: US 9,982,272 B2
(45) Date of Patent: May 29, 2018

(54) ALGAL MUTANTS HAVING A LOCKED-IN HIGH LIGHT ACCLIMATED PHENOTYPE

(71) Applicant: Synthetic Genomics, Inc., La Jolla, CA (US)

(72) Inventors: Shaun Bailey, San Diego, CA (US); Jay McCarren, Cardiff, CA (US); Soyan Leung Lieberman, Solana Beach, CA (US); Jonathan E. Meuser, San Diego, CA (US); Anna E. Romano, Honolulu, HI (US); Daniel Yee, San Diego, CA (US); Leah Soriaga, San Diego, CA (US); Robert C. Brown, San Diego, CA (US); Ariel S. Schwartz, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days. days.

(21) Appl. No.: 14/099,879

(22) Filed: Dec. 6, 2013

(65) Prior Publication Data

US 2014/0220638 A1 Aug. 7, 2014

Related U.S. Application Data

(60) Provisional application No. 61/733,956, filed on Dec. 6, 2012, provisional application No. 61/810,216, filed on Apr. 9, 2013, provisional application No. 61/869,590, filed on Aug. 23, 2013, provisional application No. 61/881,342, filed on Sep. 23, 2013.

(51) Int. Cl.

| | |
|---|---|
| ***C12N 15/82*** | (2006.01) |
| ***C12N 1/12*** | (2006.01) |
| ***C12N 15/01*** | (2006.01) |
| ***C12N 1/36*** | (2006.01) |
| ***C07K 14/405*** | (2006.01) |
| ***C07K 14/415*** | (2006.01) |

(52) U.S. Cl.

CPC .......... *C12N 15/825* (2013.01); *C07K 14/405* (2013.01); *C07K 14/415* (2013.01); *C12N 1/12* (2013.01); *C12N 1/36* (2013.01); *C12N 15/01* (2013.01); *C12N 15/8269* (2013.01)

(58) Field of Classification Search

None

See application file for complete search history.

(56) References Cited

U.S. PATENT DOCUMENTS

| | | | | |
|---|---|---|---|---|
| 5,629,179 A * | 5/1997 | Mierendorf ........ | C12N 15/1096 435/91.2 |
| 7,745,696 B2 | 6/2010 | Melis et al. | |
| 2009/0023180 A1 | 1/2009 | Dillon | |
| 2010/0317073 A1 | 12/2010 | Sayre et al. | |
| 2010/0323387 A1 | 12/2010 | Bailey et al. | |
| 2011/0197306 A1 | 8/2011 | Bailey et al. | |
| 2012/0151635 A1 | 6/2012 | Coruzzi et al. | |
| 2014/0273113 A1 | 9/2014 | Vick et al. | |
| 2014/0295448 A1 | 10/2014 | Melis et al. | |

FOREIGN PATENT DOCUMENTS

| | | |
|---|---|---|
| WO | WO 2010/008490 A1 | 1/2010 |
| WO | WO 2013/016267 A3 | 4/2013 |

OTHER PUBLICATIONS

GenBank AFJ68612.1. hypothetical protein NGATSA_2006400. 2012. p. 1-2.*

Beckmann J et al. Improvement of light to biomass conversion by de-regulation of light-harvesting protein translation in Chlamydomonas reinhardtii. 2009. Journal of Biotechnology. 142:70-77.*

Perrine et al,: "*Optimization of photosynthetic light energy utilization by microalgae*"; Algal Research, Oct. 2012, vol. 1 No. 2 pp. 134-142.

Sandesh et al.: "*Enhancement of carotenoids by mutation and stress induced carotenogenic genes in Haematococcus pluvialis mutants*"; Bioresour Technol, Dec. 2008 vol. 99 No. 18 pp. 8667-8673. Abstract only.

Dent et al.: "Functional genomics of eukaryotic photosynthesis using insertional mutagenesis of Chlamydomonas reinhardti"; Plant Physio;l Feb. 2005 vol. 137 No. 2 pp. 545-556.

Uniprot Accession No. I2CNX9 [online] Nov. 28, 2012 [retrieved Feb. 18, 2014]. Available on the intemet: <URL: www.uniprot.org/uniprotJI2CNX9.txt?version=3>.

Uniprot Accession No. B7S450 [Apr. 18, 2012. Available on the Internet: <URL: http://www.uniprot.org/uniprot/B7S450.bd?version=10>, retried on Apr. 10, 2014.

NM 180129.3 ("*Arabidopsis thaliana* protein CCA1 (CCA1) rnRNA, complete cds") [May 28, 2011; available on the Internet: <URL: Http://www.ncbi.nlm.nih.gov/nuccore/186508741?sat=17&satkey=24067453>; retried on Apr. 10, 2014].

International Search Report regarding PCT/US2013/073741.

(Continued)

*Primary Examiner* — Paul J Holland

(74) *Attorney, Agent, or Firm* — DLA Piper LLP (US)

(57) ABSTRACT

Mutant photosynthetic microorganisms having reduced chlorophyll and increased photosynthetic efficiency are provided. The mutants have a locked in high light-acclimated phenotype, in which many of the photosynthetic parameters characteristic of high light acclimated wild type cells are found in the LIHLA mutants when acclimated to low light, such as reduced chlorophyll, reduced NPQ, higher qP, higher $E_k$, higher $P_{max}$ per unit chlorophyll with little to no reduction in $P_{max}$ per cell, and higher rates of electron transport through photosystem II over a wide range of light intensities. Provided herein are constructs for attenuating or disrupting genes are provided for generating mutants having the LIHLA phenotype. Also provided are methods of culturing LIHLA mutants for the production of biomass or other products.

30 Claims, 45 Drawing Sheets

(56) References Cited

OTHER PUBLICATIONS

Beckmann, J. et al: "*Improvement of light to biomass conversion by de-regulation of light-harvesting protein translation in Chlamydomonas reinhardtii*",; J. Biotechnology, vol. 142, No. 1, Mar. 9, 2009, pp. 70-77.

Forster, Britta et al.: "*Mutants of Chlamydomonas reinhardtii resistant to very high light*"; J. Photochemistry and Photobiology B:Biology, vol. 48, No. 2-3, Jun. 24, 1999, pp. 127-135.

Kirst, H. et al: "*Truncated Photosystem Chlorophyll Antenna Size in the Green Microalga Chlamydomonas reinhardtii upon Deletion of the TLA3-CpSRP43 Gene*"; Plant Physiology, vol. 160, No. 4, Dec. 2012, pp. 2251-2260.

Maxwell, K., et al.: "*Chlorophyll fluorescence—a practical guide*"; J. Experimental Botany, vol. 51, No. 345, Apr. 2000, pp. 659-668.

Mussgnug, Jan H. et al.: "*Engineering photosynthetic light capture: impacts on improved solar energy to biomass conversion*"; Plant Biotechnology Journal, Aug. 31, 2007, vol. 5, No. 6, pp. 802-814.

Navakoudis et al.: "*Changes in the LHCII-mediated energy utilization and dissipation adjust the methanol-induced biomass increase*"; Biochimica Et Biophysica Acta. Bioenergetics, Amsterdam, NL, vol. 1767, No. 7, May 13, 2007, pp. 948-955. XP022148519, ISSN: 0005-2728, DOI: 10.1016/J.BBABI0.2007.05.003.

Polle, J. E. W. et al.: "*tla1, a DNA insertional transformant of the green alga Chiamydomonas reinhardtii with a truncated light-harvesting chlorophyll antenna size*"; Planta, Feb. 12, 2003, vol. 217, No. 1, pp. 49-59.

Radakovits et al.: "*Draft genome sequence and genetic transformation of the oleaginous alga Nannochloropis gaditana*"; Nature Communications, Feb. 21, 2012, vol. 3, 10 Pgs, XP055138208, ISSN: 2041-1723, DOI:10.1038/ncomms1688.

Supplementary Partial European Search Report dated Jul. 1, 2016, regarding EP 13 86 0017.

XP002758904: "*TSA: Nannochloropsis gaditana CCMP526 NGA Contig12817 mRNA sequence.*" Database EMBL [Online] May 17, 2012, retrieved from EBI accession No. EMBL:JU963148.

Armbrust, Virginia E. et al.: "*The Genome of the diatom Thalassiosira Pseudonana: Ecology, Evolution, and Metabolism*"; Science, vol. 306. No. 5963, Oct. 1, 2004, pgs. 79-86, XP055302056.

Cock, J. Mark et al.: "*The Ectocarpus genome and the independent evolution of multicellularity in brown algae*"; Nature, Jun. 3, 2010, vol. 465, No. 7298, pp. 617-621, XP055020932.

Supplementary European Search Repor dated Oct. 18, 2016, regarding EP 13 86 0017.

XP002761724: SubName: Full=Uncharacterized protein {ECO:0000313:EMBL:EED89972.1}; Mar. 3, 2009, Retrieved from EBI accession No. UNIPROT:B8C919.

XP002761725: SubName: Full=Uncharacterized protein {ECO:00003131 EMBL:CBJ27465.1}; Aug. 10, 2010, retrieved from EBI accession No. UNIPROT:D7G656.

Arziman et al.: "*E-RNAi: a web application to design optimized RNAi constructs*"; Nucl. Acids Res.: Jul. 1;33(Web Server issue):W582-8, 2005.

Bailey et al.: "*Acclimation of Arabidopsis thaliana to the light environment: the existence of separate low light and high light responses*"; Planta Sep.;213(5):794-801, 2001.

Bailey et al. "*Acclimation of Arabidopsis thaliana to the light environment: the relationship between photosynthetic function and chloroplast composition*"; Planta Mar.;218(5):793-802. Epub 2003 Nov. 27, 2004.

Bellafiore et al.: "*Loss of Albino3 leads to the specific depletion of the light-harvesting system*"; The Plant Cell Sep.;14(9):2303-14, 2002.

Bonente et al.: "*Mutagenesis and phenotypic selection as a strategy toward domestication of Chlamydomonas reinhardtii strains for improved performance in photobioreactors*"; Photosynthesis Res. Sep.;108(2-3):107-20. doi: 10.1007/s11120-011-9660-2. Epub May 6, 2011.

Bonente et al.: "*Acclimation of Chlamydomonas reinhardtii to different growth irradiances*"; J. Biological Chemistry Feb. 17;287(8):5833-47. doi: 10.1074/jbc.M111.304279. Epub Dec. 28, 2012.

Formighieri et al.: "*Regulation of the pigment optical density of an algal cell: filling the gap between photosynthetic productivity in the laboratory and in mass culture*"; J. Biotechnology Nov. 30;162(1):115-23. doi: 10.1016/j.jbiotec.2012.02.021. Epub Mar. 7, 2012.

Gordon & Polle: "*Ultrahigh bioproductivity from algae*"; Appl. Microbiol. Biotechnol. 2007 Oct.;76(5):969-75. Epub Jul. 24, 2007.

Kirst et al.: "*Assembly of the light-harvesting chlorophyll antenna in the green alga Chlamydomonas reinhardtii requires expression of the TLA2-CpFTSY gene*"; Plant Physiology Feb. 2012;158(2):930-45. doi: 10.1104/pp. 111.189910. Epub Nov. 23, 2011.

McIntyre and Fanning: "*Design and cloning strategies for constructing shRNA expression vectors*"; BMC Biotechnology Jan. 5, 2006; 6:1, 8 pages.

Mitra and Melts: "*Genetic and biochemical analysis of the TLA1 gene in Chlamydomonas reinhardtii*"; Planta Feb. 2010;231(3):729-40. doi: 10.1007/s00425-0091083-3. Epub Dec. 15, 2009.

Nag-Jong et al.: "*Pigment Reduction to Improve Photosynthetic Productivity of Rhodobacter Sphaeroides*"; J. Microbiol. Biotechnol, Jun. 2004, 14(3):442-449.

Oey et al.: "*RNAi knock-down of LHCBM1, 2 and 3 increases photosynthetic H2 production efficiency of the green alga Chlamydomonas reinhardtii*"; PLOS ONE Apr 16; 2013, 8(4):e61375. doi: 10.1371/journal.pone.0061375. Print 2013.

Schellenberger et al.: "*Aureochrome 1a Is Involved in the Photoacclimation of the Diatom Phaeodactylum tricornutum*"; PLOS ONE 2013; 8(9): e74451.

Tetali et al.: "*Development of the light-harvesting chlorophyll antenna in the green alga Chlamydomonas reinhardtii is regulated by the novel Tla1 gene*"; Planta, Mar. 2007, 225(4):813-29.

Wang and Mu: "*A Web-based design center for vector-based siRNA and siRNA cassette*"; Bioinformatics Jul. 22, 2004;20(11):1818-20. Epub Mar. 4, 2004.

* cited by examiner

Figure 6

| LIMS ID | Genotype (mutation detected) | ETRmax (X higher than WT) | pmol O2/min/ cell | umol O2/min/mg chl | Avg total Chl (pg)/cell | WT pmol O2/min/ cell2 | WT umol O2/min/mg chl | WT Avg total Chl (pg)/cell |
|---|---|---|---|---|---|---|---|---|
| GE4574 | LAR1 | 2.62 | 0.017 | 405 | 0.04 | 0.019 | 161 | 0.13 |
| GE4904 | LAR1 | 2.44 | 0.023 | 353 | 0.07 | 0.028 | 150 | 0.21 |
| GE4908 | LAR1 | 2.23 | 0.024 | 330 | 0.07 | 0.028 | 150 | 0.21 |
| GE4911 | LAR1 | 2.1 | 0.022 | 320 | 0.07 | 0.028 | 150 | 0.21 |
| GE5099 | LAR1 | 2.1 | 0.086 | 1654 | 0.05 | 0.086 | 534 | 0.16 |
| GE5117 | LAR1 | 2.6 | 0.094 | 1753 | 0.05 | 0.086 | 534 | 0.16 |
| NE5282 | LAR1 | 2.00 | 0.029 | 374 | 0.08 | 0.029 | 145 | 0.20 |
| NE5284 | LAR1 | 2.22 | 0.026 | 429 | 0.06 | 0.029 | 145 | 0.20 |
| NE5287 | LAR1 | 2.03 | 0.024 | 347 | 0.07 | 0.029 | 145 | 0.20 |
| NE5292 | LAR1 | 2.76 | 0.031 | 422 | 0.07 | 0.029 | 145 | 0.20 |
| GE5406 | LAR1 | 2.22 | 0.019 | 254 | 0.08 | 0.017 | 107 | 0.16 |
| GE5409 | LAR1 | 2.5 | 0.026 | 444 | 0.06 | 0.025 | 163 | 0.16 |
| GE5438 | LAR1 | 2.51 | 0.022 | 391 | 0.06 | 0.025 | 163 | 0.16 |
| GE5439 | LAR1 | 2.79 | 0.020 | 374 | 0.05 | 0.025 | 163 | 0.16 |
| GE5440 | LAR1 | 2.7 | 0.022 | 389 | 0.06 | 0.029 | 145 | 0.20 |
| GE5441 | LAR1 | 2.81 | 0.023 | 395 | 0.06 | 0.029 | 145 | 0.20 |
| GE5492 | LAR1 | 2.91 | N/A | 225 | 7.18 mg/L | N/A | 101 | 19.34 mg/L |
| GE5494 | LAR1 | 2.95 | N/A | 239 | 2.72 mg/L | N/A | 86 | 11.75 mg/ml |
| GE5838 | LAR1 | 1.53 | 0.033 | 492 | 0.13 | 0.037 | 229 | 0.16 |
| GE4906 | LAR2 | 2.33 | 0.023 | 358 | 0.07 | 0.028 | 150 | 0.21 |
| GE5408 | LAR2 | 2.1 | 0.035 | 294 | 0.12 | 0.025 | 163 | 0.16 |
| GE5098 | LAR2 | 1.47 | 0.094 | 1341 | 0.07 | 0.086 | 534 | 0.16 |
| GE5404 | LAR2 | 2.28 | 0.025 | 244 | 0.10 | 0.017 | 107 | 0.16 |
| GE5405 | LAR2 | 1.88 | 0.026 | 220 | 0.12 | 0.017 | 107 | 0.16 |
| GE5407 | LAR2 | 2.1 | 0.026 | 232 | 0.11 | 0.017 | 107 | 0.16 |
| GE5491 | LAR2 | 2.47 | N/A | 237 | 7.8 mg/L | N/A | 101 | 19.34 mg/L |
| GE5489 | LAR3 | 1.99 | N/A | 203 | 8.59 mg/L | N/A | 101 | 19.34 mg/L |

Lar1 and Lar2 Mutant Graphs of qP, ETR, and NPQ and Lar1 PI Curve

```
N. gaditana R59     ---MSNILAAGDYDMHRSSDVELKQEASANMKSNAQVGLHPSQNQQLLQQQVQQPQ---- 53
N. oceanica 83      MSSPKNILAPASLSLNNYN--KPSHDLGSPKTQHHHHGLHHQHQHKQQYQHQQQLQHAHV 58
                        .****... .::. .  : .:: .:  ..: : *** .::::   *: ** *

N. gaditana R59     --GQEERGPKTATP--PCLSEGRYTS--------------FLAPLKSLTSPVASSVFEAD 95
N. oceanica 83      LGGKSVAGSNKILPFTSSMDEVKYAAGGLIKPGTQGLGSMLSTPLTPSASLIASSVVEAD 118
                      *:.  *.:.  *  ..:.* :*::              : :**.. :* :****.***

N. gaditana R59     AKQQQLLKDSLTADLKLLLHEFERFQQATALVSREGS-KEVEAMERAAKVEFFLGYIGKV 154
N. oceanica 83      AKQQQLLKDSLTADLKLLLHEFERFQQATAAAGTGGVGEEEAAERSTKVEFFLGYIERV 178
                    ****************************** .:  *.  * ** **::********* :*

N. gaditana R59     LQELAGADAPKLQELEVRIKTSLLPLKGQVVNKLASSLLSSSALGGLQHEP-SSSASIPS 213
N. oceanica 83      LHDLAGADASKLQDLEVRIKTSLLPLKGQVVSQLAAQNNNSPPPHKEQQSSWFHPSSTCS 238
                    *::******.***:*****************.:**:.  .*..    *:..   .:*  *

N. gaditana R59     PSSSPSSSCSTHTTPPISPVSGEKMTVQDDGRRERTHPTAAA------------LMPSVR 261
N. oceanica 83      SLSSSSSVSSVHTTPPGSPLAREETVMSTYGPFTHSRVAAADAVFLSSSSAASRLMPPVS 298
                    . **.** .*.***** **:: *: .:.  *   ::: :**             ***.*

N. gaditana R59     VQRLDSSSSGATTCSENS-----EEGRGQLD--DMECLSLLMEEDGQGLGRPQDRTAGGR 314
N. oceanica 83      FRRDQSDISGITSCSSSSSSCGGEGGAGHMDDLDLECFSLIMDE-AAATAPFTTAGNGGK 357
                    .:* :*. ** *:**..*     * * *::*  *:**:**:*:* . . .       **:

N. gaditana R59     EW---GLGPDEDVTDAASLVSEESSNVFAPSPGEASEMLETISRGL-----GLGQKR-LA 365
N. oceanica 83      DLPANGSCVDDDMTDAGSLTSEESS-VFVSSPRESSSSLSTVSTGLDPTSSNSGNKRTLP 416
                    :    *   *:*:***.**.***** **..** *:*. *.*:* **     . *:** *.

N. gaditana R59     L------SEGSTGSLGLASASFTSVESMQQ-LKRARSTVIPSISSNS-----------IS 407
N. oceanica 83      LEFPSSSSSSSSSLSLATASSVSTDTLQQPLKRARSVILPTSSSSSSSCATHAPPCLAS 476
                    *      *..*:.**.**:** .*.:::** ******.::*: **.*            *

N. gaditana R59     TTTTSSVSIGHGSSEVSEPSMSVASAEKPQVRQVEYQCGVCAESYSAAASLNPWWALEKQ 467
N. oceanica 83      SSTSSSSSFSSPFSSSSVATVAAADVSKPLLRQVEYQCGACADTYTAASSLNPWWALERQ 536
                    ::*:** *:.   *. * .:::.*...** :********.**::*:**:*********:*

N. gaditana R59     ECPQCKKLQIPRIDINLPANTMDYHPALLAEEGDDDDEEE--GLGLGGSGLVPGEEFRGM 525
N. oceanica 83      ECPKCKKVQVPRIDINLPANTMEYHPALLAEEGDDDDDDEVGGGREGGMMMMPGG---GD 593
                    ***:***:*:************:**************::*  *   **  ::**    *

N. gaditana R59     GKG-------GEDSAVG-GGIGVPEEEDGQAFSPAQASQILELMSHARTCPGHHHSEAHR 577
N. oceanica 83      GHGHLEEREEGETSEKGSGGSSVLEEDEEAVLSPMQASQLLSLLEHARTCPGNHAAEKHQ 653
                    *:*       ** *  * ** .* **::  .:** ****:*.*:.*******:*  :* *:

N. gaditana R59     AVCTSTKYLMLHVRDCDGKTLDGEACGFSWCRPCKHLLGHLVRCYESEQCSIC---RPQK 634
N. oceanica 83      AVCTSAKYLMLHVRDCDGRTLDGEACGFSWCRPCKHLLGHLVRCYEAEKCQICCFSHQEE 713
                    *****:************:***************************:*:*.**   :  ::

N. gaditana R59     REPCEEAVACKRET---SGAVREGVYRALTSLC 664  (SEQ ID NO:4)
N. oceanica 83      EEKVEKKVMMSVEEMIEEKGMRVDTYRSLTSLS 746  (SEQ ID NO:8)
                    .*  *: *  . *    . .:* ..**:****.
```

FIG. 16

```
EMRE1EUKT5308216  MGIGSEAVAEVGSGTSSAPCGSNSASPMMPVVTASQNAAESVAGSMLPVSCVASAAIAPQ 60
EMRE1EUKT5787835  ----------------------------MPMVTLSQDATTTAAGSMM-------LPLLPS 25
                                              **:** **:*: :.****:        .: *.

EMRE1EUKT5308216  TSSTTVGVAASAPAASPTTSKLHKGTSSMTQLGETGRENTGRWTCEEHVLFLKGLEMHGK 120
EMRE1EUKT5787835  IPASATSASFTAPSASSTTTKSPKGTSSMTQLGETGRENTGRWTCEEHVLFLKGLEMHGK 85
                   .:::...: :**:**.**:*  *************************************

EMRE1EUKT5308216  GWKKIAKLIKTRTVVQIRTHAQKYFQKLAKAKKNGHHGDMLGMEGTRFGGKRVKFTGKRR 180
EMRE1EUKT5787835  GWKKIAKLIKTRTVVQIRTHAQKYFQKLAKAKKNGHHGDMLGMEGSHFGGKRVKFTGKRR 145
                  *********************************************::*************

EMRE1EUKT5308216  GLVYGSYLVGAEATSAAISPALQSYMPGSWAGREEGEAL-SDKEEDAAIEKGLYRFLSPV 239
EMRE1EUKT5787835  GLVYNSYLVGAEATSAAISPALQTFMPANLGMEGERVGLMTDKEEDAAIEKGLYRFLSPV 205
                  ****.******************::**.. . . *  .* :*******************

EMRE1EUKT5308216  VLDAAASNLDATAPEV--LPPSTPGTGVHANGVVGA-----DGETT-EEDGSSGGDNVDV 291
EMRE1EUKT5787835  VLDPATRNLDASAPEILPLPPSTPAMGVHHTSSRGSSRGGLDGETTGEEDGGSDSIVMGD 265
                  ***.*: ****:***:  ******. ***  ..  *:     ***** ****.*..  :.

EMRE1EUKT5308216  SETIDDADSSSGEPLPRLARVTNDMYERCSVPTWFMKGGDIEELLADAAAIDWREDSGGD 351
EMRE1EUKT5787835  GGSDQDAESSLGEPLPTLARVTPEMYTRCGVPEWFKKGGDIDELLIDAAGLDWRSDSGGD 325
                  . : :**:** ***** ***** :** **.** ** *****:*** ***.:***.*****

EMRE1EUKT5308216  AVKAEERGASILNANIESSDQAQSHRNGEKVAVPNRVAAVKVAGNISADSSYITSGASQC 411
EMRE1EUKT5787835  ARKVVDQGTSILNANINGSNCATVAPAVVRKGCGSNTNKMNSAAPVLNMTGLAGAGGLSG 385
                  * *. ::*:*******:.*: *       : .  ...  :: *. :   :.   :*. .

EMRE1EUKT5308216  VNHPPTTNTIDGKRSNMNSGQSLPTANGRNGAASGR-----CVTGRGQQQKKKQPKTQES 466
EMRE1EUKT5787835  WKGK-GSDTSEGSSSNGSSKNMALTANASAGCGQGSWGVRGGAQKKQQQQQHEVPTQQQQ 444
                   :    ::* :*. ** .* :   ***.  *...*       .  : ***::  *. *:.

EMRE1EUKT5308216  GNHGKQQLVNKHSAPTG-DMFQSKAGAGTIVLQGDI---NCFASLDPHHVELKEEHSHHE 522
EMRE1EUKT5787835  VPTQQQQVHGIHVKEEGMELLRVMADRGTV--HGHVHEEDGFAAFDPHHVELKEEHSHHD 502
                      :**: . *    * ::::  *. **:  :*.:   : **::**************:

EMRE1EUKT5308216  LRLEELQQSGVNDDTFAHMDFLANDEAPVDH-------HAGHLHT----ISTHDDVHSHA 571
EMRE1EUKT5787835  LLLEELPHDSNHDDALAHIVFSVNGESDLHSLPRGAGGGGAHVHAPPVVVGGRQHHYHHN 562
                  * **** :.. :**::**: * .*.*: :.         ..*:*:    :. ::. : *

EMRE1EUKT5308216  DHDVHMRNYDVFWKDTVPDGDHG-LLLDDFDGGIEF 606  (SEQ ID NO:6)
EMRE1EUKT5787835  DNDIHLHAYDAYLEEEGADGGHGLLLLEDLDGGIEF 598  (SEQ ID NO:21)
                  *:*:*:: **.: ::  .**.** ***:*:******
```

```
H3GY58    -------------------ASADASAQPPAA-------------------MRKGKWTAEESAYCDR
D8LN59    --SAMGAAAAAAAAAAAAAAAVQAKAKKPNG-------------------LRRGKWTSEEEDYANR
F0Y497    NVDALEAAAAAPLPDESQIEASAEKSPPRSPRSRKADGDKPAPKPRRENGLRRGKWTVEEEAYANR
EUKT352   --GNAKQGSVVSPGETSALTSANKAGKVKNG-------------------LRRGKWTPEEEAYANR
B8BSI5    -------------------SAADRRRAP----------------------LRRGKWTAEEEAYASR
B7S450    -------------PALDVIPNNKKKGPP----------------------LRRGKWTPEEEAYANR
K0T5L8    --PVAGLSHYTIPPDASSISTKKKGGQP----------------------LRRGKWTTEEEAYAAR
                                                            :*. ****  ** . *.  *

H3GY58    LIEEFKKGNLPLAEGTTLRTFLSKLLNCDPMRISKKYTGDQCIGKIIFRRR-EDDVSK---DDMES
D8LN59    LIQEFKSGLLPLTDGTTLRTFLSKLLNCDPMRISKKFVGSNCIGKQVFRRR-QADMDRLQPADIER
F0Y497    LIHEFKLGLLPLTDGTTLRTFLSKLLNCDPMRISKKFVGSNCIGKQVFRRR-QADMDRLTPDDIKR
EUKT352   LIVEFKSGLLPLTDGTTLRTFLSKLLNCDPMRISKKFVGQNCIGKQVFRRRQQADLDRLSTDEIER
B8BSI5    LIQEFKAGLLPLTDGTTLRTFLSKLLNCDPMRISKKFVGSNCIGKQVFRRR-GADVNNLTPAQIQQ
B7S450    LILEFKSGLLPLTDGTTLRTFLSKLLNCDPMRISKKFVGSNCIGKQVFRRR-TADLNRLTPEQIQQ
K0T5L8    LIHEFKSGLLPLTDGTTLRNFLSKLLNCDPMRISKKFVGNNCIGKQVFRRK-VADINSLTPAQISQ
          **  *** * ***::*****.***************:.*.:****:***.*:.: :.

H3GY58    IRKDLAELEKTYLEREQYNQRRREKRLESELSRDKSRFAATRSIGYAA
D8LN59    SRSQLADLERRFLERVAMTNRCKTGGEIGSKEGGSSFDLLRPNQPPPA
F0Y497    SRYELAELERRFLTRVAQSHRSAKSGGAGAKGVKGGDGKALGGGLMQA
EUKT352   SRQELAELERRFLERVAQTNRCKNSVAGSKHGKDSAAGQVAPEVPRRQ
B8BSI5    TRLELSELEKRFLDRVSQNKKS-------------------GGSPKSE
B7S450    SRAELSELERRFLERVAQTNRVKSSGVGGAASAAPEAIIMGRPKIEHE
K0T5L8    IRVELSE-----------------------------------------
          *  :*::
```

H3GY58, amino acids 126-263 of SEQ ID NO:68
D8LN59, amino acids 234-391 of SEQ ID NO:70
F0Y497, amino acids 541-719 of SEQ ID NO:72
EUKT352, amino acids 302-404 of SEQ ID NO:63
B8BSI5, amino acids 107-225 of SEQ ID NO:74
B7S450, amino acids 40-183 of SEQ ID NO:76
K0T5L8, amino acids 150-263 of SEQ ID ON:78

FIG. 38

ALGAL MUTANTS HAVING A LOCKED-IN HIGH LIGHT ACCLIMATED PHENOTYPE

CROSS-REFERENCE TO RELATED APPLICATIONS

This application claims priority under U.S.C. § 119(e) to U.S. Provisional Patent Application No. 61/733,956, filed Dec. 6, 2012; to U.S. Provisional Patent Application No. 61/810,216, filed Apr. 9, 2013; to U.S. Provisional Patent Application No. 61/869,590, filed Aug. 23, 2013; and to Provisional Patent Application No. 61/881,342 filed Sep. 23, 2013, the entire contents of each of which is herein incorporated by reference.

REFERENCE TO A SEQUENCE LISTING

This application contains references to nucleic acid sequences which have been submitted concurrently herewith as the sequence listing text file "SGI1700-4 Sequence Listing_ST25.txt", file size 4 kilobytes (kb), created on 6 Dec. 2013. The aforementioned sequence listing is hereby incorporated by reference in its entirety pursuant to 37 C.F.R. § 1.52(e)(iii)(5).

FIELD OF THE INVENTION

The present invention relates to algal mutants having reduced chlorophyll content and increased photosynthetic efficiency. The present invention also relates, in some embodiments, to genes encoding regulators of light acclimation, to constructs that include at least a portion of the regulator genes, and to methods of engineering photosynthetic microorganisms using such constructs.

BACKGROUND

The present invention relates to mutant algae strains having novel photosynthetic traits, to methods of generating, identifying and/or isolating such mutants and to genes encoding proteins that regulate photosynthesis.

In large scale open algal growth systems, cultures must be grown at reasonably high culture densities and depths in the region of 20-30 cm. This culturing environment provides significant self-shading, ensuring that each cell experiences only a low average irradiance level. The predominant photo-physiological status of an algal cell under these conditions is the low light-acclimated state, which is characterized by a relatively large auxiliary light harvesting antenna system associated with the photosynthetic reaction centers. However, a larger light harvesting antenna in each individual cell exacerbates the self-shading of the culture, leading to an even lower average irradiance level, which prompts further increases in the antenna size of the algal cells in response. The overall result is a culture with very poor light penetration, ensuring that the majority of the open growth system is in darkness. Furthermore, the large and efficient light harvesting antenna drives saturation of photosynthesis at relatively low light intensities. Therefore in the surface layer of the ponds, where light is available, a significant portion of the incident light is in excess of the light required to drive maximum photosynthetic rates. This excess irradiance dissipates through thermal channels and is lost as heat. The light use efficiency in open growth systems is very low and it has been suggested that up to 80% of photosynthetic active irradiance, incident upon the pond surface, is lost as heat.

Thus, the low light acclimation response decreases the overall light use efficiency of a pond culture by increasing self-shading and lowering the saturating irradiance level for photosynthesis. Prior methods for decreasing light harvesting antenna size in algae have focused solely on the antenna, targeting the biosynthesis of light harvesting polypeptides directly, or reducing their assembly or function indirectly by disrupting chlorophyll biosynthesis, protein translational control, or protein localization mechanisms. As a result, the reduced-pigment strains obtained are often imbalanced in light harvesting, electron transport, and carbon fixation, which can adversely affect culture productivity.

Most photoautotrophs acclimate to differing levels of irradiance in order to maximize light capture under light limited conditions or to avoid the potentially deleterious effects of harvesting excitation energy in excess under high irradiance. The most obvious feature of the acclimation response to irradiance is a change in the level of pigmentation, typically associated with changes in the abundance of the auxiliary light harvesting antenna. Acclimation to irradiance is, however, a largely pleiotropic response, involving changes in composition and function at multiple levels within the photosynthetic machinery and throughout the organism. The regulation of acclimation to irradiance in oxygenic photoautotrophs is poorly defined and a greater understanding of the underlying regulatory network may enable the beneficial manipulation of the composition and function of the photosynthetic machinery.

SUMMARY

The present invention describes the results of a screening procedure biased toward isolating mutants that retain as many features as possible of the natural high light acclimated photo-physiological state, including a decreased light harvesting antenna, in balance with all other aspects of the photosynthetic process. This forward genetic screen (termed the Locked In High Light Acclimated (LIHLA) screen), was specifically designed to isolate global regulatory components associated with photosynthetic acclimation to irradiance. Based on the implementation of the LIHLA screen, we provide genes encoding novel Light Acclimation Regulators (LAR1, LAR2, and LAR3). These genes are demonstrated, through transcriptomic and photo-physiological analysis, to be global regulators of photosynthetic acclimation to irradiance.

In one aspect, provided herein are algal mutants have a "Locked-in High Light Acclimated or "LIHLA" phenotype, in which the mutants exhibit photosynthetic properties of high light acclimated algal cells at both high and low light intensities. The mutants are characterized by a reduced amount of chlorophyll per cell, and can exhibit, for example, a 20% or greater reduction in chlorophyll per cell, and preferably a 25% or greater, a 30% or greater, 40% or greater, or 50% or greater reduction in chlorophyll per cell under low light conditions, as compared with a wild type cells. Additionally, LIHLA mutants have at least one of the following photosynthetic properties with respect to wild type cells, when both LIHLA mutants and wild type cells are acclimated to low light: increased photochemical quenching (qP) over all physiologically relevant light intensities greater than 400 $\mu E \cdot m^{-2} \cdot s^{-1}$ (for example, over all physiologically relevant light intensities greater than 350 $\mu E \cdot m^{-2} \cdot s^{-1}$, greater than 300 $\mu E \cdot m^{-2} \cdot s^{-1}$, greater than 250 $\mu E \cdot m^{-2} \cdot s^{-1}$, or greater than 200 $\mu E \cdot m^{-2} \cdot s^{-1}$); increased maximal photosynthetic rate ($P_{max}$) on a per chlorophyll basis, with the mutants having at least 70% of the $P_{max}$ of wild type cells on a per cell basis, and preferably with 75% or greater, 80% or greater, 85% or greater, 90% or greater, or substantially the same maximal photosynthetic rate ($P_{max}$) as wild type cells or a higher $P_{max}$ as compared to wild type cells on a per cell basis; saturation of photosynthesis at higher irradiance levels (higher Ek); delayed onset of nonphotochemical quenching (NPQ) in response to increasing light intensity; reduced levels of NPQ at all physiologically relevant irradiances greater than 500 $\mu E \cdot m^{-2} \cdot s^{-1}$, for example, greater than 450 $\mu E \cdot m^{-2} \cdot s^{-1}$, greater than 400 $\mu E \cdot m^{-2} \cdot s^{-1}$, greater than 350 $\mu E \cdot m^{-2} \cdot s^{-1}$, greater than 300 $\mu E \cdot m^{-2} \cdot s^{-1}$, greater than 250 $\mu E \cdot m^{-2} \cdot s^{-1}$, greater than 200 $\mu E \cdot m^{-2} \cdot s^{-1}$, greater than 150 $\mu E \cdot m^{-2} \cdot s^{-1}$, or greater than 100 $\mu E \cdot m^{-2} \cdot s^{-1}$. Additionally, a LIHLA mutant can have a maximal electron transport rate for photosystem II ($ETR_{PSII}$) that is at least as high as the $ETR_{PSII}$ of a wild type cell, and preferably at least about 1.5 times the rate of the wild type $ETR_{PSII}$, or at least about 2 times the rate of the wild type $ETR_{PSII}$.

In some examples, a LIHLA mutant has at least a 20%, 25%, 30%, 35%, 40%, 45%, or 50% reduction in chlorophyll with respect to a wild type cell, exhibits increased photochemical quenching (qP) over all physiologically relevant light intensities greater than 400 $\mu E \cdot m^{-2} \cdot s^{-1}$ with respect to a wild type cell; has an increased maximal photosynthetic rate ($P_{max}$) on a per chlorophyll basis (e.g., at least 1.5 fold the $P_{max}$ of wild type cells, for example at least 2 fold the $P_{max}$ of wild type cells), with at least 75% or at least 80% of the $P_{max}$ of wild type cells on a per cell basis; experiences saturation of photosynthesis at higher irradiance levels (higher Ek) than wild type; exhibits delayed onset of NPQ in response to increasing light intensity as compared with wild type cells; and has lower levels of NPQ over all irradiances greater than about 500 $\mu E \cdot m^{-2} \cdot s^{-1}$ than wild type cells, when both the LIHLA mutants and wild type cells are acclimated to low light. Additionally, a LIHLA mutant may have a maximal PSII electron transport rate ($ETR_{PSII}$) that is at least equivalent to the wild type PSII electron transport rate, and may be, for example, approximately 1.5 fold the wild type PSII electron transport rate or greater. Additionally, a LIHLA mutant may have a maximal PSI electron transport rate ($ETR_{PSI}$) that is substantially equivalent to or greater than the wild type PSI electron transport rate. Additionally, a culture comprising a LIHLA mutant, where the culture is exposed to light from a light source, may have a greater amount of light penetration into the culture than does a culture comprising a comparable wild type alga (i.e., a wild type alga of the progenitor strain).

Additionally to any of the above traits, a LIHLA mutant can have any combination of the following traits with respect to wild type or control cells: higher Fv/Fm, increased ΦPSII, and a lower a, or initial slope of the P/I curve. For example, a low light acclimated LIHLA mutant can have a higher Fv/Fm, increased ΦPSII, and, optionally, a lower a with respect to low light acclimated wild type or control cells.

In another aspect, provided herein are mutants having a LIHLA phenotype (e.g., with respect to low light acclimated wild type cells, the low light acclimated mutants have chlorophyll reduced by at least 20%, a higher qP over irradiances greater than 400 $\mu E \cdot m^{-2} \cdot s^{-1}$, at least 1.5 times or at least 2 times the $P_{max}$ of wild type cells on a per chlorophyll basis and at least 70% or at least 80% $P_{max}$ of wild type cells on a per cell basis, onset of NPQ at higher irradiance and lower NPQ at all irradiances above 500 $\mu E \cdot m^{-2} \cdot s^{-1}$, higher Ek, and preferably, a higher $ETR_{PSII}$, in which the mutants are deregulated in the expression of at least twenty, at least thirty, at least forty, at least fifty, at least sixty, at least seventy, at least eighty, at least ninety, or at least 100 genes that are regulated in response to light intensity in wild type cells. For example, mutants provided herein can be deregulated in the expression of genes that are differentially expressed when high light-acclimated wild type cells are acclimated to low light intensity.

Further, provided herein are mutants having at least one mutation in a gene encoding a regulatory protein, in which a regulatory protein can be a protein that directly or indirectly affects transcription of multiple genes, e.g., at least ten, at least twenty, at least thirty, at least forty, at least fifty, at least sixty, at least eighty, or at least 100 genes. In some nonlimiting examples, the mutant is mutated in a gene encoding a transcription factor or a transcriptional activator.

A mutant as provided herein can be a spontaneously arising mutant, derived from classical mutation (e.g., UV, gamma irradiation, or chemical mutagenesis), or obtained by genetic engineering (e.g., homologous recombination, gene attenuation by antisense or RNAi, or genome modification, for example, using meganucleases, zinc finger nucleases, talens, or CRISPR/cas systems).

Also provided herein is a mutant or recombinant algal strain exhibiting altered photosynthetic properties with respect to a wild type or control strain, for example, the progenitor strain from which the mutant was derived, in which the strain includes a mutated or attenuated gene that in the wild type strain encodes a polypeptide that includes a TAZ zinc finger domain. The polypeptide can include an amino acid sequence that can have at least 40%, at least 45%, at least 50%, at least 55%, at least 60%, at least 65%, at least 70%, at least 75%, for example at least 80%, at least 85%, at least 90%, or at least 95% sequence identity with the amino acid sequence of SEQ ID NO:9 or SEQ ID NO:10. In various examples the polypeptide can have at least 30%, at least 35%, at least 40%, at least 45%, or at least 50%, at least 55%, at least 60%, at least 65%, at least 70%, at least 75%, at least 80% or at least 85%, at least 90%, or at least 95% sequence identity to an amino acid sequence encoded by LAR1 genes as provided herein, e.g., SEQ ID NO:4 or SEQ ID NO:8. In some examples, a mutant algal strain can have a mutated or attenuated gene that in a wild type strain encodes a polypeptide having at least 65%, at least 70%, at least 75%, at least 80%, at least 85%, at least 90%, or at least 95% amino acid sequence identity to SEQ ID NO:4, SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. The polypeptide can include a TAZ zinc finger domain. The mutant or recombinant algal strain having a mutated or attenuated gene encoding a polypeptide having a TAZ zinc finger domain can exhibit altered acclimation to low light with respect to wild type cells of the same strain, and can have a LIHLA phenotype as disclosed herein.

Also provided herein is a mutant or recombinant algal strain exhibiting altered photosynthetic properties with respect to wild type cells or control cells of the same background strain, for example the wild type strain that is a progenitor to the mutant or recombinant strain, wherein the mutant or recombinant strain includes a mutated or attenuated gene than in the wild type or control strain encodes a polypeptide that includes a myb-like DNA-binding domain. The polypeptide can include an amino acid sequence that can have at least 65%, at least 70%, at least 75%, at least 80%, at least 85%, at least 90%, or at least 95% sequence identity with the amino acid sequence of SEQ ID NO:22 or SEQ ID NO:23. In various examples the polypeptide can have at least 50%, at least 55%, at least 60%, at least 65%, or at least 70%, at least 75%, at least 80%, at least 85%, at least 90%, or at least 95% sequence identity to a polypeptide encoded by a LAR2 gene as provided herein, e.g., SEQ ID NO:6 or SEQ ID NO:21. In some examples a mutant algal strain can have a mutated or attenuated gene in a gene encoding in a wild type strain a polypeptide having at least 65%, at least 70%, at least 75%, at least 80%, at least 85%, at least 90%, or at least 95% amino acid sequence identity to SEQ ID NO:6 or SEQ ID NO:21 SEQ ID NO:26, SEQ ID NO:27, SEQ ID NO:28, SEQ ID NO:29, SEQ ID NO:30, SEQ ID NO:31, or SEQ ID NO:32. The polypeptide can include a myb-like DNA-binding domain. The mutant or recombinant algal strain having a mutated or attenuated gene encoding a polypeptide having a myb-like DNA-binding domain can exhibit altered acclimation to low light, and can have a LIHLA phenotype as disclosed herein.

Further provided herein is a mutant or recombinant algal strain exhibiting altered photosynthetic properties with respect to wild type cells or control cells of the same background strain, for example the wild type strain that is a progenitor to the mutant or recombinant strain, wherein the mutant or recombinant strain includes a mutated or attenuated gene that in the wild type or control strain encodes a polypeptide having a domain having at least 65%, at least 70%, at least 75%, at least 80%, at least 85%, at least 90%, or at least 95% sequence identity with the amino acid sequence of SEQ ID NO:64. In various examples, the mutant or recombinant strain includes a mutated or attenuated gene encoding a polypeptide having at least 65%, at least 70%, at least 75%, at least 80%, at least 85%, at least 90%, or at least 95% amino acid sequence identity to a polypeptide selected from the group consisting of SEQ ID NO:63, SEQ ID NO:66, SEQ ID NO:68, SEQ ID NO:70, SEQ ID NO:72, SEQ ID NO:74, SEQ ID NO:76, and SEQ ID NO:78. In some examples a mutant algal strain can have a mutated or attenuated gene that in a wild type strain encodes a polypeptide having at least 65%, at least 70%, at least 75%, at least 80%, at least 85%, at least 90%, or at least 95% sequence identity with the amino acid sequence of SEQ ID NO:63 or SEQ ID NO:66. The mutant or recombinant algal strain having a mutated or attenuated gene encoding a polypeptide at least 65%, at least 70%, at least 75%, at least 80%, at least 85%, at least 90%, or at least 95% amino acid sequence identity to SEQ ID NO:63, SEQ ID NO:66, SEQ ID NO:68, SEQ ID NO:70, SEQ ID NO:72, SEQ ID NO:74, SEQ ID NO:76, or SEQ ID NO:78 can exhibit altered acclimation to low light, and can have a LIHLA phenotype as disclosed herein.

A mutant as provided herein having a mutated gene encoding a regulatory protein or a recombinant cell engineered to have an altered structure or expression of a gene encoding a regulatory protein can be mutated in a gene encoding a global regulator of the light acclimation response, in which, for example, at least ten, at least fifteen, at least twenty, at least thirty, at least forty, at least fifty, or at least 100 genes can be deregulated in the mutant strain in low light conditions (e.g., less than or equal to about 200 $\mu E \cdot m^{-2} \cdot s^{-1}$, less than or equal to about 150 $\mu E \cdot m^{-2} \cdot s^{-1}$, less than or equal to about 100 $\mu E \cdot m^{-2} \cdot s^{-1}$, or less than or equal to about 50 $\mu E \cdot m^{-2} \cdot s^{-1}$) with respect to the wild type or control strain in low light conditions. For example, the expression level of at least ten, at least fifteen, at least twenty, at least thirty, at least forty, at least fifty, or at least 100 genes can be differ by a $\log_2$ fold of 1 or greater in the mutant strain in low light conditions with respect to the wild type or control strain in low light conditions. The mutant or recombinant cell can have, for example, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least thirty, at least forty, or at least fifty genes that are downregulated in the mutant strain with respect to the wild type strain under low light conditions. For example, at least two, at least three, at least four, at least five, at least six, at least seven, at least eight, at least nine, at least ten, at least eleven, or at least twelve light harvesting chlorophyll-binding (LHC) protein genes can be downregulated in a LIHLA mutant in low light as compared with a wild type or control cell in low light. Additionally, at least two, at least three, at least four, at least five, or at least six non-LHC protein genes that encode proteins that function in photosynthesis can be downregulated in a LIHLA mutant. Further, at least two, at least three, at least four, at least five, at least six, at least seven, at least eight, at least nine, or at least ten genes encoding proteins that do not function in photosynthesis can be upregulated in the mutant with respect to the wild type or control strain under low light conditions. At least five, at least ten, at least twenty, or at least thirty deregulated genes can have an expression level (e.g., a transcript abundance level) that differs by a $\log_2$ fold of at least 1, for example, can be present in the LIHLA mutant at a level of two-fold or more of the wild type level, or 50% or less of the wild type or control level, under the same conditions.

A LIHLA mutant having a mutated gene encoding a regulatory protein can further be a mutant that allows greater light penetration into the culture. For example, a culture of a LIHLA mutant can allow more light into the culture than is able to penetrate a culture of a comparable wild type or control strain. For example, at least 50% more light, at least 60% more light, at least 70% more light, at least 80% more light, at least 90% more light, or at least 100% more light, can penetrate approximately 2 cm below the surface of a pond of a LIHLA mutant culture having a density of approximately $4.5 \times 10^7$ cells/mL as compared to the amount of light that can penetrate approximately 2 cm below the surface of a pond of a culture or wild type or control cells having approximately the same cell density.

Further, a LIHLA mutant having a mutated gene encoding a regulatory protein in some examples can grow to a higher cell density than a wild type or control strain. For example, a LIHLA mutant can grow to a higher cell density than a wild type or control strain after at least five, at least six, at least seven, at least eight, at least nine, at least ten, at least eleven, at least twelve, at least thirteen, at least fourteen, or at least fifteen days in culture.

In various examples, a LIHLA mutant that is disrupted in the expression or function of a global regulator of the light acclimation response has at least a 25% reduction in chlorophyll with respect to wild type cells under low light (e.g., less than about 200 $\mu E \cdot m^{-2} \cdot s^{-1}$), and is deregulated in the expression of multiple light regulated genes, for example, exhibits deregulation of at least ten, at least fifteen, or at least twenty genes that are regulated in response to light intensity in a wild type cell, where the difference in the level of expression of the genes under low light conditions between the LIHLA mutant and a wild type cell is at least two-fold. Additionally, in these examples, the LIHLA mutant exhibits a higher qP that wild type at all light intensities greater than 200 $\mu E \cdot m^{-2} \cdot s^{-1}$, exhibits delayed onset of NPQ with respect to light intensity as compared with wild type cells and lower NPQ at all irradiances greater than about 200 $\mu E \cdot m^{-2} \cdot s^{-1}$, and exhibits a higher per chlorophyll $P_{max}$ and a per cell $P_{max}$ that is not less than 70%, 75%, or 80% of wild type $P_{max}$.

Additionally, the LIHLA mutant can have a maximal $ETR_{PSII}$ that is greater than the maximal $ETR_{PSII}$ of wild type cells when both the LIHLA mutant and wild type cells are acclimated to low light.

An algal LIHLA mutant can be, for example, a microalga such as but not limited to a species of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyanidioschyzon, Cyclotella, Cylindrotheca, Cymatopleura, Dixoniella, Dunaliella, Ellipsoidon, Emiliania, Entomoneis Eremosphaera, Ernodesmius, Euglena, Eustigmatos, Franceia, Fragilaria, Fragilariopsis, Gloeothamnion, Haematococcus, Halocafeteria, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. For example, the mutant may be a diatom (Bacillariophyte) such as, but not limited to, a species of *Achnanthes, Amphora, Chaetoceros, Cyclotella, Cylindrotheca, Cymatopleura, Entomoneis, Fragilaria, Fragilariopsis, Navicula, Nitzschia, Phceodactylum*, or *Thalassiosira*. Alternatively, a LIHLA mutant can be a eustigmatophyte, such as, for example, a species of *Eustigmatos, Monodus, Nannochloropsis* or *Vischeria.*

Also provided is a method of isolating an algal mutant deregulated in low light acclimation. The method includes: mutagenizing a population of algae; screening the mutagenized population of algae for low chlorophyll fluorescence; selecting mutants that retain low chlorophyll fluorescence when acclimated to low light conditions; and screening the selected mutants by fluorometry to identify low light stable low chlorophyll fluorescence algal mutants having photochemical quenching coefficients (qP) at least as high as wild type algae. In some embodiments, the method includes identifying low light stable low chlorophyll fluorescence algal mutants having photochemical quenching coefficients (qP) that are higher than wild type algae at light intensities greater than about 400 $\mu E \cdot m^{-2} \cdot s^{-1}$, greater than about 300 $\mu E \cdot m^{-2} \cdot s^{-1}$ or greater than about 200 $\mu E \cdot m^{-2} \cdot s^{-1}$. In some embodiments, screening for low chlorophyll fluorescence is by fluorescence activated cell sorting (FACS). The method further includes screening the low chlorophyll algae for a reduction in chlorophyll, for example, a 20% or greater reduction, a 30% or greater reduction, a 40% or greater reduction, or a 50% or greater reduction, in chlorophyll per cell, under low light conditions. The method further includes screening low chlorophyll algal mutants for increased $P_{max}$ per chlorophyll with respect to wild type cells, and for $P_{max}$ per cell at least 70%, at least 75%, at least 80%, at least 85%, at least 90% or at least 95% of the $P_{max}$ per cell of wild type cells. The method further includes screening low chlorophyll algal mutants for delayed onset of NPQ in response to increasing light intensity as compared to the onset of NPQ in response to light intensity to wild type cells, and for lower levels of NPQ with respect to wild type cells acclimated to low light at all irradiances greater than about 500 $\mu E \cdot m^{-2} \cdot s^{-1}$, greater than about 400 $\mu E \cdot m^{-2} \cdot s^{-1}$, greater than about 300 $\mu E \cdot m^{-2} \cdot s^{-1}$, or greater than about 200 $\mu E \cdot m^{-2} \cdot s^{-1}$.

In various examples, the method can include screening for one or more of higher Ek, higher maximal $ETR_{PSII}$, higher Fv/Fm (photosynthetic efficiency), and greater photosynthetic quantum yield of photosystem II, ΦPSII, with respect to wild-type cells. In some examples, the method can include screening for a decreased slope (alpha) of the photosynthesis irradiance (P/I) curve.

Further provided are methods of producing algal products, comprising culturing an algal mutant that is deregulated in low light acclimation as provided herein and isolating at least one product from the culture. The product can be a lipid, a terpenoid, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a colorant, or the product can be algal biomass. The mutant alga can be cultured phototrophically and can be cultured in a pond or raceway. Also provided is a product made by an algal mutant as disclosed herein. Further included herein is an algal biomass comprising a mutant alga deregulated in acclimation to low light, such as any of the LIHLA mutants provided herein.

In other aspects, the invention provides isolated nucleic acid molecules. For example, the invention includes an isolated nucleic acid molecule comprising a nucleotide sequence that encodes a polypeptide that includes an amino acid sequence having at least 40%, at least 45%, at least 50%, at least 55%, at least 60%, at least 65%, at least 70%, at least 75%, or at least 80% or at least 85%, at least 90%, or at least 95% sequence identity with the amino acid sequence of SEQ ID NO:9 or SEQ ID NO:10. The nucleic acid can be a cDNA, for example. The polypeptide encoded by the nucleotide sequence can have at least at 30%, at least 35%, at least 40%, at least 45%, or at least 50%, at least 55%, at least 60%, at least 65%, at least 70%, at least 75%, at least 80% or at least 85%, at least 90%, or at least 95% sequence identity to a polypeptide encoded by a naturally occurring gene in which the nucleotide sequence is different from the sequence of a naturally occurring gene. Additionally, the nucleotide sequence can encode a polypeptide having an altered amino acid sequence with respect to the amino acid sequence encoded by the naturally occurring gene with which it has sequence similarity (e.g., SEQ ID NO:4; SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18). The isolated nucleic acid molecule can include a nucleotide sequence mutation that can result, for example, in an amino acid substitution, addition, or deletion. In some examples, the nucleic acid molecule encodes a truncated (e.g., N-terminally or C-terminally truncated) or internally deleted polypeptide. In some examples, the nucleic acid molecule can encode a polypeptide having at least 30%, at least 35%, at least 40%, at least 45%, or at least 50%, at least 55%, at least 60%, at least 65%, at least 70%, at least 75%, at least 80% or at least 85%, at least 90%, or at least 95% sequence identity to SEQ ID NO:4 or SEQ ID NO:8. Additionally, the encoded polypeptide can include a TAZ zinc finger domain and in some examples can include a mutated TAZ zinc finger domain. Further, the nucleic acid molecule can comprise a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, or SEQ ID NO:40, or a portion thereof, wherein the nucleotide sequence differs from that of a naturally-occurring gene.

An isolated nuclei acid molecule as provided herein can comprise a nucleotide sequence encoding a polypeptide having at least 30%, at least 35%, at least 40%, at least 45%, or at least 50%, at least 55%, at least 60%, at least 65%, at least 70%, at least 75%, at least 80% or at least 85%, at least 90%, or at least 95% sequence identity to SEQ ID NO:4; SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 and/or a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, or SEQ ID NO:40, or a portion thereof or a complement of at least a portion thereof, operably linked to a heterologous expression sequence. Alternatively or in addition, an isolated nucleic acid molecule comprise a vector that includes a nucleic acid sequence encoding a polypeptide having at least 30%, at least 35%, at least 40%, at least 45%, or at least 50%, at least 55%, at least 60%, at least 65%, at least 70%, at least 75%, at least 80% or at least 85%, at least 90%, or at least 95% sequence identity to SEQ ID NO:4; SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 and/or a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, or SEQ ID NO:40, or a portion thereof or a complement of at least a portion thereof.

In additional aspects, the invention provides isolated nucleic acid molecules comprising a nucleotide sequence encoding a polypeptide that includes an amino acid sequence having at least 40%, at least 45%, at least 50%, at least 55%, at least 60%, at least 65%, at least 70%, at least 75%, or at least 80% or at least 85%, at least 90%, or at least 95% sequence identity with the amino acid sequence of SEQ ID NO:22 or SEQ ID NO:23. The nucleic acid can be a cDNA, for example. Additionally, the polypeptide encoded by the nucleotide sequence can have at least at 30%, at least 35%, at least 40%, at least 45%, or at least 50%, at least 55%, at least 60%, at least 65%, at least 70%, at least 75%, at least 80% or at least 85%, at least 90%, or at least 95% sequence identity to a polypeptide encoded by a naturally occurring gene in which the nucleotide sequence is different in sequence from a naturally occurring gene. The nucleotide sequence can encode a polypeptide having an altered amino acid sequence with respect to the amino acid sequence encoded by the naturally occurring gene with which it has sequence similarity (e.g., SEQ ID NO:6; SEQ ID NO:21, SEQ ID NO:26, SEQ ID NO:27, SEQ ID NO:28, SEQ ID NO:29, SEQ ID NO:30, SEQ ID NO:31, or SEQ ID NO:32). The isolated nucleic acid molecule can include a nucleotide sequence mutation that can result, for example, in an amino acid substitution, addition, or deletion. In some examples, the nucleic acid molecule encodes a truncated (e.g., N-terminally or C-terminally truncated) or internally deleted polypeptide. In some examples, the nucleic acid molecule can encode a polypeptide having at least 30%, at least 35%, at least 40%, at least 45%, or at least 50%, at least 55%, at least 60%, at least 65%, at least 70%, at least 75%, at least 80% or at least 85%, at least 90%, or at least 95% sequence identity to SEQ ID NO:6 or SEQ ID NO:21. Additionally, the encoded polypeptide can include a myb-like DNA binding domain and in some examples can include a mutated a myb-like DNA binding domain. Further, the nucleic acid molecule can comprise a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, or SEQ ID NO:40, or a portion thereof, wherein the nucleotide sequence differs from that of a naturally-occurring gene.

In further aspects, the invention provides isolated nucleic acid molecules comprising a nucleotide sequence encoding a polypeptide that includes an amino acid sequence having at least 70%, at least 75%, or at least 80% or at least 85%, at least 90%, or at least 95% sequence identity with the amino acid sequence of SEQ ID NO:64. The nucleic acid can be a cDNA, for example. Additionally, the polypeptide encoded by the nucleotide sequence can have at least at least 65%, at least 70%, at least 75%, at least 80% or at least 85%, at least 90%, or at least 95% sequence identity to a polypeptide encoded by a naturally occurring gene in which the nucleotide sequence is not 100% identical to the sequence of a naturally occurring gene. The nucleotide sequence can encode a polypeptide having an altered amino acid sequence with respect to the amino acid sequence encoded by the naturally occurring gene with which it has sequence similarity (e.g., of SEQ ID NO:63, SEQ ID NO:66, SEQ ID NO:68, SEQ ID NO:70, SEQ ID NO:72, SEQ ID NO:74, SEQ ID NO:76, or SEQ ID NO:78). The isolated nucleic acid molecule can include a nucleotide sequence mutation that can result, for example, in an amino acid substitution, addition, or deletion. In some examples, the nucleic acid molecule encodes a truncated (e.g., N-terminally or C-terminally truncated) or internally deleted polypeptide. In some examples, the nucleic acid molecule can encode a polypeptide having at least 65%, at least 70%, at least 75%, at least 80% or at least 85%, at least 90%, or at least 95% sequence identity to SEQ ID NO:63 or SEQ ID NO:66. Further, the nucleic acid molecule can comprise a nucleotide sequence having at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:63, SEQ ID NO:66, SEQ ID NO:68, SEQ ID NO:70, SEQ ID NO:72, SEQ ID NO:74, SEQ ID NO:76, or SEQ ID NO:78, or a portion thereof, wherein the nucleotide sequence differs from that of a naturally-occurring gene.

Also included herein are nucleic acid constructs for homologous recombination (including but not limited to knock out and gene substitution constructs), genome modification, and gene attenuation (e.g., RNAi, antisense, and ribozyme constructs), that include at least a portion of the nucleotide sequences provided herein or their complements.

A nucleic acid construct for homologous recombination can include a nucleic acid sequence that includes at least a portion of a naturally-occurring gene encoding a polypeptide as provided herein that directly or indirectly regulates the light acclimation response, e.g., a LAR gene or homolog thereof as provided herein. Alternatively or in addition, a construct for homologous recombination can include a nucleic acid sequence that includes a sequence that is positioned in a host genome adjacent to a naturally-occurring gene encoding a polypeptide as provided herein that directly or indirectly regulates the light acclimation response. In some examples, a construct for homologous recombination includes a nucleic acid sequence that includes at least a portion of a naturally-occurring gene encoding a polypeptide as provided herein, in which the gene has at least one amino acid substitution, deletion, insertion, or addition with respect to a wild type polypeptide. For example, the gene or a portion thereof can include the insertion of a selectable marker gene.

A nucleic acid construct for gene attenuation, e.g., a ribozyme, RNAi, or antisense construct can include at least fifteen, at least twenty, at least thirty, at least forty, at least fifty, or at least sixty nucleotides having at least 80% identity, such as at least 85%, at least 90%, at least 95%, or at least 99% or complementarity to at least a portion of the sequence of a naturally-occurring gene, such as a gene having encoding a polypeptide that includes an amino acid sequence having at least an amino acid sequence having at least 40%, at least 45%, at least 50%, at least 55%, at least 60%, at least 65%, at least 70%, at least 75%, or at least 80% or at least 85%, at least 90%, at least 95%, at least 96%, at least 97%, at least 98%, or at least 99% sequence identity with the amino acid sequence of SEQ ID NO:9, SEQ ID NO:10, SEQ ID NO:22, SEQ ID NO:23, or SEQ ID NO:64. A nucleic acid construct for gene attenuation, e.g., a ribozyme, RNAi, or antisense construct can include at least fifteen, at least twenty, at least thirty, at least forty, at least fifty, or at least sixty nucleotides having at least 80%, such as at least 95% or about 100%, identity or complementarity to the sequence of a naturally-occurring gene, such as a gene having encoding a polypeptide having at least 50%, at least 55%, at least 60%, at least 65%, at least 70%, at least 75%, at least 80% or at least 85%, at least 90%, or at least 95% sequence identity to SEQ ID NO:4; SEQ ID NO:8, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:6; SEQ ID NO:21, SEQ ID NO:26, SEQ ID NO:27, SEQ ID NO:28, SEQ ID NO:29, SEQ ID NO:30, SEQ ID NO:31, SEQ ID NO:32, SEQ ID NO:63, SEQ ID NO:66, SEQ ID NO:68, SEQ ID NO:70, SEQ ID NO:72, SEQ ID NO:74, SEQ ID NO:76, or SEQ ID NO:78. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 80% identity or complementarity to the sequence of a naturally-occurring gene, such as a gene encoding a light acclimation regulator (e.g., a LAR gene) as provided herein. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity with SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:5, SEQ ID NO:20, SEQ ID NO:41, SEQ ID NO:42, SEQ ID NO:43, SEQ ID NO:44, SEQ ID NO:45, SEQ ID NO:46, SEQ ID NO:47, SEQ ID NO:62, SEQ ID NO:65, SEQ ID NO:67, SEQ ID NO:69, SEQ ID NO:71, SEQ ID NO:73, SEQ ID NO:75, or SEQ ID NO:77, or a portion thereof.

BRIEF DESCRIPTION OF THE DRAWINGS

FIG. 6 provides a summary of photophysiological properties of LIHLA mutants obtained by screening of low chlorophyll mutants after low light acclimation. The table provides maximal $ETR_{PSII}$ (presented as fold difference from wild type), $P_{max}$ per cell and $P_{max}$ per milligram chlorophyll values, and amount of chlorophyll per cell for each mutant. The three rightmost columns provide wild type values $P_{max}$ per cell and $P_{max}$ per milligram chlorophyll values, and amount of chlorophyll per cell from the same low light acclimation.

FIG. 16 provides a sequence alignment of the *N. gaditana* LAR1 protein sequence with the *N. oceanica* LAR1 ortholog ("No-LAR1") protein sequence.

FIG. 18 provides a sequence alignment of the *N. gaditana* LAR2 protein sequence with the *N. oceanica* LAR2 ortholog ("No-LAR2") protein sequence.

FIG. 38 is a sequence alignment of the conserved domain of the LAR3 gene with the homologous regions of other heterokont genes.

DETAILED DESCRIPTION

Definitions

Figure 1:
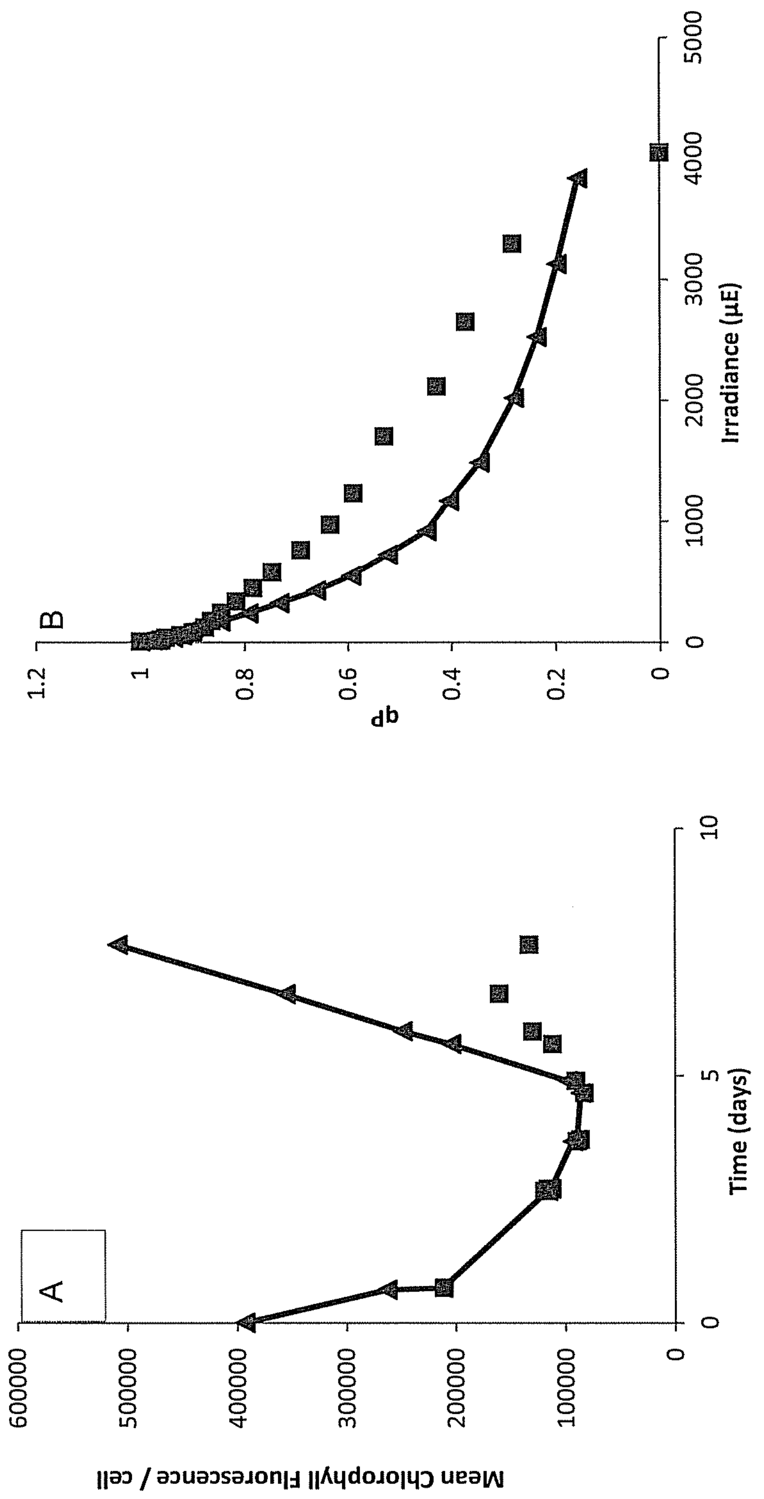
FIG. 1 (A) Light shift experiment of wild type *Nannochloropsis* experiencing high light (squares) and light limited (triangles) acclimation physiologies. Cultures were grown for 4.6 days at 500 $\mu E \cdot m^{-2} \cdot s^{-1}$ (high light) prior to reducing intensities to 100 $\mu E \cdot m^{-2} \cdot s^{-1}$ (low light, triangles) for one of the cultures to demonstrate difference in mean chlorophyll fluorescence between treatments. (B) On Day 8, photo-physiological measurements of qP over 20 irradiances was measured to illustrate how high light cultured cells (squares) have higher qP compared to light limited cultured cells (triangles).

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. All ranges provided within the application are inclusive of the values of the upper and lower ends of the range.

The term "and/or" as used in a phrase such as "A and/or B" herein is intended to include "A and B", "A or B", "A", and "B".

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, a gene may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) or having decreased expression due to alteration of gene regulatory sequences.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or exogenous recombinant nucleic acid sequence into the organism, and includes gene knockouts, targeted mutations, and gene replacement, promoter replacement, deletion, or insertion, as well as introduction of transgenes or synthetic genes into the organism. Recombinant or genetically engineered organisms can also be organisms into which constructs for gene "knock down" have been introduced. Such constructs include, but are not limited to, RNAi, microRNA, shRNA, siRNA, antisense, and ribozyme constructs. Also included are organisms whose genomes have been altered by the activity of meganucleases or zinc finger nucleases. An exogenous or recombinant nucleic acid molecule can be integrated into the recombinant/genetically engineered organism's genome or in other instances are not integrated into the recombinant/genetically engineered organism's genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided herein in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Tip; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free –NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an As used herein, "mutant" refers to an organism that has a mutation in a gene that has arisen spontaneously or is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se/ (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 26.0 (November 2011) based on the UniProt protein database release 15.6, a composite of Swiss-Prot release 57.6 and TrEMBL release 40.6. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) *Nucleic Acids Research* 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

When referring to a photosynthetic organism, such as an algal, the term "acclimated to low light" means having the increased chlorophyll and photosynthetic properties of the photosynthetic organism after being exposed to a low light intensity for a period of time that is sufficient for changes in chlorophyll and photosynthetic properties to stabilize at the low light condition. Low light can be for example, less than 200 $\mu E \cdot m^{-2} \cdot s^{-1}$ and preferably about 100 $\mu E \cdot m^{-2} \cdot s^{-1}$ or less or 50 $\mu E \cdot m^{-2} \cdot s^{-1}$ or less, and the period of time for acclimation can be for at least about four hours, at least about six hours, at least about eight hours, or at least about twelve hours, at least 24 hours, or at least 48 hours.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

An algal mutant "deregulated in low light acclimation" (or a "Locked in High Light Acclimation" or LIHLA mutant) is a mutant that does not exhibit the changes in phenotype and gene expression that are characteristic of a low light acclimated wild type algal cell, including: a substantial increase in chlorophyll and a substantial increase in the expression of the majority of light harvesting complex protein (LHCP) genes. An algal mutant deregulated in low light acclimation, when acclimated to low light, has decreased expression with respect to low light acclimated wild type cells, of multiple genes (for example, at least ten, at least twenty, at least thirty, at least forty or at least fifty genes) that are upregulated during low light acclimation of wild type cells. Further, an algal mutant deregulated in low light acclimation has increased expression of genes with respect to low light acclimated wild type cells (for example, at least five, at least six, at least seven, at least eight, at least nine, or at least ten genes) that are downregulated during low light acclimation of wild type cells. Further, as disclosed herein, an algal mutant deregulated in low light acclimation may have photosynthetic properties that are significantly different than the photosynthetic properties of wild type cells when both mutant and wild type cells are acclimated to low light.

"Photosynthetic properties", "photosynthetic properties", "photophysiological properties", or photophysiological parameters" include, without limitation, maximal photosynthetic rate, $P_{max}$ (calculated on a per cell or per mg chlorophyll basis), the intensity at which photosynthesis saturates, Ek, as measured by oxygen evolution, and a ("alpha") the initial slope of the photosynthesis (oxygen evolution) versus irradiance intensity (P/I) curve. Additional photosynthetic properties include various parameters that can be measured using fluorescence detection, including, for example, photosynthetic efficiency, Fv/Fm; the photosynthetic quantum yield of photosystem II (PSII), ΦPSII; photochemical quenching, or the proportion of open PSII centers, qP; nonphotochemical quenching, NPQ; PSII electron transport rate, $ETR_{PSII}$; PSI electron transport rate, $ETR_{PSI}$; cross-sectional size of PSI, and cross-sectional size of PSII. The listing here is not exhaustive, and the terms do not exclude other parameters that measure various aspects of photosynthesis.

Reference to properties that are "substantially the same" are intended to mean the properties are within 25%, and preferably within 20%, of the reference value.

LIHLA Mutants

Provided herein are algal mutants that are deregulated in acclimation to low light conditions. An algal mutant deregulated in acclimation to low light conditions can be a eukaryotic microalga, for example, of a marine or freshwater eukaryotic microalgal species. Transfer of wild type algae from high light to low light characteristically results in an increase in the amount of chlorophyll per cell (Chl/cell), along with higher levels of the light harvesting complex (LHC) proteins. In the algal mutants described herein, transfer from high light to low light does not result in a substantial increase in chlorophyll, and mRNA levels for nearly all of the LHC protein transcripts remain at levels similar to those of wild-type cells in the high light acclimated state. Such mutants are said to be deregulated in low light acclimation, and are referred to herein as Locked-In High Light Acclimation or "LIHLA" mutants. "Low light" or "Low light conditions" refers to the intensity of light in the photosynthetically active radiation (PAR) wavelengths (about 400 to about 700 nm), and may vary according to the algal species, but in general can be considered to be less than 200 $\mu E \cdot m^{-2} \cdot s^{-1}$, preferably less than 150 $\mu E \cdot m^{-2} \cdot s^{-1}$, and more preferably 100 $\mu E \cdot m^{-2} \cdot s^{-1}$ or less, or 50 $\mu E \cdot m^{-2} \cdot s^{-1}$ or less. "High light" or "High light conditions" can also vary by algal species, but in general is at least 350 $\mu E \cdot m^{-2} \cdot s^{-1}$, preferably at least 400 $\mu E \cdot m^{-2} \cdot s^{-1}$, and more preferably 500 $\mu E \cdot m^{-2} \cdot s^{-1}$ or greater, and can be 600 $\mu E \cdot m^{-2} \cdot s^{-1}$ or greater. The mutants have per cell maximal phohtosynthetic rate ($P_{max}$) comparable to (e.g., within 70% of wild type, within 80% or wild type, or within 90% or 95% of wild type) or higher than the $P_{max}$ of wild type cells, while allowing greater light penetration into an algal culture of mutant cells. A LIHLA mutant as provided herein can achieve higher cell density in culture as compared with a wild type strain.

The properties of a LIHLA algal mutant, including, without limitation, photosynthetic properties, gene expression profiles, chlorophyll content, growth properties, and culture characteristics, as referred to in this application, are compared to the same properties of a wild type organism of the same species as the LIHLA mutant, preferably the progenitor strain of the LIHLA mutant. The properties of a LIHLA mutant having a disrupted, attenuated, or otherwise directly or indirectly genetically manipulated LAR gene resulting in altered structure or expression of the LAR gene are also be compared with the same properties of a control cell that does not have a disrupted, attenuated, or otherwise directly or indirectly genetically manipulated LAR gene resulting in altered structure or expression of the LAR gene (regardless of whether the cell is "wild-type"). A control cell is substantially identical to the LIHLA mutant except that it does not have a disrupted, attenuated, or otherwise directly or indirectly genetically manipulated LAR gene resulting in altered structure or expression of the LAR gene. For example, a control cell may be a recombinant cell or a cell mutated in a gene other than the LAR gene whose effects are being assessed, etc.

As demonstrated herein, a LIHLA mutant, i.e., an algal photosynthetic mutant deregulated in acclimation to low light, exhibits a reduction in chlorophyll content under low light conditions with respect to a wild type or control alga of the same strain under the same light conditions. The mutants are characterized by a reduced amount of chlorophyll per cell, and can exhibit, for example, a 20% or greater reduction in chlorophyll, a 25% or greater reduction in chlorophyll, a 30% or greater reduction in chlorophyll, a 35% or greater reduction in chlorophyll, a 40% or greater reduction in chlorophyll, a 45% or greater reduction in chlorophyll, a 50% or greater reduction in chlorophyll, a 55% or greater reduction in chlorophyll, a 60% or greater reduction in chlorophyll, a 65% or greater reduction in chlorophyll, a 70% or greater reduction in chlorophyll, a 75% or greater reduction in chlorophyll, or an 80% or greater reduction in chlorophyll. Preferably, a LIHLA mutant demonstrates a reduction in chlorophyll of at least about 40%, at least about 45%, or at least about 50% on a per cell basis when compared with a wild type cell grown under low light conditions. The reduction in chlorophyll is preferably a reduction in total chlorophyll. In some examples, chlorophyll b is not selectively reduced in the mutant. In particular examples, a LIHLA mutant is in a strain of algae that does not naturally have chlorophyll b, for example, a LIHLA mutant can be a species of diatom or eustigmatophyte algae.

A LIHLA mutant also exhibits higher photochemical quenching, qP (see, for example, Maxwell and Johnson (2000) *J. Exper. Botany* 51: 659-668), at all physiologically relevant irradiances above about 400 $\mu E \cdot m^{-2} \cdot s^{-1}$, above about 350 $\mu E \cdot m^{-2} \cdot s^{-1}$, above about 300 $\mu E \cdot m^{-2} \cdot s^{-1}$, above about 250 $\mu E \cdot m^{-2} \cdot s^{-1}$, above about 200 $\mu E \cdot m^{-2} \cdot s^{-1}$, above about 150 $\mu E \cdot m^{-2} \cdot s^{-1}$, or above about 100 $\mu E \cdot m^{-2} \cdot s^{-1}$ with respect to a wild type or control alga of the same strain when both mutant an wild type are acclimated to low light. A LIHLA strain can also exhibit a higher maximal photochemical efficiency, Fv/Fm, when compared to a wild type strain acclimated to low light. Further, a LIHLA strain can have a higher value for ΦPSII, the operating efficiency of photosystem II, than the value for ΦPSII of a wild type strain.

In addition to low chlorophyll content and higher qP with respect to the wild type or control algal strain, the onset of nonphotochemical quenching, or NPQ, of a LIHLA mutant can occur at a higher light intensity as compared to the light intensity of NPQ onset in a wild type or control strain. Further, in addition to exhibiting onset of NPQ under higher light intensity, a LIHLA mutant exhibits less NPQ than wild type or control cells at all physiologically relevant light intensities greater than about 400 $\mu E \cdot m^{-2} \cdot s^{-1}$, such as light intensities greater than about 300 $\mu E \cdot m^{-2} \cdot s^{-1}$, greater than about 250 $\mu E \cdot m^{-2} \cdot s^{-1}$, greater than about 200 $\mu E \cdot m^{-2} \cdot s^{-1}$, greater than 150 $\mu E \cdot m^{-2} \cdot s^{-1}$, or greater than 100 $\mu E \cdot m^{-2} \cdot s^{-1}$, e.g., can exhibit lower NPQ at light intensities from about 200 $\mu E \cdot m^{-2} \cdot s^{-1}$ to 2000 $\mu E \cdot m^{-2} \cdot s^{-1}$ or from about 100 $\mu E \cdot m^{-2} \cdot s^{-1}$ to 2000 $\mu E \cdot m^{-2} \cdot s^{-1}$.

Additionally, a LIHLA mutant has a higher maximal photosynthetic rate on a per chlorophyll basis than does a wild type or control cell. For example, a LIHLA mutant can have about 1.5 fold or greater, between about 1.5 fold and about five fold, between about 1.5 fold and about 4 fold, between about 2 fold and about 4 fold, between about 2 fold and about 3.5 fold, or between about 2 fold and about 3 fold the $P_{max}$ of a wild type or control cell. Additionally, a LIHLA mutant can have at least about 70%, at least about 75%, or at least about 80% of the maximal photosynthetic rate on a per cell basis as a wild type alga of the same strain (e.g., the progenitor strain) or a control strain. The photosynthetic rate can be measured as the rate of oxygen evolution, which is measured over a range of light intensities, to saturate photosynthesis, to obtain the maximal rate, or $P_{max}$. A LIHLA mutant can have, for example, substantially the same maximal photosynthetic rate as a wild type or control cell or a higher maximal photosynthetic rate than a wild type or control cell. By "substantially the same maximal photosynthetic rate" is meant that the maximal photosynthetic rate is at least about 80% or at least about 85% of the wild type maximal photosynthetic rate, and preferably at least about 90% of the wild type rate or at least about 95% of the wild type rate. Additionally, the algal photosynthetic mutant can have a higher saturating irradiance for photosynthesis (Ek) than a wild type alga of the same strain or a control strain, and in some examples can also demonstrate a decrease in the initial slope of the photosynthetic irradiance curve (alpha, a) with respect to wild type cells or control cells.

In some examples, a LIHLA mutant has at least a 20%, 25%, 30%, 35%, 40%, 45%, or 50% reduction in chlorophyll with respect to a wild type cell, exhibits increased photochemical quenching (qP) over all physiologically relevant light intensities greater than 400 $\mu E \cdot m^{-2} \cdot s^{-1}$ with respect to a wild type cell; has an increased maximal photosynthetic rate ($P_{max}$) on a per chlorophyll basis (e.g., at least 1.5 fold the $P_{max}$ of wild type cells, for example at least 2 fold the $P_{max}$ of wild type cells), with at least 75% of the $P_{max}$ of wild type cells on a per cell basis; experiences saturation of photosynthesis at higher irradiance levels (higher Ek) than wild type; exhibits delayed onset of NPQ in response to increasing light intensity as compared with wild type cells; and has lower levels of NPQ over all irradiances greater than about 500 $\mu E \cdot m^{-2} \cdot s^{-1}$ than wild type cells, when both the LIHLA mutants and wild type cells are acclimated to low light. In some examples, a LIHLA mutant has at least a 40%, 45%, or 50% reduction in chlorophyll with respect to a wild type cell, exhibits increased photochemical quenching (qP) over all physiologically relevant light intensities greater than 200 $\mu E \cdot m^{-2} \cdot s^{-1}$ with respect to a wild type cell; has an increased maximal photosynthetic rate ($P_{max}$) on a per chlorophyll basis (e.g., at least 2 fold the $P_{max}$ of wild type cells, for example, between about two fold and about three fold the $P_{max}$ of wild type cells), with at least 80% of the $P_{max}$ of wild type cells on a per cell basis; experiences saturation of photosynthesis at higher irradiance levels (higher Ek) than wild type; exhibits delayed onset of NPQ in response to increasing light intensity as compared with wild type cells; and has lower levels of NPQ than wild type cells over all irradiances greater than about 200 $\mu E \cdot m^{-2} \cdot s^{-1}$ or greater than about 100 $\mu E \cdot m^{-2} \cdot s^{-1}$, when both the LIHLA mutants and wild type cells are acclimated to low light. In some examples a LIHLA mutant has a mutation in a gene encoding a regulator of the light acclimation response and the foregoing characteristics are in comparison with a control cell not having a mutation in a gene encoding a regulator of light acclimation.

Additionally, a LIHLA mutant can have PSII activity (electron transport rate through PSII, $ETR_{PSII}$) substantially equivalent to or greater than that of the wild type or control cells. For example, $ETR_{PSII}$ of a LIHLA mutant can be between about 1 and about 4 fold the $ETR_{PSII}$ of a wild type or control cell, for example, between about 1.5 fold and about 3.5 fold, or between about 1 and about 2 fold the $ETR_{PSII}$ of a wild type or control cell, between about 1.5 fold and about 3.5 3 fold the $ETR_{PSII}$ of a wild type or control cell, or more than 3 fold the $ETR_{PSII}$ of a wild type or control cell, for example, between about 3 and 4 about fold. Alternatively or in addition, in various examples, a LIHLA mutant can have PSI activity (electron transport rate through PSI, $ETR_{PSI}$) substantially equivalent to that of the wild type or a control strain.

A culture of an algal LIHLA mutant as provided herein can allow greater penetration of light into the culture than a wild type or control alga when the wild type or control alga is cultured in the same way and light penetration into the culture is measured at the same culture density as the cell density of the LIHLA mutant strain. Additionally, an algal LIHLA mutant can achieve higher cell densities in a liquid culture over a period of, for example, at least five, at least six, at least seven, at least eight, at least nine, at least ten, at least eleven, at least twelve, at least thirteen, at least fourteen, at least fifteen, between fifteen and twenty, at least twenty, between twenty and thirty, or at least thirty days for a culture of at least 0.5 liters, for example, at least 1 liter, at least 2 liters, at least 5 liters, at least 10 liters, at least 20 liters, at least 50 liters, or at least 100 liters.

Additionally to the above properties, an algal LIHLA mutant can be globally transcriptionally deregulated under low light conditions, that is, a LIHLA mutant can be deregulated in the expression of multiple genes that are differentially regulated in the wild type strain during acclimation to low light. For example, a LIHLA mutant can exhibit deregulated expression of at least ten, at least twenty, at least thirty, at least forty, at least fifty, or at least 100 genes that are differentially expressed in response to light intensity, for example, that are differentially expressed in wild type cells during acclimation to low light. Genes that are deregulated in an algal LIHLA mutant under low light include but are not limited to genes encoding light harvesting complex (LHC) proteins. For example, under low light conditions, with respect to a wild type cell, a LIHLA mutant can have decreased expression of at least ten, at least twelve, at least fifteen, or at least twenty light-responsive genes, including at least five, at least ten, or at least twelve, LHC protein genes, and can have increased expression with respect to a wild type cell of at least two, at least three, at least four, at least five, or at least six genes that do not encode light harvesting complex proteins. A LIHLA mutant can exhibit deregulation of at least twenty, at least thirty, at least forty, at least fifty, at least sixty, at least seventy, at least eighty, at least ninety, or at least 100 genes genes where the difference in the transcript level of the genes is at least a $\log_2$ of 1. Additionally, at least five, at least ten, at least twelve, at least fourteen, at least sixteen, at least eighteen, at least twenty, or at least twenty-two, genes encoding LHC proteins can be downregulated in the mutant with respect to the wild type when both are cultured under low light by at least a $\log_2$ of 1. Additionally, at least five, at least six, at least seven, at least eight, at least nine, or at least ten genes can be upregulated in a LIHLA mutant with respect to a wild type cell when both are cultured under low light by at least a $\log_2$ of 1.

An algal LIHLA mutant can be, for example, a microalga such as, but not limited to, a species of a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Fragilaropsis, Gloeothamnion, Haematococcus, Halocafeteria, Hantzschia, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. In some examples, a LIHLA mutant is a species that does not naturally have chlorophyll b, such as a diatom or eustigmatophyte. In some examples, a LIHLA mutant is eustigmatophyte such as *Ellipsoidon, Eustigmatos, Monodus, Nannochloropsis*, or *Vischeria* or a diatom such as, but not limited to, a species of *Amphora, Chaetoceros, Cyclotella, Fragilaropsis, Navicula, Nitzschia, Pavlova, Phceodactylum*, or *Thalassiosira.*

An algal photosynthetic mutant that is deregulated in low light acclimation (i.e., a LIHLA mutant) can be a mutant generated by any feasible method, including but not limited to UV irradiation, gamma irradiation, or chemical mutagenesis. Methods for generating mutants of microbial strains are well-known.

An algal LIHLA mutant as provided herein can also be a genetically engineered algal mutant in which one or more genes, such as, for example, the LAR1, LAR2, or LAR3 gene or homologs thereof, as described herein, have been targeted by homologous recombination for knock-out or gene replacement (for example with mutated form of the gene that may encode a polypeptide having reduced activity with respect to the wild type polypeptide). Included herein are aspects of engineering a microorganism in which the introduction, addition, integration, incorporation, or of certain nucleic acid molecules or particular polynucleotide sequences into microorganisms or host cells in order to affect the expression of a gene in the microorganism. For example, a microorganism of interest may be engineered by site directed homologous recombination to insert a particular gene of interest with or without an expression control sequence such as a promoter, into a particular genomic locus, or to insert a promoter into a genetic locus of the host microorganism to affect the expression of a particular gene or set of genes at the locus.

For example, gene knockout or replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

Alternatively or in addition, a LIHLA mutant can be generated by expressing a gene encoding a regulator, in which the gene has been mutated to encode a dominant negative mutant regulator. For example, a regulator gene can be mutated in a region that binds a nucleic acid or activates one or more proteins in a regulatory pathway, such that the protein may interact with (for example, bind) one or more components of a pathway but the interaction does not result in activation of further proteins in the pathway. In such instances the gene may be integrated into the chromosome of the host organism that may or not be the locus of the wild type gene, or may be introduced into the cell as part of an episomal nucleic acid molecule.

Alternatively or in addition, a genetically engineered LIHLA mutant can be engineered to include a construct for attenuating gene expression by reducing the amount, stability, or translatability of mRNA of a gene encoding a protein that regulates acclimation to low light intensity. For example, an alga can be transformed with an antisense RNA, RNAi, or ribozyme construct targeting an mRNA of a light acclimated regulator using methods known in the art. For example, an antisense RNA construct that includes all or a portion of the transcribed region of a gene can be introduced into a microalga to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a regulator gene can be introduced into an alga for reducing expression of the regulator (see, for example, Cerruti et al. (2011) *Eukaryotic Cell* (2011) 10: 1164-1172; Shroda et al. (2006) *Curr. Genet.* 49:69-84). Other genetic engineering strategies for generating LIHLA mutants include TALEN or zinc finger nuclease genome engineering (Perez-Pinera et al. (2012) *Curr. Opin. Chem. Biol.* 16: 268-277) or CRISPR technology (e.g., DiCarlo et al. (2013) *Nucl Acids Res* 41:doi:10.1093/nar/gtk135).

For antisense expression, a nucleic acid sequence of the regulator gene of interest is operably linked to a promoter such that the antsense strand of the RNA will be transcribed. The nucleic acid sequence can be only a portion of the regulator gene of interest, or may be the entire gene of interest. The nucleotide sequence can be, for example, from about 30 nucleotides to about 3 kilobases or greater, for example, from 30-50 nucleotides in length, from 50 to 100 nucleotides in length, from 100 to 500 nucleoties in length, from 500 nucleotides to 1 kb in length, from 1 kb to 2 kb in length, or from 2 to 5 kb. For example, an antisense sequence can be from about 100 nucleotides to about 1 kb in length. The construct can be transformed into algae using any feasible method, include any disclosed herein.

Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591.

In addition to the scientific literature above, the use of RNAi constructs is described in US2005/0166289 and WO 2013/016267, for example. A double stranded RNA with homology to the target gene is delivered to the cell or produced in the cell by expression of an RNAi construct, for example, an RNAi short hairpin (sh) construct. The construct can include a sequence that is identical to the target gene, or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1 kb of sequence homologous to the target gene. Expression vectors can be engineered using promoters selected for continuous or inducible expression of an RNAi construct, such as a construct that produces an shRNA.

A LIHLA mutant in some examples can be generated through targeting of a gene encoding a regulator of acclimation to low light intensity. A regulator can be any protein that directly or indirectly affects light acclimation and can be, as nonlimiting examples, a transcription factor, a transcriptional activator, an allosteric protein, a kinase, a phosphatase, an acetylase, a deacetylase, a methylase, a demethylase, a nucleotide cyclase, or a phosphodiesterase. Preferably a regulator directly or indirectly affects expression of multiple genes involved in light acclimation, including LHC protein genes as well as genes that do not encode LHC proteins.

For example, a LIHLA mutant can be mutated in a gene encoding the LAR1 ("Light Aclimation Regulator 1") protein (formerly referred to as Regulator-59) of *Nannochloropsis gaditana* (SEQ ID NO:4) or any of its orthologs, such as the LAR1 protein of *Nannochloropsis oceanica* ("No-LAR1"; SEQ ID NO:8), or a homolog of the LAR1 or No-LAR1 protein having at least 30% identity to SEQ ID NO:4 or SEQ ID NO:8 in any algal species. For example, a LIHLA mutant can be mutated in a gene encoding the polypeptide of SEQ ID NO:4, SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or can be mutated in a naturally-occurring gene encoding a polypeptide having at least 30%, at least 35%, at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with SEQ ID NO:4, SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, where the polypeptide includes an amino acid sequence having at least 40%, at least 45%, or at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with SEQ ID NO:9 or SEQ ID NO:10.

The LAR1 protein of *Nannochloropsis gaditana* (SEQ ID NO:4) and the No-LAR1 protein of *Nannochloropsis oceanica* (SEQ ID NO:8) each include a TAZ zinc finger domain (pfam domain PF02135), a domain commonly found in transcriptional activators, comprising amino acids 554-632 of SEQ ID NO:4 and 631-711 of SEQ ID NO:8. Amino acid sequences that comprise a TAZ zinc finger domain plus conserved sequences on either side of the TAZ zinc finger domain (referred to herein as an extended TAZ zinc finger domain; see Example 8), are provided herein as SEQ ID NO:9 for the *N. gaditana* LAR1 protein and SEQ ID NO:10 for the *N. oceanica* LAR1 (No-LAR1) protein.

As demonstrated in Example 12, the *N. gaditana* LAR1 protein (SEQ ID NO:4) and the No-LAR1 protein of *N. oceanica* (SEQ ID NO:8) are functional homologs, or orthologs, in different species. As detailed in Example 8, the amino acid sequences of the *N. gaditana* LAR1 protein (SEQ ID NO:4) the No-LAR1 protein of *N. oceanica* (SEQ ID NO:8) are approximately 49.7% identical, while the *N. gaditana* LAR1 protein extended TAZ zinc finger domain (SEQ ID NO:9) and the *N. oceanica* No-LAR1 protein extended TAZ zinc finger domain (SEQ ID NO:10) of these orthologs have approximately 81.8% amino acid sequence identity. Further analysis of related genes in both proprietary and public databases found a distinct phylogenetic grouping of genes encoding proteins having TAZ zinc finger domains with at least 40% identity to SEQ ID NO:9 (Table 3). These genes encode putative orthologs of the LAR1 protein.

Thus, in various examples, the gene that is mutated in a LIHLA mutant can be a gene encoding a polypeptide having at least 30%, at least 35%, at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:4 or SEQ ID NO:8, or at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18. The polypeptide encoding the regulator gene can include a TAZ zinc finger domain and can recruit to pfam PF02135, e.g., with a bit score greater than the gathering cutoff (19.0), and an E value of less than 1.00E-2 or less than 1.00E-10. Further, the encoded polypeptide that is at least at least 30% identical to SEQ ID NO:4 or SEQ ID NO:8, or is at least 80% or at least 85% identical to SEQ ID NO:4, SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 can include an amino acid sequence having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:9 or SEQ ID NO:10.

In particular examples, a LIHLA mutant can be mutated in a gene encoding a polypeptide that includes an amino acid sequence encoding a TAZ zinc finger domain having at least 40%, at least 64%,at least 50%, at least 55%, at least 60%, at least 65%, at least 70%, at least 75%, or at least 80%, or at least 85%, for example at least 86%, at least 87%, at least 88%, at least 89%, at least 90%, at least 91%, at least 92%, at least 93%, at least 94%, or at least 95% identity with the amino acid sequence of SEQ ID NO:9 or SEQ ID NO:10, where the polypeptide includes a TAZ zinc finger domain. For example, a LIHLA mutant can be mutated in a gene encoding a polypeptide having at least 50% identity to SEQ ID NO:4 or SEQ ID NO:8, and the polypeptide can include an amino acid sequence encoding a zinc finger domain, in which the amino acid sequence has at least 80%, or at least 85%, for example at least 86%, at least 87%, at least 88%, at least 89%, at least 90%, at least 91%, at least 92%, at least 93%, at least 94%, at least 95% identity with the amino acid sequence of SEQ ID NO:9 or SEQ ID NO:10.

The invention also provides LIHLA mutants that are mutated in genes comprising a nucleotide sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:3 or SEQ ID NO:7, in which the gene encodes a polypeptide that includes an amino acid sequence having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:9 or SEQ ID NO:10. Additionally, the polypeptide encoded by the gene can recruit to pfam PF02135. Further, the polypeptide encoded by the gene can have at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:4 or SEQ ID NO:8.

Further, the invention provides LIHLA mutants that are mutated in genes comprising a nucleotide sequence having at at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:33, SEQ ID NO:34, SEQ ID NO:35, SEQ ID NO:36, SEQ ID NO:37, SEQ ID NO:38, SEQ ID NO:39, or SEQ ID NO:40, or a portion thereof. The gene that is mutated in the LIHLA mutant can encode, in a wild type alga, a polypeptide that includes an amino acid sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:9 or SEQ ID NO:10.

In additional examples, a LIHLA mutant can be mutated in a gene encoding the LAR2 ("Light Aclimation Regulator 2") protein (formerly referred to as Regulator-216) of *Nannochloropsis gaditana* (SEQ ID NO:6) or any of its orthologs, such as the LAR2 protein of *Nannochloropsis oceanica* (No-LAR2; SEQ ID NO:21), or a homolog of the LAR2 protein or the No-LAR2 protein from any algal species having at least 50% identity to SEQ ID NO:6 or SEQ ID NO:21.

The LAR2 protein of *Nannochloropsis gaditana* (SEQ ID NO:6) and the No-LAR2 protein of *Nannochloropsis oceanica* (SEQ ID NO:21) each include a myb-like DNA-binding domain (pfam domain PF00249), a domain commonly found in transcriptional regulators, comprising amino acids 101-144 of SEQ ID NO:6, and amino acids 66-109 of SEQ ID NO:21. An extended version of this domain in *N. gaditana* (SEQ ID NO:22) is 81% identical to the extended myb-like DNA binding domain of *N. oceanica* (SEQ ID NO:23).

As demonstrated in Example 12, the *N. gaditana* LAR2 protein (SEQ ID NO:6) and the No-LAR2 protein of *N. oceanica* (SEQ ID NO:21) are functional homologs in different species, or "orthologs". As detailed in Example 8, the amino acid sequences of the *N. gaditana* LAR2 protein (SEQ ID NO:6) and the No-LAR2 protein of *N. oceanica* (SEQ ID NO:21) are approximately 69% identical, while the extended myb-like DNA-binding domains of the *N. gaditana* LAR2 protein (SEQ ID NO:22) and the *N. oceanica*

No-LAR2 protein (SEQ ID NO:23) are approximately 81% identical. Further analysis of related genes in both proprietary and public databases found a distinct phylogenetic grouping of genes encoding proteins having myb-like DNA-binding domains with at least 80% identity to SEQ ID NO:22 (Table 4). These genes encode putative orthologs of the LAR2 protein.

Thus, in various examples, the gene that is mutated in a LIHLA mutant can be a gene encoding a polypeptide having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:6 or SEQ ID NO:21, or at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:26, SEQ ID NO:27, SEQ ID NO:28, SEQ ID NO:29, SEQ ID NO:30, SEQ ID NO:31, or SEQ ID NO:32. The polypeptide encoded by the gene can include a myb-like DNA-binding domain and can recruit to pfam PF00249, e.g., with a bit score higher than the gathering cutoff (24.4) and an E value of less than 1.00E-2 or less than 1.00E-10. Further, the encoded polypeptide that is at least 50% identical to SEQ ID NO:6 or SEQ ID NO:21, or at least 80% or at least 85% identical to SEQ ID NO:6, SEQ ID NO:21, SEQ ID NO:26, SEQ ID NO:27, SEQ ID NO:28, SEQ ID NO:29, SEQ ID NO:30, SEQ ID NO:31, or SEQ ID NO:32 can include a sequence having at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:22 or SEQ ID NO:23.

In particular examples, a LIHLA mutant can be mutated in a gene encoding a polypeptide that includes a myb-like DNA-binding domain, in which the amino acid sequence has at least 65%, at least 70%, at least 75%, at least 80%, at least 80%, or at least 85%, for example at least 86%, at least 87%, at least 88%, at least 89%, at least 90%, at least 91%, at least 92%, at least 93%, at least 94%, at least 95% identity with the amino acid sequence of SEQ ID NO:22 or SEQ ID NO:23. For example, a LIHLA mutant can be mutated in a gene encoding a polypeptide having at least 65% identity to SEQ ID NO:6 or SEQ ID NO:21, and the polypeptide can include an amino acid sequence encoding a myb-like DNA-binding domain, in which the amino acid sequence has at least 80%, or at least 85%, for example at least 86%, at least 87%, at least 88%, at least 89%, at least 90%, at least 91%, at least 92%, at least 93%, at least 94%, at least 95% identity with the amino acid sequence of SEQ ID NO:22 or SEQ ID NO:23.

The invention further provides LIHLA mutants that are mutated in genes comprising nucleotide sequence having at least 50%, at least 55%, at least 60%, at least 65%, at least 70%, at least 75%, for example, at least 80%, or at least 85%, at least 86%, at least 87%, at least 88%, at least 89%, at least 90%, at least 91%, at least 92%, at least 93%, at least 94%, or at least 95% sequence identity with SEQ ID NO:5 or SEQ ID NO:20, in which the gene encodes a polypeptide that includes an amino acid sequence having at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:22 or SEQ ID NO:23. Additionally, the polypeptide encoded by the gene can recruit to pfam PF00249. Further, the polypeptide encoded by the gene can have at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:6 or SEQ ID NO:21.

Further, the invention provides LIHLA mutants that are mutated in genes comprising a nucleotide sequence having at at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:5, SEQ ID NO:20, SEQ ID NO:41, SEQ ID NO:42, SEQ ID NO:43, SEQ ID NO:44, SEQ ID NO:45, SEQ ID NO:46, or SEQ ID NO:47, or a portion thereof. The gene that is mutated in the LIHLA mutant can encode, in a wild type alga, a polypeptide that includes an amino acid sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:22 or SEQ ID NO:23.

The invention further provides LIHLA mutants that are mutated in genes comprising nucleotide sequence having at least 50%, at least 55%, at least 60%, at least 65%, at least 70%, at least 75%, for example, at least 80%, or at least 85%, at least 86%, at least 87%, at least 88%, at least 89%, at least 90%, at least 91%, at least 92%, at least 93%, at least 94%, or at least 95% sequence identity with SEQ ID NO:64, in which the gene encodes a polypeptide that includes an amino acid sequence having at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:63 or SEQ ID NO:66.

Further, the invention provides LIHLA mutants that are mutated in genes comprising a nucleotide sequence having at at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:62, SEQ ID NO:65, SEQ ID NO:67, SEQ ID NO:69, SEQ ID NO:71, SEQ ID NO:73, SEQ ID NO:75, or SEQ ID NO:77, or a portion thereof. The gene that is mutated in the LIHLA mutant can encode, in a wild type alga, a polypeptide that includes an amino acid sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:64.

In additional examples, a LIHLA mutant can be mutated in a gene encoding the LAR3 ("Light Aclimation Regulator 3") protein of *Nannochloropsis gaditana* (SEQ ID NO:63) or any of its orthologs, such as the LAR3 protein of *Nannochloropsis oceanica* (No-LAR2; SEQ ID NO:66), or a homolog of the LAR3 protein or the No-LAR2 protein from any algal species having at least 50% identity to SEQ ID NO:63 or SEQ ID NO:66.

The LAR3 protein of *Nannochloropsis gaditana* (SEQ ID NO:63) and the No-LAR3 protein of *Nannochloropsis oceanica* (SEQ ID NO:66) each include a conserved domain of approximately 100 amino acids (SEQ ID NO:64), comprising amino acids 302-404 of SEQ ID NO:63, and amino acids 303-405 of SEQ ID NO:66.

As demonstrated in Example 16, the *N. gaditana* LAR3 protein (SEQ ID NO:63) and the No-LAR3 protein of *N. oceanica* (SEQ ID NO:66) are functional homologs in different species, or "orthologs". As detailed in Example 17, the amino acid sequences of the *N. gaditana* LAR3 protein (SEQ ID NO:63) and the No-LAR3 protein of *N. oceanica* (SEQ ID NO:66) are approximately 56% identical, while the conserved domain of the *N. gaditana* LAR3 protein (SEQ ID NO:64) and the *N. oceanica* No-LAR3 protein (amino acids 303-405 of SEQ ID NO:66) are approximately 96% identical.

Thus, in various examples, the gene that is mutated in a LIHLA mutant can be a gene encoding a polypeptide having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:63 or SEQ ID NO:66, or at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:63, SEQ ID NO:66, SEQ ID NO:68, SEQ ID NO:70, SEQ ID NO:72, SEQ ID NO:74, SEQ ID NO:76, or SEQ ID NO:78. Further, the encoded polypeptide that is at least 50% identical to SEQ ID NO:63 or SEQ ID NO:66, or at least 80% or at least 85% identical to SEQ ID NO:63, SEQ ID NO:66, SEQ ID NO:68, SEQ ID NO:70, SEQ ID NO:72, SEQ ID NO:74, SEQ ID NO:76, or SEQ ID NO:78 can include a sequence having at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:64.

In particular examples, a LIHLA mutant can be mutated in a gene encoding a polypeptide that includes an amino acid sequence having at least 65%, at least 70%, at least 75%, at least 80%, at least 80%, or at least 85%, for example at least 86%, at least 87%, at least 88%, at least 89%, at least 90%, at least 91%, at least 92%, at least 93%, at least 94%, at least 95% identity to SEQ ID NO:64. For example, a LIHLA mutant can be mutated in a gene encoding a polypeptide having at least 65% identity to SEQ ID NO:63 or SEQ ID NO:66.

The invention further provides LIHLA mutants that are mutated in genes comprising nucleotide sequence having at least 50%, at least 55%, at least 60%, at least 65%, at least 70%, at least 75%, for example, at least 80%, or at least 85%, at least 86%, at least 87%, at least 88%, at least 89%, at least 90%, at least 91%, at least 92%, at least 93%, at least 94%, or at least 95% sequence identity with SEQ ID NO:62 or SEQ ID NO:65, in which the gene encodes a polypeptide having an amino acid sequence having at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO:64. Further, the polypeptide encoded by the gene can have at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:63 or SEQ ID NO:66.

Further, the invention provides LIHLA mutants that are mutated in genes comprising a nucleotide sequence having at at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity with SEQ ID NO:62, SEQ ID NO:65, SEQ ID NO:67, SEQ ID NO:69, SEQ ID NO:71, SEQ ID NO:73, SEQ ID NO:75, or SEQ ID NO:77, or a portion thereof. The gene that is mutated in the LIHLA mutant can encode, in a wild type alga, a polypeptide that includes an amino acid sequence having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity to SEQ ID NO:64.

Methods of Isolating LIHLA Mutants

A further aspect of the invention is a method of isolating algal mutants that are deregulated in acclimation to low light. The methods include: mutagenizing a population of algae; screening the mutagenized population of algae for low chlorophyll fluorescence; selecting mutants that retain low chlorophyll fluorescence when the mutants are maintained under low light conditions; and screening said selected mutants by fluorometry to identify low light stable low chlorophyll fluorescence algal mutants having photochemical (qP) coefficients that are higher than the qP coefficients of wild type algae. For example, mutants can be screened for having qP coefficients higher than wild type algae at light intensities greater than 400 $\mu E \cdot m^{-2} \cdot s^{-1}$, greater than 350 $\mu E \cdot m^{-2} \cdot s^{-1}$, greater than 300 $\mu E \cdot m^{-2} \cdot s^{-1}$, greater than 250 $\mu E \cdot m^{-2} \cdot s^{-1}$, or greater than 200 $\mu E \cdot m^{-2} \cdot s^{-1}$, greater than 150 $\mu E \cdot m^{-2} \cdot s^{-1}$, for example, or greater than 100 $\mu E \cdot m^{-2} \cdot s^{-1}$.

Mutagenesis can be by any method, for example insertional mutagenesis, chemical mutagenesis, or by irradiation with gamma or ultraviolet radiation. Methods for generating mutants of microbial strains are well-known. For example, gamma irradiation, UV irradiation, and treatment with any of a large number of possible chemical mutagens (e.g., 5-bromo deoxyuridine, ethyl methane sulfonate (EMS), methyl methane sulfonate (MMS), diethylsulfate (DES), nitrosoguanidine (NTG), ICR compounds, etc.) or treatment with compounds such as enediyne antibiotics that cause chromosome breakage (e.g., bleomycin, adriamycin, neocarzinostatin) are methods that have been employed for mutagenesis of algae, fungi, and chytrids (see, for example, U.S. Pat. No. 8,232,090; US Patent Application 20120088831; US Patent Application 20100285557; US Patent Application 20120258498). A large number of chemical mutagens are known in the art including but not limited to, intercalating agents, alkylating agents, deaminating agents, base analogs. Intercalating agents include, as non-limiting examples, the acridine derivatives or the phenanthridine derivatives such as ethidium bromide (also known as 2,7-diamino-10-ethyl-6-phenylphenanthridium bromide or 3,8-diamino-5-ethyl-6-phenylphenantridinium bromide). Nonlimiting examples of alkylating agents include nitrosoguanidine derivatives (e.g., N-methyl-N'-nitro-nitrosoguanidine), ethyl methanesulfonate (EMS), ethyl ethanesulfonate, diethylsulfate (DES), methyl methane sulfonate (MMS), nitrous acid, or $HNO_2$, and the nitrogen mustards or ICR compounds. Nonlimiting examples of base analogs that can be used as mutagens include the compound 5-bromo-uracil (also known as deoxynucleoside 5-bromodeoxyuridine), 5-bromo deoxyuridine, and 2-aminopurine.

Mutagenesis can additionally or alternately include introduction of exogenous nucleic acid molecules into the microbial cell of interest, as exemplified herein. For example, an exogenous nucleic acid molecule introduced into the cell can integrate into a genetic locus by random or targeted integration, affecting expression of genes into which the foreign DNA inserts or genes that are proximal to foreign DNA inserted into the genome (e.g., U.S. Pat. No. 7,019,122; U.S. Pat. No. 8,216,844). Typically the introduced nucleic acid molecule includes a selectable marker gene for selection of transformants that have integrated the exogenous nucleic acid molecule construct. The exogenous nucleic acid molecule in some embodiments can include a transposable element or a component thereof, such as, for example, inverted repeats that can be recognized by a transposase and/or a gene encoding a transposase, or the exogenous nucleic acid molecule can be based at least in part on a virus, such as an integrating virus.

For random insertional mutagenesis, a construct preferably includes a selectable marker that can be used to select for transformants having an integrated construct, and optionally can also serve as a segregation marker and molecular tag for isolation and identification of a gene interrupted by the integrated selectable marker gene. Alternatively, a specific genetic locus may be targeted, as illustrated in Example 12 herein. The genetic locus can encode a regulator of light acclimation, such as, but not limited to, LAR1 or a homolog thereof, or LAR2 or a homolog thereof. The construct for gene disruption can include, for example, a selectable marker gene flanked by sequences from the genetic locus of interest, e.g., at least a portion of the gene that encodes a regulator, and, optionally, additional genomic sequences surrounding the gene. Such flanking sequences can comprise, for example, at least 50 nucleotides, at least 100 nucleotides, at least 500 nucleotides, or at least 1 kilobase of genomic sequence.

Alternatively or in addition, a nucleic acid molecule encoding a variant of a light acclimation regulator (e.g., LAR1 or a homolog of LAR1, LAR2 or a homolog of LAR2, or another regulator) can be introduced into an algal cell to generate a LIHLA mutant. The gene encoding a variant can be targeted to the corresponding gene locus to effect gene replacement, or can be transformed into the cell to integrate randomly or targeted to another locus, or can be provided on an episome. As nonlimiting example, the gene can encode a variant that is truncated, internally deleted, or includes one or more amino acid changes. In some examples the variant acts as a dominant negative to inhibit, wholly or in part, the regulatory pathway that the low light acclimation regulator participates in.

In yet other examples, a nucleic acid molecule encoding a low light acclimation regulator an antisense, RNAi, or ribozyme construct can be introduced to generate a LIHLA mutant. For example, a construct that includes sequences that are complementary (“antisense”) with respect to a light acclimation regulator gene coding strand can include antisense sequences corresponding to at least a portion of a native algal gene encoding an LAR1 protein or a homolog thereof, an LAR2 protein or a homolog thereof, or another light acclimation regulator.

Algae and photosynthetic bacteria can be transformed by any suitable methods, including, as nonlimiting examples, natural DNA uptake (Chung et al. (1998) *FEMS Microbiot Lett.* 164: 353-361; Frigaard et al. (2004) *Methods Mol. Biol.* 274: 325-40; Zang et al. (2007) *J. Microbiol.* 45: 241-245), conjugation (Wolk et al. (1984) *Proc. Natl. Acad. Sci. USA* 81, 1561-1565), transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) *Proc. Natl. Acad. USA* 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017) electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly(amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation can also be performed on algal cells, for example after removing or wounding the algal cell wall (e.g., WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; WO 2003/091413; WO 2005/005643; and WO 2007/133558, all incorporated herein by reference in their entireties).

Preferably, the population that has been subjected to a mutagenesis procedure, whether by physical or chemical means, or by genetic engineering, is screened is by fluorescence activated cell sorting (FACS). The FACS procedure can use a gate, by which cells having fluorescence above a certain value are excluded, or the FACS procedure can take, for example, the lowest 0.1, 0.2, 0.3, 0.4, 0.5, 1.0, 1.5, 2.0, 2.5, 3.0. 4.0, 5.0, or lowest 10% of cells, in terms of chlorophyll fluorescence intensity on a per cell basis. Alternatively the gate can be the level of chlorophyll fluorescence of the wild type cells when acclimated to high light. A FACS screening can be followed by single-colony isolate screening for reduced chlorophyll content, which can be by visual inspection, for example, using visible light to observe pale coloration, or by fluorescence, for example, with the aid of a camera. Alternatively or in addition, chlorophyll level of clonal isolates can be quantitatively measured and compared. Chlorophyll levels are assessed (biochemically, visually, and/or by fluorescence) after low light acclimation to ensure a deregulated low light acclimation phenotype.

The photochemical quenching coefficient qP can be measured by fluorometry (e.g., Dual PAM fluorometry). Assessment of qP is preferably performed after isolates are acclimated to growth at low light, for example, at light of less than or about 400 μE $m^{-2}$ $sec^{-1}$, less than or about 350 μE $m^{-2}$ $sec^{-1}$, less than or about 300 μE $m^{-2}$ $sec^{-1}$, or less than or about 250 μE $m^{-2}$ $sec^{-1}$, or less than or about 200 μE $m^{-2}$ $sec^{-1}$, less than or about 150 μE $m^{-2}$ $sec^{-1}$, less than or about 100 μE $m^{-2}$ $sec^{-1}$, or less than or about 50 μE $m^{-2}$ $sec^{-1}$. Preferably, isolates are screened for a stable low chlorophyll phenotype after one to five days of acclimation at low light prior to measuring qP. Isolates having qP greater than that of low light-acclimated wild type cells, at least at irradiances greater than about 400 μE $m^{-2}$ $sec^{-1}$, or greater than about 350 μE $m^{-2}$ $sec^{-1}$, greater than about 300 μE $m^{-2}$ $sec^{-1}$, greater than about 250 μE $m^{-2}$ $sec^{-1}$, and preferably at irradiances greater than about 200 μE $m^{-2}$ $sec^{-1}$ are identified as putative LIHLA mutants.

Isolates having a stable low chlorophyll phenotype under low light conditions, for example at least a 20% reduction in chlorophyll, preferably at least a 30% reduction in chlorophyll, and more preferably at least a 40%, at least a 45%, or at least a 50% reduction in chlorophyll with respect to wild type cells under low light conditions, and exhibiting a higher qP at irradiances greater than 400 μE $m^{-2}$ $sec^{-1}$, for example, greater than 200 μE $m^{-2}$ $sec^{-1}$, are further screened for photosynthetic rate by measuring oxygen evolution.

Oxygen evolution is measured across a range of irradiances. The irradiance at which photosynthesis saturates (Ek) can also be calculated, and mutants can be selected for having a higher Ek than wild type cells acclimated to low light. Isolates demonstrating $P_{max}$ (the maximal rate of photosynthesis) greater that the $P_{max}$ of the wild type strain on a per chlorophyll basis, and substantially the same $P_{max}$ as the wild type strain on a per cell basis, are selected as LIHLA mutants. A LIHLA mutant can have a $P_{max}$ on a per cell basis that is at least 70% of the wild type $P_{max}$, at least 75% of the wild type $P_{max}$, at least 80% of the wild type $P_{max}$, at least 85% of the wild type $P_{max}$, or at least 90% or at least 95% of the wild type $P_{max}$, and can have a $P_{max}$ per cell that is higher than the $P_{max}$ per cell of a comparable wild type strain.

Mutants can additionally be assessed for differences in nonphotochemical quenching (NPQ) with respect to wild type cells. Preferably, a selected mutant initiates NPQ at a higher irradiance than does the wild type strain, and preferably, NPQ is lower at all irradiances greater than about 500 μE $m^{-2}$ $sec^{-1}$, greater than 450 μE $m^{-2}$ $sec^{-1}$, greater than about 400 μE $m^{-2}$ $sec^{-1}$, greater than 350 μE $m^{-2}$ $sec^{-1}$, greater than about 300 μE $m^{-2}$ $sec^{-1}$, greater than 250 μE $m^{-2}$ $sec^{-1}$, greater than about 200 μE $m^{-2}$ $sec^{-1}$, greater than 150 μE $m^{-2}$ $sec^{-1}$, or greater than 100 μE $m^{-2}$ $sec^{-1}$ in a selected mutant with respect to the wild type strain.

In some examples, mutagenized cells are screened for a decrease in the amount of chlorophyll per cell, an increase in $P_{max}$ per mg chlorophyll without substantially no reductionin $P_{max}$ per cell, higher qP and Ek than wild type cells, along with a decrease in alpha, the slope of the photosynthetic irradiance curve, and onset of NPQ at a higher irradiance than in wild type cells. Further, the cells can be screened for increased light penetration into the culture.

In addition, electron transport rates for photosystem II and/or PSI can be measured by fluorometry to identify mutants that are not substantially impaired in photosystem function.

Mutants can also be analyzed for gene expression, for example, after acclimation to low light, and gene expression profiles can be compared with gene expression profiles of high and low light acclimated wild type cells to identify mutants having expression profiles in low light that demonstrate a difference with respect to the expression profile of wild type cells in low light similar to the difference in expression profiles of wild type cells acclimated to high light as compared with wild type cells acclimated to low light.

Nucleic Acid Molecules

The present invention also includes isolated nucleic acid molecules encoding regulators that function in the acclimation of photosynthetic cells to light intensity, including the complement sequences of such nucleic acid sequences. The nucleic acid molecules provided herein can be used, for example, to generate gene targeting constructs as described herein, and for RNAi, and ribozyme constructs as well as for expression constructs. The nucleic acid molecules can also encode variant regulators that act as dominant negative proteins that can be produced in an algal cell to produce a LIHLA mutant phenotype, and may also be used in strategies for obtaining additional genes encoding polypeptides that play a role in light acclimation.

In some examples, an isolated nucleic acid molecule as provided herein comprises a nucleic acid sequence encoding a polypeptide comprising an amino acid sequence encoding an extended TAZ zinc finger domain having at least 40%, at least 45%, at least 50%, at least 55%, at least 60%, at least 65%, at least 70%, at least 75%, or at least 80% identity to SEQ ID NO:9 or SEQ ID NO:10. The nucleic acid molecule can encode a polypeptide having a mutation, with respect to a wild type polypeptide, e.g., the gene can encode a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:4; SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, in which the polypeptide has at least one mutation with respect to a wild type polypeptide. The mutation can optionally be in a TAZ zinc finger domain (e.g., in a sequence having at least 50%, at least 65%, at least 70%, at least 75%, or at least 80% identity to SEQ ID NO:9 or SEQ ID NO:10). The polypeptide encoded by the gene can recruit to pfam PF02135 with a bit score at least as high as the gathering cutoff for pfam PF02135 (e.g., 19.0) when queried against the Pfam database. Further, the polypeptide encoded by the gene can have at least 30%, at least 35%, at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:4 or SEQ ID NO:8. The nucleic acid molecule in some embodiments can encode a polypeptide having a mutation, with respect to a wild type polypeptide, in a TAZ zinc finger domain (e.g., in a sequence having at least 50%, at least 65%, at least 70%, at least 75%, or at least 80% identity to SEQ ID NO:9 or SEQ ID NO:10). Alternatively or in addition, the nucleic acid molecule in some embodiments can encode a truncated, frameshifted, or internally deleted polypeptide.

The invention provides, in various examples, nucleic acid molecules encoding polypeptides having at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:4, SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, in which the polypeptides include an extended TAZ zinc finger domain having an amino acid sequence with at least 40% identity to SEQ ID NO:9 or SEQ ID NO:10. The polypeptides can have, for example, at least 85%, at least 90%, or at least 95%, sequence identity with the amino acid sequence of SEQ ID NO:4, SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, in which the polypeptides include an extended TAZ zinc finger domain having an amino acid sequence with at least 40% identity to SEQ ID NO:9 or SEQ ID NO:10. The nucleic acid molecules in various examples are cDNAs, do not have the sequence of a naturally occurring gene, and/or are constructs for homologous recombination or gene attenuation.

The invention further provides isolated nucleic acid molecules comprising nucleotide sequences having at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, or SEQ ID NO:40, as well as nucleic acid molecules comprising nucleotide sequences complementary to any thereof, where the nucleotide sequence preferably is not identical to the nucleotide sequence of the naturally-occurring gene. Also included are nucleic acid molecules comprising nucleotide sequences having at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with at least a portion of a naturally-occurring gene, in which the nucleic acid molecule is a construct for homologous recombination or gene attenuation (e.g., a construct for RNAi, antisense, or ribozyme expression), and in which the naturally-occurring gene encodes a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:4; SEQ ID NO:8, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. The naturally-occurring gene that is targeted by the antisense, RNAi, or ribozyme construct can in some examples have at least 30%, at least 35%, at least 40%, at least 45%, at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:3, SEQ ID NO:7, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

In some exemplary embodiments, a nucleic acid provided herein encodes a polypeptide having at least 50% identity to SEQ ID NO:4 or SEQ ID NO:8, in which the polypeptide includes an extended TAZ zinc finger domain having at least 80% identity to SEQ ID NO:9 or SEQ ID NO:10. For example, a nucleic acid as provided herein can encode a polypeptide having at least 85% identity to SEQ ID NO:4 or SEQ ID NO:8, where the polypeptide includes an extended TAZ zinc finger domain having an amino acid sequence with at least 85% identity to SEQ ID NO:9 or SEQ ID NO:10.

In other examples, an isolated nucleic acid molecule as provided herein comprises a nucleic acid sequence encoding a polypeptide comprising an amino acid sequence encoding an extended myb-like DNA-binding domain having at least 80% or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO:22 or SEQ ID NO:23. The nucleic acid molecule can encode a polypeptide having a mutation, with respect to a wild type polypeptide, e.g., a gene encoding a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:6, SEQ ID NO:21, SEQ ID NO:26, SEQ ID NO:27, SEQ ID NO:28, SEQ ID NO:29, SEQ ID NO:30, SEQ ID NO:31, or SEQ ID NO:32, in which the polypeptide has at least one mutation with respect to a wild type polypeptide. The mutation can optionally be in a myb-like DNA binding domain (e.g., in a sequence having at least 80% or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO:22 or SEQ ID NO:23). The polypeptide encoded by the gene can recruit to pfam PF00249 with a bit score at least as high as the gathering cutoff for pfam PF00249 (e.g., 24.4) when queried against the Pfam database. Further, the polypeptide encoded by the gene can have at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:6 or SEQ ID NO:21. The nucleic acid molecule in some embodiments can encode a polypeptide having a mutation, with respect to a wild type polypeptide, in a myb-like DNA-binding domain (e.g., in a sequence having at least 50%, at least 65%, at least 70%, at least 75%, or at least 80% identity to SEQ ID NO:22 or SEQ ID NO:23). Alternatively or in addition, the nucleic acid molecule can encode a truncated, frameshifted, or internally deleted polypeptide.

The invention provides, in various examples, nucleic acid molecules encoding polypeptides having at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:6, SEQ ID NO:21, SEQ ID NO:26, SEQ ID NO:27, SEQ ID NO:28, SEQ ID NO:29, SEQ ID NO:30, SEQ ID NO:31, or SEQ ID NO:32, in which the polypeptides include an extended myb-like DNA-binding domain having an amino acid sequence with at least 40% identity to SEQ ID NO:22 or SEQ ID NO:23. The polypeptides can have, for example, at least 85%, at least 90%, or at least 95%, sequence identity with the amino acid sequence of SEQ ID NO:6, SEQ ID NO:21, SEQ ID NO:26, SEQ ID NO:27, SEQ ID NO:28, SEQ ID NO:29, SEQ ID NO:30, SEQ ID NO:31, or SEQ ID NO:32, in which the polypeptides include an extended myb-like DNA-binding domain having an amino acid sequence with at least 40% identity to SEQ ID NO:22 or SEQ ID NO:23. The nucleic acid molecules in various examples are cDNAs, do not have the sequence of a naturally occurring gene, and/or are constructs for homologous recombination or gene attenuation.

The invention further provides isolated nucleic acid molecules comprising nucleotide sequences having at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:5, SEQ ID NO:20, SEQ ID NO:41, SEQ ID NO:42, SEQ ID NO:43, SEQ ID NO:44, SEQ ID NO:45, SEQ ID NO:46, or SEQ ID NO:47, as well as nucleic acid molecules comprising nucleotide sequences complementary to any thereof, where the nucleotide sequence is not identical to the nucleotide sequence of the naturally-occurring gene. Also included are nucleic acid molecules comprising nucleotide sequences having at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with at least a portion of a naturally-occurring gene, in which the nucleic acid molecule is a construct for homologous recombination or gene attenuation (e.g., a construct for RNAi, antisense, or ribozyme expression), and in which the naturally-occurring gene encodes a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:6; SEQ ID NO:21, SEQ ID NO:26, SEQ ID NO:27, SEQ ID NO:28, SEQ ID NO:29, SEQ ID NO:30, SEQ ID NO:31, or SEQ ID NO:32. The naturally-occurring gene that is targeted by the antisense, RNAi, or ribozyme construct can have at least 30%, at least 35%, at least 40%, at least 45%, at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:5, SEQ ID NO:20, SEQ ID NO:41, SEQ ID NO:42, SEQ ID NO:43, SEQ ID NO:44, SEQ ID NO:45, SEQ ID NO:46, or SEQ ID NO:47.

In some exemplary embodiments, a nucleic acid provided herein encodes a polypeptide having at least 65% identity to SEQ ID NO:6 or SEQ ID NO:21, in which the polypeptide includes an extended myb-like DNA-binding domain having at least 85% identity to SEQ ID NO:22 or SEQ ID NO:23. For example, a nucleic acid as provided herein can encode a polypeptide having at least 85% identity to SEQ ID NO:6 or SEQ ID NO:21, where the polypeptide includes an extended myb-like DNA-binding domain having an amino acid sequence with at least 95% identity to SEQ ID NO:22 or SEQ ID NO:23.

In other examples, an isolated nucleic acid molecule as provided herein comprises a nucleic acid sequence encoding a polypeptide comprising an amino acid sequence encoding domain having at least 80% or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO:64. The nucleic acid molecule can encode a polypeptide having a mutation, with respect to a wild type polypeptide, e.g., a gene can encode a polypeptide having at least at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:63, SEQ ID NO:66, SEQ ID NO:68, SEQ ID NO:70, SEQ ID NO:72, SEQ ID NO:74, SEQ ID NO:76, or SEQ ID NO:78, in which the polypeptide has at least one mutation with respect to a wild type polypeptide. The mutation can optionally be in a conserved domain of the polypeptide (e.g., in a sequence having at least 80% or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO:64). Further, the polypeptide encoded by the gene can have at least 40%, at least 45%, at least 50%, at least 55%, having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the amino acid sequence of SEQ ID NO:63 or SEQ ID NO:66. The nucleic acid molecule in some embodiments can encode a polypeptide having a mutation, with respect to a wild type polypeptid, in a conserved domain of the polypeptide (e.g., in a sequence having at least 50%, at least 65%, at least 70%, at least 75%, or at least 80% identity to SEQ ID NO:64). Alternatively or in addition, the nucleic acid molecule can encode a truncated, frameshifted, or internally deleted polypeptide.

The invention provides, in various examples, nucleic acid molecules encoding polypeptides having at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of SEQ ID NO:63, SEQ ID NO:66, SEQ ID NO:68, SEQ ID NO:70, SEQ ID NO:72, SEQ ID NO:74, SEQ ID NO:76, or SEQ ID NO:78, in which the polypeptides include domain having an amino acid sequence with at least 40% identity to SEQ ID NO:64. The polypeptides can have, for example, at least 85%, at least 90%, or at least 95%, sequence identity with the amino acid sequence of SEQ ID NO:63, SEQ ID NO:66, SEQ ID NO:68, SEQ ID NO:70, SEQ ID NO:72, SEQ ID NO:74, SEQ ID NO:76, or SEQ ID NO:78, in which the polypeptides include a conserved domain having an amino acid sequence with at least 40% identity to SEQ ID NO:64. The nucleic acid molecules in various examples are cDNAs, do not have the sequence of a naturally occurring gene, and/or are constructs for homologous recombination or gene attenuation.

The invention further provides isolated nucleic acid molecules comprising nucleotide sequences having at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:62, SEQ ID NO:65, SEQ ID NO:67, SEQ ID NO:69, SEQ ID NO:71, SEQ ID NO:73, SEQ ID NO:75, or SEQ ID NO:77, as well as nucleic acid molecules comprising nucleotide sequences complementary to any thereof, where the nucleotide sequence is not identical to the nucleotide sequence of the naturally-occurring gene. Also included are nucleic acid molecules comprising nucleotide sequences having at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with at least a portion of a naturally-occurring gene, in which the nucleic acid molecule is a construct for homologous recombination or gene attenuation (e.g., a construct for RNAi, antisense, or ribozyme expression), and in which the naturally-occurring gene encodes a polypeptide having at least 40%, at least 45%, at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the amino acid sequence of any of SEQ ID NO:63, SEQ ID NO:66, SEQ ID NO:68, SEQ ID NO:70, SEQ ID NO:72, SEQ ID NO:74, SEQ ID NO:76, or SEQ ID NO:78. The naturally-occurring gene that is targeted by the antisense, RNAi, or ribozyme construct can have at least 30%, at least 35%, at least 40%, at least 45%, at least 50%, at least 55%, at least 60%, at least 65%, at least 70%, at least 75%, at least 80%, or at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with the nucleotide sequence of SEQ ID NO:62, SEQ ID NO:65, SEQ ID NO:67, SEQ ID NO:69, SEQ ID NO:71, SEQ ID NO:73, SEQ ID NO:75, or SEQ ID NO:77.

In some exemplary embodiments, a nucleic acid provided herein encodes a polypeptide having at least 65% identity to SEQ ID NO:63 or SEQ ID NO:66, in which the polypeptide includes a domain having at least 85% identity to SEQ ID NO:64. For example, a nucleic acid as provided herein can encode a polypeptide having at least 85% identity to SEQ ID NO:63 or SEQ ID NO:66, where the polypeptide includes a domain having an amino acid sequence with at least 95% identity to SEQ ID NO:64.

The invention also encompasses variations of the nucleotide sequences of the invention, such as those encoding functional fragments or variants of the polypeptides as described herein. Such variants can be naturally-occurring, or non-naturally-occurring, such as those induced by various mutagens and mutagenic processes. Intended variations include, but are not limited to, addition, deletion, and substitution of one or more nucleotides which can result in conservative or non-conservative amino acid changes, including additions and deletions. Codon-optimization of nucleotide sequences encoding polypeptides for expression in a host cell of interest is also contemplated.

The invention also provides constructs comprising a nucleic acid sequence as provided herein that can further include one or more sequences that regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that may be operably linked to a gene of interest or antisense or shRNA-encoding sequence in an expression construct or "expression cassette." Various algal promoters are disclosed in U.S. Patent Application Publication US 2013/0023035; U.S. patent application Ser. No. 13/486,930, filed Jun. 1, 2012; U.S. Ser. No. 13/693,585, filed Dec. 4, 2012; and U.S. application Ser. No. 13/915,522, filed Jun. 11, 2013. A promoter used in a construct may in some instances be regulatable, e.g., inducible.

An inducible promoter can be responsive to, e.g., light intensity or high or low temperature, and/or can be responsive to specific compounds. The inducible promoter may be, for example, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (U.S. Pat. No. 5,750,385, U.S. Pat. No. 5,639,952; U.S. Pat. No. 8,314,228), metals (*Eukaryotic Cell* 2:995-1002 (2003)) or temperature (U.S. Pat. No. 5,447,858; Abe et al. *Plant Cell Physiol.* 49: 625-632 (2008); Shroda et al. *Plant J.* 21: 121-131 (2000)). The foregoing examples are not limiting as to the types of promoters or specific promoters that may be used. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

In aspects where the nucleic acid construct does not contain a promoter in operable linkage with the nucleic acid sequence encoding the gene of interest (e.g., a dehydrogenase gene) the nucleic acid sequence can be transformed into the cells such that it becomes operably linked to an endogenous promoter by, e.g., homologous recombination, site specific integration, and/or vector integration. In some instances, genomic host sequences included in a nucleic acid construct for mediating homologous recombination into the host genome may include gene regulatory sequences, for example, a promoter sequence, that can regulate expression of a gene or antisense or RNAi sequence of the nucleic acid construct. In such examples, the transgene(s) of the construct can become operably linked to a promoter that is endogenous to the host microorganism. The endogenous promoter(s) may be regulatable, e.g., inducible.

Constructs for homologous recombination into an algal genome (e.g., for disruption or gene replacement of a regulator gene) can include a nucleotide sequence of a regulator gene, such as any provided herein, or sequences from the algal genome that are adjacent to the regulator gene in the host organism. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a regulator gene that includes a TAZ zinc finger domain, such as any disclosed herein, and/or genomic DNA adjacent thereto. For example, the sequences for mediating homologous recombination in a construct can include one or more nucleotide sequences from or adjacent to a naturally-occurring algal gene encoding a TAZ zinc finger domain protein, wherein the TAZ zinc finger domain protein comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to SEQ ID NO:9 or SEQ ID NO:10. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:3 or SEQ ID NO:7 and/or an adjacent region of the *Nannochloropsis* genome.

Alternatively, the sequences for mediating homologous recombination in a construct can include one or more nucleotide sequences from or adjacent to a naturally-occurring algal gene encoding a myb-like DNA-binding domain protein, wherein the myb-like DNA-binding domain protein comprises an amino acid sequence having at least 80%, for example, at least 85%, at least 90%, at least 95% identity, or at least 99% to SEQ ID NO:22 or SEQ ID NO:23. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a regulator gene that includes a myb-like DNA-binding domain, such as any disclosed herein, and/or genomic DNA adjacent thereto. For example, the sequences for mediating homologous recombination in a construct can include one or more nucleotide sequences from or adjacent to a naturally-occurring algal gene encoding a myb-like DNA-binding domain protein, wherein the myb-like DNA-binding domain protein comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to SEQ ID NO:6; SEQ ID NO:21, SEQ ID NO:26, SEQ ID NO:27, SEQ ID NO:28, SEQ ID NO:29, SEQ ID NO:30, SEQ ID NO:31, or SEQ ID NO:32. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:5 or SEQ ID NO:20 and/or an adjacent region of the *Nannochloropsis* genome.

Further alternatively, the sequences for mediating homologous recombination in a construct can include one or more nucleotide sequences from or adjacent to a naturally-occurring algal or heterokont gene encoding a protein comprising an amino acid sequence having at least 80%, for example, at least 85%, at least 90%, at least 95% identity, or at least 99% to SEQ ID NO:64. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a gene that includes a conserved domain, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a protein that comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to SEQ ID NO:63, SEQ ID NO:66, SEQ ID NO:68, SEQ ID NO:70, SEQ ID NO:72, SEQ ID NO:74, SEQ ID NO:76, or SEQ ID NO:78. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:62 or SEQ ID NO:65 and/or an adjacent region of the *Nannochloropsis* genome.

Constructs for expressing antisense or interfering RNA (RNAi) or ribozymes are also provided for generating LIHLA mutants. Such constructs can include one or more sequences that are complementary, or antisense, with respect to the nucleic acid sequences provided herein that encode regulator polypeptides. For example, provided herein are nucleic acid molecule constructs for expression of antisense RNA, shRNA, microRNA, or a ribozyme comprising a nucleotide sequence complementary to at least a portion of a naturally-occurring algal gene encoding a TAZ zinc finger domain protein, where the TAZ zinc finger domain protein comprises an amino acid sequence having at least 40% for example, at least 45%, at least 50%, at least 55%, at least 60%, at least 65%, at least 70%, at least 75%, at least 80%, at least 85%, at least 90%, at least 95%, or at least 99% identity to identity to SEQ ID NO:9 or SEQ ID NO:10. In exemplary embodiments, the construct can include a sequence complementary to at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:3 or SEQ ID NO:7 and/or a noncoding region of an mRNA that comprises SEQ ID NO:3 or SEQ ID NO:7.

Additional constructs for expressing antisense or interfering RNA (RNAi) or ribozymes to generate LIHLA mutants can include one or more sequences that are complementary, or antisense, with respect to the nucleic acid sequences provided herein that encode regulator polypeptides. For example, provided herein are nucleic acid molecule constructs for expression of antisense RNA, shRNA, microRNA, or a ribozyme comprising a nucleotide sequence complementary to at least a portion of a naturally-occurring algal gene encoding a myb-like DNA-binding domain protein, where the myb-like DNA-binding domain protein comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to identity to SEQ ID NO:22 or SEQ ID NO:23. In exemplary embodiments, the construct can include a sequence complementary to at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:5 or SEQ ID NO:20 and/or a noncoding region of an mRNA that comprises SEQ ID NO:5 or SEQ ID NO:20.

Additional constructs for expressing antisense or interfering RNA (RNAi) or ribozymes to generate LIHLA mutants can include one or more sequences that are complementary, or antisense, with respect to the nucleic acid sequences provided herein that encode regulator polypeptides. For example, provided herein are nucleic acid molecule constructs for expression of antisense RNA, shRNA, microRNA, or a ribozyme comprising a nucleotide sequence complementary to at least a portion of a naturally-occurring algal gene encoding a polypeptide comprising an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to identity to SEQ ID NO:64. In exemplary embodiments, the construct can include a sequence complementary to at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of SEQ ID NO:62 or SEQ ID NO:65 and/or a noncoding region of an mRNA that comprises SEQ ID NO:62 or SEQ ID NO:65.

Methods of Producing Algal Products

Also provided herein are methods of producing algal products by culturing algae having increased photosynthetic efficiency, such as the LIHLA mutants disclosed herein. The methods include culturing an algal photosynthetic mutant deregulated in acclimation to low light in a suitable medium to provide an algal culture and recovering biomass or at least one product from the culture. The algal culture is preferably a photoautotrophic culture, and the culture medium preferably does not include a substantial amount of reduced carbon, that is, the culture does not include reduced carbon in a form or at a level that can be used by the algae for growth.

The algae may be cultured in any suitable vessel, including flasks or bioreactors, where the algae may be exposed to artificial or natural light. The culture comprising mutant algae that are deregulated in their response to low light may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the mutants provided herein exhibiting deregulated adaptation to low light intensity can achieve higher cell density of the culture over time, for example, over a period of a week or more, with respect to a culture wild type algal cells of the same strain that are not deregulated in low light acclimation. For example, a LIHLA mutant may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms deregulated in acclimation to low light intensity can be cultured in a "photobioreactor" equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The algal LIHLA mutants can include one or more non-native genes encoding a polypeptide for the production of a product, such as, but limited to, a lipid, a colorant or pigment, an antioxidant, a vitamin, a nucleotide, an nucleic acid, an amino acid, a hormone, a cytokine, a peptide, a protein, or a polymer. For example, the encoded polypeptide can be an enzyme, metabolic regulator, cofactor, carrier protein, or transporter.

The methods include culturing a LIHLA mutant that includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending, commonly-assigned U.S. patent application Ser. No. 13/407,817 entitled "Solvent Extraction of Products from Algae", filed on Feb. 29, 2012, which is incorporated herein by reference in its entirety.

Biomass can be harvested, for example, by centrifugation or filtering. The biomass may be dried and/or frozen. Further products may be isolated from biomass, such as, for example, lipids or one or more proteins.

Also included in the invention is an algal biomass comprising biomass of an algal LIHLA mutant, such as any disclosed herein, for example, an algal LIHLA mutant that includes a mutation in a gene encoding a polypeptide having at least 40% identity to SEQ ID NO:4 or SEQ ID NO:8, a gene encoding a polypeptide having at least 50% identity to SEQ ID NO:6 or SEQ ID NO:21, a gene encoding a polypeptide having at least 50% identity to SEQ ID NO:63 or SEQ ID NO:66. Further included is an algal product produced by a LIHLA mutant, such as any disclosed herein, including an algal LIHLA mutant that includes a mutation in a gene encoding a polypeptide having at least 40% identity to SEQ ID NO:4 or SEQ ID NO:8, a gene encoding a polypeptide having at least 50% identity to SEQ ID NO:6 or SEQ ID NO:21, or. a gene encoding a polypeptide having at least 50% identity to SEQ ID NO:64.

EXAMPLES

The following examples are illustrative, and do not limit this disclosure in any way.

Example 1. Determining Useful Metrics for the High Light Acclimated State

A wild type *Nannochloropsis gaditana* strain, WT-3730, which is a subcultured isolate of the *N. gaditana* strain CCMP1894, obtained from the Provasoli-Guillard National Center for Marine Algae and Microbiota (NCMA, Maine, U.S.A.), formerly the Culture Collection of Marine Phytoplankton (CCMP), was used as the wild type background for all experiments and genetic manipulation. *N. gaditana* WT-3730 cells were acclimated to high light (500 $\mu E \cdot m^{-2} \cdot s^{-1}$) and low light (100 $\mu E \cdot m^{-2} \cdot s^{-1}$) intensities in order to assess the features of the high light acclimated state that could be exploited during the screening for LIHLA derivatives. As shown in FIG. 1A, two wild type cultures were grown under high light intensity for 4 days to achieve high light acclimation. Chlorophyll fluorescence was monitored as a metric for the high light acclimation process, which is characterized by a decrease in fluorescence associated with a decrease in light harvesting chlorophyll binding proteins.

Once the chlorophyll fluorescence had reached a minimal level (at about 4.6 days), one culture was retained at high light while the other was transferred to low light intensity. The cultures were allowed to grow for several days following the light shift and the chlorophyll fluorescence continued to be monitored. For the low light shifted culture the chlorophyll fluorescence increased throughout the growth period (represented by the triangles in FIG. 1A), indicating a low light acclimation response, with increasing antenna size. The culture that was maintained at high light showed a small increase over time in chlorophyll fluorescence (represented by the squares in FIG. 1A) reflecting a small increase in light harvesting antenna associated with self-shading as the cells grew to higher densities. By Day 8 the chlorophyll fluorescence was approximately 3 fold higher in the cells growing under low light conditions compared to the chlorophyll fluorescence of cells maintained in high light. At this point a number of Pulse Amplitude Modulated (PAM) fluorescence parameters were monitored to reveal the physiological differences associated with the high light acclimated state. Differences were observed in a number of PAM fluorescence parameters; however the qP parameter, reflecting PSII excitation pressure, proved a particularly reliable indicator of high light acclimation relative to the low light acclimated state. FIG. 1B shows the high light shifted cells, represented by squares, have higher qP at all irradiances greater than about 200 $\mu E \cdot m^{-2} \cdot s^{-1}$. The qP parameter was therefore chosen as an initial secondary screening parameter to compare low light acclimated cultures of wild type and putative LIHLA mutant algae.

Example 2. Insertional Mutagenesis of *Nannochloropsis gaditana*

Figure 2:
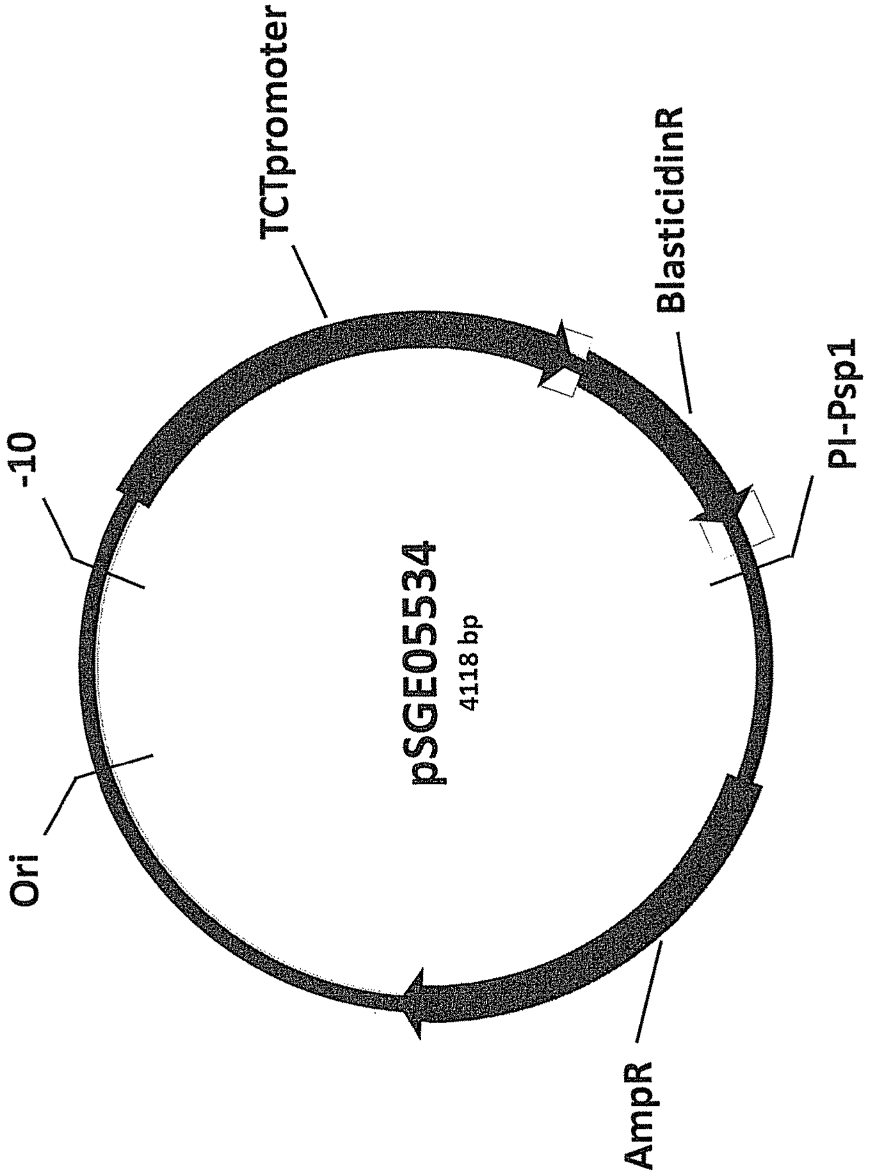
FIG. 2 provides a map of vector pSG-5534 (SEQ ID NO:1), one of several vectors used for insertional mutagenesis of *Nannochloropsis gaditana*, which included a TCTP promoter (SEQ ID NO:2) driving an *Apergillus* blasticidin resistance gene (SEQ ID NO:59), codon optimized for *Nannochloropsis*. The PI-PspI site was used for linearization prior to transformation.

In separate experiments, various constructs that included either a blasticidin or bleomycin resistance gene, codon optimized for *Nannochloropsis* expression and cloned downstream of a *Nannochloropsis* promoter (see, for example, U.S. patent application Ser. No. 13/915,522, filed Jun. 11, 2013, and U.S. patent application Ser. No. 13/486,930, filed Jun. 1, 2012) were transformed into *Nannochloropsis gaditana* cells. An example of one such construct is provided in FIG. 2, and the sequence of one such construct is provided as SEQ ID NO:1. The construct includes the *Aspergillus* blasticidin resistance gene codon-optimized for *Nannochloropsis* expression, operably linked to a *Nannochloropsis* TCTP promoter (SEQ ID NO:2). For transformation, *Nannochloropsis gaditana* cells were grown in PM064 media and harvested at a concentration between 1-3×$10^7$ cells/mL. Cells were centrifuged at 2500×g for 10 minutes at 25° C. to pellet the cells. Cells were then resuspended in a sterile solution of 385 mM sorbitol and centrifuged again, then washed two more times in sorbitol to remove all traces of media. The cell pellet was resuspended in sorbitol to a final concentration of 1×$10^{10}$ cells/mL. Linearized plasmid DNA of the construct was aliquoted into microfuge tubes at a concentration between 0.5-5 μg DNA, and 100 mL of cell mixture was mixed with the DNA. The mixture was transferred to chilled electroporation cuvettes with a gap distance of 2 mm. The electroporator was set to 50 μF capacitance, 500 ohms resistance and 2.2 kV voltage. Following electroporation, samples were resuspended in 1 mL of sorbitol and incubated on ice for a few minutes. Cells were transferred to 15 mL conical tubes containing 10 mL of fresh media, and allowed to recover overnight in dim light (~5 μmol photons $m^{-2}$ $sec^{-1}$). The next day, cells were plated on PM024 plates containing either 5 μg/mL zeocin or 100 μg/mL blasticidin at a concentration between 5-7×$10^8$ cells/mL. Plates were incubated under constant light (~80 μmol photons $m^{-2}$ $sec^{-1}$) until colonies appeared (about 2-3 weeks).

In a separate experiment, *Nannochloropsis gaditana* cells were treated with UV to induce mutations and subjected to the LIHLA screen. For UV mutagenesis, cells were grown to mid-log phase and then diluted to 1×$10^6$ cells/mL with growth medium PM064. The cell suspensions were transferred by pipet to a 100 mm Petri dish and placed within a Stratalinker 2400 with the plate lid removed. UV irradiation was carried out with 10,000, 25,000, and 50,000 μJ/$cm^{-2}$. After irradiation, cell suspensions were pipetted into a shake flask wrapped in foil to prevent light exposure for twenty-four hours following irradiation.

PM024 media includes: 35 ppt Instant Ocean Salts, 10× Guillard's F/2 marine water enrichment solution (50× stock from Sigma-Aldrich, St. Louis, Mo., cat. No. G0154; final concentrations of components in media: 8.825 mM Sodium nitrate; 0.32 mM Sodium phosphate monobasic; 0.205 μM Biotin; 0.420 μM Cobalt chloride.$6H_2O$; 0.400 μM Cupric sulfate.$5H_2O$; 0.11713 mM Disodium EDTA.$2H_2O$; 9.095 μM Manganese chloride.$4H_2O$; 0.248 μM Sodium molybdate.$2H_2O$; 2.965 μM Thiamine.HCl; 0.037 μM Vitamin $B_{12}$; 0.765 μM Zinc sulfate.$7H_2O$).)

PM064 media includes: 35 ppt Instant Ocean Salts, 5× Guillard's F/2 marine water enrichment solution (50× stock from Sigma-Aldrich, St. Louis, Mo., cat. No. G0154; final concentrations of components in media: 4.413 mM Sodium nitrate; 0.16 mM Sodium phosphate monobasic; 0.103 μM Biotin; 0.240 μM Cobalt chloride.$6H_2O$; 0.200 μM Cupric sulfate.$5H_2O$; 0.0585 mM Disodium EDTA.$2H_2O$; 4.54 μM Manganese chloride.$4H_2O$; 0.124 μM Sodium molybdate.$2H_2O$; 1.48 μM Thiamine.HCl; 0.0185 μM Vitamin $B_{12}$; 0.382 μM Zinc sulfate.$7H_2O$).

Example 3. Screens and Physiological Assessment of LIHLA Mutant GE-4574

Figure 3:
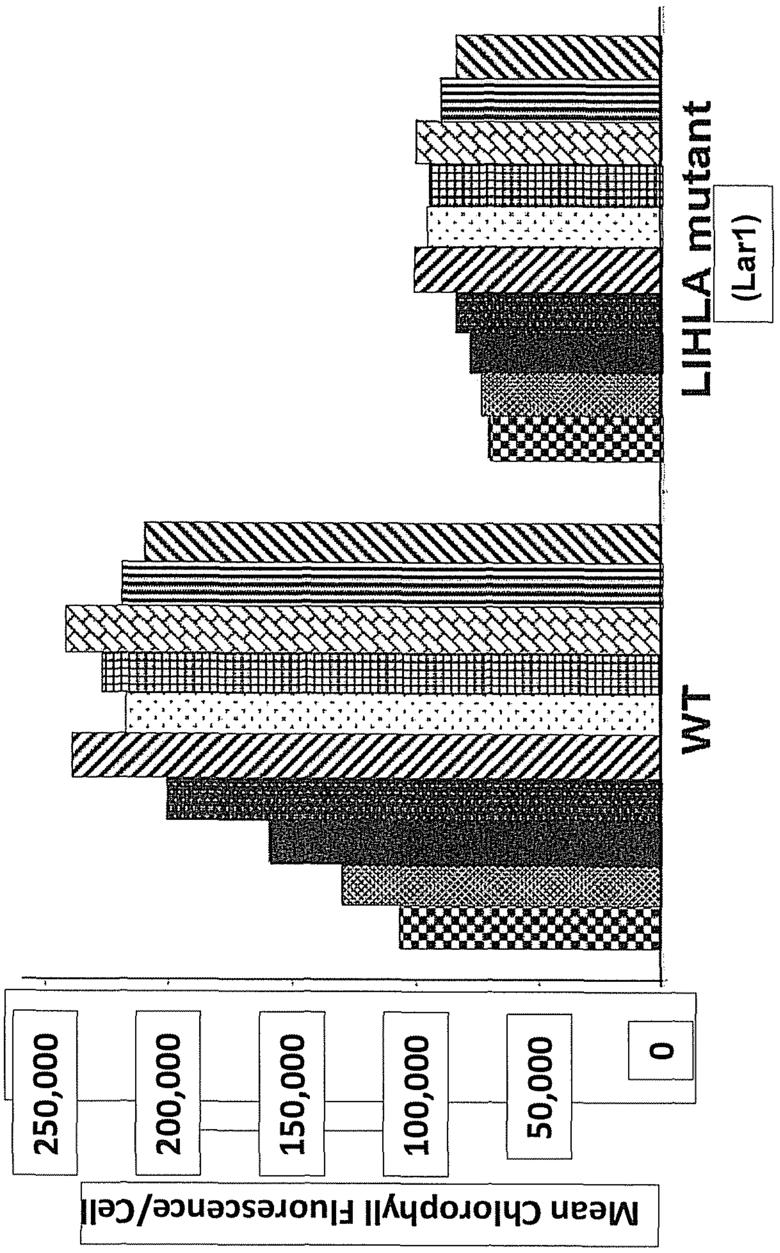
FIG. 3 shows the increase in chlorophyll fluorescence per cell in wild type culture during acclimation to low irradiance alongside a potential LIHLA mutant. The bars represent successive days after transfer to low light. While the wild type culture acclimates by increasing its chlorophyll content approximately 2.5 fold, the mutant chlorophyll content remains very low, showing only a modest increase.

Initially, random insertion tagged mutant libraries of transformed *Nannochloropsis* were screened for reduced pigmentation using flow cytometric techniques. Antibiotic resistant colonies appearing on transformation plates were resuspended into liquid culture and acclimated to low light intensities and sorted by flow cytometry using a BD FACSAria II flow cytometer (BD Biosciences, San Jose, Calif.) such that low chlorophyll fluorescence cells were selected. In general, approximately 0.5 to 2% of the total population of cells was selected as having the lowest chlorophyll fluorescence from this first screening procedure. In some instances, low light acclimated transformants were selected by FACS in which the sorting was gated to the level of chlorophyll fluorescence from a wild-type high light acclimated culture. Further primary screening of putative LIHLA colonies isolated through flow cytometry was conducted through the selection of pale green or yellow visual phenotypes on plates. In order to screen putative LIHLA colonies from other reduced pigment mutants and false positives, selected colonies were subjected to a medium-throughput secondary cultivation screen to acclimate the isolates to low light conditions prior to photo-physiological measurements. Chlorophyll fluorescence was monitored during low light acclimation to select colonies that retained the reduced chlorophyll fluorescence characteristic of the high light acclimated state. FIG. 3 shows an example of a LIHLA mutant and wild type culture undergoing acclimation from high to low light intensity, where chlorophyll fluorescence was monitored daily. Under these conditions, the wild type culture increased its chlorophyll per cell over ten days, whereas in the the LIHLA mutant, chlorophyll increased only slightly. This trait, of retaining substantially the same low chlorophyll content of a high light acclimated cell even when acclimated to low light conditions, is an identifying characteristic of the LIHLA mutants. Under the same conditions of transfer from high to low light and subsequent low light acclimation, wild type cells characteristically dramatically increase their chlorophyll content on a per cell basis.

Cell lines that retained reduced chlorophyll fluorescence at higher culture density (which promotes a low light acclimation response in wild type) were then further screened through more advanced photo-physiological measurements following acclimation to low light.

Example 4. Physiological Assessment of Clones Having Reduced Chlorophyll Under Low Light Conditions Fluorescence based PSII photo-physiological parameters were used to identify strains with similar or increased maximal PSII quantum yield ($F_v/F_m$) and higher photochemical quenching coefficient (qP) than the wild type strain, determined over 12 irradiance levels. Fv/Fm was measured using a Dual PAM fluorometer (Walz, Effeltrich, Germany). A 3 ml aliquot of cells with a cell density 1×$10^8$ cells per ml (approximately 5 mg chlorophyll per ml) was dark adapted for five minutes, after which a low intensity measuring beam was used to obtain $F_0$. The cells were then exposed to saturating light to close all reaction centers, and then a second low intensity measuring beam was used for obtaining $F_m$ (Maxwell and Johnson, (2000) *J. Exper. Bot.* 51: 659-668). Photochemical quenching, or qP, is a measure of the proportion of open PSII centers, and was also measured using the Dual PAM fluorometer (Walz, Effeltrich, Germany).

Chlorophyll content of mutants was determined by extracting frozen cells with 80% acetone buffered with $Na_2CO_3$, centrifuging, and analyzing the supernatant by HPLC (Lafarde et al. (2000) *Appl Environ Microbiol* 66: 64-72).

Nonphotochemical quenching, or NPQ, was also measured using a Dual PAM fluorometer (Walz, Effeltrich, Germany) over a range of light intensities. LIHLA mutants exhibited onset of NPQ at a higher light intensity than was required for NPQ onset in wild type cells. Further, LIHLA mutants exhibited higher NPQ at all light intensites higher than 100 μmol photons $m^{-2}$ $sec^{-1}$.

Oxygen evolution was measured using a Clark-type oxygen electrode. An aliquot of cells containing 5 μg chlorophyll per ml, or $10^8$ cells, was transferred into the oxygen electrode chamber which was illuminated with a lamp at 1500 μmol photons $m^{-2}$ $sec^{-1}$. Sodium bicarbonate (5 mM) was also added to the chamber to ensure the cells were not carbon-limited. The algal cells were exposed to increasing light intensity while oxygen concentration was continuously measured. Oxygen concentration was then plotted as a function of light intensity to provide a photosynthesis irradiance (P/I) curve demonstrating the light saturation of photosynthesis in the strains, where the light saturated rate of oxygen evolution is referred to as $P_{max}$. The $P_{max}$ value was calculated on a per mg of chlorophyll basis and on a per cell basis. Ek, the saturating irradiance for photosynthesis, was also calculated from the oxygen evolution v. light intensity curve (P/I curve) (Talling J. (1957) *New Phytologist* 56: 29-50. LIHLA mutants were observed to have a decreased a, the initial slope of the P/I curve.

Example 5. Functional Characterization of LIHLA Mutant GE-4574

Figure 4:
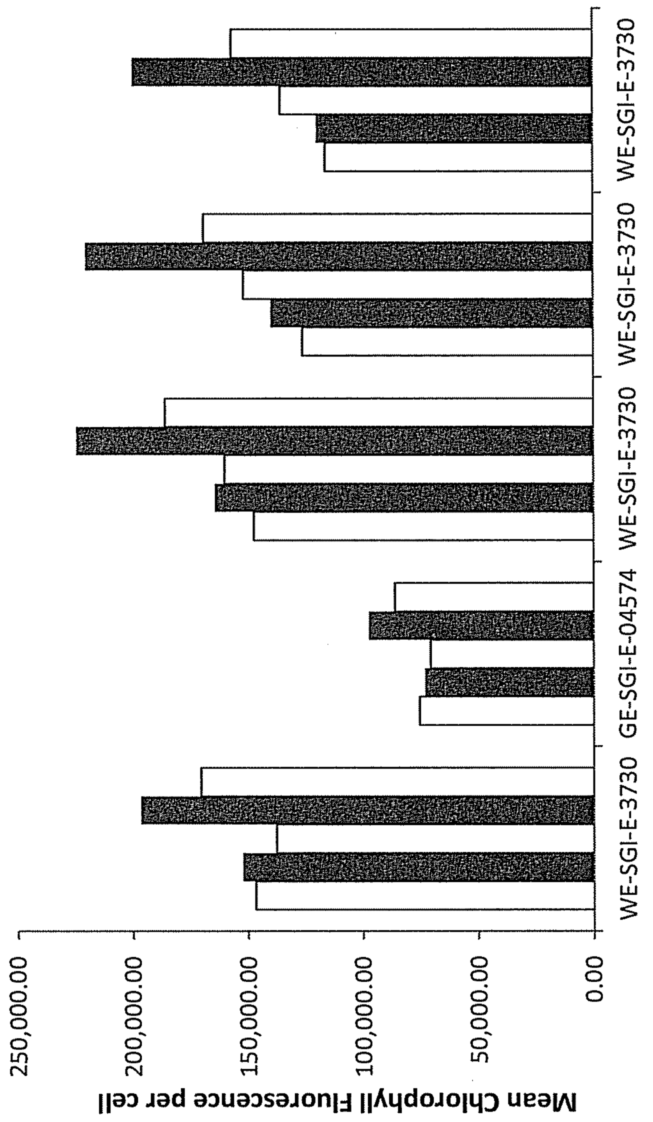
FIG. 4 depicts the results of monitoring chlorophyll fluorescence for 5 days (left to right columns: day 1, day 2, day 3, day 4, day 5) during low light acclimation cultivation of LIHLA strain GE-4574 and four biological replicates of wild type controls (WT-3730). Mean chlorophyll fluorescence per cell was determined by flow cytometry.

One of the isolates selected for further characterization, strain GE-4574, was found to have an approximately 45% reduction in mean chlorophyll fluorescence per cell compared to wild type following low light acclimation (see for example FIG. 4). In addition to reduced chlorophyll content, this strain also demonstrated higher $F_v/F_m$ (Table 1) and higher qP (FIG. 5) at all light intensities greater than 200 μmol photons $m^{-2}$ $sec^{-1}$ that were tested. The qP value was measured essentially according to Maxwell and Johnson, (2000) *J. Exper. Bot.* 51: 659-668.

TABLE 1

Maximum PSII quantum yield for strain GE-4574 and biological duplicates of wild type control *Nannochloropsis* (WT-3730).

| Strain | $F_v/F_m$ |
|---|---|
| WT-3730 | 0.74 |
| WT-3730 | 0.74 |
| GE-4574 | 0.81 |

Figure 5:
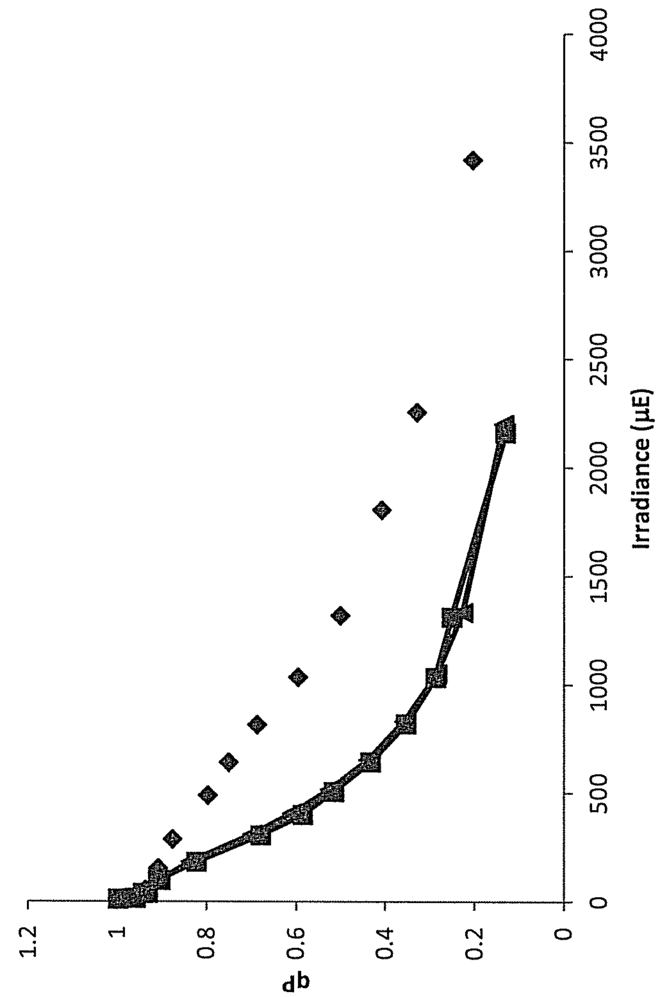
FIG. 5 provides a graph of the photochemical quenching coefficient (qP) for 12 different irradiances for light limited cultures of strain GE-4574 (diamonds) and biological replicates of wild type control WT-3730 (squares and triangles).

It is noteworthy that the qP value of the GE-4574 LIHLA mutant is significantly higher than the qP of the wild type, over a range of irradiance levels (FIG. 5). For example, at an irradiance of ~650 μmol photons $m^{-2}$ $sec^{-1}$, the GE-4574 strain has a qP value 1.7 fold higher than wild type, and at ~1000 μmol photons $m^{-2}$ $sec^{-1}$ and even ~2200 μmol photons $m^{-2}$ $sec^{-1}$, the qP of the GE-4574 strain is more than twice that observed in the wild type strain.

Further photo-physiological screens were implemented to verify the maintenance of balanced photosynthesis, consistent with a LIHLA phenotype, as opposed to photosynthetic impairments that might reduce productivity. Maximal oxygen evolution per cell ($P_{max}$) and photosystem I (PSI) measurements were performed on low light acclimated cultures. $P_{max}$ for GE-4574 was reduced by approximately 10% on a per cell basis with respect to wild type but was 2.5 fold the wild type value when normalized to chlorophyll concentration (Table 2). PSI parameters were measured by monitoring the difference between 875 nm and 830 nm transmittance signals. This provides the ratio of oxidized to reduced PSI centers, and can be converted into an electron transport rate (ETR) for PSI. PSI parameters for GE-4574 indicated no deficiencies that would impair growth or the ability to perform photosynthesis. Electron transport rates through both PSI ($ETR_{PSI}$) and PSII ($ETR_{PSII}$) in LIHLA mutants were found to be substantially equivalent to or greater than $ETR_{PSI}$ and $ETR_{PSII}$ of wild type cells.

TABLE 2

Maximum oxygen evolution per cell and chlorophyll concentration for LIHLA mutant GE-4574 and biological duplicates of wild type control *Nannochloropsis* (WT-3730).

| Strain ID | $P_{max}$/cell (μmol $O_2$ $hour^{-1}$ $cell^{-1}$) | $P_{max}$/[chlorophyll] (μmol $O_2$ $hour^{-1}$ $mg^{-1}$) | Total Chlorophyll (pg/cell) |
|---|---|---|---|
| WT-3730 | 0.18 | 151.1 | 0.12 |
| WT-3730 | 0.19 | 161.0 | 0.12 |
| GE-4574 | 0.17 | 404.9 | 0.04 |

A total of 35 mutants were originally isolated using the screen for reduced chlorophyll, increased qP over irradiances greater than 200 μmol photons $m^{-2}$ $sec^{-1}$, an increase in $P_{max}$ per chlorophyll with $P_{max}$ per cell at least 70% of wild type cells, higher Ek than wild type cells, and onset of NPQ at higher irradiance than was required for wild type cells, with reduced NPQ over irradiances greater than 200 μmol photons $m^{-2}$ $sec^{-1}$. Many of the mutants that were isolated had the following characteristics as compared to wild type cells under low light acclimated conditions: chlorophyll content reduced to from about 30% to about 75% of wild type levels, (typically, an approximately two to three fold decrease in chlorophyll per cell); an approximately two to three fold increase in $P_{max}$ per chlorophyll, with less than about 25%, and typically not greater than about a 15% decrease in $P_{max}$ per cell; approximately the same or increased rate of photosynthetic electron transport (e.g., $ETR_{PSII}$ typically at least 1.5 times or at least 2 times the wild type rate); increased qP at all irradiances greater than 200 μmol photons $m^{-2}$ $sec^{-1}$; higher Ek with respect to wild type cells; decreased a (initial slope of the photosynthesis irradiance curve); onset of NPQ at higher irradiance; decreased NPQ at all irradiances greater than 200 μmol photons $m^{-2}$ $sec^{-1}$, and typically at all irradiances greater than 100 μmol photons $m^{-2}$ $sec^{-1}$. FIG. 6 provides a listing of mutants having these characteristics along with their chlorophyll content, $ETR_{PSII}$, and $P_{max}$. The mutants in the table are characterized by the genetic locus that was found to be responsible for the mutant phenotype (LAR1, LAR2, or LAR3), as described below in Examples 7 and 10.

Figure 7:
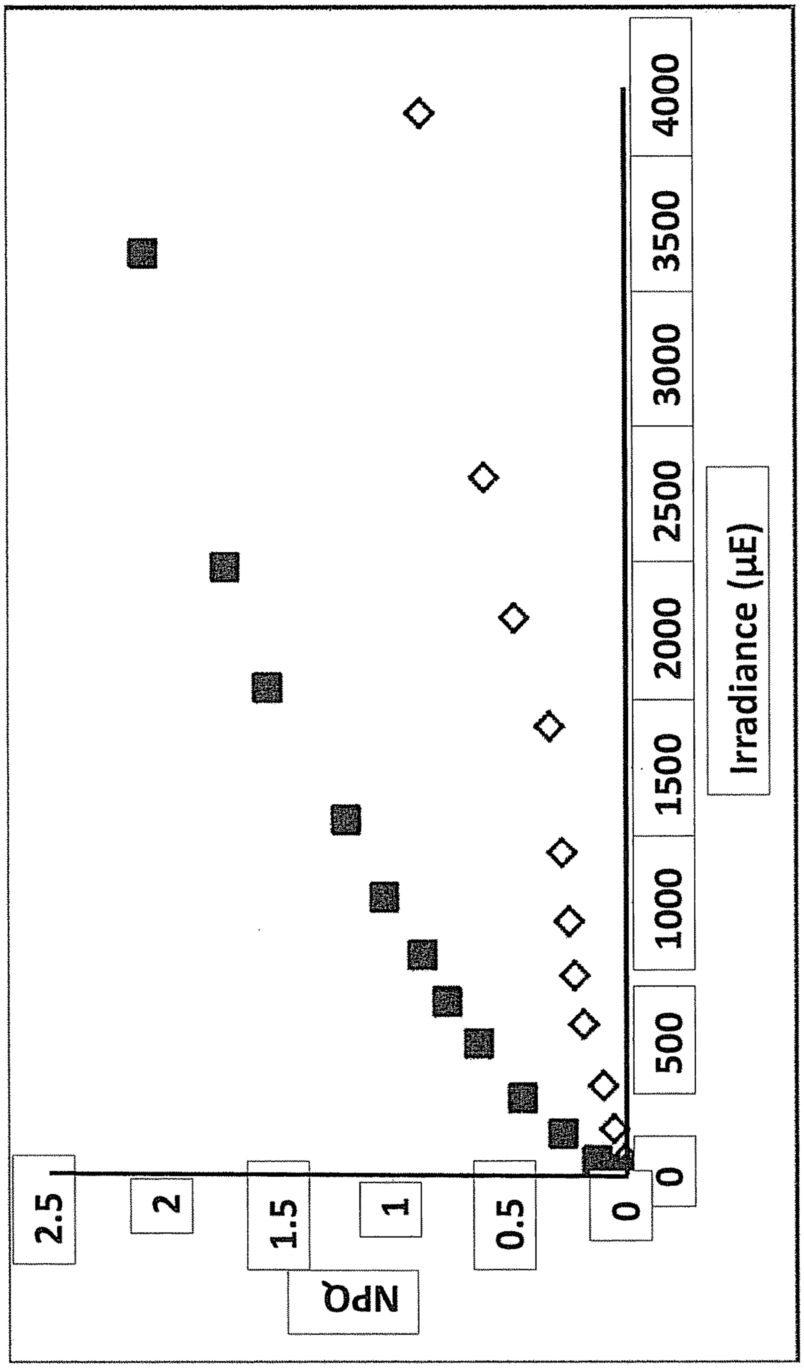
FIG. 7 provides an NPQ curves for a LIHLA mutant having a mutation in the LAR1 gene (open diamonds) as compared with wild type cells (black squares) when both LIHLA mutant and wild type cells are acclimated to low light.

FIG. 7 is a graph of NPQ versus light intensity for one of the LIHLA mutants (open diamonds), later determined to be a LAR1 mutant, and the wild type progenitor strain (black squares). The LIHLA mutant demonstrates late onset of NPQ with respect to irradiance, and demonstrates drastically lower NPQ than the wild type over all irradiances greater than 200 μmol photons $m^{-2}$ $sec^{-1}$.

Figure 8:
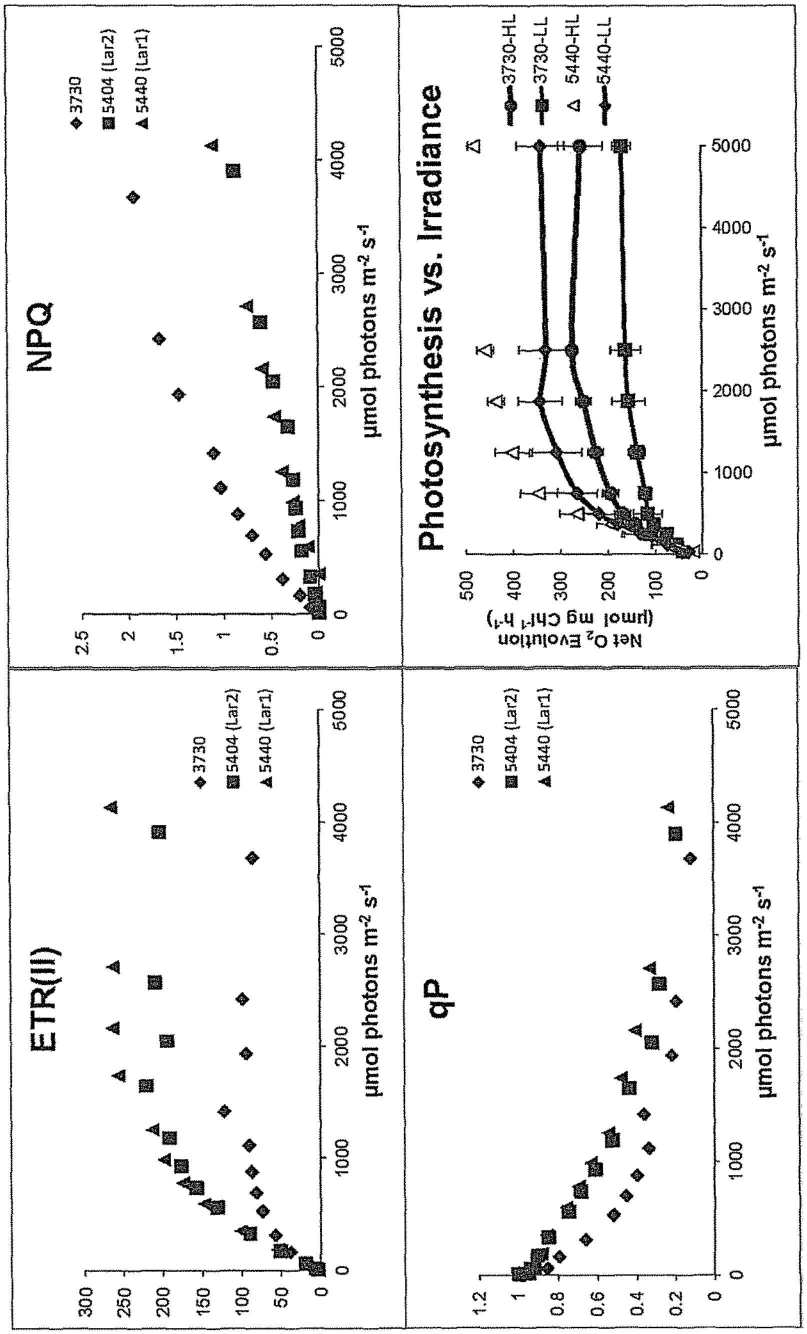
FIG. 8 provides a graph of the $ETR_{PSII}$ for LAR1 LIHLA mutant strain GE-5440 (triangles), LAR2 LIHLA mutant strain GE-5404 (squares), and the wild type strain (WT-3730, diamonds) over a range of irradiances (see Northwest Quadrant); the Northeast Quadrant is a graph depicting NPQ over a range of irradiances for LAR1 LIHLA mutant 5440 (triangles), LAR2 LIHLA mutant 5404 (squares), and the wild type strain WT-3730 (diamonds); the Southwest Quadrant is a graph showing qP in response to irradiance for LAR1 LIHLA mutant 5440 (triangles), LAR2 LIHLA mutant 5404 (squares), and the wild type strain WT-3730 (diamonds); and the Southeast Quadrant shows P/I curves for a LAR1 mutants acclimated to high light (open triangles) or low light (black diamonds) as well as for high light acclimated wild type cells (black circles) and low light acclimated wild type cells (black squares).

FIG. 8*a* provides a graph of the $ETR_{PSII}$ for a LAR1 LIHLA mutant (triangles), a LAR2 LIHLA mutant (squares), and the wild type strain (diamonds) over all irradiances greater than 200 μmol photons $m^{-2}$ $sec^{-1}$. FIG. 8*b* shows NPQ is drastically reduced for the LIHLA mutants over a range of irradiances greater than 100 μmol photons $m^{-2}$ $sec^{-1}$ as compared with wild type (LAR1 mutant, triangles; LAR2 mutant, squares; wild type, diamonds). FIG. 8*c* is a graph showing higher qP in response to irradiance for irradiances greater than 200 μmol photons $m^{-2}$ $sec^{-1}$ for a LAR1 LIHLA mutant (triangles), a LAR2 LIHLA mutant (squares), and the wild type strain (diamonds). FIG. 8*d* provides P/I curves for a LAR1 mutants acclimated to high light (open triangles) or low light (dark diamonds) as well as high light acclimated (dark circles) and low light acclimated (dark squares) wild type cells, with the LIHLA mutant demonstrating higher Ek and higher $P_{max}$ per chlorophyll than wild type cells at both high and low light intensities.

Figure 9:
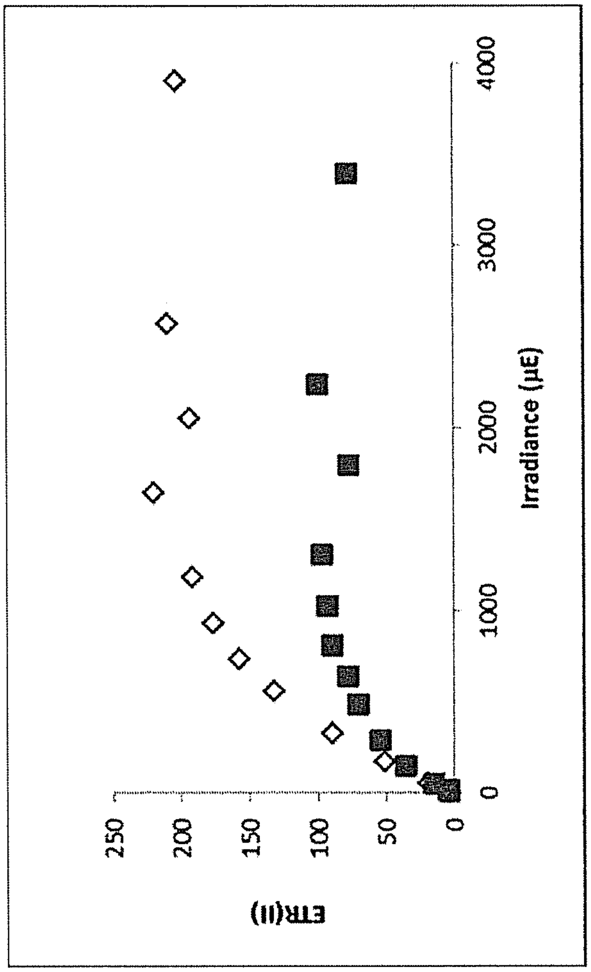
FIG. 9 is a graph depicting Photosystem II electron transport rates ($ETR_{PSII}$) as a function of irradiance for LIHLA LAR1 mutant GE-5440 (open diamonds) and wild type WT-3730 (black squares) over a range of light intensities.
Figure 10:
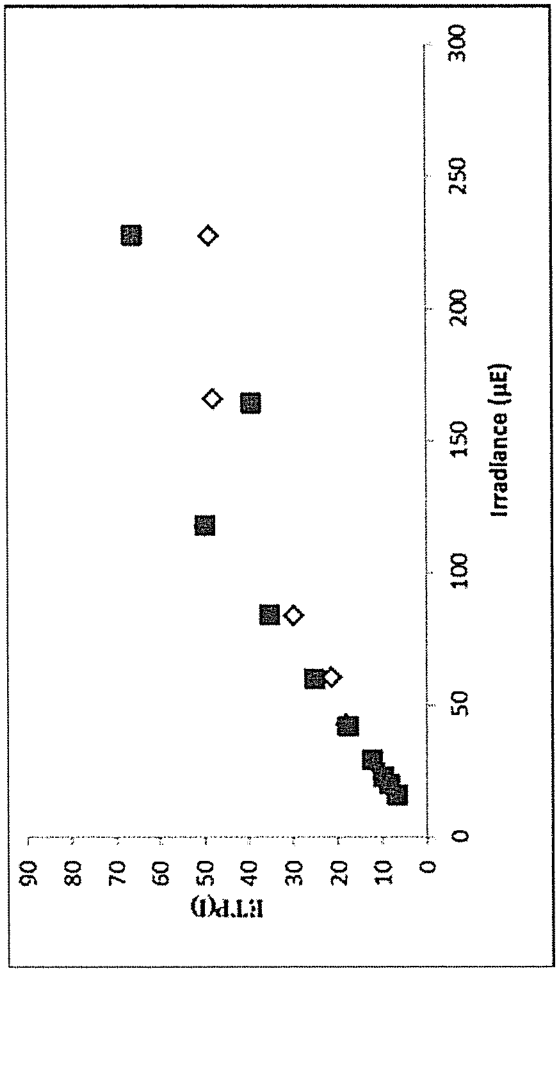
FIG. 10 is a graph depicting Photosystem I electron transport rates as a function of irradiance for LIHLA LAR1 mutant GE-5440 (open diamonds) and wild type WT-3730 (black squares) over a range of light intensities.

FIG. 9 and FIG. 10 show exemplary results of testing electron transport through Photosystem II ($ETR_{PSII}$) and Photosystem I ($ETR_{PSI}$) respectively in a LIHLA LAR1 mutant. The LIHLA mutant demonstrates higher $ETR_{PSII}$ over a wide range of irradiances and demonstrates no discernible impairment of $ETR_{PSI}$.

Example 6. Light Penetration into LIHLA Mutant Culture Ponds

Figure 11:
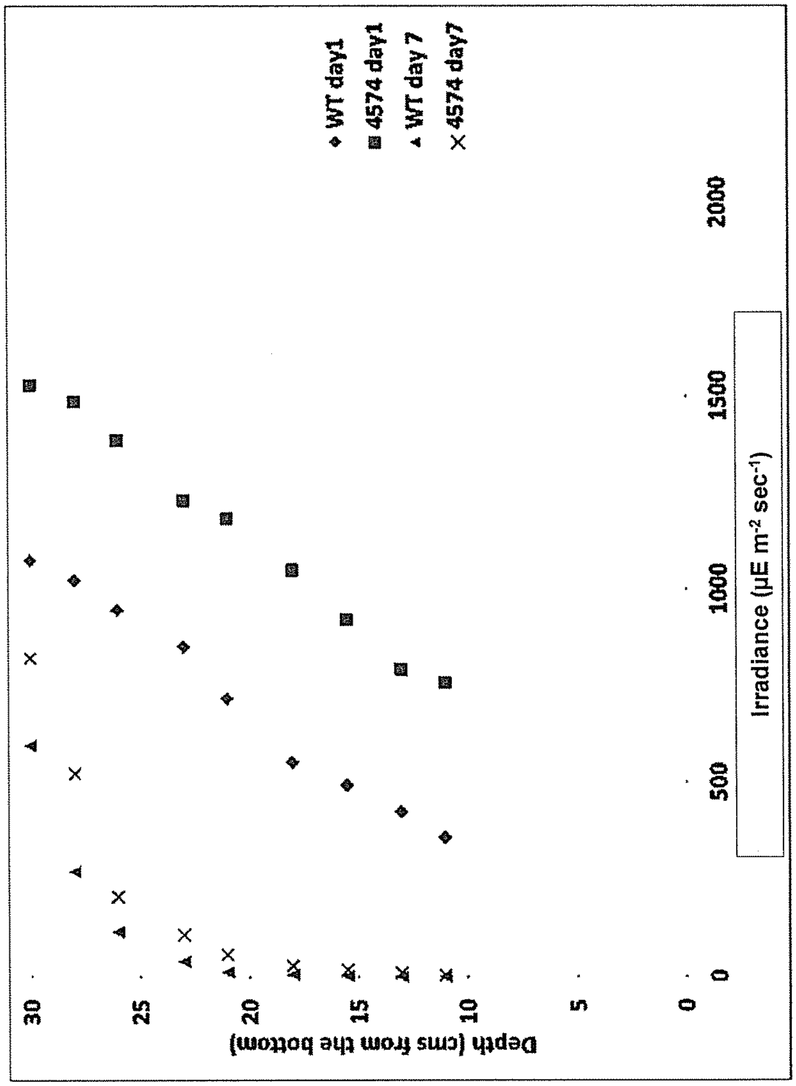
FIG. 11 shows the penetration of light to various depths (centimeters from the bottom) on two different days post inoculation with wild type (diamonds [day 1] and triangles [day 7]) and LAR1 mutant GE-4574 (squares [day 1] and Xs [day 7]) cultures. Cell density on day 1 was $2\times10^6$ cells/mL. Cell density on day 7 was $4.5\times10^7$ cells/mL.

Cultures of mutant strains were also screened for better light penetration into the culture with respect to light penetration into wild type strain cultures. Light penetration into an open growth system used to culture wild type *Nannochloropsis* as well as the GE-4574 mutant was also assessed. *Nannochloropsis gaditana* wild type (WT-3730) and GE-4574 mutant cultures were grown in 400 L greenhouse ponds in nitrogen replete growth medium for seven days on a 14 hour light/10 hour dark cycle. Wild type *Nannochloropsis* and GE-4574 mutant cells were used to inoculate ponds at a cell density of $2\times10^6$ cells/mL. Penetration of light into the pond was measured using a 4 Pi spherical quantum sensor on day 1 as well as on day 7 (providing cell densities of $2\times10^6$ and $4.5\times10^7$ cells/mL, respectively). FIG. 11 shows that on day one of culturing, immediately after inoculation, the difference in light penetration into the cultures is substantial, with the GE-4574 mutant culture experiencing much higher light levels, with respect to the wild type culture, at all depths measured. For example, the amount of light at approximately 20 cm from the bottom of the pond (i.e., approximately 10 cm below the surface) of the wild type culture is equivalent to that found at approximately 10 cm from the bottom (i.e., approximately 20 cm below the surface of the pond) of the mutant culture.

When the cultures reached a higher density (day 7), the difference in light penetration into wild type and mutant cultures was less pronounced, but still significant, at depths above 20 centimeters from the bottom of the pond (i.e., within approximately 10 cm of the pond surface). For example, approximately 500 μE $m^{-2}$ $sec^{-1}$ of light was available 28 cm from the bottom of the pond holding the GE-4574 mutant culture, whereas at the same depth only about 250 μE $m^{-2}$ $sec^{-1}$ of light was available in the pond holding the wild type culture. Thus, the LIHLA mutant allows greater penetration of light into the pond than does the wild type strain grown under identical conditions, which allows photosynthesis to occur at greater distances from the pond surface and at higher cell densities.

In a separate experiment, wild type and GE4906 (a LAR2 mutant) cultures were grown in 400 L greenhouse miniponds (5 ponds per strain) with supplemental illumination by two overhead lamps on a 14 hour light/10 hour dark cycle. The algae were grown in PM074 media (10×F/2) with 4 mM additional nitrate added to the cultures on day 7. Initially, each of the ponds was diluted daily for two days to allow the wild type strain to acclimate to high light conditions. One set of the lamp simulator cultures was allowed to grow past the onset of light limitation; the remaining ponds were allowed to asymptote and then were diluted daily to keep the strains within their optimal productivity range. The depth profile for the wild type and mutant cultures was recorded at a standing biomass density of 300 mg/L, which corresponded to an $OD_{730}$ of 0.75.

Figure 12:
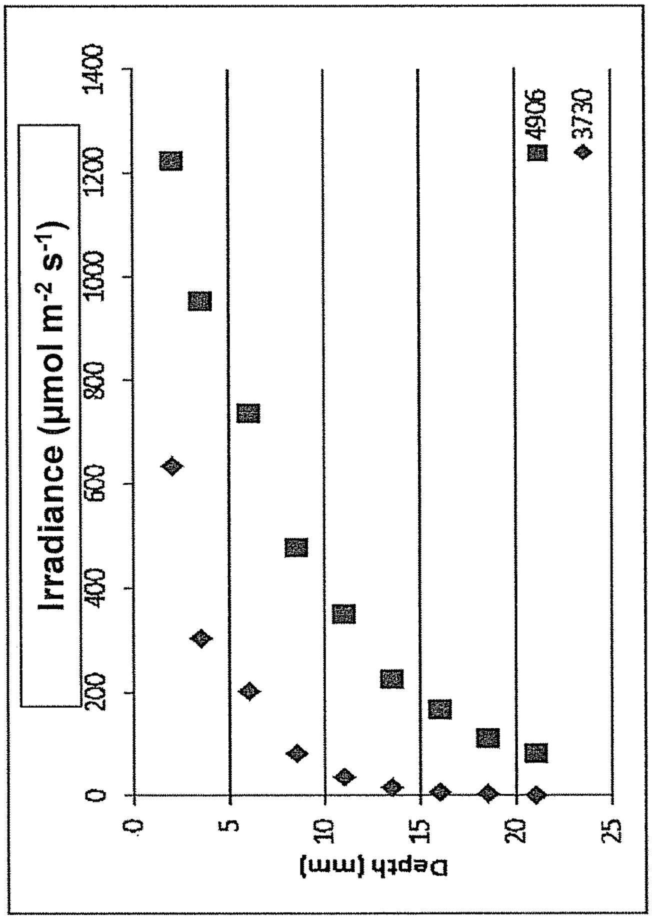
FIG. 12 graphically depicts the amount of light reaching various depths of 400 L miniponds operated in a greenhouse. Squares are light intensities measured from a culture of LIHLA mutant 4906 (mutated in the LAR2 gene), and diamonds are light intensities measured from a culture of wild type *Nannochloropsis* (WT-3730). The y-axis shows depth (distance from the surface) in centimeters.

The data providing the irradiance (measured using a 4 Pi spherical quantum sensor) at various depths of the pond is provided in FIG. 12 and demonstrates that, as for the LAR1-mutated LIHLA mutant GE4574 (FIG. 11), the LAR2-mutated LIHLA GE4906 mutant allows greater light penetration into the culture, with the GE4906 mutant culture experiencing much higher light levels, with respect to the wild type culture, at all depths measured.

Example 7. Genotyping of LIHLA LAR1 and LAR2 Mutants

Figure 13:
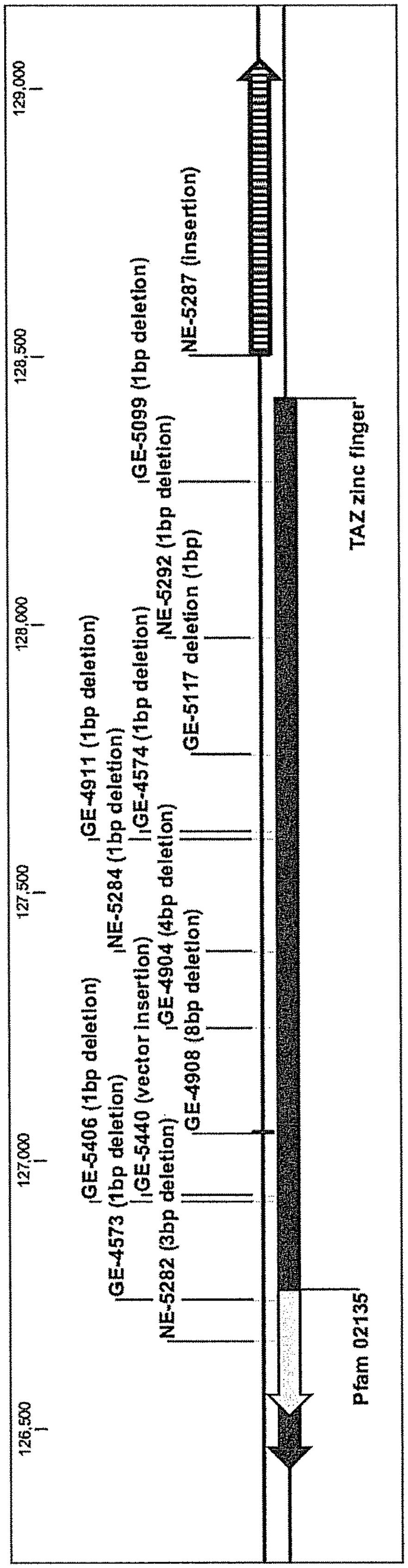
FIG. 13 is a map of the genetic locus encoding the LAR1 gene in *Nannochloropsis gaditana* showing the sites of genetic lesions found in various LIHLA mutants. The pfam PF02135 TAZ zinc finger domain (blue region, labeled "Pfam 02135") is in the C-terminal portion of the protein.

Multiple mutants were isolated having the LIHLA phenotype of 1) at least a 40% reduction in chlorophyll per cell with respect to wild type as measured by fluorescence and spectroscopy, 2) higher qP with respect to wild type over physiologically relevant irradiances (e.g., greater than about 200 μE $m^{-2}$ $sec^{-1}$ or greater than about 100 μE $m^{-2}$ $sec^{-1}$), 3) equivalent (a difference of 20% or less, and preferably difference of about 10% or less) or greater $P_{max}$ per cell as compared to wild type and at least two fold higher $P_{max}$ per unit chlorophyll as compared to a wild type cell, 4) higher $E_k$ with respect to wild type, and 5) onset of NPQ at higher irradiances with respect to wild type, with lower NPQ at all irradiance higher than about 200 μE $m^{-2}$ $sec^{-1}$. Of all the mutants that were confirmed through photo-physiological analysis to have the LIHLA phenotypes based on these parameters, all but one were mapped by DNA sequencing to show lesions in one of just two genes. Thirteen distinct mutations were mapped to a single gene as annotated in a proprietary *Nannochloropsis gaditana* genome sequence. The identified gene, referred to herein as "Light Acclimation Regulator 1" or LAR1 (SEQ ID NO:3) (previously called Regulator 59), was found to encode a polypeptide (SEQ ID NO:4) that recruited to pfam PF02135 or the "TAZ zinc finger" pfam, and thus was determined to encode a putative TAZ Zinc finger transcriptional regulator (Ponting et al. (1996) *Trends Biochem. Sci.* 21: 11-13). The mutations found in the LAR1 gene included tagged insertions, untagged insertions, and short deletions resulting in frame shift mutations, as well as one short deletion which created both a missense and deletion point mutation. FIG. 13 shows the position and type of mutations confirmed for 13 LAR1-associated LIHLA mutants. Confirmation of the position of the genetic lesion was through a combination of chromosome walking techniques, PCR, and DNA sequencing, including genome sequencing using an in-house MiSeq sequencer (Illumina, San Diego, Calif.).

For LIHLA strain genome re-sequencing, whole genomic DNA of *Nannochloropsis gaditana* mutants were used for Nextera DNA library preparation according to the recommended protocol (Illumina Inc., San Diego, Calif.) The libraries generated were sequenced by paired-end sequencing on an Illumina MiSeq instrument.

Figure 14:
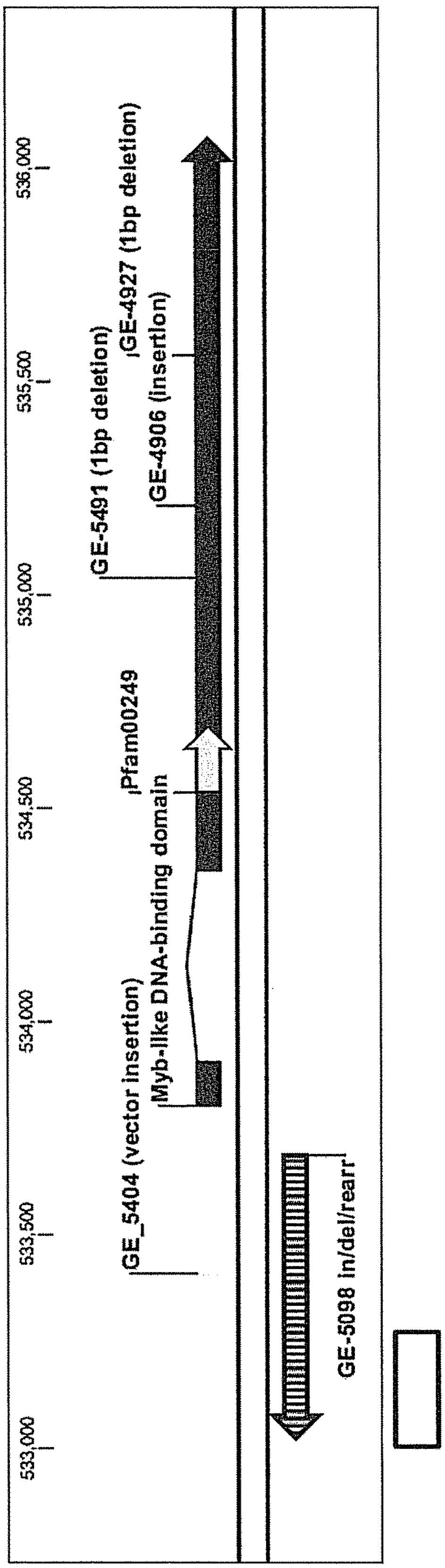
FIG. 14 is a map of the genetic locus encoding the LAR2 gene in *Nannochloropsis gaditana* showing the sites of genetic lesions found in various LIHLA mutants. The pfam PF00249 myb-like DNA-binding domain (blue, labeled "Pfam 00249") is in the N-terminal portion of the protein.

In addition to the mutations found in the LAR1 gene, five distinct mutations were identified in a gene referred to herein as "Light Acclimation Regulator 2" or LAR2 (SEQ ID NO:5) (previously called Regulator 216), among the LIHLA mutants isolated. This locus was identified in the proprietary *Nannochloropsis gaditana* genome sequence as encoding a myb-like transcription factor. The polypeptide encoded by this gene (SEQ ID NO:6), was found to recruit to pfam PF00249 ("myb-like DNA-binding domain"). The LAR2 genetic lesions were also identified by a combination of chromosome walking and sequencing approaches; the positions and nature of the LAR2 genetic lesions are shown in FIG. 14.

Figure 15:
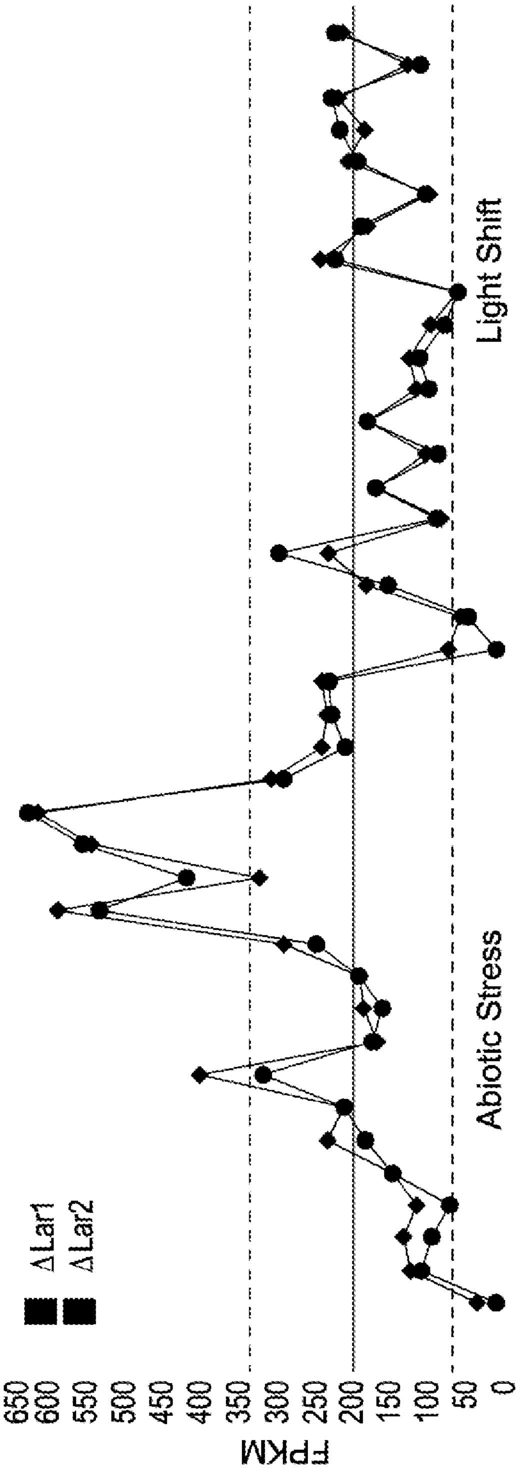
FIG. 15 is a plot of LAR1 and LAR2 expression values from RNA-seq analysis using RNA libraries for a number of abiotic conditions as well as during light shifts that demonstrates the highly significant similarity of their expression profiles.

*Nanncochloropsis* transcriptomics data sets (n=113 RNA-seq libraries) were analyzed to predict genes with likely similar function to LAR1 by performing co-expression analysis. Co-expression analysis was performed in two ways: 1) by calculating pairwise distance metrics between LAR1 and all other genes and 2) by performing gene network inference on all *Nannochloropsis gaditana* genes using the GENIE3 algorithm (Huynh-Thu et al. (2010) PLOS One 5(9) e12776.doi:10). By all metrics LAR2 was ranked the most similar gene to LAR1, and the converse was also true. Plotting LAR1 and LAR2 expression values for all abiotic conditions (e.g., temperature, nutrient limitation, light intensity, etc.) demonstrates the significant similarity of their expression profiles suggesting potential co-regulation of these factors (FIG. 15). Results of the network inference analysis also ranked LAR2 as the top gene with a dependent expression pattern relative to LAR1. This indicates (as supported by their highly similar phenotype of the mutants) that the proteins encoded by the LAR1 and LAR2 genes are on the same pathway, and suggests that they may interact with one another. This analysis can be pursued further to identify other potential members of the photoacclimation regulatory network. LAR mutants as provided herein can provide a useful background for further genetic manipulation.

Example 8. LAR1 and LAR2 Homologs

Figure 17:
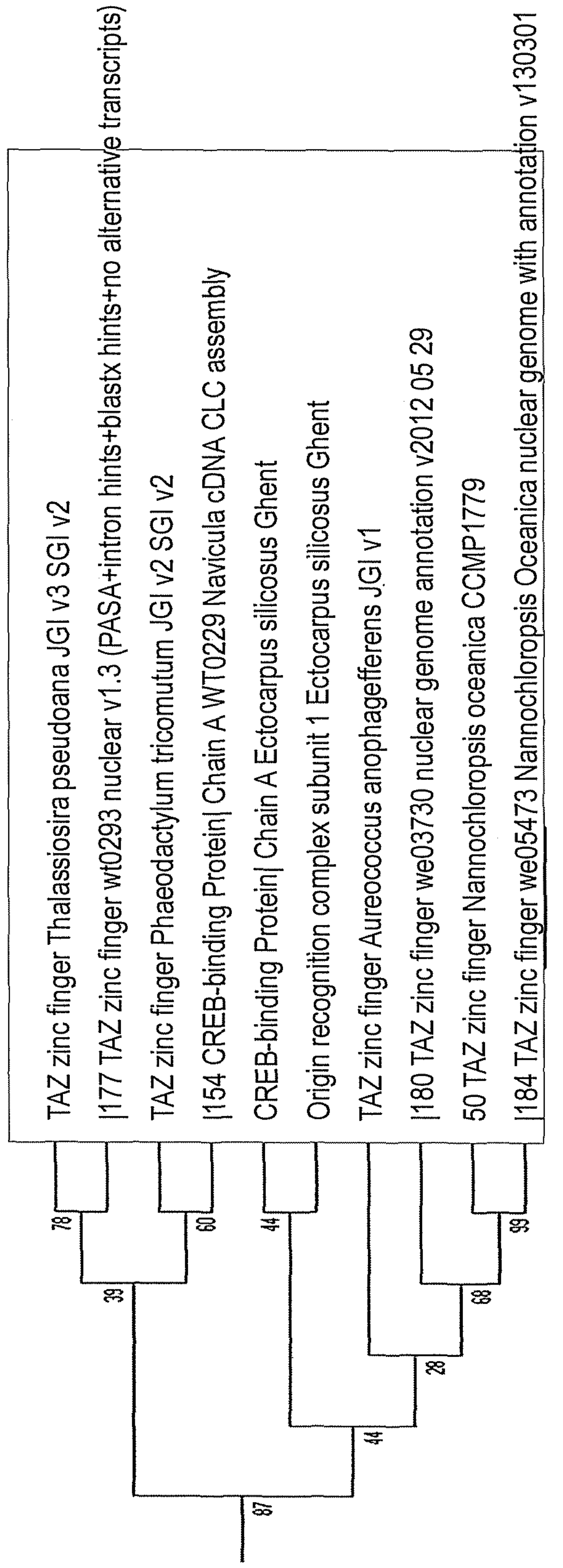
FIG. 17 provides a bioinformatics phylogenetic tree showing relationships among homologs of LAR1.

There is significant similarity between the *N. gaditana* WT-3730 LAR1 gene and a gene identified in *Nannochloropsis oceanica* (strain ID WT5473) (No-LAR1, SEQ ID NO:7, encoding the polypeptide of SEQ ID NO:8) over the annotated PF02135 TAZ zinc finger (Transcription Adaptor putative Zinc finger) domain near the C terminus according to pairwise alignment of the full-length protein sequences (FIG. 16). The pfam PF02135 TAZ zinc finger domain of the *N. gaditana* WT-3730 LAR1 polypeptide, amino acids 554-632, is provided as SEQ ID NO:9. The pfam PF02135 TAZ zinc finger domain of the *N. oceanica* WT5473 No-LAR1 polypeptide, amino acids 630-706, is provided as SEQ ID NO:10. (Functional validation of the *N. oceanica* LAR1 ortholog No-LAR1 is demonstrated in Example 13, below.) To uncover additional potential orthologs of LAR1, we searched 66 in-house and publicly available eukaryotic assemblies (mostly algae and plants) for protein sequences annotated with the PF02135 domain (as scored by hmmscan at I-Evalue<0.01). Three hundred and sixty-four TAZ domain-containing protein sequences were extracted, and aligned using Muscle (Edgar (2004) *Nucl. Acids Res.* 32: 1792-1797. A maximum likelihood phylogenetic tree (with 100 bootstrap replicates) was built using Mega (Kumar et al. (2008) *Briefings in Bioinformatics* 9: 299-306). One particular branch containing the WT-3730 LAR1 protein grouped together the same set of proteins 87/100 times and therefore represents a likely grouping of LAR1 orthologs in other stramenopiles and diatoms (FIG. 17). Each protein appears to be from a unique sequence library (corresponding to a unique cDNA or gDNA assembly, strain or species) except in the case of two proteins from *Ectocarpus silicosus* (Ghent genome assembly).

Using the LAR1 TAZ domain sequence (SEQ ID NO:9) as a query to the full-length sequences of proteins with predicted TAZ domains, the top hits correspond to the sub-tree defined from the TAZ zinc finger phylogenetic tree. There seems to be a substantial difference in E-value and bit score for blastp similarity matches outside the putative TAZ orthologs branch. Despite sequence identity as low as 42% over the TAZ domain, the analysis suggests that the proteins highlighted in the table are likely orthologs in other species (Table 3).

TABLE 3

LAR1 Homologs

| Library_ID | % Identity of pfam Domain | % ID of entire protein | alignment length | mismatches | gap openings | q.start | q.end | s.start | s.end | E-value | bit score |
|---|---|---|---|---|---|---|---|---|---|---|---|
| SEQ ID NO: 4 WT-3730 *Nannochloropsis gaditana* | 100.0 | | 79 | 0 | 0 | 1 | 79 | 554 | 632 | 1.00E−46 | 175 |
| SEQ ID NO: 8 WT5473 *Nannochloropsis oceanica* | 81.8 | 49.7 | 77 | 14 | 0 | 1 | 77 | 630 | 706 | 1.00E−37 | 145 |
| SEQ ID NO: 11 CCMP1779 *Nannochloropsis oceanica* | 81.8 | 49.5 | 77 | 14 | 0 | 1 | 77 | 555 | 631 | 2.00E−37 | 145 |
| SEQ ID NO: 12 *Ectocarpus silicosus* | 62.0 | | 79 | 30 | 0 | 1 | 79 | 581 | 659 | 8.00E−26 | 106 |
| SEQ ID NO: 13 *Thalassiosira pseudonana* | 56.1 | | 82 | 33 | 1 | 1 | 79 | 942 | 1023 | 1.00E−23 | 99.4 |
| SEQ ID NO: 14 *Phaeodactylum tricornutum* | 53.2 | | 79 | 37 | 0 | 1 | 79 | 1011 | 1089 | 1.00E−20 | 89.4 |

TABLE 3-continued

| LAR1 Homologs | | | | | | | | | | | |
|---|---|---|---|---|---|---|---|---|---|---|---|
| Library_ID | % Identity of pfam Domain | % ID of entire protein | alignment length | mismatches | gap openings | q.start | q.end | s.start | s.end | E-value | bit score |
| SEQ ID NO: 15 WT0293 *Cyclotella* sp. | 55.0 | | 80 | 33 | 1 | 1 | 77 | 744 | 823 | 2.00E−20 | 88.6 |
| SEQ ID NO: 16 *Ectocarpus silicosus* | 55.4 | | 74 | 33 | 0 | 1 | 74 | 444 | 517 | 7.00E−20 | 86.7 |
| SEQ ID NO: 17 WT 0229 *Navicula* species | 51.9 | | 79 | 38 | 0 | 1 | 79 | 521 | 599 | 2.00E−19 | 85.5 |
| SEQ ID NO: 18 *Aureococcus anopagefferens* | 42.1 | | 76 | 41 | 1 | 2 | 77 | 137 | 209 | 1.00E−14 | 69.3 |

There is also considerable sequence identity/similarity between the *N. gaditana* (WT-3730) and *N. oceanica* (WT-5473) orthologs at the N terminus of LAR1, including a perfectly conserved stretch of thirty amino acids: AKQQQLLKDSLTADLKLLLHEFERFQQATA (SEQ ID NO:19). Using the N-terminus sequence (first 300 amino acids) of LAR1 as query in a DELTA-Blast (Domain Enhanced Lookup Time Accelerated BLAST) search over the NCBI non-redundant protein database, a significant match to a protein XP_001952448.1, annotated as "PREDICTED: nucleosome-remodeling factor subunit NURF301-like isoform 1 [*Acyrthosiphon pisum*]", was identified. The sequence similarity region in XP_001952448.1 is adjacent to the annotated PHD domain. NURF301 is thought to mediate histone H3 lysine recognition through the PHD domain.

A similar approach was undertaken to identify putative orthologs of LAR2 in other species. Alignment of *N. gaditana* (WT-3730) LAR2 with an identified ortholog of *N. oceanica* (WT-5473) (No-LAR2, gene sequence provided as SEQ ID NO:20; encoded polypeptide provided as SEQ ID NO:21) show complete identity over the predicted PF00249 Myb-like DNA-binding domain (FIG. 18). An extended version of the pfam PF00249 myb-like domain of the *N. gaditana* WT-3730 LAR2 polypeptide, amino acids 71-351, is provided as SEQ ID NO:22. An extended version of the pfam PF00249 myb-like domain of the *N. oceanica* WT-5473 No-LAR2 polypeptide, amino acids 36-325, is provided as SEQ ID NO:23. (Functional validation of the *N. oceanica* LAR2 ortholog is demonstrated in Examples 12 and 13.) A notable feature of this particular kind of Myb-like DNA-binding proteins is a "SHAQKY" (SEQ ID NO:24) amino acid motif at the end of the Myb-like domain. For LAR2 the motif is slightly different: "THAQKY" (SEQ ID NO:25). Thus, we searched 66 in-house and public eukaryotic assemblies (mostly algae and plants) for protein sequences annotated with the PF00249 domain (as scored by hmmscan at I-Evalue<0.01) which contain a THAQKY (SEQ ID NO:25) or SHAQKY (SEQ ID NO:24) six amino acid motif. A total of 1,409 proteins were identified with the PF00249 domain and the six amino acid motif.

We used both the annotated PFAM domain and an extended version of the PFAM domain as queries for blastp comparison against the set of 1,409 Myb-like DNA-binding proteins. An extended version of the PF00249 domain was used because the PF00249 model is relatively short (48 amino acids) and there appears to be extended sequence similarity between the WT-3730 and WT-5473 orthologs over a larger region. However, using both sequence versions as query, the same top results as shown in Table 4 were obtained.

Putative homologs in other species (diatoms and stramenopiles) are identified at a higher level of sequence identity (>80%) over the Myb-like domain compared with the homologies observed for the TAZ domain. Matches in other strains and species with a higher blastp similarity score by E-value to the LAR2 Myb-like domain compared to other proteins with similar domains within WT-3730 are considered putative orthologs as highlighted in Table 4.

TABLE 4

| LAR2 Homologs | | | | | | | | | | | |
|---|---|---|---|---|---|---|---|---|---|---|---|
| Subject | % ID of pfam PF00249 domain | % ID of entire protein | alignment length | mismatches | gap openings | q.start | q.end | s.start | s.end | E-value | bit score |
| SEQ ID NO: 6/ WT-3730 *Nannochloropsis gaditana* | 100.0 | | 44 | 0 | 0 | 1 | 44 | 101 | 144 | 3.00E−24 | 101 |
| SEQ ID NO: 21| WT5473 *Nannochloropsis oceanica* | 100.0 | 69 | 44 | 0 | 0 | 1 | 44 | 66 | 109 | 1.00E−23 | 99.4 |
| SEQ ID NO: 26| CCMP1779 *Nannochloropsis oceanica* | 100.0 | | 44 | 0 | 0 | 1 | 44 | 66 | 109 | 1.00E−23 | 99.4 |
| SEQ ID NO: 27| *Ectocarpus silicosus* | 86.4 | | 44 | 6 | 0 | 1 | 44 | 7 | 50 | 3.00E−20 | 88.2 |

TABLE 4-continued

| LAR2 Homologs | | | | | | | | | | | |
|---|---|---|---|---|---|---|---|---|---|---|---|
| Subject | % ID of pfam PF00249 domain | % ID of entire protein | alignment length | mismatches | gap openings | q.start | q.end | s.start | s.end | E-value | bit score |
| SEQ ID NO: 28\| WT0229 *Cyclotella* sp. | 86.4 | | 44 | 6 | 0 | 1 | 44 | 72 | 115 | 4.00E−20 | 87.8 |
| SEQ ID NO: 29 *Phaeodactylum tricornutum* | 86.4 | | 44 | 6 | 0 | 1 | 44 | 118 | 161 | 4.00E−20 | 87.8 |
| SEQ ID NO: 30 *Phaeodactylum tricornutum* | 86.4 | | 44 | 6 | 0 | 1 | 44 | 118 | 161 | 4.00E−20 | 87.8 |
| SEQ ID NO: 31 *Thalassiosira pseudonana* | 86.4 | | 44 | 6 | 0 | 1 | 44 | 419 | 462 | 6.00E−20 | 87.4 |
| SEQ ID NO: 32 *Ectocarpus silicosus* | 81.8 | | 44 | 8 | 0 | 1 | 44 | 32 | 75 | 1.00E−19 | 85.9 |

The transcriptomics data demonstrating strong co-expression of LAR1 and LAR2 genes in WT-3730 (FIG. 15) suggests a likely interaction or related function of the encoded proteins. Among the species profiled, likely orthologs for both LAR1 (Taz domain) and LAR2 (Myb-like domain) are predicted in *Ectocarpus silicosus, Navicula* (WT-0229 strain), *Thalassiosira pseudonana*, and *Phaeodactylum tricornutum*. Under the hypothesis that the LAR1 and LAR2 proteins interact, the TAZ phylogenetic analysis suggests that there could be orthologs for the LAR2 Myb-like protein as well in *Cyclotella* (WT-0293 strain) and *Aureococcus anophagefferens.*

Example 9. Transcriptomics of High and Low Light Acclimated Wild Type and LIHLA Mutant *Nannochloropsis*

In order to assess the genome-wide transcriptional response of wild type *Nannochloropsis gaditana* during acclimation to low and high light, transient light shift experiments were conducted. Cells were separately acclimated to both low and high irradiance by culturing at the indicated light intensity for 5 days with culture dilution on day 3 to ensure consistent light exposure of the cells, with all other variables (e.g., temperature) tightly controlled, and then experimental flasks were transferred from high to low (H-L) and low to high (L-H) irradiance, while the control flasks were maintained under the previously acclimated irradiance conditions (low or high light).

A range of high light intensities were previously tested to determine the appropriate level of high light irradiance to obtain a sustained high light acclimated state in WT-3730 within the cell density range of 96 hours of logistic growth and to test the capacity of this strain to adapt to high irradiance. A light intensity of 500 μmol photons·$m^{-2}$·$s^{-1}$ PAR was selected because 1) this was the highest maximum irradiance the wild type cells could be cultured without stress-induced clumping at the desired starting cell density of $2\times10^6$ cells/ml, while still maintaining high-light acclimation at the final cell density following 96 h of logistic growth; and both 2) the highest maximum oxygen evolution rates per unit chlorophyll ($P_{max}$), and 3) the greatest difference in the amount of chlorophyll per cell (Chl/cell) (from the 50 μmol photons·$m^{-2}$·$sec^{-1}$ PAR low light control) were determined at this intensity. Both $P_{max}$ and Chl/cell are widely accepted indicators of photosynthetic acclimation to changes in light intensity. In wild-type cells, an approximately 2-fold increase in $P_{max}$ was induced, while the amount of chlorophyll per cell (Chl/cell) decreased 2-3 fold over the course of 48 h after shifting from low to high light. These changes were consistently reproduced when *Nannochloropsis* cells were shifted from low to high light.

The WT-3730 transcriptomics-scale low to high light and high to low light shift experiments were repeated 3 times to generate biological triplicates for four time points during acclimation to high light and low light. Cultures were acclimated for 48 h before the light shift. Cultures were grown in 100 mL volumes starting at approximately $2\times10^6$ cells/mL and grown to approximately $1\times10^7$ cells/mL at the time of the shift. Cells were grown axenically in Corning low profile 100 $cm^2$ tissue culture flasks (Part#3816), sealed with previously-autoclaved rubber stoppers penetrated by red PTFE tubing 1⁄16"ID×1⁄8"OD (Cole-Parmer part #EW-96130-02) and mixed via bubbling with 0.2 μM-filtered 1% $CO^2$:air mixtures at a rate of 15 mL/min (+/−3 mL/min). For each experiment, 40 ml culture samples were pelleted and immediately frozen in liquid nitrogen at 4 time points (0 h ($T_0$), 4 h, 24 h, and 48 h). The reproducibility of a desired response to the high light and low light conditions was again validated in this experiment: $O_2$ evolution was enhanced in the high light adapted flasks, and a 2-3 fold decrease in Chl/cell was observed at 24 and 48 h post high light shift. These changes were fully reversible during the high to low light shift.

Chlorophyll content, photosynthetic rate ($P_{max}$) and Dual PAM chlorophyll fluorescence parameters (e.g., qP) were also monitored to show that physiologically successful acclimation took place. RNA was extracted from sacrificial samples removed at various time points during the light shift and submitted for genome-wide deep sequencing using HiSeq.

RNA was extracted from low and high light-adapted samples harvested at 0, 4, 24, and 48 h after the light shift from all experiments. Final RNA quality was determined by Agilent Bioanalyzer 2100 analysis. All samples had RNA integrity numbers greater than 7, with most between 8 and 9. At least 10 μg of RNA from each sample was sent to Ambry Genetics (San Diego, Calif.) for transcript sequencing. In addition to sequencing of polyA RNA, 16 of the 24 samples were also treated by RiboZero™ rRNA (Plant Leaf Kit) depletion of rRNA for total RNA sequencing. RiboZero-treated total RNA sequencing allowed for quantitation of chloroplast encoded transcripts not captured by polyA sequencing of RNA. Analysis of Ribo-Zero treated versus polyA RNA purified samples revealed similar patterns of nuclear-encoded gene transcripts, though RiboZero-treated samples allowed for additional analysis of chloroplast and mitochondrial gene transcription.

In addition, the LIHLA mutant GE-4574 was low light acclimated using the same conditions that were used for the wild type low light acclimation. RNA was extracted from both wild type (WT-3730) and LIHLA mutant GE-4574 cells at various time points during light acclimation and submitted for transcriptomic profiling.

RNA samples were depleted of rRNA by two independent methods. Samples were split into two aliquots and either polyA purified or treated using the RiboZero™ Magnetic Kit (Plant Leaf) after which both were fragmented and sequenced by Ambry Genetics (Aliso Viejo, Calif.). mRNA was sequenced using sequencing-by-synthesis (Illumina HiSeq) to generate 100 bp paired-end reads using the mRNA-Seq procedure (described in Mortazavi et al. (2008) *Nature Methods* 5:621-628. Mappable reads were aligned to the *N. gaditana* reference genome sequence using TopHat (tophat.cbcb.umd.edu/). Expression levels were computed for every annotated gene normalized for gene length and total number of mappable reads per sample using the Cuffdiff component of the Cufflinks software (cufflinks.cbcb.umd.edu). Expression levels in units of fragments per kilobase per million (FPKM) were reported for every gene in each sample using standard parameters. FPKM is a measure of relative transcriptional levels that normalizes for differences in transcript length.

Global analysis of the transcripts with significant differences (FDR less than or equal to 0.05) in their expression levels between the LIHLA GE-4574 mutant and wild type progenitor strain WT-3730 under the same low light conditions, demonstrated the pattern of differential expression of these genes. The edgeR software package was used to test genes for differential expression between the two strains, see Robinson et al. (2009) *Bioinformatics* 26: 139-140. Of the 340 expressed genes that were analyzed, the abundance of transcripts of the LIHLA GE-4574 mutant grown under low light relative to their abundance in wild type cells under low light conditions appeared discernibly similar to the WT during the low to high light (L-H) shift and opposite to the WT during the high to low light (H-L) shift. That is, based on the transcriptomics analysis, the majority of light regulated genes that were found to have altered transcript levels in low light acclimated wild type cultures with respect to their transcript levels in high light, were found to be deregulated in the LIHLA mutant, i.e., they did not have, in low light acclimated mutant cells, the transcript abundance seen in low light acclimated wild type cells. This large scale de-regulation of the genes that are differentially regulated by light, in a mutant with a locked in high light transcriptional profile strongly suggested that the LAR1 protein is a global positive regulator of the low light acclimation response in *Nannochloropsis*. The transcriptional profile of the genes annotated as light harvesting polypeptides under the light shift conditions was particularly striking, with almost all of the LHCP transcripts reduced in abundance in the mutant under low light growth with respect to wild type levels and similarly reduced in the wild type under high light growth but present in higher abundance in the wild type under low light growth.

Example 10. qRT-PCR of Genes Regulated During Low Light Acclimation

One of the isolated LIHLA mutants (GE5440) carried a single insertion in the LAR1 gene ("Light Acclimation Regulator—Zinc finger domain") (SEQ ID NO:3) and had just one additional conservative point mutation in an intergenic region of another region of the genome (as determined by genome sequencing (MiSeq)). In order to find out whether this mutant was also de-regulated in the transcriptomic response to low light, we performed RT-PCR on a selection of gene transcripts (provided in Table 5) that were representative of the transcriptional response to light in wild type. An additional LAR1 mutant with good growth properties, GE5409, and a LAR2 mutant, GE4906, were also included in this analysis.

TABLE 5

Genes Differentially regulated in LIHLA mutant cells relative to wild type

| Gene ID | Gene | Relative Abundance (up/down) | $Log_2$ fold change in abundance |
|---|---|---|---|
| 7003 | Unknown protein | ↑ | 3.1 |
| 2936 | Predicted protein | ↑ | 1.9 |
| 4948 | Metabolic Enzyme | ↑ | 1.7 |
| 5289 | Protein with peptidoglycan binding domain | ↑ | 1.3 |
| 4070 | Enzyme subunit | ↑ | 1.1 |
| 2286 | Photosynthesis-related protein | ↓ | −1.4 |
| 1517 | Photosynthesis-related protein | ↓ | −1.5 |
| 1584 | Photosynthesis-related protein | ↓ | −1.6 |
| 2281 | Predicted protein | ↓ | −1.7 |
| 1091 | Photosynthesis-related protein | ↓ | −1.8 |
| 9309 | Light Harvesting Complex Protein 3 | ↓ | −2.1 |
| 8780 | Light Harvesting Complex Protein 2 | ↓ | −2.4 |
| 2073 | Light Harvesting Complex Protein (VCP1) | ↓ | −2.5 |
| 0480 | Light Harvesting Complex Protein 3 | ↓ | −2.6 |
| 8185 | Light Harvesting Complex Protein 3 | ↓ | −2.6 |
| 6440 | Light Harvesting Complex Protein 3 | ↓ | −2.7 |
| 0651 | Early Light Inducible Protein HV60 | ↓ | −2.7 |
| 0881 | Light Harvesting Complex Protein 2 | ↓ | −2.8 |
| 3534 | Light Harvesting Complex Protein 2 | ↓ | −2.9 |
| 7454 | Light Harvesting Complex Protein (VCP2) | ↓ | −3.1 |
| 2796 | Light Harvesting Complex Protein 10 | ↓ | −3.1 |
| 4746 | Light Harvesting Complex Protein 2 | ↓ | −3.6 |
| 0194 | Light Harvesting Complex Protein 5 | ↓ | −3.9 |
| 0499 | Light Harvesting Complex Protein 5 | ↓ | −4.4 |

Figure 19:
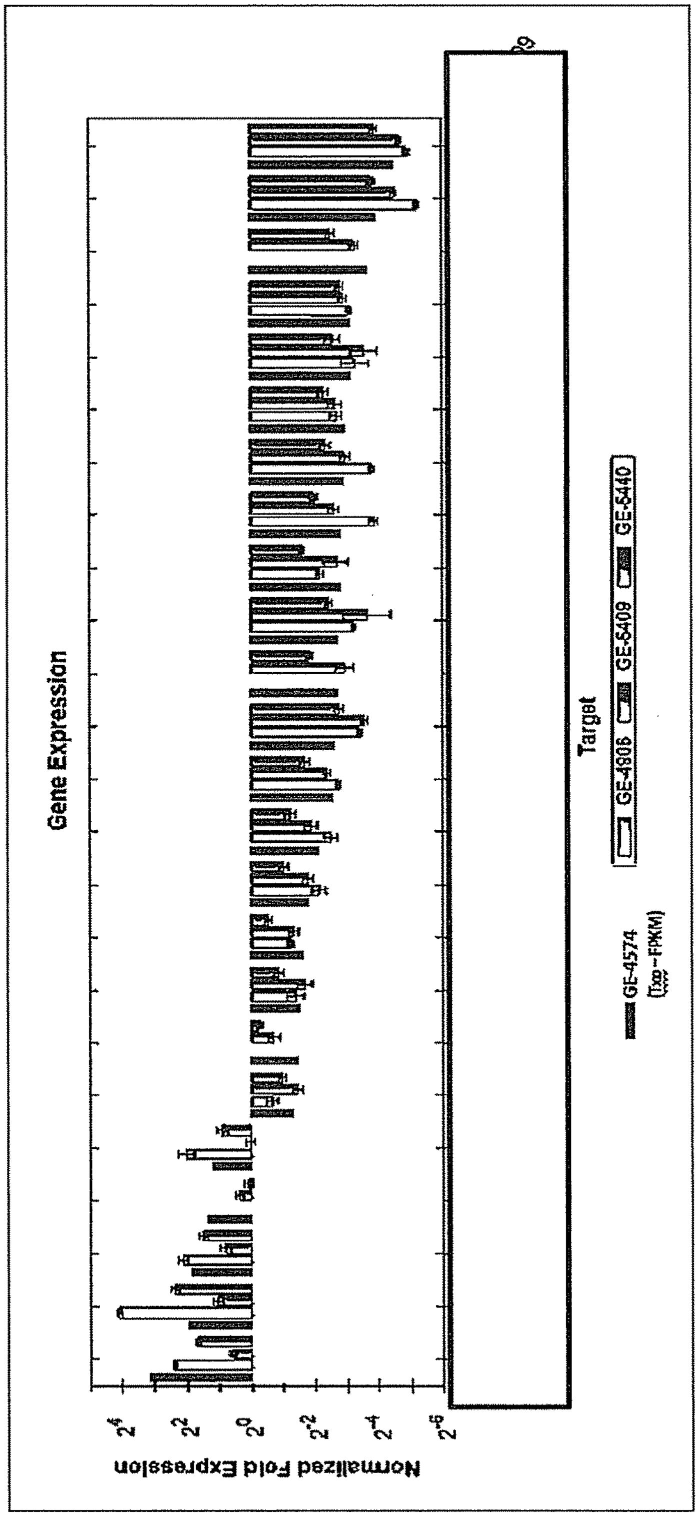
FIG. 19 graphically depicts normalized fold expression with respect to wild type expression levels of several genes as measured by qRT-PCR in LIHLA mutants GE-4906 (mutated in the LAR2 gene), GE-5409 (mutated in the LAR1 gene), and GE-5440 (insertional mutation in the LAR1 gene). Normalized fold expression for these same genes from transcriptomics data for GE-4574 (mutated in the LAR1 gene) is provided for reference.

As provided in a summary graph in FIG. 19, all of the mutants tested demonstrated de-regulation, with respect to the wild type strain, of genes that were differentially expressed when wild type cells were shifted from high to low light. The global transcriptional response was similar for all mutants examined, i.e. all genes tested that were upregulated relative to wild-type in the original LAR1 mutant GE4574 transcriptomic data set (Example 9) were upregulated in these additional mutant strains that were profiled. Furthermore all genes downregulated relative to wild-type in the original LAR1 mutant GE4574 transcriptomic data set were also downregulated, and downregulated to a similar extent, in these mutant strains.

Example 11. Transcriptomics for Analysis of Genes Regulated by LAR1

Figure 20:
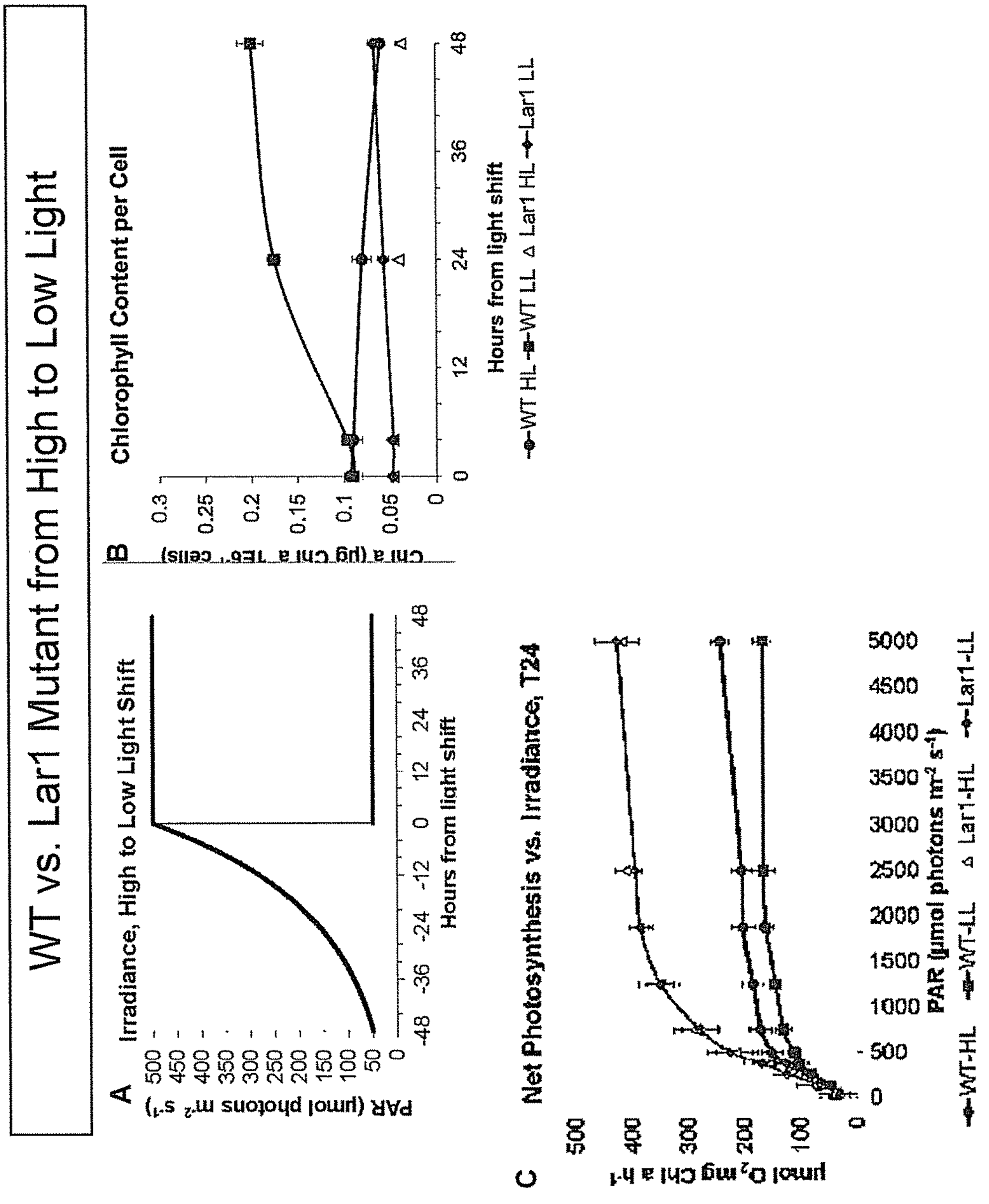
FIG. 20 a) is a diagram showing the acclimation of *Nannochloropsis* cells (in parallel experiments, both wild type and a LIHLA LAR1 mutant) to high light (500 μmol photons $m^{-2}$ $s^{-1}$), after which (at time 0 on the x axis) cells were transferred to low light for two days, while control cells were maintained under high light conditions for two days. b) provides the chlorophyll a content of cells during the light shift: circles, wild type cells maintained in high light after time 0; squares, wild type cells transferred from high light to low light time 0, where they remained for two days; open triangles, LAR1 mutant cells maintained in high light after time 0; diamonds, LAR1 mutant cells transferred from high light to low light at time 0, where they remained for two days. c) provides the P/I curves for the mutant and wild type cells two days after the light shift (time 0): circles, wild type cells maintained in high light after time 0; squares, wild type cells transferred from high light to low light time 0, where they remained for two days; open triangles, LAR1 mutant cells maintained in high light after time 0; diamonds, LAR1 mutant cells transferred from high light to low light at time 0, where they remained for two days.

In further transcriptomics experiments, the LIHLA LAR1 mutant GE5440 was grown in high light (500 $\mu E \cdot m^{-2} \cdot s^{-1}$) prior to either shifting to low light (50 $\mu E \cdot m^{-2} \cdot s^{-1}$) and culturing for two additional days, or, as a control, maintaining the high light acclimated cells in high light for an additional two days. Wild type *N. gaditana* cells were subjected to exactly the same regimen: either acclimated to high light prior to shifting to low light and culturing for two days, or maintained continuously in high light (diagrammed in FIG. 20A). FIG. 20B shows the amount of chlorophyll per cell over the time course of theses light shift experiments, where the high light acclimated wild type cells (squares) increased their chlorophyll content approximately two-fold over the two day period following a shift from high to low light, but decreased their chlorophyll slightly when, instead of being shifted to low light, they were maintained under high light for the additional two days (circles). In contrast, the LAR1 mutant increased its chlorophyll only slightly over the two day period following a shift from high to low light (diamonds), resulting in a chlorophyll level that was essentially the same as the chlorophyll level of wild type cells maintained in high light, demonstrating clearly the "Locked in High Light Acclimation" phenotype. Control LAR1 mutant cells that remained in high light during the experiment (triangles), maintained their low level of chlorophyll, similar to wild type. Under these conditions, the irradiance curve for photosynthesis (FIG. 20C) showed that photosynthetic oxygen evolution at irradiances higher than 200 $\mu E \cdot m^{-2} \cdot s^{-1}$ was lowest in wild type cells that were shifted from high to low light (squares). $P_{max}$ per chlorophyll was somewhat higher in wild type cells that were maintained under high light (circles). Strikingly, the LAR1 LIHLA mutant demonstrated a higher $P_{max}$ and $E_k$ than wild type regardless of whether they were maintained in high light (triangles) or shifted to low light (diamonds). $P_{max}$ per chlorophyll was approximately twice the value for the LIHLA mutant as found in wild type cells, which had approximately twice the chlorophyll content, indicating that $P_{max}$ on a per cell basis was approximately equivalent to that of the $P_{max}$ of wild type cells.

RNA was extracted at the 0, 4 h, 24 h, and 48 h timepoints, where the 0 h timepoint was the time at which cells were shifted from high to low light (see FIG. 20A) and analyzed as provided in Example 9. RNA-seq was used to analyze the global transcriptional response under steady-state high light (500 $\mu E \cdot m^{-2} \cdot s^{-1}$) or the high light (500 $\mu E \cdot m^{-2} \cdot s^{-1}$) to low light (50 $\mu E \cdot m^{-2} \cdot s^{-1}$) shift conditions for the wild type and LAR1 mutant.

Figure 21:
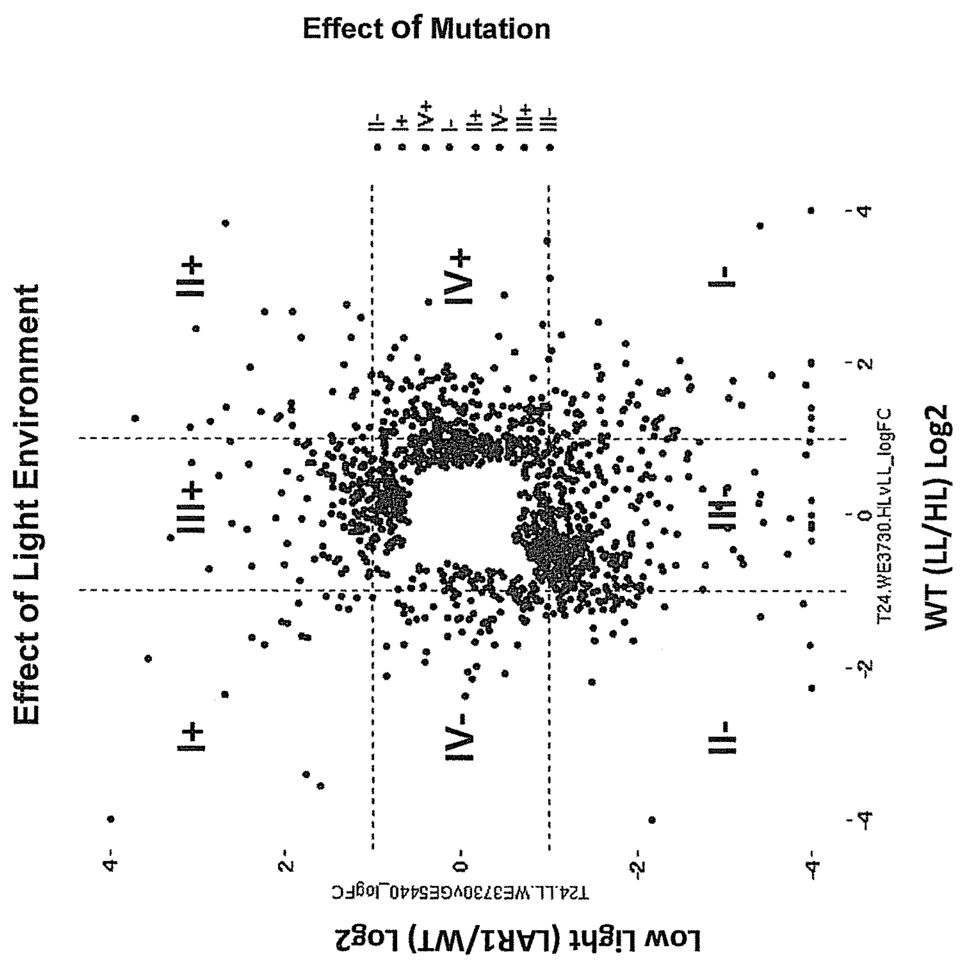
FIG. 21 provides a diagram of the results of analysis of levels of transcripts (each transcript represented by a dot) in the LAR1 mutant with respect to the wild type in low light, with relative transcript abundance in the mutant reflected in the position along the y axis. The same transcripts are positioned along the x axis to reflect their relative abundance in wild type cells acclimated to low light versus their levels in high light acclimated cells. The genes are divided into TRACs based on whether the differential expression in mutant versus wild type follows a similar or different pattern in wild type acclimated to high light versus wild type acclimated to low light. Positions along the horizontal axis differ to reflect the effect of the light environment on expression of the individual transcripts; positions along the y axis vary in relation to expression level in the mutant with respect to the wild type. The dashed lines correspond to $\log_2$ values of 1 or −1, such that points outside these limits represent genes having greater that a 2 fold increase or decrease in abundance.

The $\log_2$ fold change value of the wild type response to shifting to low light (i.e., the low light (24 hours post-shift) transcript level as compared with the high light (pre-shift) expression level) for each gene was plotted with respect to the horizontal axis relative to the $\log_2$ fold change value of the same gene for the LAR1 mutant acclimated to low light vs. the wild type acclimated to low light on the vertical axis. The resulting grouping of the graphed points, representing the differentially expressed genes at the 24 hour time point (24 hours after shifting from high to low light), revealed discrete Transcriptional Regulatory Ascendency Categories (TRACs) which were numbered –I+ to IV+ and I– to IV– (FIG. 21). The TRACs make organization of the LAR1 mutant's transcriptional regulation relative to the wild type response to light possible: TRAC 0 are null category genes which did not significantly vary in response conditions at the cut-off for significance (false discovery rate, FDR, of 0.05 or less) selected at the time points tested. TRAC I gene expression is decoupled from the abiotic variable (light intensity) by the genetic variable tested (LAR mutation). Many photosynthetic proteins are in this category, along with many unknowns. TRAC II genes are regulated by light intensity, and also differentially regulated, but to a greater degree, in the mutant. TRAC III genes are those that are found differentially expressed between the mutant and wild type when acclimated to the same environmental (low light) conditions, though are not significantly differentially expressed in the wild type in response to the light shift. TRAC IV genes did not show statistically significant differential expression between the mutant and wild type when acclimated to the same environmental (low light) conditions, however, have been found to be differentially regulated in response to the light shift.

The TRAC I genes include a significant proportion of photosynthetic light responsive genes including LHCs, VCPs, chlorophyll biogenesis genes, thylakoid assembly genes, as well as many genes encoding unknown proteins. Such genes, and others identified by this analysis, may be used for further engineering of strains, for example, for altering their expression to modulate the LIHLA phenotype. The striking similarity of expression of the TRAC I genes to genes regulated by light intensity in wild type cells is shown in the side by side graphs of FIG. 22 in which genes that are upregulated in the wild type in high light are also upregulated in the LAR1 LIHLA mutant with respect to the wild type in low light acclimation, and genes that are downregulated in the mutant in low light as compared to wild type are also downregulated in high light acclimated wild type cells.

Figure 22:
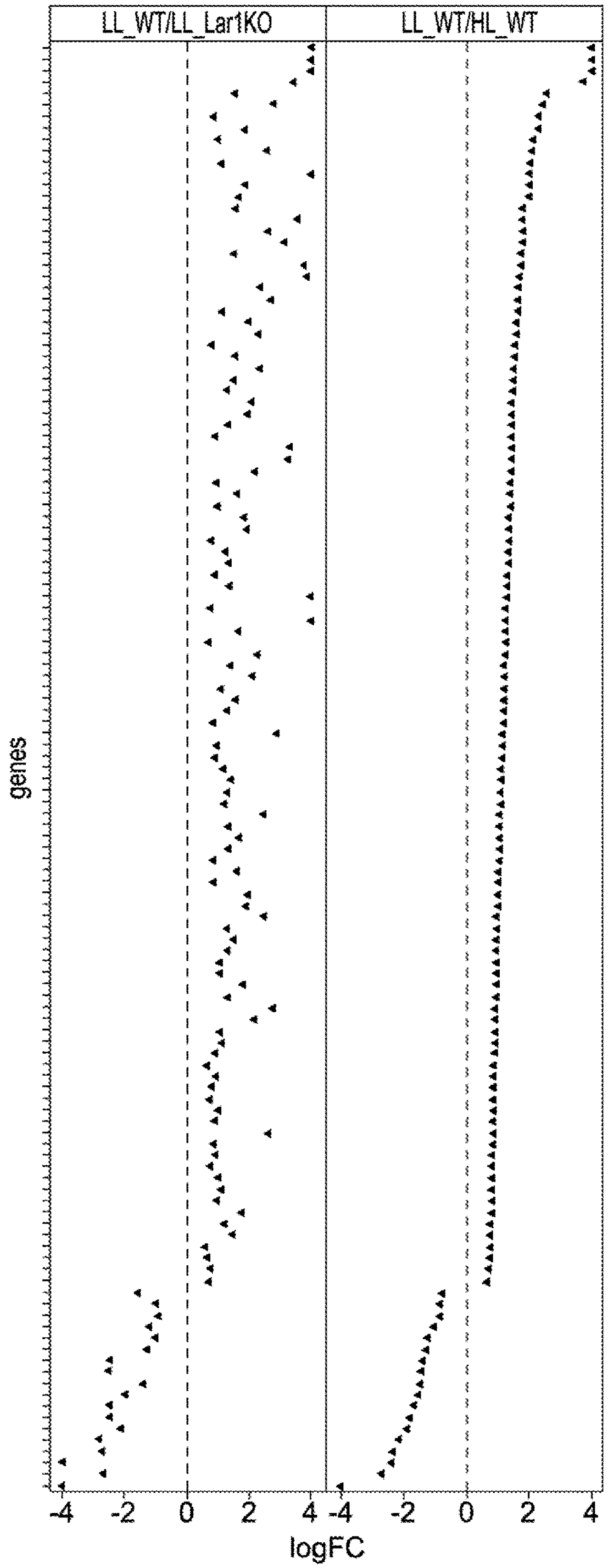
FIG. 22 provides side-by-side dot plots of "TRAC I" transcripts having the same pattern of regulation in the LAR1 mutant with respect to wild type in low light (left plot) as in wild type cells transferred to high light versus their low light levels (right plot). A dashed vertical line in each plot marks the position along the x axis where the $\log_2$ fold change is zero, where there is no difference in the expression level. indicates expression of the gene in the mutant is twice as much or more than the levels in the wild type.

FIG. 22 depicts, in side-by-side dot plot graphs, 127 individual TRAC I genes represented by dots ordered vertically. In the graph on the right, each point representing a gene is positioned horizontally according to its level of expression in wild type 24 hour low light-acclimated cells relative to its level of expression in high light-acclimated cells, with genes having higher relative expression in low light acclimated cells (i.e., the highest degree of "overexpression" in low light acclimated cells versus high light acclimated cells) represented by points positioned farther to the right ($\log_2$ positive values), and genes having lower levels of expression in low light acclimated versus high light acclimated wild type cells represented by points positioned to the left ($\log_2$ negative values). The x axis is calibrated on a log base 2 ($\log_2$) scale, such that "0" on the x axis indicates no change in expression levels based on light acclimation, "1" on the x axis represents a doubling in the level of a transcript, and "–1" on the x axis represents a halving in the level of a transcript expressed in 24 hour low light acclimated cells relative to high light acclimated cells. For example, the LHC genes are known to be overexpressed under low light acclimation with respect to their expression levels in high light acclimated cells; nearly all of the genes characterized by pfam domain as LHCs are represented by points found at the upper end of the scale shown in FIG. 22, and their horizontal position is to the right (positive side) of the vertical dashed line along the x axis. The adjacent graph on the left is aligned with the graph on the right, so that points representing the same gene are found at the same vertical position on the left graph as for the right graph, but on the left graph the points are positioned horizontally according to their relative expression level in low light-acclimated wild type cells with respect to LIHLA LAR1 mutant cells (when both are acclimated to low light). The graph shows that for a large number of genes relative expression levels in the wild type versus LIHLA LAR1 mutant is strikingly similar to the relative expression levels in low light acclimated versus high light acclimated wild type cells, with genes upregulated in low light acclimated wild type cells being upregulated in the wild type cells as compared to the LAR1 LIHLA mutant cells, and genes downregulated in low light acclimated wild type cells being downregulated in the wild type cells with respect to the LAR1 LIHLA mutant cells. Thus the pattern of gene expression in the LAR1 LIHLA mutant demonstrates that the LIHLA mutants are globally deregulated in low light acclimation, as under low light acclimation their gene expression pattern strongly resembles that of high light acclimated wild type cells.

Example 12. Transcriptomics of a LAR2 Mutant

Figure 23:
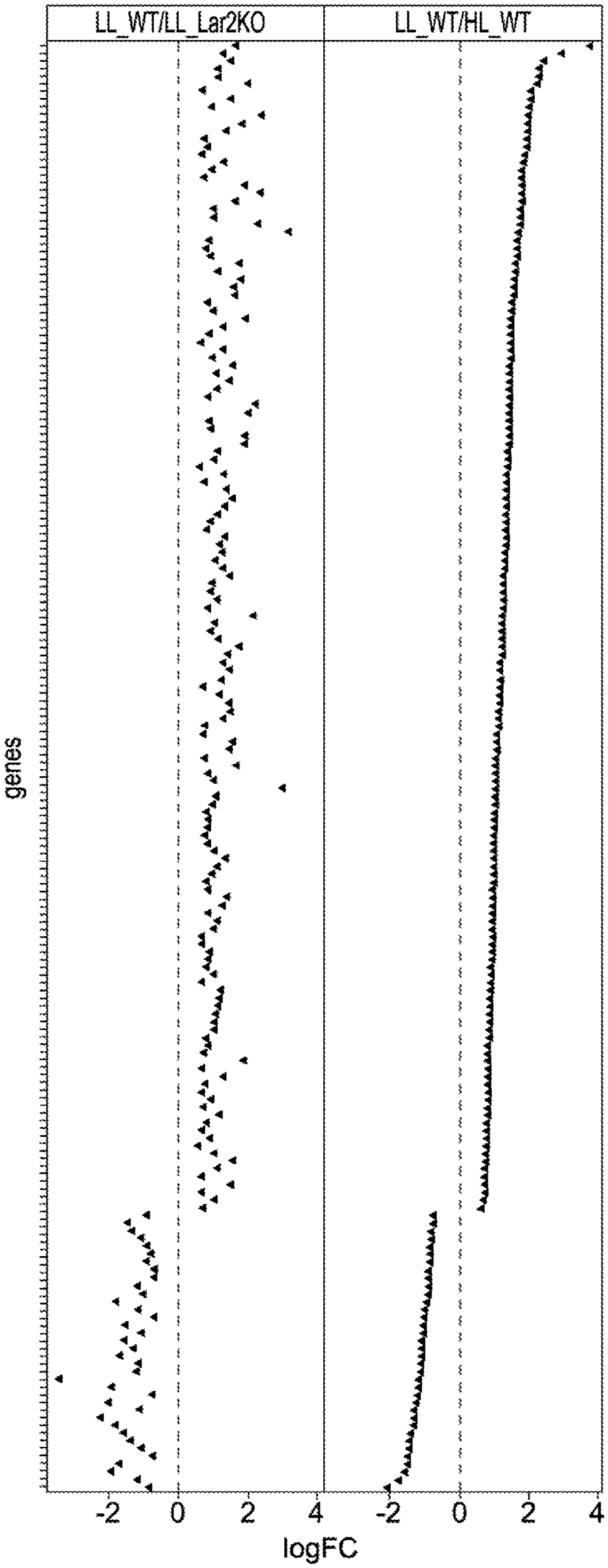
FIG. 23 provides side-by-side dot plots of "TRAC I" transcripts having the same pattern of regulation in the LAR2 mutant with respect to wild type in low light (left plot) as in wild type cells transferred to high light versus their low light levels (right plot). A dashed vertical line in each plot marks the position along the x axis where the $\log_2$ fold change is zero, where there is no difference in the expression level. indicates expression of the gene in the mutant is twice as much or more than the levels in the wild type.

Transcriptomic analyses of a LAR2 mutant was performed in a similar but simplified manner as described for LAR1 in Example 9. Triplicate cultures of WT-3730 and LAR2 mutant GE-5404 were all taken to low light acclimation as depicted in FIG. 3. Cells were pelleted by centrifugation (4000×g for 5 minutes) and cell pellets were resuspended in lysis buffer (50 mM Tris pH8.0, 20 mM EDTA pH8.0, 300 mM NaCl) after which the resuspensions were transferred to a 2 mL microcentrifuge tube containing approximately 0.5 mL of 200 gm zirconium beads. Cells were mechanically lysed by bead beating for 3 minutes and then debris pelleted for 2 min at 11.8×g. To the RNA containing supernatants SDS was added to ~1.5% w/v and incubated for 15 minute at 50° C. Following incubation RNA was extracted with an equal volume of acidic Phenol: $CHCl_3$ followed by a second extraction with 24 mL 1-bromo-3-chloropropane. Purified RNA was precipitated with a final concentration of 2.5M LiCl with incubation overnight at 20° C. The RNA pellet was washed once with 80% ethanol, dried, and then resuspended in water. RNA was DNAse treated with DNA-free following the manufacturer's protocol (Life Technologies; Carlsbad, Calif.). Final RNA quality was determined by Agilent Bioanalyzer 2100 analysis according to the manufacturer's instructions (Agilent Technologies; Santa Clara, Calif.). mRNA was enriched using polyA selection and then subsequently used to generate Illumina TruSeq Stranded mRNA LT libraries (following manufacturer's instructions; Illumina Inc., San Diego, Calif.). RNA-seq was used to analyze the global transcriptional response under a steady-state low light (50 $\mu E \cdot m^{-2} \cdot s^{-1}$) acclimated condition for the wild type and LAR2 mutant. FIG. 23 is another graphical dot plot depiction (as described in Example 11, FIG. 22), in this case of the similarity of gene expression patterns in a LAR2 LIHLA mutant (GE-5404 which contains a vector insertion in the promoter region of the LAR2 gene, see FIG. 14) as compared with wild type. FIG. 23 depicts, in side-by-side graphs to be viewed together, 186 individual genes represented by points ordered vertically. The depicted genes are TRAC I genes from transcriptomic analysis of low light v. high light acclimated wild type cells, and wild type v. GE5404 LAR2 mutant cells under low light, i.e., they are deregulated in the LAR2 LIHLA mutant under low light acclimation. On the right hand graph, each point representing a gene is positioned horizontally according to its level of expression in low light-acclimated wild type cells relative to its level of expression in high light-acclimated cells, with genes having the highest relative expression in low light acclimated cells (i.e., the highest degree of "overexpression" in low light acclimated cells versus high light acclimated cells) represented by points positioned to the right ($\log_2$ positive values), and genes having lower levels of expression in low light acclimated versus high light acclimated wild type cells represented by points positioned to the left ($\log_2$ negative values). The graph on the left side is aligned with the graph on the right, so that points representing the same gene are found at the same vertical position on the left graph as for the right graph, but on the left graph the points are positioned horizontally according to their relative expression level in wild type versus LIHLA LAR2 mutant cells (when both are acclimated to low light). The graph shows that for a large number of genes relative expression levels in the wild type versus LIHLA LAR2 mutant is strikingly similar to the relative expression levels in low light acclimated versus high light acclimated wild type cells, with genes upregulated in low light acclimated wild type cells being upregulated in the wild type cells as compared to the LAR2 LIHLA mutant cells, and genes downregulated in low light acclimated wild type cells being downregulated in the wild type cells with respect to the LAR2 LIHLA mutant cells. Thus the pattern of gene expression in the LAR2 LIHLA mutant demonstrates that the LIHLA mutants are globally deregulated in low light acclimation, as under low light acclimation their gene expression pattern resembles that of high light acclimated wild type cells.

Example 13. Knock-Out of LAR1 and LAR2 Orthologs in *Nannochloropsis oceanica*

To further demonstrate that mutations in LAR1 and LAR2 are responsible for the LIHLA phenotype, and also to determine the functionality of homologous genes from another algal species, orthologs of these regulators were identified in *Nannochloropsis oceanica*, a species in which homologous recombination has been demonstrated. Constructs that included the *N. oceanica* LAR1 ortholog (No-LAR1 gene, SEQ ID NO:7) interrupted by a blasticidin resistance gene (SEQ ID NO:48) and *N. oceanica* LAR2 ortholog (No-LAR2 gene, SEQ ID NO:20) interrupted by a blasticidin resistance gene (SEQ ID NO:49) were linearized and independently transformed into *N. oceanica* strain WE-5473 essentially according to the procedure provided in Example 2. Antibiotic resistant colonies were isolated and screened by PCR for integration of the knockout construct by homologous recombination. Recombinant knock-out isolates were screened for low chlorophyll fluorescence.

Figure 24:
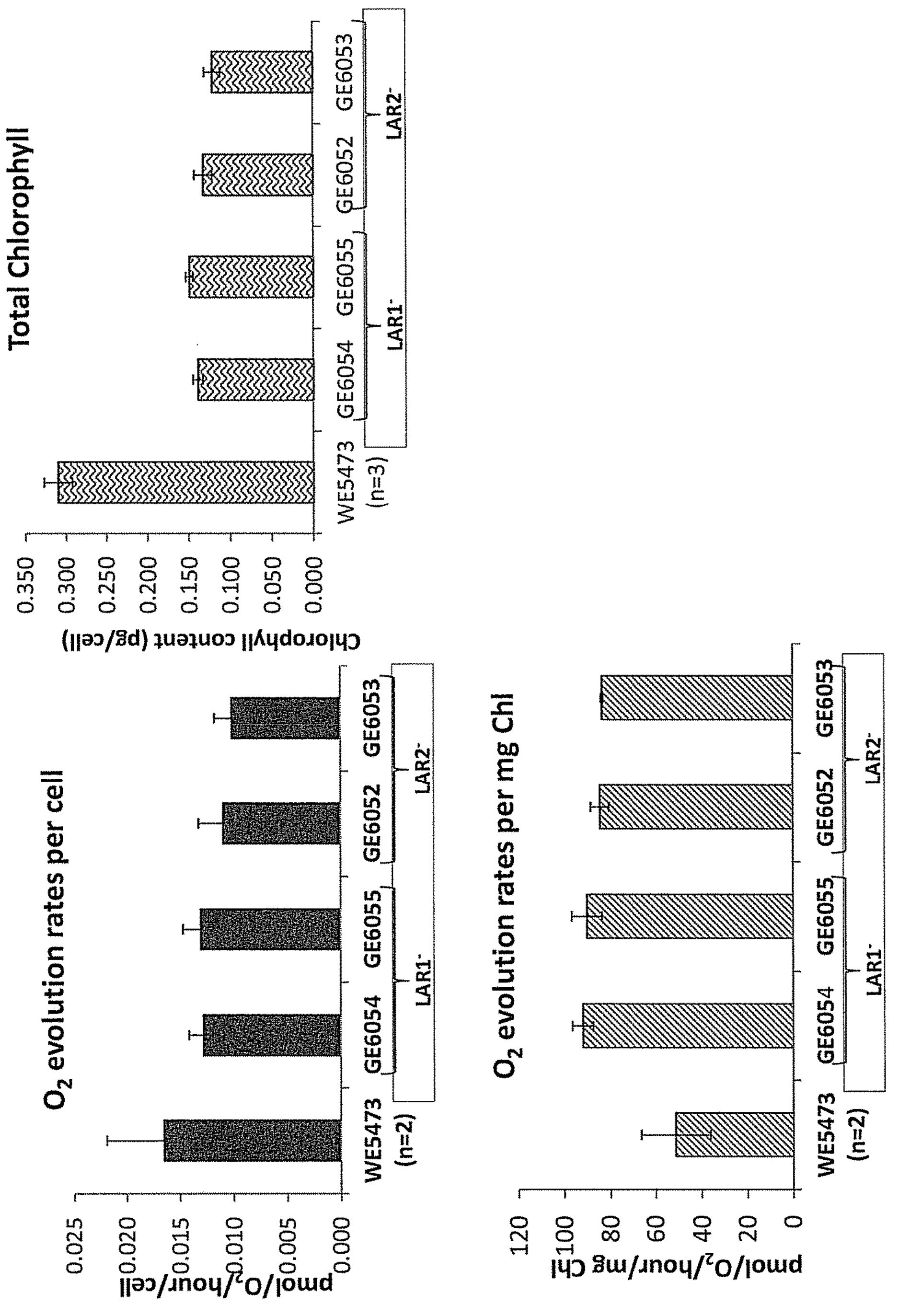
FIG. 24 provides graphs of oxygen evolution and total chlorophyll content per cell of wild type *Nannochloropsis oceanica* (WE5473) and four LIHLA knockout strains: GE6054 and GE6055 are LAR1 gene knockouts, and GE6052 and GE6053 are LAR2 gene knockouts.
Figure 25:
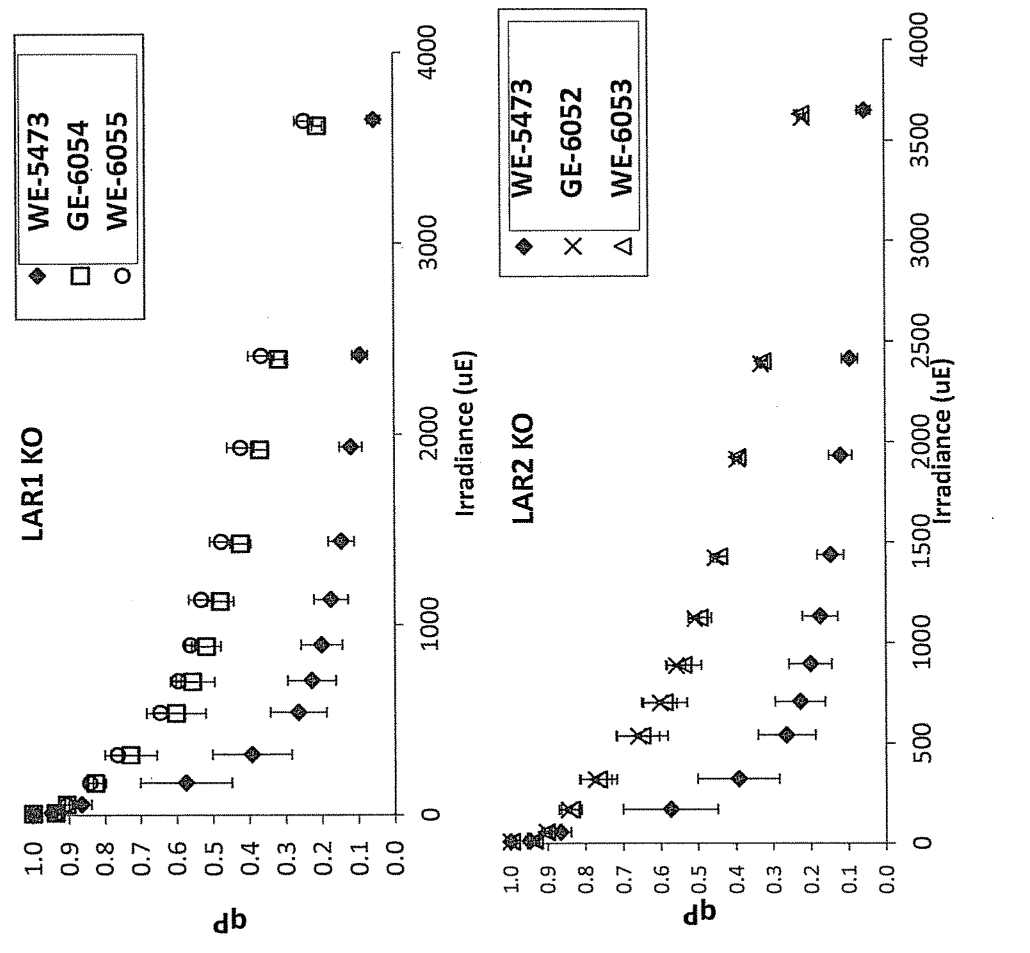
FIG. 25 depicts photochemical quenching (qP) in wild type *Nannochloropsis oceanica* (WE5473) (solid diamonds), a) depicts two LIHLA LAR1 knockout strains, GE6054 and GE6055; and b) depicts two LAR2 knockout strains, GE6052 and GE6053.
Figure 26:
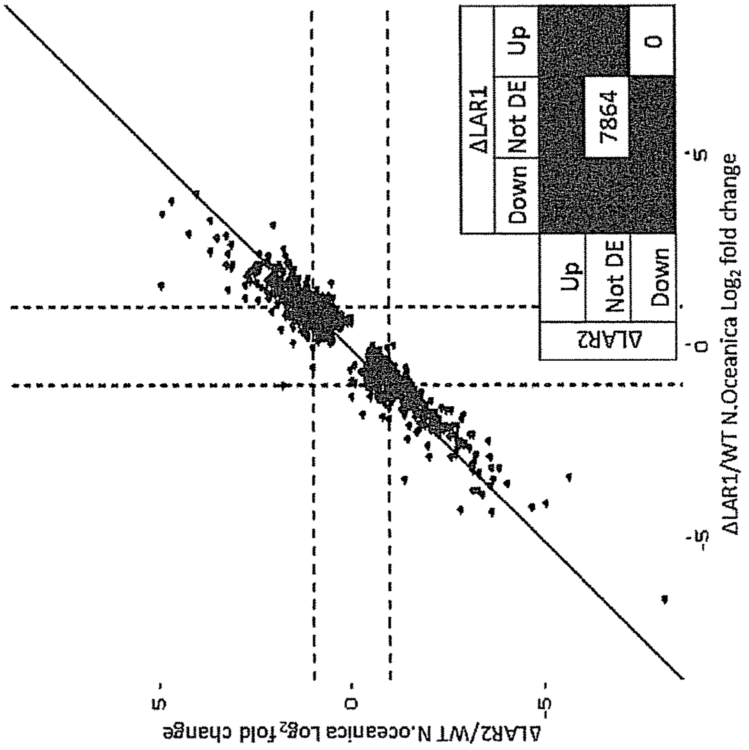
FIG. 26 is a graph depicting the correlation in deregulated expression levels of transcripts in LAR1 mutants to the expression levels in LAR2 mutants.

FIG. 24B shows the total chlorophyll per cell of low-light acclimated *Nannochloropsis oceanica* wild type strain WE-5473, which was used to generate the knockouts, as well as the chlorophyll per cell of low-light acclimated LAR1 knock-out mutants (GE-6054 and GE-6055), and LAR2 knock-out mutants (GE6052 and GE6053). In all knockout strains, consistent with the LIHLA phenotype, the amount of chlorophyll per cell is reduced by at least 50%. FIG. 24 also provides graphs showing oxygen evolution rates for the wild type and knock out strains. On a per cell basis, oxygen evolution rates of the knockout mutants are somewhat lower than wild type (FIG. 24A), although oxygen evolution rates per chlorophyll of the knockout mutants are significantly higher than oxygen evolution rates per chlorophyll of the wild type (FIG. 24C). FIG. 25 shows the results of fluorescence studies to determine qP of two LAR1 gene knockout strains and two LAR2 gene knockout strains. Fluorescence parameters of the wild type *N. oceanica* strain WE-5473 are provided in the same graphs for comparison. For both knock-outs, consistent with the LIHLA phenotype seen in the *N. gaditana* mutants, qP is significantly higher in the knockouts at all irradiances over 100 μmol photons $m^{-2}$ $sec^{-1}$ than in the wild type progenitor strain. Thus the LAR1 homolog in *N. oceanica*, demonstrating approximately 49.5% identity to the *N. gaditana* LAR1 polypeptide and approximately 82% identity over the extended TAZ domain (Table 3), was demonstrated to be a functional homolog, or ortholog, of *N. gaditana* LAR1. The LAR2 homology in *N. oceanica*, demonstrating approximately 69% identity to the *N. gaditana* LAR1 polypeptide and 100% identity over the extended myb-like DNA binding domain domain (Table 4), was demonstrated to be a functional homolog, or ortholog, of N. gaditana LAR2.

Figure 28:
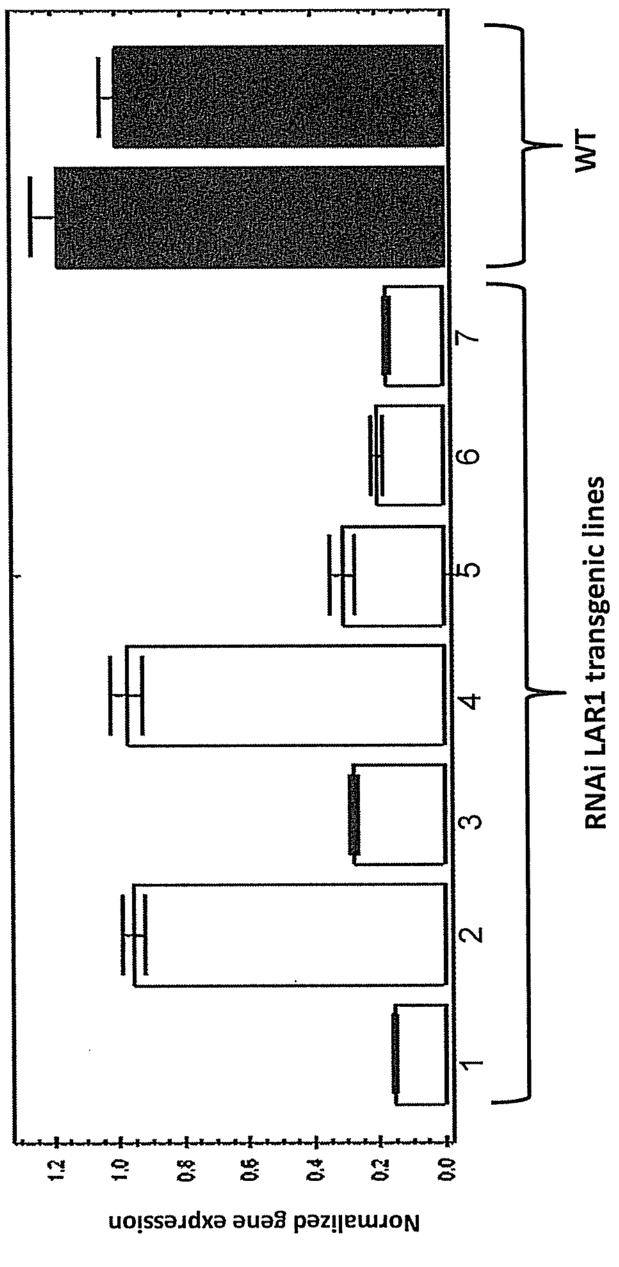
FIG. 28 depicts expression levels of the LAR1 gene in *Nannochloropsis gaditana* isolates (1-7) transformed with RNAi constructs targeting the LAR1 gene, with two wild type (WT) isolates shown as controls.

The LAR1 and LAR2 knockouts in N. oceanica were used in further transcriptomics experiments to analyze gene expression patterns in these globally deregulated light acclimation mutants. Genes that were differentially expressed in the LAR1 knockout mutant under low light acclimation with respect to wild type N. oceanica under low light acclimation were strikingly similar to genes that were differentially expressed in the LAR2 knockout mutant under low light acclimation with respect to wild type N. oceanica under low light acclimation. This is depicted in FIG. 28, where the value for the LAR1 $\log_2$ fold change in expression level (mutant v. wild type) for each gene is plotted against the LAR2 $\log_2$ fold change in expression level (mutant v. wild type) for the same gene. It can be seen that the plotting of the differential expression for LAR1 v. LAR2 shows nearly all of the points fall on a straight 1:1 diagonal line, indicating that these gene knockouts produce nearly identical global transcriptional effects.

Figure 27:
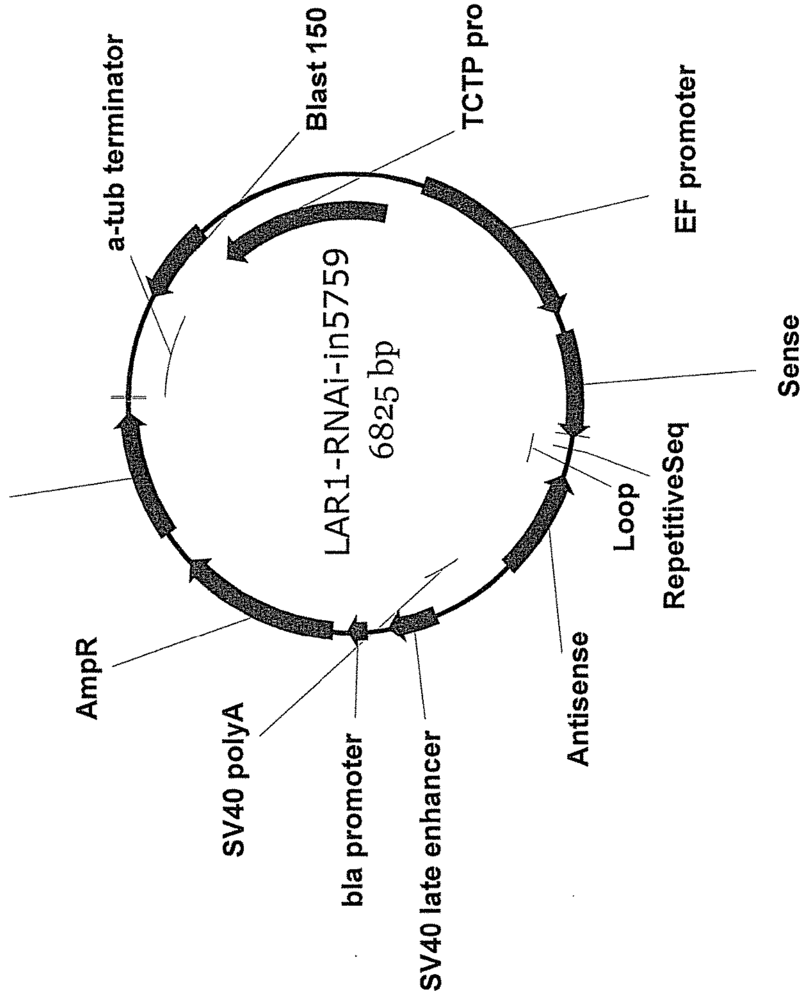
FIG. 27 is a map of an RNAi construct used to knockdown the LAR1 gene in *N. gaditana.*

In addition to the N. oceanica knock-outs, N. gaditana knock-down lines were generated that exhibited the LIHLA characteristics of the LAR1 mutant (see FIG. 6) using the RNAi construct shown in FIG. 27. The RNAi construct targeting the LAR1 gene (SEQ ID NO:50) was introduced into N. gaditana, resulting in varying levels of LAR1 transcript in different knockdown lines (FIG. 28). Table 6 provides data showing that the LAR1-RNAi knockdown exhibited photophysiological characteristics of other LAR1 mutants, including a more than doubling of Pmax per chlorophyll with no decrease in Pmax per cell, higher maximal $ETR_{PSII}$, and higher Ek.

TABLE 6

Photo-physiology of N. gaditana LAR1 RNAi knockdown line

| | Cells/ml | av. Chl mg/L | pmol $O_2$/ hour/cell | µmol $O_2$/ hour/mg chl | $ETR_{PSII}$ max | $ETR_{PSII}$ max Fold Change | Ek (µE) |
|---|---|---|---|---|---|---|---|
| WT-3730 | 4.84 E07 | 15.717 | 0.022 | 68.72 | 45.3 | 1.00 | 190.4 |
| LAR1-RNAi | 1.05 E08 | 15.314 | 0.023 | 154.76 | 93.5 | 2.06 | 353.9 |

Example 14. LIHLA Mutant Cultures in Scaled-Down Culture System

For laboratory testing of LIHLA cultures, a light box was positioned next to a series of culture flasks that included 500 mls of PM074 (10×f/2) media to replicate a sunny day in a greenhouse having a 12 hour light/12 hour dark cycle with a maximum irradiance of 1800 µmol photons m$^{-2}$ sec$^{-1}$. A 1% $CO_2$ mixture was fed continuously. Cultures were diluted to a cell density of 2×10$^7$ cells ml$^{-1}$ for 3 days for steady state acclimation. On day 7, an additional 4 mM nitrate was added. The cells were allowed to grow for 12 days and cell counts were recorded daily.

Figure 29:
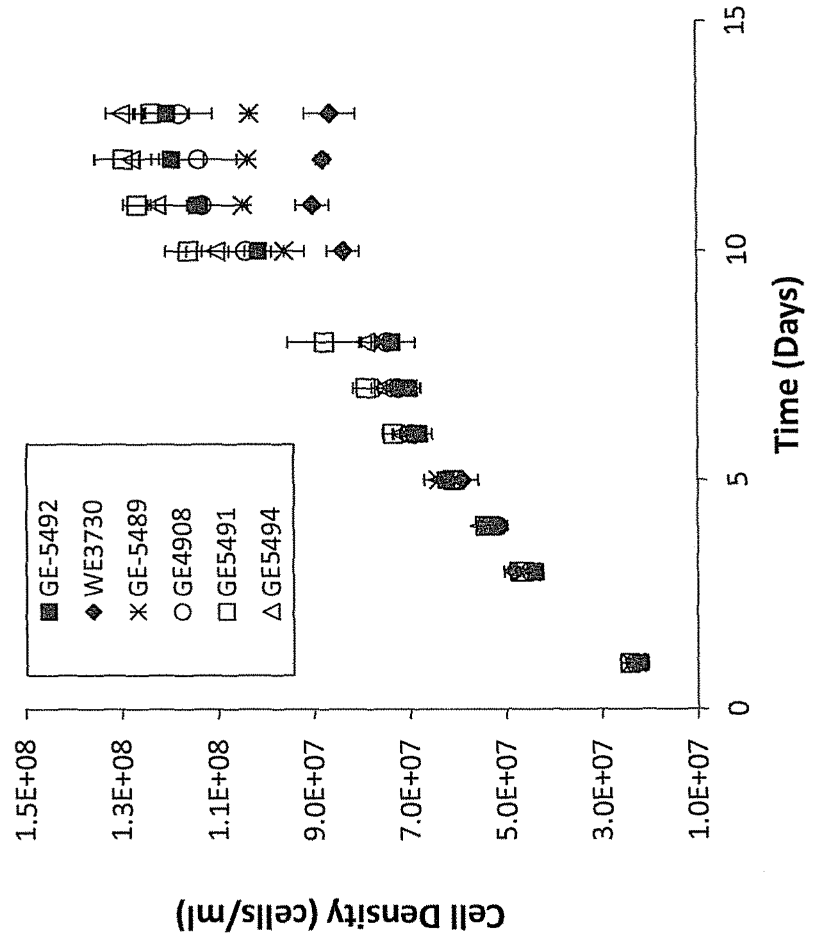
FIG. 29 depicts cell densities of wild type (WT-3730) (solid diamonds) and five LIHLA mutants in cultures grown for 14 days in scaled down laboratory cultures simulating pond conditions.

Nannochloropsis gaditana LIHLA mutants GE-5492, GE-4908, and GE-5494 (disrupted LAR1 gene), GE5491 (disrupted LAR2 gene), and GE5489 (disrupted LAR3 gene, described below in example 16), were all found to reach a higher cell density than did wild type strain WT-3730, as depicted graphically in FIG. 29.

Figure 30:
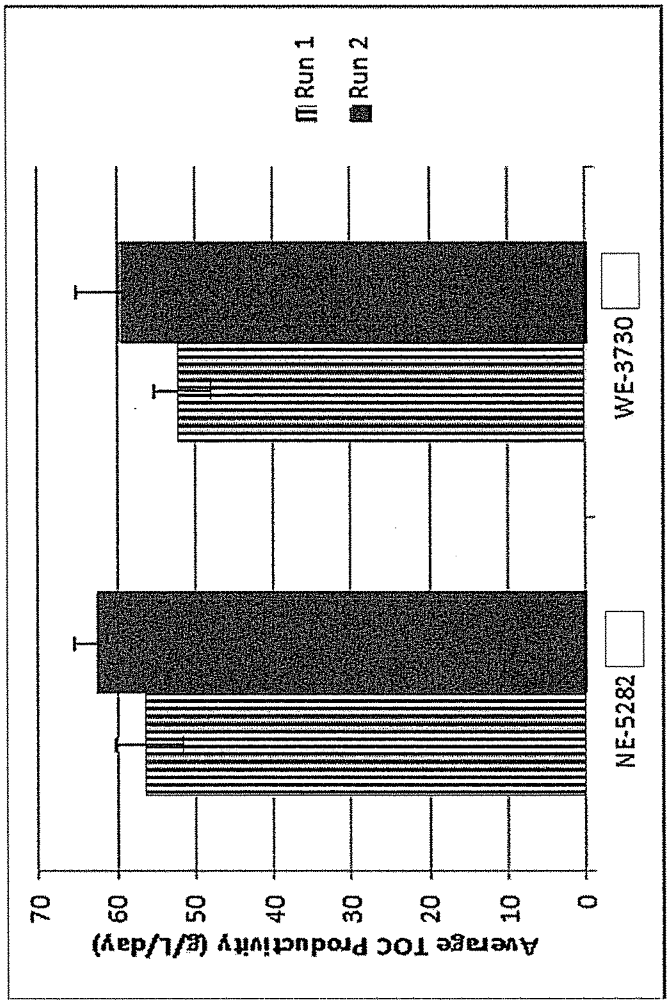
FIG. 30 is a bar graph providing the average productivity per day as measured by total organic carbon accumulation by a LIHLA mutant and wild type *Nannochloropsis* strain WT-3730 grown in scaled down laboratory cultures simulating pond conditions, in which the cultures were diluted back daily by 15%. The results of two independent experiments are shown.

In a separate experiment, wild type strain WT-3730 and LIHLA LAR1 mutant NE-5282 were grown in a series of culture flasks in the same scaled-down system that included 500 mls of PM074 (10×f/2) media to replicate a sunny day in a greenhouse (14 hours light to 10 hours dark) with a maximum irradiance of ~1800 nmol photons m$^{-2}$ sec$^{-1}$. A 1% $CO_2$ mixture was fed to the cultures continuously. Cultures were diluted daily by removing 15% by volume of the culture and replacing it with 15% to a cell density of 2$^7$ for 3 days for steady state volume of the culture and replacing it with fresh media. The cells were allowed to grow for 10 days and total organic carbon was measured daily by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999. The experiment was repeated once. FIG. 30 shows that the LIHLA mutant had a slightly higher average daily biomass accumulation. Although the increase was small on a per day basis, such increases can accumulate to provide advantages in long term cultures.

Example 15. Complementation of LIHLA Mutants

In order to further confirm that the lesions in the LAR1 gene and the LAR2 gene are responsible for the LIHLA phenotype, N. gaditana mutant GE5440, which has a vector construct insertion in the LAR1 gene (FIG. 13), was transformed with an expression construct in which the LAR1 gene (SEQ ID NO:3) was operably linked to a Nannochloropsis TCTP promoter (SEQ ID NO:2). The construct was transformed into N. gaditana mutant GE5440 essentially according to the methods provided in Example 2. qRT-PCR analysis was performed to confirm the transformed intact LAR1 genes were expressed in the cells. Complemented LAR1 strains, parental mutant LAR1 strains, and "grand-parental" wild type cells were grown under moderately low irradiance levels (100 µE m$^{-2}$ s$^{-1}$) for 10 days and diluted on a daily basis to a cell density of 1×10$^8$ cells ml$^{-1}$. During this semi-continuous growth, to low light acclimate the WT control, chlorophyll auto-fluorescence per cell was monitored until it was high and stable, indicating that steady state low light acclimation had been achieved. Cells were then dark adapted and monitored by fluoescence, as described above.

Figure 31:
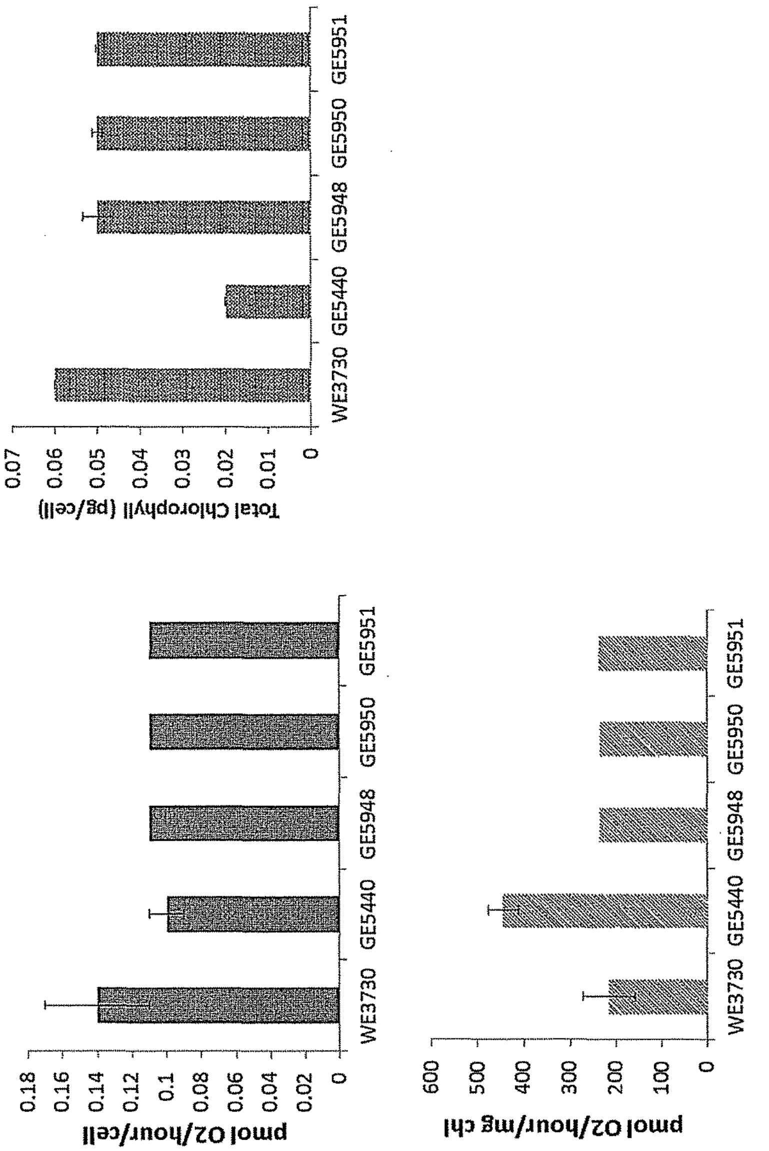
FIG. 31 provides graphs of oxygen evolution and total chlorophyll content per cell of wild type *Nannochloropsis oceanica* (WE5473), LIHLA mutant GE-5440, and three rescued mutant strains: GE5948, GE5950, and GE5951 all overexpressing the LAR1 protein in the GE-5440 mutant background.
Figure 32:
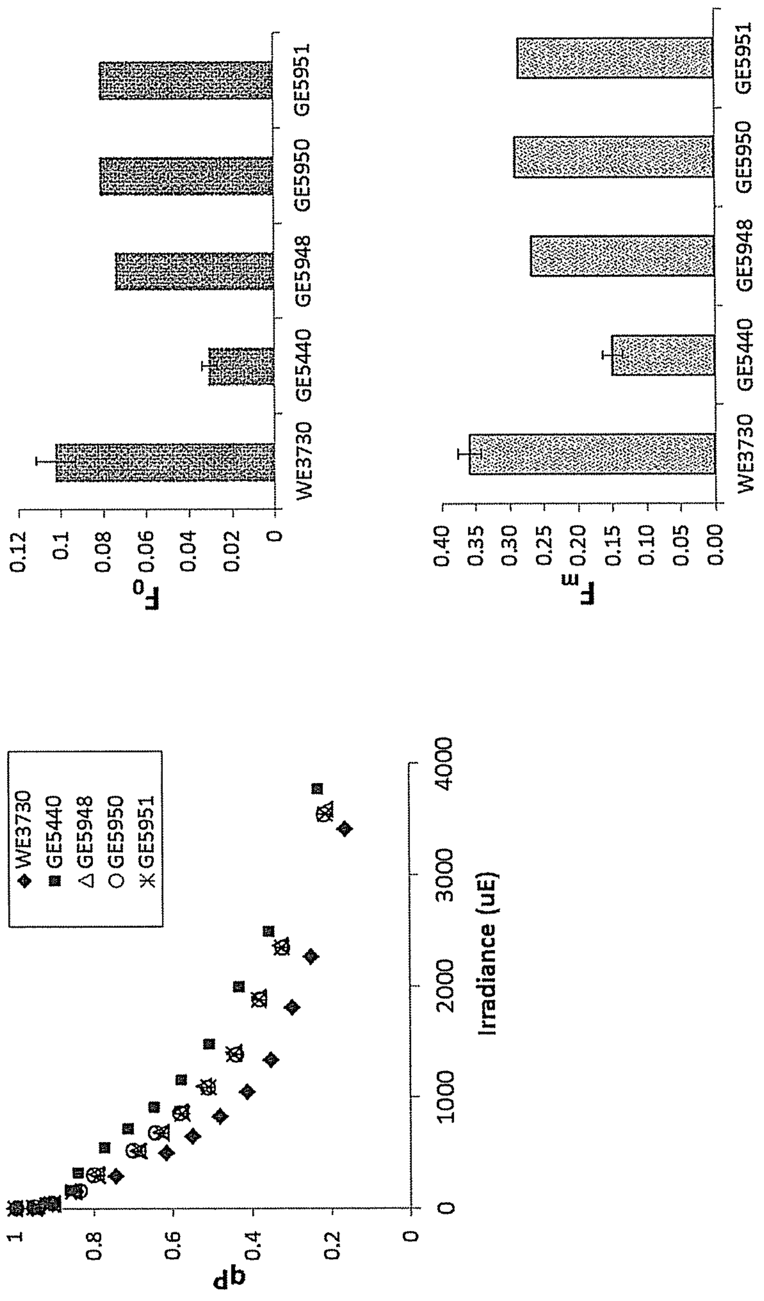
FIG. 32 provides graphs depicting photochemical quenching (qP), minimal flourescence ($F_0$) and maximal fluorescence (Fm) in wild type *Nannochloropsis oceanica* (WE5473), LIHLA mutant GE-5440, and three rescued mutant strains: GE5948, GE5950, and GE5951, all overexpressing the LAR1 protein in the GE-5440 mutant background.

As shown in FIG. 31, the complemented mutants GE-5948, GE-5950, and GE-5951 have increased chlorophyll per cell compared to mutant GE-5440, although the wild type level of chlorophyll per cell has not been completely restored in the complemented mutants. Similarly, the rescued mutants (GE5948, GE5950, GE5951) have $O_2$ evolution rates on a per cell basis with that approach wild type rates, and $O_2$ evolution rates on a per cell basis is very similar to the wild type rate. FIG. 32 shows that the complemented mutants have largely restored $F_0$ and $F_m$ values, as well as qP values that approach the wild type values, providing further confirmation that LAR1 is a regulator of light acclimation, and that mutations in the LAR1 gene are responsible for the Locked in High Light Acclimation phenotype.

Example 16. Genotyping a LAR3 Mutant

Among the thirty-five LIHLA strains isolated, all except one strain, GE-5489, had a mutation in either the LAR1 or LAR2 locus. Re-sequencing of the LAR1 and LAR2 loci in strain GE-5489 indicated that the LAR1 and LAR2 genes were intact in GE-5489, indicating that a different genetic locus was responsible for the LIHLA phenotype in this strain.

Figure 33:
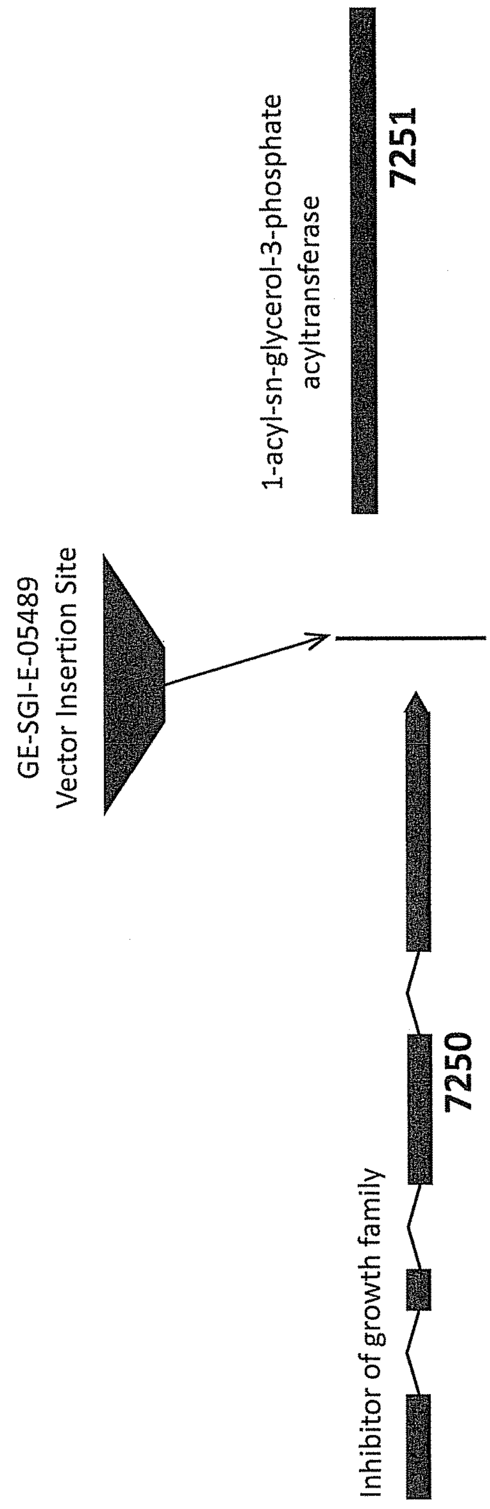
FIG. 33 provides a diagram of a region of the *Nannochloropsis gaditana* genome showing where the mutagenizing vector in a LAR3 mutant inserted between genes 7250 and 7251.

Whole genome sequencing of GE-5489 identified the genomic location of the inserted vector as well as several single base-pair deletions and single nucleotide polymorphisms elsewhere in the genome. GE-5489 was found to have the introduced vector inserted into an intergenic region ~200 bp downstream of locus 7250 and ~300 bp upstream of locus 7251 (FIG. 33). Additionally, genome resequencing identified, with high confidence, several additional mutations present in this strain relative to the parental strain WT-3730 including single base pair frameshift deletions in conserved predicted proteins E2-352 and E2-2665.

To determine the identity of the gene whose disruption was responsible for the LIHLA phenotype, the possibility that the vector insertion site which might have affected expression of the downstream putative LPAAT gene 7251 was investigated. Quantitative reverse transcription PCR (qRT-PCR) analysis of GE-5489 was performed to determine whether transcript abundance of gene 7251 differed from that observed in wild-type strain WT-3730. In addition to gene E1-7251, three LHC genes were included in this qRT-PCR experiment, which in other LIHLA mutants have been shown to lack the characteristic up-regulation in low-light conditions seen in wild type strains.

For qRT-PCR, RNA was isolated from low light (50 μE) acclimated *N. gaditana* wild type WT-3730 cells and LAR3 mutant GE-5489 as described in Example 12. DNAse-treated RNA was reverse transcribed using Bio-Rad iScript according to manufacturer's protocols (Bio-Rad, Hercules, Calif.). The resulting cDNA was then used as template in qPCR reactions using Bio-Rad SsoAdvanced, again according to manufacturer's protocols.

TABLE 6

Primers for qRT-PCR of differentially expressed genes

| Gene target | Primer | Sequence |
|---|---|---|
| 5307251 | 5-19 | GTGAAACCAGCACTCAATCTCTC (SEQ ID NO: 51) |
| 5307251 | 5-20 | AGTTCGAATATCCTGCAATCGT (SEQ ID NO: 52) |
| 5310499 | F3 | GGGAGGCTGAGATCAAGCAC (SEQ ID NO: 53) |
| 5310499 | F4 | CAGGAGCCCTACCGTCATGT (SEQ ID NO: 54) |
| 5310194 | F5 | TACTTGCAGGAGGCCGAGAT (SEQ ID NO: 55) |
| 5310194 | F6 | AGGGAGCTAACAGCGTGGAC (SEQ ID NO: 56) |
| 5312796 | G1 | TGCCCCGAAGAAGCTAGATG (SEQ ID NO: 57) |
| 5312796 | G2 | CACGACCCAGCCTAGGAAAC (SEQ ID NO: 58) |

Figure 34:
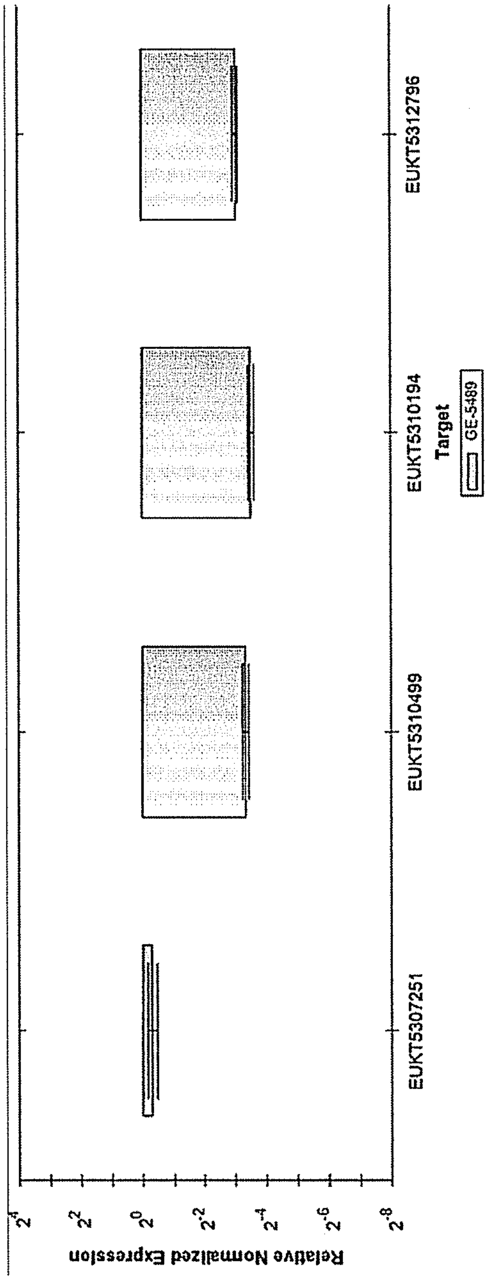
FIG. 34 is a bar graph depicting expression levels determined by qRT-PCR of gene 7251 and three LHC genes relative to wild type levels. The y axis is $\log_2$ scaled.

The analysis demonstrated that all three LHC protein transcripts assayed by qRT-PCR were similarly downregulated with respect to wild type, as was observed in the other investigated LIHLA strains. The graph shown in FIG. 34 provides a $\log_2$ scale on the y axis, and the bars represent the fold expression of the tested genes in the LAR3 mutant GE-5489 with respect to wild type WT-3730. FIG. 34 demonstrates that the putative LPAAT gene E1-7251 is expressed in LAR3 mutant GE-5489 at a level essentially identical to wild-type, whereas each of the tested LHC genes 10499, 10194, and 12796 are expressed at levels several fold lower in the LAR3 GE-5489 mutant with respect to wild type strain WT-3730, as expected for LIHLA mutants, when both the LAR3 mutant and the wild type strain are low light-acclimated. Additional experiments also failed to identify consistent changes in transcript abundance for either sense or antisense transcripts from gene E1-7250 lying upstream of the vector insertion site or a putative non-coding RNA flanking the site of vector insertion. Similar analysis of transcript levels for the gene E1-7250 which is upstream of the vector insertion site also failed to show any difference in the expression of that locus relative to wild-type.

Although transcript analysis failed to provide clear indications of the responsible locus, two additional approaches both confirmed the identity of the LAR3 gene responsible for the LIHLA phenotype in GE-5489. In one approach, complementation experiments were undertaken to recover the wild-type phenotype in strain GE-5489. In a second approach, directed knockouts of various loci were created in the related species *Nannochloropsis oceanica*. In both cases, a conserved predicted protein (E2-352 in *N. gaditana* and ortholog E1-8005 in *N. oceanica*) was identified as the locus responsible for the LIHLA phenotype (Table 6).

TABLE 6

Genetic Validation of Gene E2-352 as LAR3 Locus

| Target Gene | Gene ID | Complementation, *N. gaditana* mutant GE-5489 | Knock out (KO) *N. oceanica* ortholog |
|---|---|---|---|
| PHD-finger Protein | E1-7250 | Did not complement | Wild type chlorophyll fluorescence |
| Putative LPAAT | E1-7251 | Did not complement | KO unsuccessful |
| Putative noncoding RNA | | Did not complement | Wild type chlorophyll fluorescence |
| Conserved predicted protein "1" | E2-352 | Partial complementation | LIHLA Phenotype |
| Conserved predicted protein "2" | E2-2665 | Unable to clone | Unable to clone |

Figure 35:
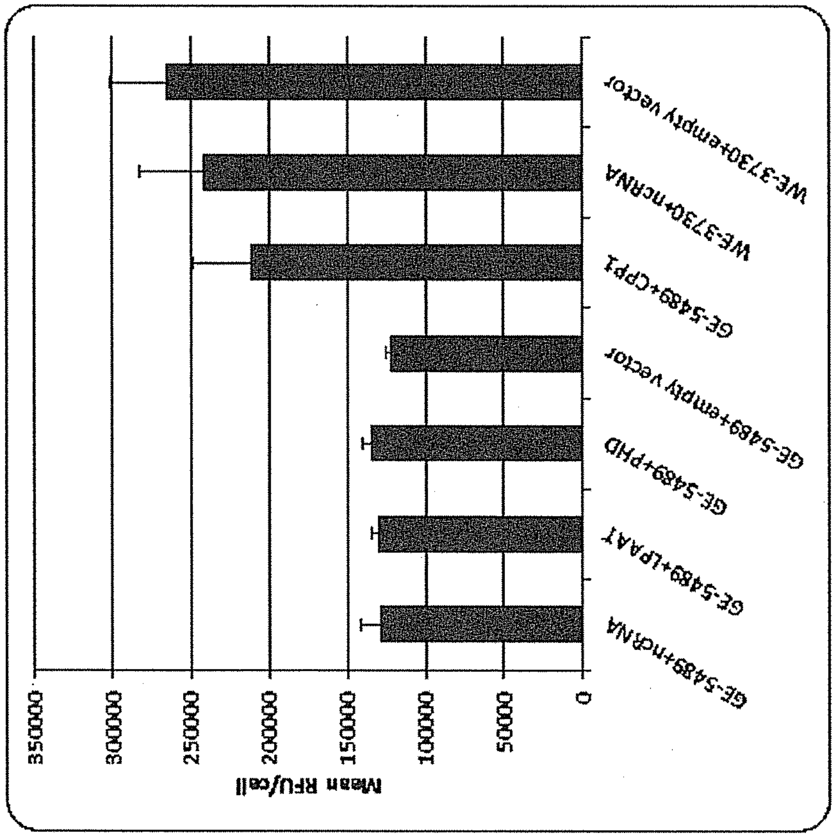
FIG. 35 is a bar graph depicting chlorophyll fluorescence levels of the GE-5489 LAR3 mutant transformed with various genes considered possible loci of the LAR3 mutation.

Complementation experiments in *N. gaditana* resulted in partial complementation to recover close to wild-type per cell chlorophyll levels through heterologous expression of open reading frame E2-352 ("conserved predicted protein 1") in GE5489. In these experiments, linearized vectors that included the gene to be tested for along with native promoter and terminator sequences, which were transformed into the LIHLA mutant GE-5489 essentially according to the procedure provided in Example 2. Transformants were plated on plates containing hygromycin and after 2-3 weeks, colonies were picked, streaked, and then grown in liquid culture for low light-acclimation prior to screening using a BD Accuri C6 (BD Biosciences, San Jose, Calif.) flow cytometer to determine mean culture chlorophyll fluorescence on a per cell basis. Wild type cells (*N. gaditana* strain WT-3730), which contain an empty vector, were also low light acclimated to use as a control for per cell chlorophyll fluorescence levels. FIG. 35 provides a graph showing the mean chlorophyll fluorescence per cell of strains transformed with the putative noncoding RNA, the putative LPAAT gene (E1-7251, the PHD-finger protein (E1-7250), an empty vector as control, and the "conserved predicted protein 1" (gene E2-352). FIG. 35 shows clearly that complementation with an intact conserved predicted protein (E2-352) resulting in the recovery of near wild-type levels of mean chlorophyll per cell.

Figure 36:
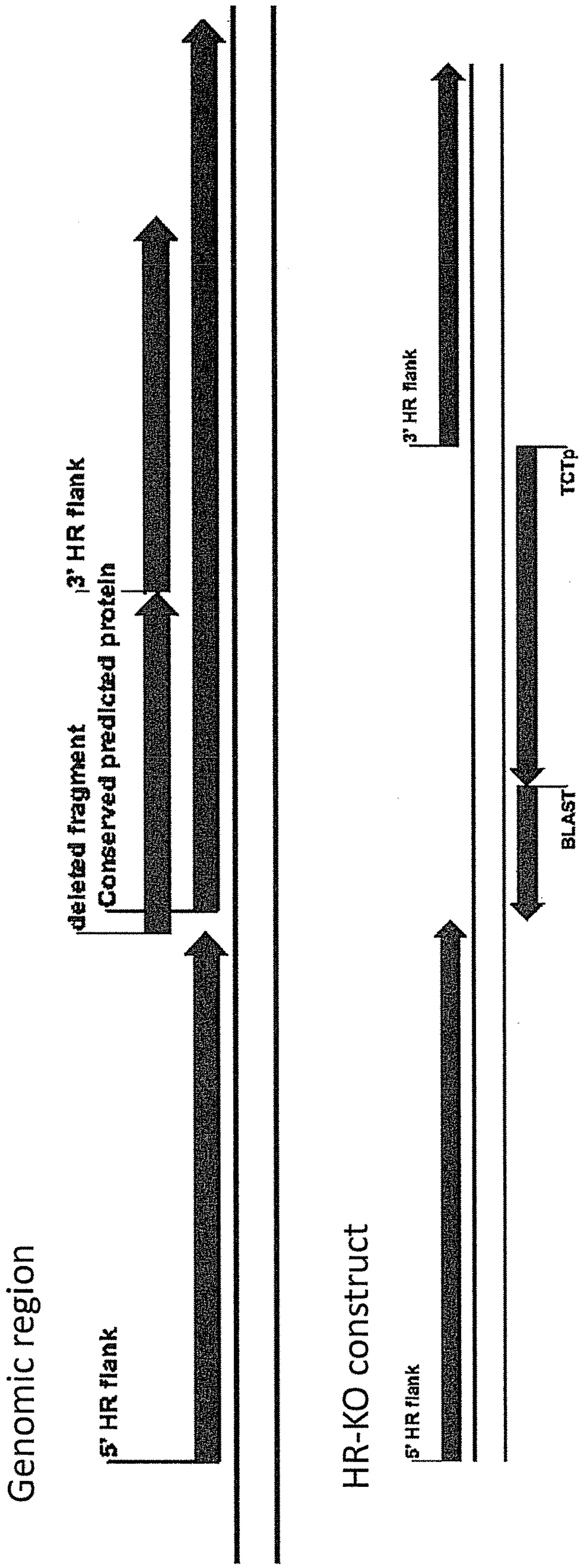
FIG. 36 provides a map of the LAR3 locus (see Genomic region) and a construct designed for homologous recombination into the LAR3 locus that includes the "blast" gene (SEQ ID NO:59) driven by the *Nannochloropsis* TCTP promoter (SEQ ID NO:2) as a selectable marker (see HR-KO construct).

Directed knock-outs of orthologous genes in a related species confirmed these results (Table 5). Knockout constructs for the *N. oceanica* LAR3 locus included a blasticidin resistance gene (SEQ ID NO:59) flanked on either side by sequences ranging from 1-2 kb of the locus being tested. FIG. 36 provides a diagram of the LAR3 knockout construct showing the *N. oceanica* LAR3 locus sequences (left flank, SEQ ID NO:60) on either side of the blasticidin resistance gene (SEQ ID NO:61). The linear knockout fragment was generated by PCR and transformed into *N. oceanica* essentially according to the protocol in Example 2.

Figure 37:
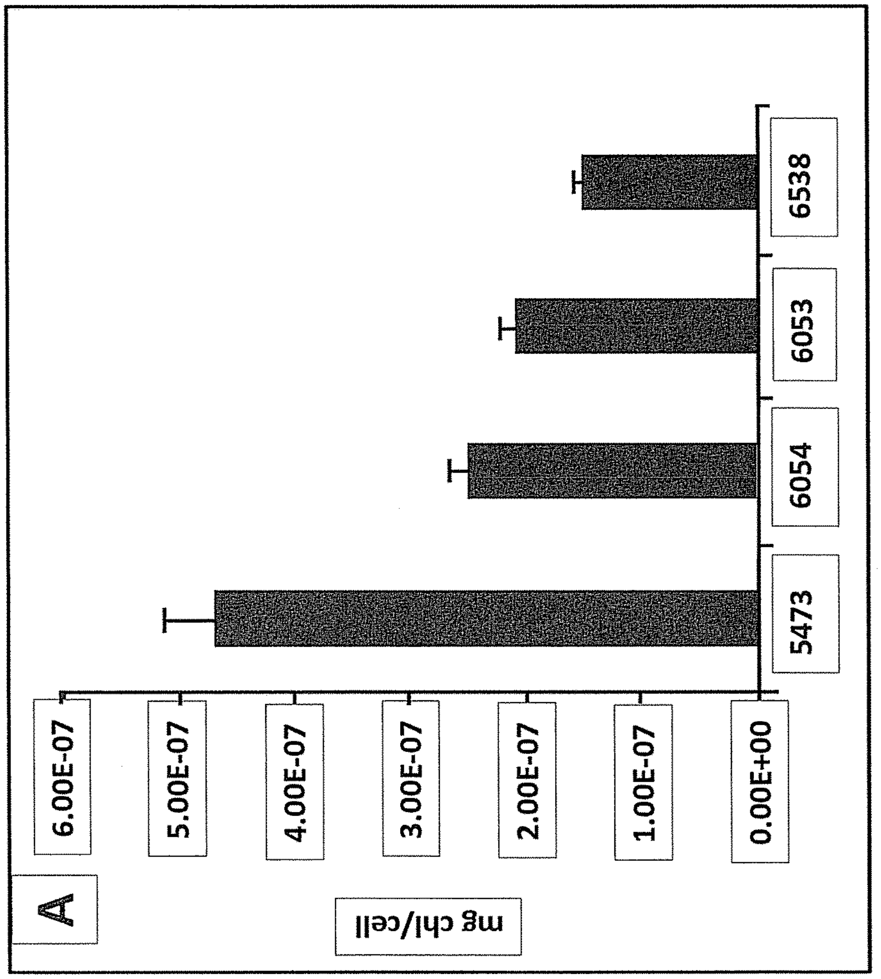
FIG. 37 provides photophysiological parameters of *Nannochloropsis oceanica* wild type strain 5473 and engineered mutants of LAR1 (knockout strain 6054), LAR2 (knockout strain 6053) and LAR3 (knockout strain 6038) in the *Nannochloropsis oceanica* background. A) provides the chlorophyll per cell of wild type and engineered LAR1, LAR2, and LAR3 mutants. B) provides Pmax per mg chlorophyll for the wild type strain and engineered LAR1 and LAR3 mutants. C) provides average Ek values for wild type and engineered LAR1, LAR2, and LAR3 mutants. D) provides $ETR_{PSII}$ over a range of light intensities for wild type and engineered LAR1, LAR2, and LAR3 mutants. E) provides qP values over a range of light intensities for wild type and engineered LAR1, LAR2, and LAR3 mutants.
Figure 37:
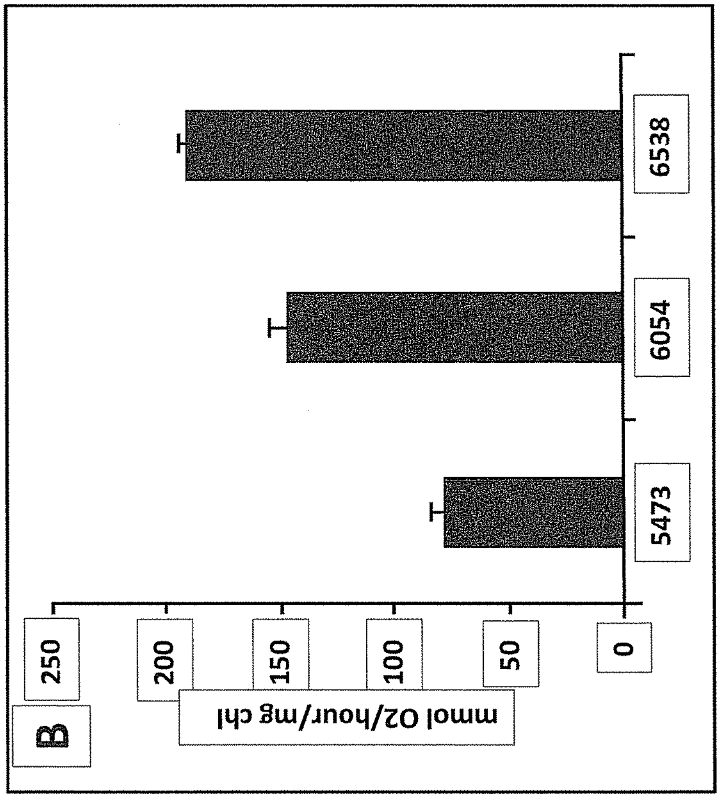
Figure 37:
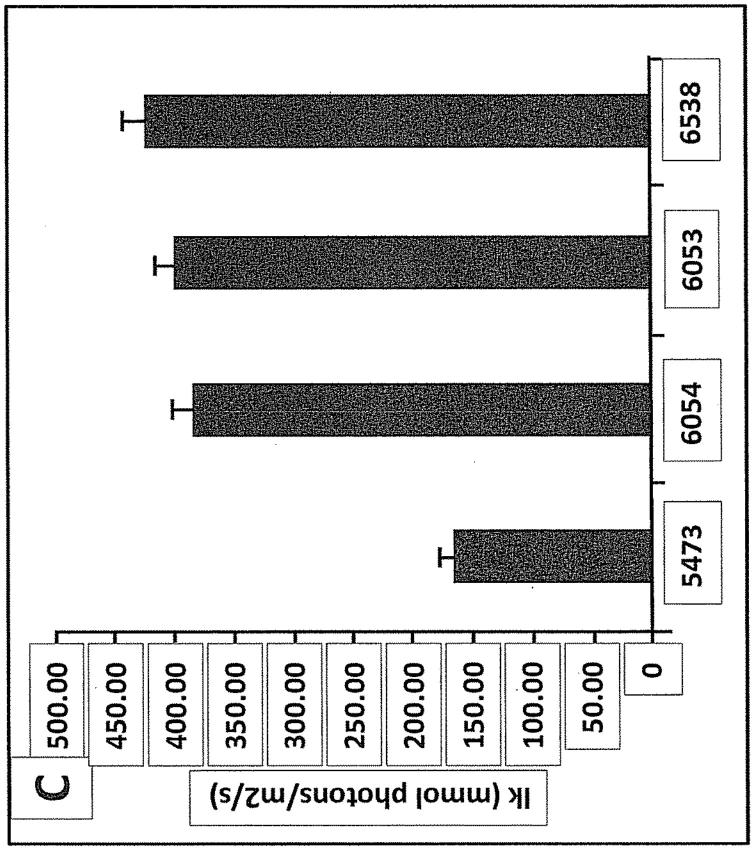
Figure 37:
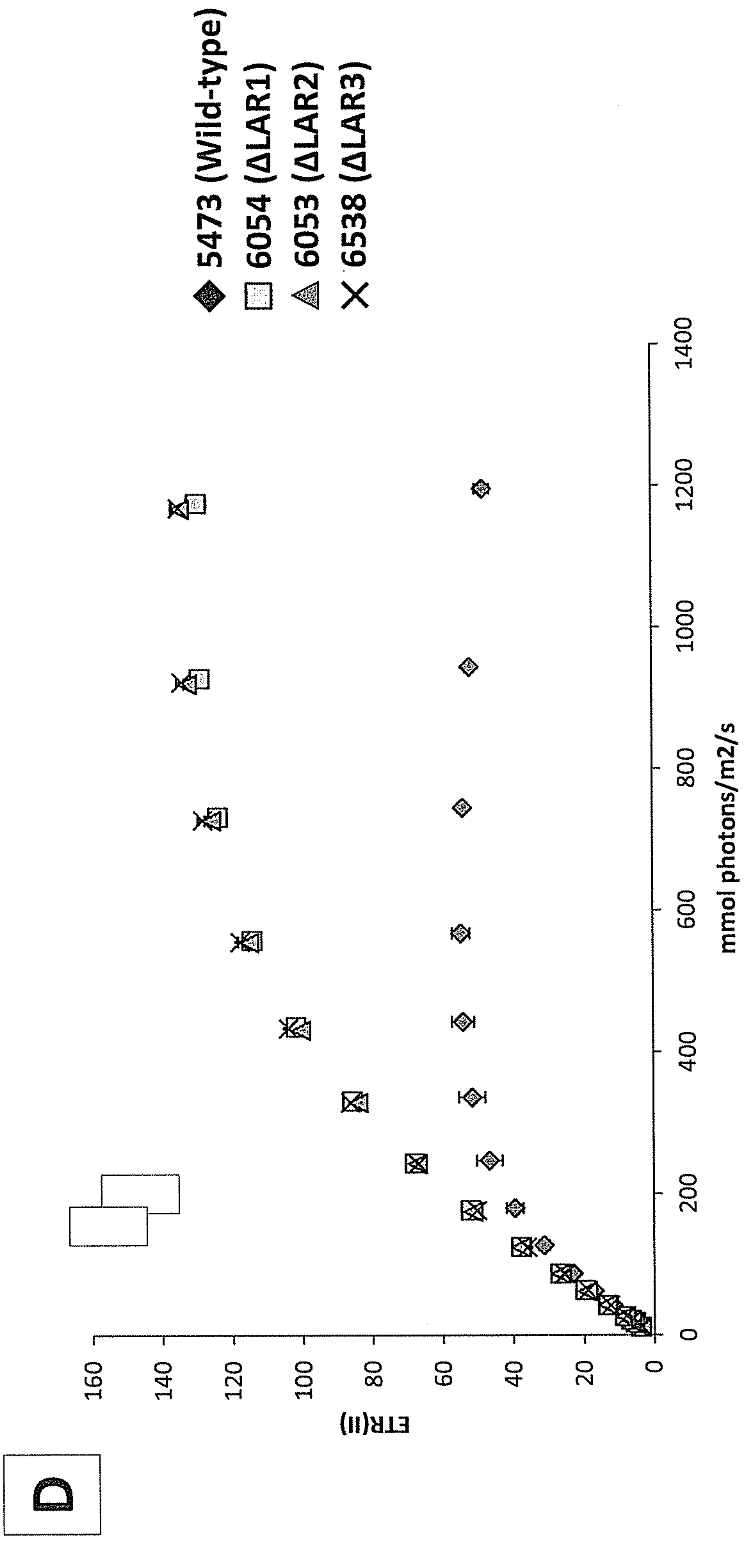
Figure 37:
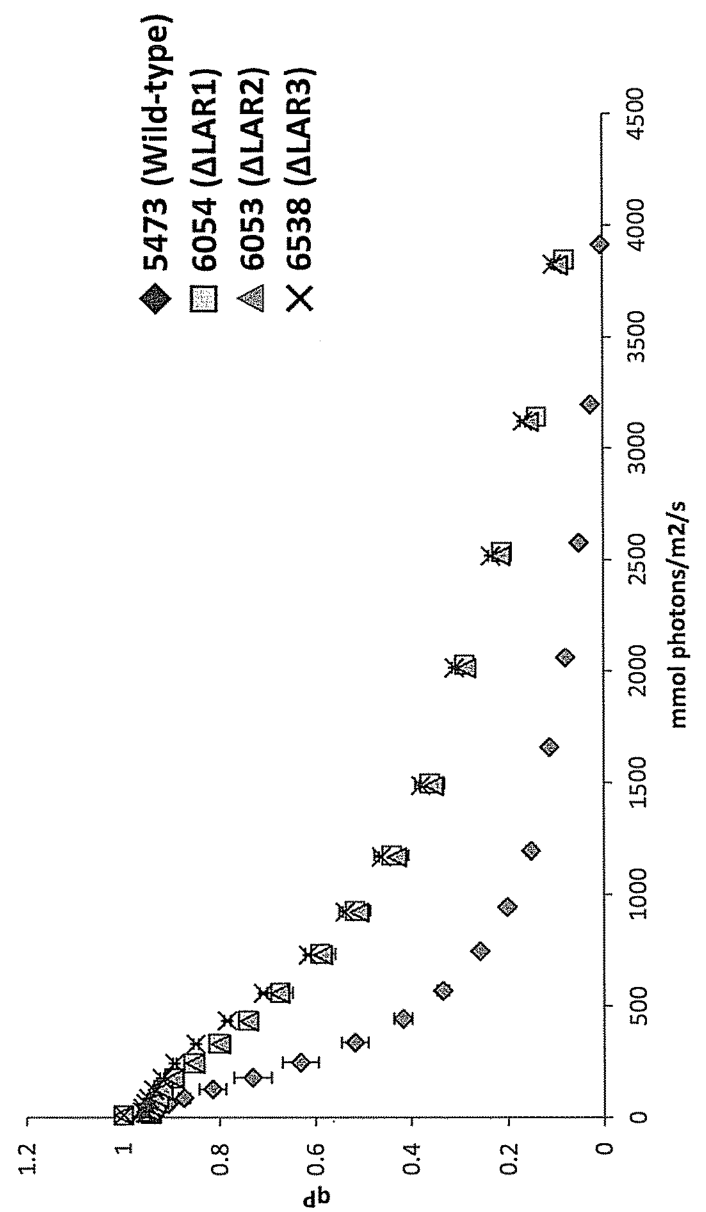

Detailed physiological analysis of the *N. oceanica* LAR3 knockout strain alongside LAR1 and LAR2 *N. oceanica* knockout strains clearly shows that the directed knockout of this gene produces a similar physiology as that identified in the other LIHLA strains (FIG. 37). The genetically engineered LAR1 (6054), LAR2 (6053) and LAR3 (6538) knockout strains are all demonstrated to have significantly reduced chlorophyll per cell (FIG. 37A) and a higher Ek (FIG. 37C) with respect to wild type *N. oceanica* strain 5473. In addition, electron transport rates of photosystem II ($ETR_{PSII}$) are also increased at light intensities above 100 or above 200 for the LAR1, LAR2, and LAR3 knockouts (FIG. 37D), as is qP (FIG. 37E). FIG. 37B shows the higher levels of oxygen evolution ($P_{max}$) per chlorophyll for the LAR1 and LAR3 knockouts.

Example 17. LAR3 Homologs

E2-352 (the LAR3 gene, SEQ ID NO:62) encodes a predicted protein (SEQ ID NO:63) of 841 amino acids and molecular weight of 86.23 kDa. Multiple sequence alignment (MUSCLE) of LAR3 translated sequences and the top 5 homology hits from other heterokonts/stramenopiles shows a ~100 aa sequence that is highly conserved (FIG. 38). This section corresponds to residues 302-405 of LAR3 (SEQ ID NO:64). This conserved region can be used as a hook for identifying putative homologs in other species such as *Cyclotella* and *Navicula*. Sequence identity over this region is approximately 80% for best matches in these strains. At E-value <1, there are no matches to known PFAM-A domains over this highly conserved region. There is a significant match to a PFAM-B domain (Pfam-B 10967) over residues 299 to 414 of LAR3 at E-value<2.1E-12, but this automated PFAM-B alignment is uncharacterized.

The conserved domain of the *N. gaditana* LAR3 protein (SEQ ID NO:64) has 96% identity to amino acids 303 to 405 of the *Nannochloropsis oceanica* LAR3 ortholog (SEQ ID NO:66, encoded by SEQ ID NO:65). Across the entire LAR3 protein, the *N. gaditana* and *N. oceanica* LAR3 ortholog are 56% identical at the amino acid level. The functional equivalence of these proteins is demonstrated by the knockout experiments performed in *N. oceanica* in Example 16, above, that resulted in the LIHLA phenotype.

The conserved domain of the *N. gaditana* LAR3 protein (SEQ ID NO:64) has 62% identity with amino acids 138 to 236 of an "unnamed protein product" of *Phytophthora ramorum* (SEQ ID NO:68, encoded by SEQ ID NO:67); 86% identity to amino acids 263 to 364 of a "putative uncharacterized protein" of *Ectocarpus siliculosus* (SEQ ID NO:70, encoded by SEQ ID NO:69); 86% identity to amino acids 591 to 692 of a "hypothetical protein" of *Aureococcus anophagefferens* (SEQ ID NO:72, encoded by SEQ ID NO:71); 76% identity to amino acids 116 to 217 of a "predicted protein" of *Thalassiosira pseudonana* (SEQ ID NO:74, encoded by SEQ ID NO:73); 87% identity to amino acids 55 to 156 of a "predicted protein" of *Phaeodactylum tricornutum* (SEQ ID NO:76, encoded by SEQ ID NO:75); and 78% identity to amino acids 176 to 263 of an "uncharacterized protein" of *Thalassiosira oceanica* (SEQ ID NO:78, encoded by SEQ ID NO:77). These polypeptides are putative orthologs of the *Nannochloropsis* LAR3 polypeptides.

Example 18. LAR3 Transcriptomics

Figure 39:
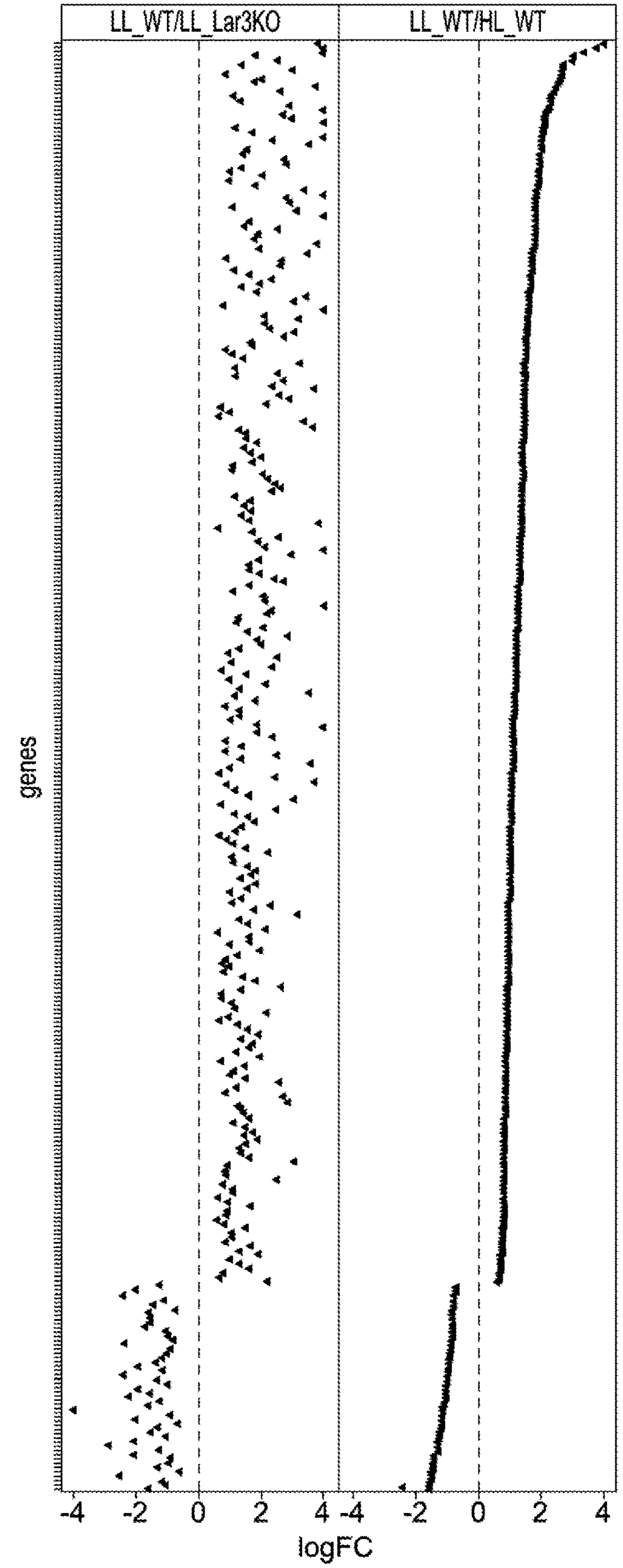
FIG. 39 provides side-by-side dot plots of "TRAC 1" transcripts having the same pattern of regulation in the LAR3 mutant with respect to wild type in low light (left plot) as in wild type cells transferred to high light versus their low light levels (right plot). A dashed vertical line in each plot marks the position along the x axis where the $\log_2$ fold change is zero, where there is no difference in the expression level. indicates expression of the gene in the mutant is twice as much or more than the levels in the wild type.
Figure 40:
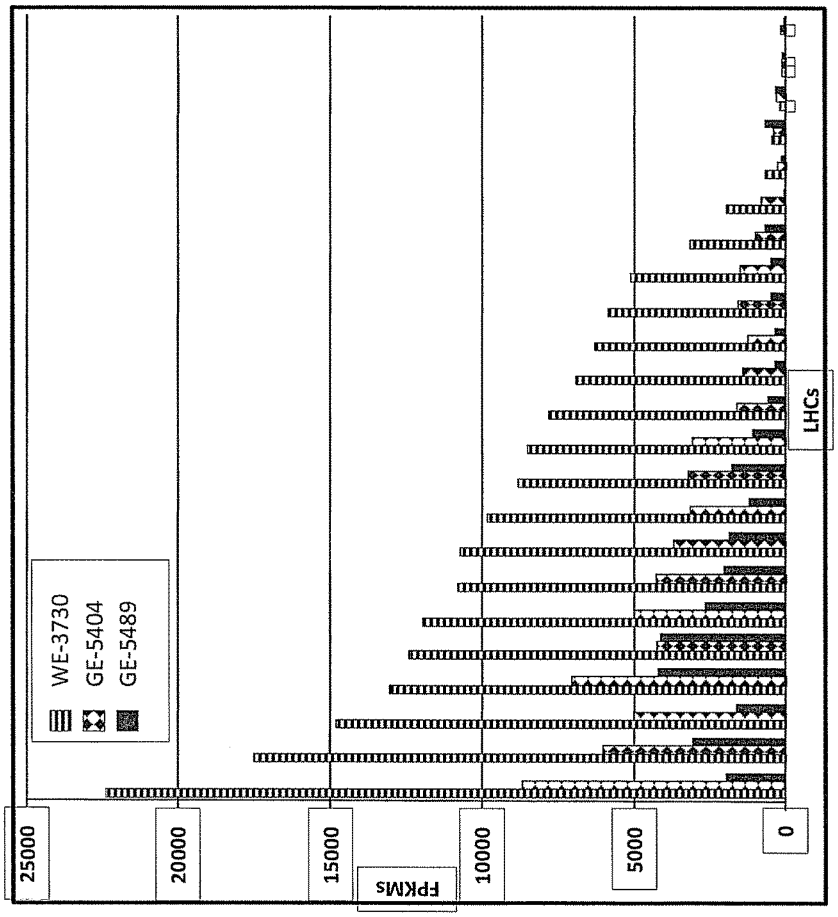
FIG. 40 is a graph providing expression data from RNA-seq experiments using RNA isolated from wild type ("WE-3730"), LAR2 mutant (GE-5404) and LAR3 mutant (GE-5489) cells, demonstrating the characteristic reduced expression of at least eighteen LHCs in the LAR mutants with respect to wild type cells acclimated to low light.

Transcriptomic profiling of LAR3 mutant GE-5489 was performed exactly as for the LAR2 mutant described in Example 12. FIG. 39 is the same type of dot plot graphical depiction of the similarity of gene expression patterns in a LIHLA mutant as compared with wild type as is provided for a LAR1 LIHLA mutant in FIG. 22 and the LAR2 mutant in FIG. 23. FIG. 39 depicts, in side-by-side graphs to be viewed together, 327 individual genes represented by points ordered vertically. The depicted genes are TRAC I genes from transcriptomic analysis of low light v. high light acclimated wild type cells, and wild type v. GE5489 LAR3 mutant cells under low light, i.e., they are deregulated in the LAR3 LIHLA mutant under low light acclimation. On the right hand graph, each point representing a gene is positioned horizontally according to its level of expression in low light-acclimated wild type cells relative to its level of expression in high light-acclimated cells, with genes having the highest relative expression in low light acclimated cells (i.e., the highest degree of "overexpression" in low light acclimated cells versus high light acclimated cells) represented by points positioned to the right ($log_2$ positive values), and genes having lower levels of expression in low light acclimated versus high light acclimated wild type cells represented by points positioned to the left ($log_2$ negative values). The graph on the left side is aligned with the graph on the right, so that points representing the same gene are found at the same vertical position on the left graph as for the right graph, but on the left graph the points are positioned horizontally according to their relative expression level in wild type versus LIHLA LAR3 mutant cells (when both are acclimated to low light). The graph shows that for a large number of genes relative expression levels in the wild type versus LIHLA LAR3 mutant is strikingly similar to the relative expression levels in low light acclimated versus high light acclimated wild type cells, with genes upregulated in low light acclimated wild type cells being upregulated in the wild type cells as compared to the LAR3 LIHLA mutant cells, and genes downregulated in low light acclimated wild type cells being downregulated in the wild type cells with respect to the LAR3 LIHLA mutant cells. Thus the pattern of gene expression in the LAR3 LIHLA mutant demonstrates that the LIHLA mutants are globally deregulated in low light acclimation, as under low light acclimation their gene expression pattern resembles that of high light acclimated wild type cells. In addition to all the phenotypic and physiological hallmarks of a LIHLA strain, GE-5489 shows a similar global deregulation of photosynthesis genes and specifically those involved in low light acclimation. Even under low light acclimation conditions the vast majority of Light Harvesting Complex (LHC) proteins are significantly downregulated in this strain (FIG. 40). This global deregulation of photosynthesis-related genes is also evident among all genes found to be in photosynthetic stramenopiles but not in nonphotosynthetic stramenopiles, the "photocut" genes.

Figure 41:
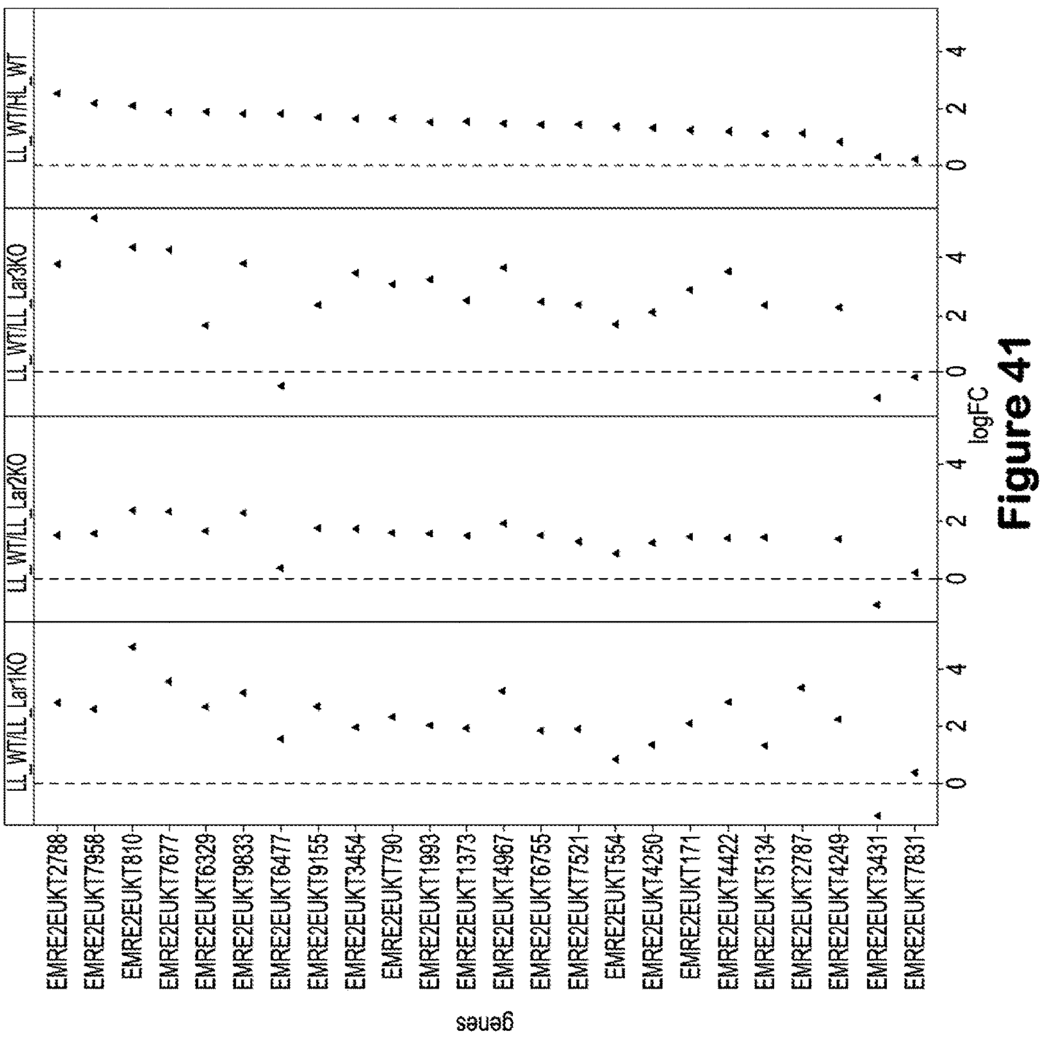
FIG. 41 provides side-by-side dot plots relative expression levels of LHC transcripts in wild type low light acclimated cells versus, in graphs proceding from left to right, a LAR1 mutant, a LAR2 mutant, and a LAR3 mutant, in which the LAR mutants are also low light-acclimated. The rightmost graph depicts expression levels of LHC transcripts in low light acclimated cells versus high light-acclimated wild type cells. A dashed vertical line in each plot marks the position along the x axis where the $\log_2$ fold change is zero, where there is no difference in the expression level. Low light acclimated wild type cells demonstrate increased expression, relative to low light acclimated wild type cells of LHCs (rightmost graph). This general pattern is seen in all three LAR mutants, where low light acclimated wild type LHC expression levels for nearly all of the LHCs exceed the expression levels in low light-acclimated LAR mutants. The exemplified *Nannochloropsis* LHCs are, proceeding from top to bottom: 2788 (SEQ ID NO:79); 7958 (SEQ ID NO:80); 810 (SEQ ID NO:81); 7677 (SEQ ID NO:82); 6329 (SEQ ID NO:83); 9833 (SEQ ID NO:84); 6477 (SEQ ID NO:85); 9115 (SEQ ID NO:86); 3454 (SEQ ID NO:87); 790 (SEQ ID NO:88); 1993 (SEQ ID NO:89); 1373 (SEQ ID NO:90); 4967 (SEQ ID NO:91); 6755 (SEQ ID NO:92); 7521 (SEQ ID NO:93); 554 (SEQ ID NO:94); 4250 (SEQ ID NO:95); 171 (SEQ ID NO:96); 4422 (SEQ ID NO:97); 5134 (SEQ ID NO:98); 2787 (SEQ ID NO:99); 4249 (SEQ ID NO:100); 3431 (SEQ ID NO:101); and 7831 (SEQ ID NO:102).

Three independent LIHLA mutants having mutations in different genes (LAR1, LAR2, and LAR3) have been demonstrated to be globally deregulated in low light acclimation. It is demonstrated that over 100 genes that are either up or down regulated by wild type cells on low light acclimation are deregulated, that is, are not similarly differentially regulated, by low light acclimated LAR1, LAR2, and LAR3 mutants. Among the deregulated genes are genes encoding light harvesting chlorophyll binding proteins or LHCs. The LHC sequences analyzed in this experiment were identified in the in-house *Nannochloropsis gaditana* genome assembly by the inclusion of the pfam domain PF00504 (chlorophyll a-b binding protein) in the encoded polypeptide sequences. The nucleic acid sequences are provided as SEQ ID NO:79-SEQ ID NO:102. FIG. 41 provides aligned dot plots for LAR1, LAR2, and LAR3 mutants as well as wild type cells, in which the analyzed genes encode LHCs or related proteins. From top to bottom, the *Nannochloropsis* genes analyzed are, proceeding from the top to the bottom of the plot, are SEQ ID NO:79, annotated as encoding a fucoxanthin chlorophyll a/c binding protein; SEQ ID NO:80, also annotated as encoding a fucoxanthin chlorophyll a/c binding protein; SEQ ID NO:81, annotated as encoding a light harvesting complex protein 5 (precursor); SEQ ID NO:82, also annotated as encoding a light harvesting complex protein 5 (precursor); SEQ ID NO:83, annotated as encoding a light harvesting complex protein 10 (precursor); SEQ ID NO:84, also annotated as encoding a light harvesting complex protein 10 (precursor); SEQ ID NO:85, annotated as encoding a Beta-Ig-H3/fasciclin protein; SEQ ID NO:86, annotated as encoding a low molecular mass early light-inducible protein HV60; SEQ ID NO:87, annotated as encoding a light harvesting complex protein 2; SEQ ID NO:88, annotated as encoding light harvesting complex protein 3; SEQ ID NO:89, annotated as encoding a light harvesting complex protein 3; SEQ ID NO:90, annotated as encoding a light harvesting complex protein 2; SEQ ID NO:91, annotated as encoding a light-harvesting complex I chlorophyll a/b binding protein; SEQ ID NO:92, annotated as encoding a light harvesting complex protein 2; SEQ ID NO:93, also annotated as encoding a light harvesting complex protein 2; SEQ ID NO:94, annotated as encoding a light harvesting complex protein; SEQ ID NO:95, also annotated as encoding a light harvesting complex protein 2; SEQ ID NO:96, annotated as encoding a light harvesting complex protein 3; SEQ ID NO:97, annotated as encoding a light harvesting complex protein 2; SEQ ID NO:98, annotated as encoding a light harvesting complex protein 2; SEQ ID NO:99, annotated as encoding a fucoxanthin chlorophyll a/c binding protein; SEQ ID NO:100, annotated as encoding a light harvesting complex protein 3; SEQ ID NO:101, annotated as encoding a light harvesting complex protein; and SEQ ID NO:102, annotated as encoding a beta-Ig-H3/fasciclin precursor.

The leftmost plot shows along the x axis the ratio of expression of each of 22 LHC genes in low light-acclimated wild type as compared to low light-acclimated LAR1 cells, the next plot shows low light-acclimated wild type expression of each LHC gene as a ratio of its expression in low light-acclimated LAR2 cells, the third plot shows low light-acclimated wild type expression of each LHC gene as a ratio of its expression in low light-acclimated LAR3 cells, and the rightmost plot shows low light-acclimated wild type expression of each LHC gene as a ratio of its expression in high light-acclimated wild type cells. The plots show that the expression of at least 20 LHC genes in low light acclimated wild type cells differs from the expression of the LHC in low light acclimated LIHLA mutant cells in a manner very similar to the difference between low light acclimated and high light acclimated wild type cells. That is, the LIHLA mutants resemble high light acclimated wild type cells in their pattern of LHC expression, even though they are acclimated to low light.

Example embodiments are provided so that this disclosure will be thorough, and will fully convey the scope of the invention to those who are skilled in the art. Numerous specific details are set forth such as examples of specific components and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known structures, and well-known technologies are not described in detail.

We claim:

1. An algal mutant deregulated in acclimation to low light, wherein said algal mutant is derived from classical mutagenesis or genetic engineering and comprises:

(a) a disrupted gene encoding a polypeptide having at least 85% amino acid sequence identity to the amino acid sequence of SEQ ID NO: 4 or the amino acid sequence of SEQ ID NO: 8;

(b) a disrupted gene encoding a polypeptide having at least 85% amino acid sequence identity to the amino acid sequence of SEQ ID NO: 6 or the amino acid sequence of SEQ ID NO: 21; or (c) a disrupted gene encoding a polypeptide having at least 85% amino acid sequence identity to the amino acid sequence of SEQ ID NO: 63 or the amino acid sequence of SEQ ID NO: 66; and further wherein said algal mutant exhibits:

a reduction in chlorophyll under low light conditions, and higher photochemical quenching (qP) at all physiologically relevant irradiances above 300 $\mu E^*m^{-2}*s^{-1}$, with respect to a wild type alga of the same strain.

2. The algal mutant of claim 1, wherein said reduction in chorophyll is at least a 20% reduction with respect to a wild type alga of the same strain.

3. The algal mutant of claim 2, wherein said reduction in chlorophyll is at least a 30% reduction with respect to a wild type alga of the same strain.

4. The algal mutant of claim 1, wherein said algal mutant exhibits onset of nonphotochemical quenching (NPQ) at a higher irradiance than a wild type alga of the same strain.

5. The algal mutant of claim 1, wherein said algal mutant exhibits lower NPQ at all physiologically relevant irradiances above 400 $\mu E^*m^{-2}*s^{-1}$ than a wild type alga of the same strain.

6. The algal mutant of claim 1, wherein said algal mutant has at least 70% of the maximal photosynthetic rate ($P_{max}$) per cell as a wild type alga of the same strain.

7. The algal mutant of claim 1, wherein said algal mutant has a higher saturating irradiance for photosynthesis (Ek) than a wild type alga of the same strain.

8. The algal mutant of claim 1, wherein a culture of said algal mutant has greater penetration of light into said culture than does a culture of a wild type alga of the same strain.

9. The algal mutant of claim 1, wherein said algal mutant has been generated by UV irradiation, gamma irradiation, or chemical mutagenesis.

10. The algal mutant of claim 1, wherein said algal mutant is a genetically engineered algal mutant.

11. The algal mutant of claim 10, wherein said algal mutant has been genetically engineered by a means for disrupting a gene encoding a regulator of light acclimation.

12. The algal mutant of claim 11, wherein said algal mutant has been genetically engineered by insertional mutagenesis.

13. The algal mutant of claim 1, wherein said algal mutant belongs to a genus selected from the group consisting of: *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, and *Volvox.*

14. The algal mutant of claim 13, wherein said algal mutant belongs to a genus selected from the group consisting of: *Amphora, Chaetoceros, Cyclotella, Ellipsoidon, Fragilaria, Monodus, Nannochloropsis, Navicula, Nitzschia, Phaeodactylum*, and *Thalassiosira.*

15. An algal biomass comprising the algal mutant of claim 1.

16. A method of producing an algal product, comprising culturing the algal mutant of claim 1 and isolating at least product produced by said algal mutant from said culture.

17. The method of claim 16, wherein said product is algal biomass.

18. The method of claim 16, wherein said product is a lipid, a protein, a peptide, one or more amino acids, a carbohydrate, one or more nucleotides, a vitamin, a cofactor, a hormone, an antioxidant, or a pigment or colorant.

19. The method of claim 16, wherein said product is a lipid.

20. The method of claim 19, wherein said algal mutant is engineered to include at least one exogenous gene encoding a polypeptide that participates in the production of a lipid.

21. The method of claim 16, wherein said algal mutant is cultured phototrophically.

22. The method of claim 21, wherein said algal mutant is cultured in a pond or raceway.

23. The algal mutant of claim 11, wherein said algal mutant has been genetically engineered by insertional mutagenesis, gene replacement, RNAi, antisense RNA, meganuclease genome engineering, one or more ribozymes, and/or a CRISPR/cas system.

24. The algal mutant of claim 1, wherein said algal mutant is a diatom or *Eustigmatophyte* species.

25. The algal mutant of claim 1, wherein said algal mutant is mutated in a gene encoding a polypeptide having at least 85% amino acid sequence identity to the amino acid sequence of SEQ ID NO: 4 or the amino acid sequence of SEQ ID NO: 8, wherein said polypeptide recruits to pfam PF02135 and comprises an extended TAZ zinc finger domain comprising an amino acid sequence having at least 85% amino acid sequence identity to the amino acid sequence of SEQ ID NO: 9 or the amino acid sequence of SEQ ID NO: 10.

26. The algal mutant of claim 25, wherein said TAZ zinc finger domain comprises an amino acid sequence having at least 90% amino acid sequence identity to the amino acid sequence of SEQ ID NO: 9 or the amino acid sequence of SEQ ID NO: 10.

27. The algal mutant of claim 1, wherein said algal mutant is mutated in a gene encoding a polypeptide having at least 85% amino acid sequence identity to the amino acid sequence of SEQ ID NO: 6 or the amino acid sequence of SEQ ID NO: 21, wherein said polypeptide recruits to pfam PF00249 and comprises an extended myb-like DNA-binding domain comprising an amino acid sequence having at least 85% amino acid sequence identity to the amino acid sequence of SEQ ID NO: 22 or the amino acid sequence of SEQ ID NO: 23.

28. The algal mutant of claim 1, wherein said extended myb-like DNA-binding domain comprises an amino acid sequence having at least 90% amino acid sequence identity to the amino acid sequence of SEQ ID NO: 22 or the amino acid sequence of SEQ ID NO: 23.

29. The algal mutant of claim 1, wherein said algal mutant is mutated in a gene encoding a polypeptide having at least 85% amino acid sequence identity to the amino acid sequence of SEQ ID NO: 63 or the amino acid sequence of SEQ ID NO: 66, wherein said polypeptide comprises a domain comprising an amino acid sequence having at least 85% amino acid sequence identity to the amino acid sequence of SEQ ID NO: 64.

30. The algal mutant of claim 29, wherein said domain comprises an amino acid sequence having at least 90% amino acid sequence identity to SEQ ID NO: 64.

* * * * *

SEQUENCE LISTING

```
<160> NUMBER OF SEQ ID NOS: 102

<210> SEQ ID NO 1
<211> LENGTH: 4118
<212> TYPE: DNA
<213> ORGANISM: Artificial Sequence
<220> FEATURE:
<223> OTHER INFORMATION: pSG-05534 Construct for Insertional Mutagenesis

<400> SEQUENCE: 1
```

-continued

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcctgcag gtcgactcta gagcgtgcag gtgtacagat tgaaggaaac aatggagata    300
tctttggcag ttgaaaaccg tgttcgaatc atgctcttct actctccaac tgagacgaaa    360
tttatagcgc catctcgctt ctgactacca ggcttaggaa ggcctcatca caagctggat    420
cggttcgaat taagcaggca ctgaagccaa gcttgcaaga cagccacctt ttaattctct    480
caaaacactt tctcaattca gcccggtaaa tatgccgatt cacagcggcc aagatagagg    540
ggaggttagc aagaatgttg cgatccctcc ccagtcgttg cctcgcacac aacctaggac    600
ttcacctttc catggaaaat tgagaagtga atattggttt tcttacggca tatcagatga    660
aatcatgacc cctaaacatg aagagctgca ggcaaaacac ctgctctgga cgagcacgat    720
gaaatctcga gaacccgccg tacttcagtt gatcccgcat gatgacggcc gccattgaaa    780
taagccacct cactttattc tagcaccgat ttccaccgtt gtgagggccg aacgaggaca    840
atttcgtgcg aaacaagcac gaacgcgcac acgattagta ggacagacga gcagatcgat    900
ggcatgcggc acggtctcgc gttctcggcg accaggacaa cggagcagag ggaggcctgc    960
cgagttccga ggggcatttt agtcccaaaa ttgtgttgac acgtgaacaa gtggcttgaa   1020
aagaggaagg aaatgcctgg gtttcccttc gagagcggga actcgcttgt gcgtcatcct   1080
agctacccat ggtccctttg tgggggaggc tgtttcgtcc taccgaatgt gtggcgctcc   1140
atgcatcttc tgcctcccaa accaccaaca tgagcacgcg aaggaaggag aaaaaagtgg   1200
ccgcaacgtt ctcttctcat atttattgtc tcatcacaaa cataggtaca taatacaaca   1260
atcatggatc cccgggtacc gagctcgatg gccaagcctt tgtcccaaga ggaatccacg   1320
ctgatcgaac gtgcaactgc gaccatcaac agcataccta ttagcgagga ctactcggtg   1380
gccagtgcag ccctctcgtc cgacggtcgg atctttaccg gcgtgaatgt atatcatttc   1440
accggagggc catgcgcgga gctcgtggtc ctcggaacgg ccgctgcggc tgctgccgga   1500
aatctgacgt gcatagtggc catcgggaac gaaaaccgcg gcattctgtc tccgtgcggg   1560
cgatgtcggc aggtgctgct tgacttgcac ccggggatca aggcaattgt caaagattcc   1620
gatgggcagc ccacagcggt tggcatcagg gagttgcttc cctctggcta cgtctgggag   1680
ggttgaaatt cactggccgt cgttttacaa cgtcgtgact gggaaaaccc tggcgttacc   1740
caacttaatc gccttgcagc acatccccct ttcgccagac ccataatacc cataatagct   1800
gtttgccact ggcgtaatag cgaagaggcc cgcaccgatc gcccttccca acagttgcgc   1860
agcctgaatg gcgaatggcg cctgatgcgg tattttctcc ttacgcatct gtgcggtatt   1920
tcacaccgca tatggtgcac tctcagtaca atctgctctg atgccgcata gttaagccag   1980
ccccgacacc cgccaacacc cgctgacgcg ccctgacggg cttgtctgct cccggcatcc   2040
gcttacagac aagctgtgac cgtctccggg agctgcatgt gtcagaggtt ttcaccgtca   2100
tcaccgaaac gcgcgagacg aaagggcctc gtgatacgcc tatttttata ggttaatgtc   2160
atgataataa tggtttctta gacgtcaggt ggcacttttc ggggaaatgt gcgcggaacc   2220
cctatttgtt tatttttcta aatacattca aatatgtatc cgctcatgag acaataaccc   2280
tgataaatgc ttcaataata ttgaaaaagg aagagtatga gtattcaaca tttccgtgtc   2340
```

```
gcccttattc ccttttttgc ggcattttgc cttcctgttt ttgctcaccc agaaacgctg   2400

gtgaaagtaa aagatgctga agatcagttg ggtgcacgag tgggttacat cgaactggat   2460

ctcaacagcg gtaagatcct tgagagtttt cgccccgaag aacgttttcc aatgatgagc   2520

acttttaaag ttctgctatg tggcgcggta ttatcccgta ttgacgccgg gcaagagcaa   2580

ctcggtcgcc gcatacacta ttctcagaat gacttggttg agtactcacc agtcacagaa   2640

aagcatctta cggatggcat gacagtaaga gaattatgca gtgctgccat aaccatgagt   2700

gataacactg cggccaactt acttctgaca acgatcggag gaccgaagga gctaaccgct   2760

tttttgcaca acatggggga tcatgtaact cgccttgatc gttgggaacc ggagctgaat   2820

gaagccatac caaacgacga gcgtgacacc acgatgcctg tagcaatggc aacaacgttg   2880

cgcaaactat taactggcga actacttact ctagcttccc ggcaacaatt aatagactgg   2940

atggaggcgg ataaagttgc aggaccactt ctgcgctcgg cccttccggc tggctggttt   3000

attgctgata aatctggagc cggtgagcgt gggtctcgcg gtatcattgc agcactgggg   3060

ccagatggta agccctcccg tatcgtagtt atctacacga cggggagtca ggcaactatg   3120

gatgaacgaa atagacagat cgctgagata ggtgcctcac tgattaagca ttggtaactg   3180

tcagaccaag tttactcata tatactttag attgatttaa aacttcattt ttaatttaaa   3240

aggatctagg tgaagatcct ttttgataat ctcatgacca aaatccctta acgtgagttt   3300

tcgttccact gagcgtcaga ccccgtagaa aagatcaaag gatcttcttg agatcctttt   3360

tttctgcgcg taatctgctg cttgcaaaca aaaaaaccac cgctaccagc ggtggtttgt   3420

ttgccggatc aagagctacc aactcttttt ccgaaggtaa ctggcttcag cagagcgcag   3480

ataccaaata ctgttcttct agtgtagccg tagttaggcc accacttcaa gaactctgta   3540

gcaccgccta catacctcgc tctgctaatc ctgttaccag tggctgctgc cagtggcgat   3600

aagtcgtgtc ttaccgggtt ggactcaaga cgatagttac cggataaggc gcagcggtcg   3660

ggctgaacgg ggggttcgtg cacacagccc agcttggagc gaacgaccta caccgaactg   3720

agatacctac agcgtgagct atgagaaagc gccacgcttc ccgaagggag aaaggcggac   3780

aggtatccgg taagcggcag ggtcggaaca ggagagcgca cgagggagct tccaggggga   3840

aacgcctggt atctttatag tcctgtcggg tttcgccacc tctgacttga gcgtcgattt   3900

ttgtgatgct cgtcaggggg gcggagccta tggaaaaacg ccagcaacgc ggccttttta   3960

cggttcctgg ccttttgctg gccttttgct cacatgttct ttcctgcgtt atcccctgat   4020

tctgtggata accgtattac cgcctttgag tgagctgata ccgctcgccg cagccgaacg   4080

accgagcgca gcgagtcagt gagcgaggaa gcggaaga                           4118
```

<210> SEQ ID NO 2
<211> LENGTH: 1002
<212> TYPE: DNA
<213> ORGANISM: Artificial Sequence
<220> FEATURE:
<223> OTHER INFORMATION: TCTP promoter

<400> SEQUENCE: 2

```
cgtgcaggtg tacagattga aggaaacaat ggagatatct ttggcagttg aaaaccgtgt     60

tcgaatcatg cttttctact ctccaactga gacgaaattt atagcgccat ctcgcttctg    120

actaccaggc ttaggaaggc ctcatcacaa gctggatcgg ttcgaattaa gcaggcactg    180

aagccaagct tgcaagacag ccacctttta attctctcaa aacactttct caattcagcc    240

cggtaaatat gccgattcac agcggccaag atagagggga ggttagcaag aatgttgcga    300
```

-continued

```
tccctcccca gtcgttgcct cgcacacaac ctaggacttc acctttccat ggaaaattga    360

gaagtgaata ttggttttct tacggcatat cagatgaaat catgacccct aaacatgaag    420

agctgcaggc aaaacacctg ctctggacga gcacgatgaa atctcgagaa cccgccgtac    480

ttcagttgat cccgcatgat gacggccgcc attgaaataa gccacctcac tttattctag    540

caccgatttc caccgttgtg agggccgaac gaggacaatt tcgtgcgaaa caagcacgaa    600

cgcgcacacg attagtagga cagacgagca gatcgatggc atgcggcacg gtctcgcgtt    660

ctcggcgacc aggacaacgg agcagaggga ggcctgccga gttccgaggg gcattttagt    720

ccaaaattgt gttgacacgt gaacaagtgg cttgaaaaga ggaaggaaat gcctgggttt    780

cccttcgaga gcgggaactc gcttgtgcgt catcctagct acccatggtc cctttgtggg    840

ggaggctgtt tcgtcctacc gaatgtgtgg cgctccatgc atcttctgcc tcccaaacca    900

ccaacatgag cacgcgaagg aaggagaaaa aagtggccgc aacgttctct tctcatattt    960

attgtctcat cacaaacata ggtacataat acaacaatca tg                      1002
```

<210> SEQ ID NO 3
<211> LENGTH: 1995
<212> TYPE: DNA
<213> ORGANISM: Artificial Sequence
<220> FEATURE:
<223> OTHER INFORMATION: Gene encoding LAR1

<400> SEQUENCE: 3

```
atgagcaaca tccttgccgc aggggactac gacatgcaca gaagtagcga tgtggaactt     60

aagcaagagg cgtcagccaa catgaaatca aacgcccagg ttggcctgca tccgtcacag    120

aatcagcagc ttctgcaaca acaagtgcag cagccgcagg gacaggagga gagggggccg    180

aagacagcga cgccaccatg tctatcagag ggaagatata cctcatttct ggctccgctg    240

aaatcactga cctccccogt ggcgtcttcg gtgttcgagg cggacgcgaa gcagcagcaa    300

ctcttgaaag attccctcac cgcagacctt aaactgctct tgcacgagtt tgaacgcttc    360

cagcaagcga cagcattagt gtcgagagag ggctcgaaag aggtggaggc aatggagcgg    420

gcggcgaaag tggaattctt cctaggctac atcggaaagg tgcttcagga acttgccggc    480

gccgacgcac cgaagctcca ggaattagag gttcggatca agaccagcct ccttccattg    540

aaggggcaag tggtgaacaa gcttgcatct tccctgctct cgtcctccgc cctcggtggt    600

ctgcagcatg agccttcctc ctccgcatcc atcccgtcgc cttcctcttc tccttcctcc    660

tcatgcagca cccacaccac tccccccatc tcccccgtat caggggagaa gatgacagtc    720

caggatgatg gccggaggga gaggacgcat ccgacggccg ccgcgctcat gccctccgtg    780

cgagtccaac gcctcgacag ctcctccagt ggcgccacca cctgctcgga gaactccgag    840

gaggggcgcg gacagcttga cgatatggag tgcctgagcc tgctcatgga ggaagacggc    900

cagggactgg ggaggccaca ggacaggacg gcgggcggga gggagtgggg cctgggcccc    960

gacgaggacg tgacggacgc ggccagcctg gtgtcggagg aaagcagcaa cgtcttcgct   1020

ccctcgcccg gggaggcgtc ggagatgctg gagacgatca gcagggggct gggtctgggg   1080

caaaagaggc tggccttgtc ggagggcagc acgggcagcc tgggcttggc ctcagcgtcc   1140

ttcacctcgg ttgagagcat gcagcagctc aagagggcgc gcagcaccgt gattcccagc   1200

atcagcagca atagcatcag caccaccacc accagcagcg tgagcatcgg ccatggaagc   1260

agcgaggttt cggaaccctc catgtccgtt gcgagcgcgg agaagcctca ggtgcgacag   1320
```

```
gtcgagtatc agtgcggggt ctgtgcggaa tcgtacagcg ctgccgcctc cctgaacccc   1380

tggtgggcgc tggagaagca ggagtgccca caatgcaaga agctgcagat tcctcggatc   1440

gacattaacc tgccggccaa caccatggac tatcaccccg ccctgctcgc ggaggagggg   1500

gacgacgacg acgaggaaga ggggctgggc ctgggaggga gcggattggt ccctggggaa   1560

gagtttcggg ggatggggaa gggaggggag gactcggcgg tcggcggcgg gataggcgtc   1620

ccggaggagg aggacgggca ggccttctcc ccggcgcaag cctcgcagat attggagttg   1680

atgtcgcacg cccggacctg tcccggccac caccactcgg aggcccaccg cgcggtgtgt   1740

acctccacca agtacctgat gctgcatgtg agggactgcg acgggaagac cctggacggg   1800

gaggcctgtg gcttctcctg gtgccgccct tgcaagcacc tgctgggtca cctggtgcgt   1860

tgttatgagt cggagcagtg cagcatttgt cgtccccaga agcgtgagcc gtgcgaggaa   1920

gcggtcgcgt gcaagaggga gaccagcggg gcggtgaggg agggtgtgta tcgggcactg   1980

acgagcttgt gctaa                                                    1995
```

```
<210> SEQ ID NO 4
<211> LENGTH: 664
<212> TYPE: PRT
<213> ORGANISM: Nannochloropsis gaditana

<400> SEQUENCE: 4

Met Ser Asn Ile Leu Ala Ala Gly Asp Tyr Asp Met His Arg Ser Ser
1               5                   10                  15

Asp Val Glu Leu Lys Gln Glu Ala Ser Ala Asn Met Lys Ser Asn Ala
            20                  25                  30

Gln Val Gly Leu His Pro Ser Gln Asn Gln Gln Leu Leu Gln Gln Gln
        35                  40                  45

Val Gln Gln Pro Gln Gly Gln Glu Glu Arg Gly Pro Lys Thr Ala Thr
    50                  55                  60

Pro Pro Cys Leu Ser Glu Gly Arg Tyr Thr Ser Phe Leu Ala Pro Leu
65                  70                  75                  80

Lys Ser Leu Thr Ser Pro Val Ala Ser Ser Val Phe Glu Ala Asp Ala
                85                  90                  95

Lys Gln Gln Gln Leu Leu Lys Asp Ser Leu Thr Ala Asp Leu Lys Leu
            100                 105                 110

Leu Leu His Glu Phe Glu Arg Phe Gln Gln Ala Thr Ala Leu Val Ser
        115                 120                 125

Arg Glu Gly Ser Lys Glu Val Glu Ala Met Glu Arg Ala Ala Lys Val
    130                 135                 140

Glu Phe Phe Leu Gly Tyr Ile Gly Lys Val Leu Gln Glu Leu Ala Gly
145                 150                 155                 160

Ala Asp Ala Pro Lys Leu Gln Glu Leu Glu Val Arg Ile Lys Thr Ser
                165                 170                 175

Leu Leu Pro Leu Lys Gly Gln Val Val Asn Lys Leu Ala Ser Ser Leu
            180                 185                 190

Leu Ser Ser Ser Ala Leu Gly Gly Leu Gln His Glu Pro Ser Ser Ser
        195                 200                 205

Ala Ser Ile Pro Ser Pro Ser Ser Ser Pro Ser Ser Ser Cys Ser Thr
    210                 215                 220

His Thr Thr Pro Pro Ile Ser Pro Val Ser Gly Glu Lys Met Thr Val
225                 230                 235                 240

Gln Asp Asp Gly Arg Arg Glu Arg Thr His Pro Thr Ala Ala Ala Leu
                245                 250                 255
```

```
Met Pro Ser Val Arg Val Gln Arg Leu Asp Ser Ser Ser Ser Gly Ala
            260                 265                 270

Thr Thr Cys Ser Glu Asn Ser Glu Glu Gly Arg Gly Gln Leu Asp Asp
        275                 280                 285

Met Glu Cys Leu Ser Leu Leu Met Glu Glu Asp Gly Gln Gly Leu Gly
    290                 295                 300

Arg Pro Gln Asp Arg Thr Ala Gly Gly Arg Glu Trp Gly Leu Gly Pro
305                 310                 315                 320

Asp Glu Asp Val Thr Asp Ala Ala Ser Leu Val Ser Glu Glu Ser Ser
                325                 330                 335

Asn Val Phe Ala Pro Ser Pro Gly Glu Ala Ser Glu Met Leu Glu Thr
            340                 345                 350

Ile Ser Arg Gly Leu Gly Leu Gly Gln Lys Arg Leu Ala Leu Ser Glu
        355                 360                 365

Gly Ser Thr Gly Ser Leu Gly Leu Ala Ser Ala Ser Phe Thr Ser Val
    370                 375                 380

Glu Ser Met Gln Gln Leu Lys Arg Ala Arg Ser Thr Val Ile Pro Ser
385                 390                 395                 400

Ile Ser Ser Asn Ser Ile Ser Thr Thr Thr Thr Ser Ser Val Ser Ile
                405                 410                 415

Gly His Gly Ser Ser Glu Val Ser Glu Pro Ser Met Ser Val Ala Ser
            420                 425                 430

Ala Glu Lys Pro Gln Val Arg Gln Val Glu Tyr Gln Cys Gly Val Cys
        435                 440                 445

Ala Glu Ser Tyr Ser Ala Ala Ala Ser Leu Asn Pro Trp Trp Ala Leu
    450                 455                 460

Glu Lys Gln Glu Cys Pro Gln Cys Lys Lys Leu Gln Ile Pro Arg Ile
465                 470                 475                 480

Asp Ile Asn Leu Pro Ala Asn Thr Met Asp Tyr His Pro Ala Leu Leu
                485                 490                 495

Ala Glu Glu Gly Asp Asp Asp Asp Glu Glu Glu Gly Leu Gly Leu Gly
            500                 505                 510

Gly Ser Gly Leu Val Pro Gly Glu Glu Phe Arg Gly Met Gly Lys Gly
        515                 520                 525

Gly Glu Asp Ser Ala Val Gly Gly Gly Ile Gly Val Pro Glu Glu Glu
    530                 535                 540

Asp Gly Gln Ala Phe Ser Pro Ala Gln Ala Ser Gln Ile Leu Glu Leu
545                 550                 555                 560

Met Ser His Ala Arg Thr Cys Pro Gly His His His Ser Glu Ala His
                565                 570                 575

Arg Ala Val Cys Thr Ser Thr Lys Tyr Leu Met Leu His Val Arg Asp
            580                 585                 590

Cys Asp Gly Lys Thr Leu Asp Gly Glu Ala Cys Gly Phe Ser Trp Cys
        595                 600                 605

Arg Pro Cys Lys His Leu Leu Gly His Leu Val Arg Cys Tyr Glu Ser
    610                 615                 620

Glu Gln Cys Ser Ile Cys Arg Pro Gln Lys Arg Glu Pro Cys Glu Glu
625                 630                 635                 640

Ala Val Ala Cys Lys Arg Glu Thr Ser Gly Ala Val Arg Glu Gly Val
                645                 650                 655

Tyr Arg Ala Leu Thr Ser Leu Cys
            660
```

<210> SEQ ID NO 5
<211> LENGTH: 1821
<212> TYPE: DNA
<213> ORGANISM: Artificial Sequence
<220> FEATURE:
<223> OTHER INFORMATION: Gene encoding LAR2

<400> SEQUENCE: 5
atgggaatcg gctcagaggc cgtcgctgag gtagggagcg gcacaagcag cgcaccgtgt 60
ggcagcaact cagcaagccc aatgatgcct gtcgtgactg cgagtcagaa cgcggctgag 120
agcgtagcag gctctatgct acctgtaagt tgcgtggcct ccgctgcgat cgcccctcaa 180
acgtcctcga cgacagtggg agtcgctgcc agcgcccctg cagcgtcccc aacgacctcg 240
aagctgcaca aaggcacgtc ctctatgacc caactcggcg aaaccggtcg agagaacacg 300
ggtcgatgga cttgcgagga acatgttttg ttcttaaaag gcttggagat gcacgggaaa 360
ggctggaaaa aaattgccaa attgattaaa acccggaccg ttgtccagat ccggacccac 420
gcgcagaaat atttccaaaa attggcaaaa gcaaagaaaa atgggcacca tggggacatg 480
cttggaatgg aaggcacacg attcggggga aagcgtgtga agttcactgg gaaacggcga 540
gggttggtct acgggagcta cttggtcggt gcggaggcga cttccgcagc catctctcct 600
gccttgcagt cctacatgcc cgggtcttgg gccgggcgtg aggaagggga agcgctgtcg 660
gataaggagg aggacgccgc catcgagaaa gggctttatc gatttctgtc tcccgtcgta 720
ttggacgctg cggcgagtaa cctggacgcg accgcgccgg aagttttacc tccgagcaca 780
ccgggaacag gagtgcacgc caacggggta gtgggggcag acggcgagac gacggaggag 840
gatgggagca gcggcgggga caacgtggac gtcagtgaga cgatcgatga cgctgactcc 900
tcatcgggcg agcccctgcc gcgcttggcc cgcgtcacga atgacatgta tgagcgatgt 960
agtgtgccca cctggtttat gaagggcggg gatatcgaag agctcttggc cgatgctgcc 1020
gcgatcgact ggcgcgagga ctccggggga gacgcggtga aggctgaaga gcgcggggcg 1080
agcattttga acgccaatat tgagagttcc gaccaagctc agagccacag gaatggcgag 1140
aaagtggccg ttccgaatag ggtcgcagcc gtgaaagtgg caggaaacat ttccgcagac 1200
agttcttaca taacatcggg tgccagccaa tgcgtcaacc accctcctac gaccaacact 1260
atcgatggca agcgcagcaa catgaattcg gggcagtcgc tgccaaccgc gaatggacgg 1320
aacggtgcag cctcaggacg atgcgtcaca gggcgtggac agcagcaaaa gaaaaagcag 1380
ccaaaaacac aagaatcggg gaaccacggc aagcagcaat tagtgaacaa gcatagcgcc 1440
cctacgggag acatgttcca gtcaaaggca ggcgctggca cgatcgtcct tcaaggtgat 1500
atcaactgct ttgcatcttt ggacccgcac catgttgagc tgaaggagga gcattcccac 1560
cacgagctac gtttggaaga gttgcagcaa agcggcgtca acgatgacac gttcgcacac 1620
atggatttct tggcgaacga cgaggcgccc gtggaccatc acgcaggcca ccttcacacc 1680
atttctacgc acgatgacgt gcatagtcat gccgaccatg acgttcatat gcgcaactat 1740
gacgtctttt ggaaagatac ggtacctgac ggcgaccatg gcttgctgct cgatgatttt 1800
gacggcggaa tcgaattttg a 1821

<210> SEQ ID NO 6
<211> LENGTH: 606
<212> TYPE: PRT
<213> ORGANISM: Nannochloropsis gaditana

<400> SEQUENCE: 6

-continued

```
Met Gly Ile Gly Ser Glu Ala Val Ala Glu Val Gly Ser Gly Thr Ser
1               5                   10                  15

Ser Ala Pro Cys Gly Ser Asn Ser Ala Ser Pro Met Met Pro Val Val
            20                  25                  30

Thr Ala Ser Gln Asn Ala Ala Glu Ser Val Ala Gly Ser Met Leu Pro
        35                  40                  45

Val Ser Cys Val Ala Ser Ala Ala Ile Ala Pro Gln Thr Ser Ser Thr
    50                  55                  60

Thr Val Gly Val Ala Ala Ser Ala Pro Ala Ala Ser Pro Thr Thr Ser
65                  70                  75                  80

Lys Leu His Lys Gly Thr Ser Ser Met Thr Gln Leu Gly Glu Thr Gly
                85                  90                  95

Arg Glu Asn Thr Gly Arg Trp Thr Cys Glu Glu His Val Leu Phe Leu
            100                 105                 110

Lys Gly Leu Glu Met His Gly Lys Gly Trp Lys Lys Ile Ala Lys Leu
        115                 120                 125

Ile Lys Thr Arg Thr Val Val Gln Ile Arg Thr His Ala Gln Lys Tyr
    130                 135                 140

Phe Gln Lys Leu Ala Lys Ala Lys Lys Asn Gly His His Gly Asp Met
145                 150                 155                 160

Leu Gly Met Glu Gly Thr Arg Phe Gly Gly Lys Arg Val Lys Phe Thr
                165                 170                 175

Gly Lys Arg Arg Gly Leu Val Tyr Gly Ser Tyr Leu Val Gly Ala Glu
            180                 185                 190

Ala Thr Ser Ala Ala Ile Ser Pro Ala Leu Gln Ser Tyr Met Pro Gly
        195                 200                 205

Ser Trp Ala Gly Arg Glu Glu Gly Glu Ala Leu Ser Asp Lys Glu Glu
    210                 215                 220

Asp Ala Ala Ile Glu Lys Gly Leu Tyr Arg Phe Leu Ser Pro Val Val
225                 230                 235                 240

Leu Asp Ala Ala Ala Ser Asn Leu Asp Ala Thr Ala Pro Glu Val Leu
                245                 250                 255

Pro Pro Ser Thr Pro Gly Thr Gly Val His Ala Asn Gly Val Val Gly
            260                 265                 270

Ala Asp Gly Glu Thr Thr Glu Glu Asp Gly Ser Ser Gly Gly Asp Asn
        275                 280                 285

Val Asp Val Ser Glu Thr Ile Asp Asp Ala Asp Ser Ser Ser Gly Glu
    290                 295                 300

Pro Leu Pro Arg Leu Ala Arg Val Thr Asn Asp Met Tyr Glu Arg Cys
305                 310                 315                 320

Ser Val Pro Thr Trp Phe Met Lys Gly Gly Asp Ile Glu Glu Leu Leu
                325                 330                 335

Ala Asp Ala Ala Ala Ile Asp Trp Arg Glu Asp Ser Gly Gly Asp Ala
            340                 345                 350

Val Lys Ala Glu Glu Arg Gly Ala Ser Ile Leu Asn Ala Asn Ile Glu
        355                 360                 365

Ser Ser Asp Gln Ala Gln Ser His Arg Asn Gly Glu Lys Val Ala Val
    370                 375                 380

Pro Asn Arg Val Ala Ala Val Lys Val Ala Gly Asn Ile Ser Ala Asp
385                 390                 395                 400

Ser Ser Tyr Ile Thr Ser Gly Ala Ser Gln Cys Val Asn His Pro Pro
                405                 410                 415
```

-continued

```
Thr Thr Asn Thr Ile Asp Gly Lys Arg Ser Asn Met Asn Ser Gly Gln
            420                 425                 430

Ser Leu Pro Thr Ala Asn Gly Arg Asn Gly Ala Ala Ser Gly Arg Cys
        435                 440                 445

Val Thr Gly Arg Gly Gln Gln Gln Lys Lys Lys Gln Pro Lys Thr Gln
    450                 455                 460

Glu Ser Gly Asn His Gly Lys Gln Gln Leu Val Asn Lys His Ser Ala
465                 470                 475                 480

Pro Thr Gly Asp Met Phe Gln Ser Lys Ala Gly Ala Gly Thr Ile Val
                485                 490                 495

Leu Gln Gly Asp Ile Asn Cys Phe Ala Ser Leu Asp Pro His His Val
            500                 505                 510

Glu Leu Lys Glu Glu His Ser His His Glu Leu Arg Leu Glu Glu Leu
        515                 520                 525

Gln Gln Ser Gly Val Asn Asp Asp Thr Phe Ala His Met Asp Phe Leu
    530                 535                 540

Ala Asn Asp Glu Ala Pro Val Asp His His Ala Gly His Leu His Thr
545                 550                 555                 560

Ile Ser Thr His Asp Asp Val His Ser His Ala Asp His Asp Val His
                565                 570                 575

Met Arg Asn Tyr Asp Val Phe Trp Lys Asp Thr Val Pro Asp Gly Asp
            580                 585                 590

His Gly Leu Leu Leu Asp Asp Phe Asp Gly Gly Ile Glu Phe
        595                 600                 605


<210> SEQ ID NO 7
<211> LENGTH: 2241
<212> TYPE: DNA
<213> ORGANISM: Artificial Sequence
<220> FEATURE:
<223> OTHER INFORMATION: LAR1 ortholog

<400> SEQUENCE: 7

atgtcctccc ccaagaacat tctggccccc gcaagcttgt ccctaaacaa ttacaataaa     60

cccagccacg atctcggcag cccaaagacg caacaccatc accatggcct gcatcatcag    120

caccagcaca agcagcagta ccagcaccaa cagcaactgc agcacgccca tgttctcggt    180

ggcaaatcag tagccggttc caacaagatc cttcctttca cctcatctat ggatgaagtt    240

aaatatgccg ctggcgggct gatcaagccc gggacgcaag gcctgggcag catgctctct    300

acacccttga cgccctcggc ttctcttatt gcatcgtcgg tggtagaggc cgatgcaaag    360

caacaacaac tgctgaagga ttccctcacc gccgacctca aattgctcct gcacgaattc    420

gaacgcttcc agcaggccac tgcagcagca gcgggaacag gaggcgtggg cgaggaggag    480

gcagctgagc gatcgacgaa agtggagttc tttttgggat acattgagcg agttctccac    540

gatttggcag gggctgacgc atcgaaactg caggatctcg aggtgcggat caagacaagt    600

ctactaccac tcaagggcca ggtggttagc cagcttgcgg cgcaaaataa taactcccct    660

cctccccata aggagcagca gtcatcttgg ttccatcctt cttccacctg ctcctccctc    720

tcctcctctt cttccgtctc cagcgtgcac acaactcctc ctggatctcc cttggcaagg    780

gaggagacgg tgatgagcac ctacggtccc tttacccact cccgcgtcgc agcagcagac    840

gcagtctttc tctcctcttc ctctgctgct tctcggctga tgccgcctgt gagtttccgg    900

agggatcaga gtgacataag tgggattacg tcgtgctcgt catcatcgtc gtcatgcggg    960

ggggaaggag gtgcggggca tatggacgat ttagatttgg agtgttttag cttgataatg   1020
```

-continued

```
gacgaggctg ccgctactgc tccttttact actgcaggta atggtgggaa ggatctgccg   1080

gccaatggct catgtgttga tgatgacatg acggatgctg gctctctaac ttcagaggaa   1140

agcagcgtgt ttgtgtcctc cccccgggag tcctcctctt cgctcagcac tgttagtacg   1200

ggcttggacc caacaagcag caacagtgga aataagcgga ccttgccctt agaatttccc   1260

agcagcagca gcagcagcag cagcagcagt ctttctctgg ccacagcgtc ctccgtatct   1320

acagacactc tgcagcagcc gctcaagcgc gcccgcagcg tcatcctacc caccagcagc   1380

agcagcagca gcagttgtgc tacgcatgca cctccctgcc tcgcctcctc ctccacctcc   1440

tcctcttctt ctttctcttc ccctttctct tcctcttcgg tggcgacagt ggcagcagca   1500

gatgtcagca agcctctcct tcgtcaggtt gagtatcagt gcggtgcttg cgccgacacc   1560

tacaccgctg cctcctccct caatccctgg tgggccctcg agcgacagga gtgtcccaag   1620

tgcaagaagg ttcaagttcc acgcattgac ataaacctgc ctgccaacac catggaatac   1680

cacccggctt tgctcgcgga ggaaggcgat gatgacgatg atgatgaggt gggaggcggg   1740

agggagggag ggatgatgat gatgccgggg ggaggggatg gacatggaca tttggaggaa   1800

agagaggagg gagagacgag tgagaaaggg agcggtggaa gtagcgtact agaggaggac   1860

gaggaagcag tgttgagccc tatgcaagct tcacagctgt tgagtttgtt ggagcatgcg   1920

cggacatgcc cgggcaatca tgctgccgag aaacaccagg ctgtgtgtac gagtgccaag   1980

tatctcatgt tgcatgtgag ggattgtgat ggcaggacgt tagatgggga ggcttgtgga   2040

ttctcgtggt gcaggccttg caaacacttg ctcgggcacc tggtccggtg ttacgaagcc   2100

gagaagtgtc agatctgctg tttctcacac caagaagagg aggagaaagt ggaaaagaag   2160

gtgatgatga gtgtggagga gatgattgag gagaaaggaa tgagggtcga cacctacagg   2220

agcttgacga gcttgagctg a                                              2241
```

```
<210> SEQ ID NO 8
<211> LENGTH: 746
<212> TYPE: PRT
<213> ORGANISM: Nannochloropsis oceanica

<400> SEQUENCE: 8

Met Ser Ser Pro Lys Asn Ile Leu Ala Pro Ala Ser Leu Ser Leu Asn
1               5                   10                  15

Asn Tyr Asn Lys Pro Ser His Asp Leu Gly Ser Pro Lys Thr Gln His
            20                  25                  30

His His His Gly Leu His His Gln His Gln His Lys Gln Gln Tyr Gln
        35                  40                  45

His Gln Gln Gln Leu Gln His Ala His Val Leu Gly Gly Lys Ser Val
    50                  55                  60

Ala Gly Ser Asn Lys Ile Leu Pro Phe Thr Ser Ser Met Asp Glu Val
65                  70                  75                  80

Lys Tyr Ala Ala Gly Gly Leu Ile Lys Pro Gly Thr Gln Gly Leu Gly
                85                  90                  95

Ser Met Leu Ser Thr Pro Leu Thr Pro Ser Ala Ser Leu Ile Ala Ser
            100                 105                 110

Ser Val Val Glu Ala Asp Ala Lys Gln Gln Gln Leu Leu Lys Asp Ser
        115                 120                 125

Leu Thr Ala Asp Leu Lys Leu Leu Leu His Glu Phe Glu Arg Phe Gln
    130                 135                 140

Gln Ala Thr Ala Ala Ala Ala Gly Thr Gly Gly Val Gly Glu Glu Glu
```

-continued 145 150 155 160

Ala Ala Glu Arg Ser Thr Lys Val Glu Phe Phe Leu Gly Tyr Ile Glu
165 170 175

Arg Val Leu His Asp Leu Ala Gly Ala Asp Ala Ser Lys Leu Gln Asp
180 185 190

Leu Glu Val Arg Ile Lys Thr Ser Leu Leu Pro Leu Lys Gly Gln Val
195 200 205

Val Ser Gln Leu Ala Ala Gln Asn Asn Asn Ser Pro Pro Pro His Lys
210 215 220

Glu Gln Gln Ser Ser Trp Phe His Pro Ser Ser Thr Cys Ser Ser Leu
225 230 235 240

Ser Ser Ser Ser Ser Val Ser Ser Val His Thr Thr Pro Pro Gly Ser
245 250 255

Pro Leu Ala Arg Glu Glu Thr Val Met Ser Thr Tyr Gly Pro Phe Thr
260 265 270

His Ser Arg Val Ala Ala Ala Asp Ala Val Phe Leu Ser Ser Ser Ser
275 280 285

Ala Ala Ser Arg Leu Met Pro Pro Val Ser Phe Arg Arg Asp Gln Ser
290 295 300

Asp Ile Ser Gly Ile Thr Ser Cys Ser Ser Ser Ser Ser Ser Cys Gly
305 310 315 320

Gly Glu Gly Gly Ala Gly His Met Asp Asp Leu Asp Leu Glu Cys Phe
325 330 335

Ser Leu Ile Met Asp Glu Ala Ala Ala Thr Ala Pro Phe Thr Thr Ala
340 345 350

Gly Asn Gly Gly Lys Asp Leu Pro Ala Asn Gly Ser Cys Val Asp Asp
355 360 365

Asp Met Thr Asp Ala Gly Ser Leu Thr Ser Glu Glu Ser Ser Val Phe
370 375 380

Val Ser Ser Pro Arg Glu Ser Ser Ser Ser Leu Ser Thr Val Ser Thr
385 390 395 400

Gly Leu Asp Pro Thr Ser Ser Asn Ser Gly Asn Lys Arg Thr Leu Pro
405 410 415

Leu Glu Phe Pro Ser Ser Ser Ser Ser Ser Ser Ser Ser Ser Leu Ser
420 425 430

Leu Ala Thr Ala Ser Ser Val Ser Thr Asp Thr Leu Gln Gln Pro Leu
435 440 445

Lys Arg Ala Arg Ser Val Ile Leu Pro Thr Ser Ser Ser Ser Ser Ser
450 455 460

Ser Cys Ala Thr His Ala Pro Pro Cys Leu Ala Ser Ser Ser Thr Ser
465 470 475 480

Ser Ser Ser Ser Phe Ser Ser Pro Phe Ser Ser Ser Ser Val Ala Thr
485 490 495

Val Ala Ala Ala Asp Val Ser Lys Pro Leu Leu Arg Gln Val Glu Tyr
500 505 510

Gln Cys Gly Ala Cys Ala Asp Thr Tyr Thr Ala Ala Ser Ser Leu Asn
515 520 525

Pro Trp Trp Ala Leu Glu Arg Gln Glu Cys Pro Lys Cys Lys Lys Val
530 535 540

Gln Val Pro Arg Ile Asp Ile Asn Leu Pro Ala Asn Thr Met Glu Tyr
545 550 555 560

His Pro Ala Leu Leu Ala Glu Glu Gly Asp Asp Asp Asp Asp Asp Glu
565 570 575

```
Val Gly Gly Gly Arg Glu Gly Gly Met Met Met Met Pro Gly Gly Gly
            580                 585                 590

Asp Gly His Gly His Leu Glu Glu Arg Glu Glu Gly Glu Thr Ser Glu
        595                 600                 605

Lys Gly Ser Gly Gly Ser Ser Val Leu Glu Glu Asp Glu Glu Ala Val
    610                 615                 620

Leu Ser Pro Met Gln Ala Ser Gln Leu Leu Ser Leu Leu Glu His Ala
625                 630                 635                 640

Arg Thr Cys Pro Gly Asn His Ala Ala Glu Lys His Gln Ala Val Cys
                645                 650                 655

Thr Ser Ala Lys Tyr Leu Met Leu His Val Arg Asp Cys Asp Gly Arg
            660                 665                 670

Thr Leu Asp Gly Glu Ala Cys Gly Phe Ser Trp Cys Arg Pro Cys Lys
        675                 680                 685

His Leu Leu Gly His Leu Val Arg Cys Tyr Glu Ala Glu Lys Cys Gln
    690                 695                 700

Ile Cys Cys Phe Ser His Gln Glu Glu Glu Glu Lys Val Glu Lys Lys
705                 710                 715                 720

Val Met Met Ser Val Glu Glu Met Ile Glu Glu Lys Gly Met Arg Val
                725                 730                 735

Asp Thr Tyr Arg Ser Leu Thr Ser Leu Ser
            740                 745


<210> SEQ ID NO 9
<211> LENGTH: 77
<212> TYPE: PRT
<213> ORGANISM: Nannochloropsis gaditana

<400> SEQUENCE: 9

Ala Ser Gln Ile Leu Glu Leu Met Ser His Ala Arg Thr Cys Pro Gly
1               5                   10                  15

His His His Ser Glu Ala His Arg Ala Val Cys Thr Ser Thr Lys Tyr
            20                  25                  30

Leu Met Leu His Val Arg Asp Cys Asp Gly Lys Thr Leu Asp Gly Glu
        35                  40                  45

Ala Cys Gly Phe Ser Trp Cys Arg Pro Cys Lys His Leu Leu Gly His
    50                  55                  60

Leu Val Arg Cys Tyr Glu Ser Glu Gln Cys Ser Ile Cys
65                  70                  75


<210> SEQ ID NO 10
<211> LENGTH: 77
<212> TYPE: PRT
<213> ORGANISM: Nannochloropsis oceanica

<400> SEQUENCE: 10

Ala Ser Gln Leu Leu Ser Leu Leu Glu His Ala Arg Thr Cys Pro Gly
1               5                   10                  15

Asn His Ala Ala Glu Lys His Gln Ala Val Cys Thr Ser Ala Lys Tyr
            20                  25                  30

Leu Met Leu His Val Arg Asp Cys Asp Gly Arg Thr Leu Asp Gly Glu
        35                  40                  45

Ala Cys Gly Phe Ser Trp Cys Arg Pro Cys Lys His Leu Leu Gly His
    50                  55                  60

Leu Val Arg Cys Tyr Glu Ala Glu Lys Cys Gln Ile Cys
65                  70                  75
```

<210> SEQ ID NO 11
<211> LENGTH: 671
<212> TYPE: PRT
<213> ORGANISM: Nannochloropsis CCMP 1179

<400> SEQUENCE: 11

Met Asp Glu Val Lys Tyr Ala Ala Gly Gly Leu Ile Lys Pro Gly Thr
1 5 10 15

Gln Gly Leu Gly Ser Met Leu Ser Thr Pro Leu Thr Pro Ser Ala Ser
20 25 30

Leu Ile Ala Ser Ser Val Val Glu Ala Asp Ala Lys Gln Gln Gln Leu
35 40 45

Leu Lys Asp Ser Leu Thr Ala Asp Leu Lys Leu Leu Leu His Glu Phe
50 55 60

Glu Arg Phe Gln Gln Ala Thr Ala Ala Ala Ala Gly Thr Gly Gly Val
65 70 75 80

Gly Glu Glu Glu Ala Ala Glu Arg Ser Thr Lys Val Glu Phe Phe Leu
85 90 95

Gly Tyr Ile Glu Arg Val Leu His Asp Leu Ala Gly Ala Asp Ala Ser
100 105 110

Lys Leu Gln Asp Leu Glu Val Arg Ile Lys Thr Ser Leu Leu Pro Leu
115 120 125

Lys Gly Gln Val Val Ser Gln Leu Ala Ala Gln Asn Asn Asn Ser Pro
130 135 140

Pro Pro His Lys Glu Gln Gln Ser Ser Trp Phe His Pro Ser Ser Thr
145 150 155 160

Cys Ser Ser Leu Ser Ser Ser Ser Ser Val Ser Ser Val His Thr Thr
165 170 175

Pro Pro Gly Ser Pro Leu Ala Arg Glu Glu Thr Val Met Ser Thr Tyr
180 185 190

Gly Pro Phe Thr His Ser Arg Val Ala Ala Ala Asp Ala Val Phe Leu
195 200 205

Ser Ser Ser Ser Ala Ala Ser Arg Leu Met Pro Pro Val Ser Phe Arg
210 215 220

Arg Asp Gln Ser Asp Ile Ser Gly Ile Thr Ser Cys Ser Ser Ser Ser
225 230 235 240

Ser Ser Cys Gly Gly Glu Gly Gly Ala Gly His Met Asp Asp Leu Asp
245 250 255

Leu Glu Cys Phe Ser Leu Ile Met Asp Glu Ala Ala Ala Thr Ala Pro
260 265 270

Phe Thr Thr Ala Gly Asn Gly Gly Lys Asp Leu Pro Ala Asn Gly Ser
275 280 285

Cys Val Asp Asp Asp Met Thr Asp Ala Gly Ser Leu Thr Ser Glu Glu
290 295 300

Ser Ser Val Phe Val Ser Ser Pro Arg Glu Ser Ser Ser Ser Leu Ser
305 310 315 320

Thr Val Ser Thr Gly Leu Asp Pro Thr Ser Ser Asn Ser Gly Asn Lys
325 330 335

Arg Thr Leu Pro Leu Glu Phe Pro Ser Ser Ser Ser Ser Ser Ser Ser
340 345 350

Ser Ser Ser Leu Ser Leu Ala Thr Ala Ser Ser Val Ser Thr Asp Thr
355 360 365

Leu Gln Gln Pro Leu Lys Arg Ala Arg Ser Val Ile Leu Pro Thr Ser

```
    370                 375                 380

Ser Ser Ser Ser Ser Ser Cys Ala Thr His Ala Pro Pro Cys Leu Ala
385                 390                 395                 400

Ser Ser Ser Thr Ser Ser Ser Ser Ser Phe Ser Ser Pro Phe Ser Ser
                405                 410                 415

Ser Ser Val Ala Thr Val Ala Ala Ala Asp Val Ser Lys Pro Leu Leu
            420                 425                 430

Arg Gln Val Glu Tyr Gln Cys Gly Ala Cys Ala Asp Thr Tyr Thr Ala
        435                 440                 445

Ala Ser Ser Leu Asn Pro Trp Trp Ala Leu Glu Arg Gln Glu Cys Pro
    450                 455                 460

Lys Cys Lys Lys Val Gln Val Pro Arg Ile Asp Ile Asn Leu Pro Ala
465                 470                 475                 480

Asn Thr Met Glu Tyr His Pro Ala Leu Leu Ala Glu Glu Gly Asp Asp
                485                 490                 495

Asp Asp Asp Asp Glu Val Gly Gly Gly Arg Glu Gly Gly Met Met Met
            500                 505                 510

Met Pro Gly Gly Gly Asp Gly His Gly His Val Glu Glu Arg Glu Glu
        515                 520                 525

Gly Glu Thr Ser Glu Lys Gly Ser Gly Gly Ser Ser Val Leu Glu Glu
    530                 535                 540

Asp Glu Glu Ala Val Leu Ser Pro Met Gln Ala Ser Gln Leu Leu Ser
545                 550                 555                 560

Leu Leu Glu His Ala Arg Thr Cys Pro Gly Asn His Ala Ala Glu Lys
                565                 570                 575

His Gln Ala Val Cys Thr Ser Ala Lys Tyr Leu Met Leu His Val Arg
            580                 585                 590

Asp Cys Asp Gly Arg Thr Leu Asp Gly Glu Ala Cys Gly Phe Ser Trp
        595                 600                 605

Cys Arg Pro Cys Lys His Leu Leu Gly His Leu Val Arg Cys Tyr Glu
    610                 615                 620

Ala Glu Lys Cys Gln Ile Cys Cys Phe Ser His Gln Glu Glu Glu Glu
625                 630                 635                 640

Lys Val Glu Lys Lys Val Met Met Ser Val Glu Glu Met Ile Glu Glu
                645                 650                 655

Lys Gly Met Arg Val Asp Thr Tyr Arg Ser Leu Thr Ser Leu Ser
            660                 665                 670


<210> SEQ ID NO 12
<211> LENGTH: 787
<212> TYPE: PRT
<213> ORGANISM: Ectocarpus siliculosus

<400> SEQUENCE: 12

Met Leu Ala Gln Leu Ala Gln Gln Gln Gln Gln Ser Ser Pro Ser Thr
1               5                   10                  15

Ala Ala Thr Ala Thr Pro Ser Thr Glu Thr Ile Gly Thr Asp Ala Gly
            20                  25                  30

Gly Asn Thr Pro Pro Pro Pro Ser Gly Ser Leu Phe Leu Gly Gly Val
        35                  40                  45

Gly Gly Gly Lys Asp Gly Ala Thr Ala Val Ser Asp Gly Trp Val Val
    50                  55                  60

Gly Ser Pro Ser Pro Thr Leu Pro Pro Ser Ser Ser Asn Glu Ser Gly
65                  70                  75                  80
```

-continued

```
Gly Gly Gly Gly Gly Gly Gly Arg Val Asn Ile Ser Thr Cys Asp Ser
                85                  90                  95

Gly Gly Gln Leu Ser Gly Thr Thr Ser Ser Ala Ser Leu Pro Arg Ala
            100                 105                 110

Cys Ser Ser Leu Ser Phe Ala Asp Leu Gly Asp Leu Cys Gly Asp Gln
        115                 120                 125

Glu Gly Gly Asp Val Phe Leu Val Gly Gly Glu Asp Cys Asp Asp Asp
    130                 135                 140

Ala His Gly Ser Gly Ile Gly Leu Asp Leu Tyr Asp Leu Gly Gln Gly
145                 150                 155                 160

Gly Lys Asp Pro Phe Leu Pro Glu Gly Gln Gln Arg Ala Gly Arg Trp
                165                 170                 175

Ser Ser Ile Ser Thr Arg Ser Ser Ser Ser Thr Ala Ser Thr Asp Gly
            180                 185                 190

Glu Glu Leu Ser Asp Asp Ser Leu Ser Val Asp Ala Asp Cys Ser Gly
        195                 200                 205

Ser Ser Ser Thr Pro Cys Ser Pro Ser Ala Val Ser Ser Gly Glu Pro
    210                 215                 220

Ser Leu Leu Ala Ala Ala Ala Ala Ala Thr Arg Ala Ala Lys Ala Ile
225                 230                 235                 240

Lys Thr Glu Ala Arg Pro Asp Gly Ser Ala Gly Leu Glu Ala Gly Ala
                245                 250                 255

Val Gln Gln Gly Val Ala Ala Gly Gly Ala Ser Ala Thr Lys Ser Gly
            260                 265                 270

Ile Asp Gln Glu Met Gly Glu Leu Ser Glu Leu Phe Ala Pro Asp Ala
        275                 280                 285

Phe Leu Met Ser Thr Val Leu Asp Thr Glu Met Glu Ala Gly Gly Gly
    290                 295                 300

Gly Ala Ala Arg Ala Gly Ala Ser Gly Ile Glu Val Ser Ile Glu Pro
305                 310                 315                 320

Thr Ala Thr Glu Pro Ser Lys Ala Ser Gln His Ala Ala Ala Ala Val
                325                 330                 335

Gly Pro Arg Pro Thr Thr Ala Ala Gly Ala Ser Ala Val Ala Val Thr
            340                 345                 350

Ala Pro Ala Ala Val Val Lys Met Glu Phe Leu Pro Ala Ala Gly Ala
        355                 360                 365

Ser Ala Pro Ser Pro Ala Ser Pro Pro Ala Pro Thr Ala Ala Ala Ala
    370                 375                 380

Ala Ser Val Leu Pro Ala Pro Ala Ala Val Ala Pro Lys Gln Glu Cys
385                 390                 395                 400

Arg Cys Gly Gln Ala Ala Cys Pro Ser Leu Ile Thr Ala Ala Arg Lys
                405                 410                 415

Arg Pro Val Ala Glu Leu Ser Pro Ser Leu Ser Gly Ala Asp Gly Pro
            420                 425                 430

Ala Pro Leu Ser Met Val Thr Gly Leu Pro Phe His Gln Ser Ser Arg
        435                 440                 445

Gln Arg Lys Arg Gln Arg Ser Leu Ala Pro Val Leu Ser Ala Pro Arg
    450                 455                 460

Thr Val Ser Tyr Glu Cys Ser Leu Cys Lys Glu Ser Tyr Pro Ser Glu
465                 470                 475                 480

Ile Ala Ser Asn Pro Trp Trp Ser Leu Phe Leu His Glu Cys Pro Arg
                485                 490                 495

Cys His Arg Met Gln Ile Pro Arg Val Asp Ala Thr Ser Ala Ala Val
```

500 505 510

Ser Val Asp Tyr Ile His Ala Val Cys Ala Glu Glu Gly Glu Gly Cys
515 520 525

Asp Ser Asp Gly Tyr Gly Ser Glu Ser Cys Ser Asp Ser Asp Asp Asp
530 535 540

Val Thr Asp Asp Gly Arg Glu Arg Glu Gly Ile Ala Ala Phe Asp Thr
545 550 555 560

Asp Ile Ile Ala Gly Asp Ser Gln Ala Gly Cys Lys Glu Gly Arg Leu
565 570 575

Ser Thr Phe Gln Ala Ser Arg Leu Leu Val Leu Met Ser His Ala Arg
580 585 590

Thr Cys Pro Gly His His Ala Asn Pro Lys His Ala Glu Val Cys Arg
595 600 605

Ser Thr Lys Phe Leu Met Leu His Met Arg Asp Cys Thr Gly His Thr
610 615 620

Ala Asn Gly Asp Pro Cys Glu His Arg Trp Cys Arg Pro Cys Lys Ser
625 630 635 640

Leu Leu Ser His Leu Val Arg Cys Pro Asp Pro Asn Thr Cys Arg Ile
645 650 655

Cys Thr Pro Leu Asp Leu Pro Gly Pro Leu Arg Gln Leu Arg Asp Leu
660 665 670

Asn Val Ala Gln Ala Arg His Ala Ser Ala Ala Ala Ala Ala Ala Ala
675 680 685

Ala Ala Thr Thr Ser Thr Thr Ala Pro Ser Ser Ala Ala Val Ala Val
690 695 700

Pro Gly Val Gly Gly Val Pro Ser Ser Leu Ala Ala Ala Ala Ala Pro
705 710 715 720

Ala Ala Ala Ala Arg Val Pro Ser Met Pro Ala Pro Ala Thr Ala Val
725 730 735

Asp Ala Ala Thr Val Lys Ser Glu Glu Met Cys Arg Pro Ala Gly Ala
740 745 750

Ala Thr Ala Met Gly Leu Ala Val Ser Ala Thr Thr Thr Thr Ser Leu
755 760 765

Arg Gln Gln Leu Gln Gln Arg Val Val Gly Gly Ala Gly Gly Val Val
770 775 780

Thr Thr Arg
785

<210> SEQ ID NO 13
<211> LENGTH: 1135
<212> TYPE: PRT
<213> ORGANISM: Thalasiossira pseudonana

<400> SEQUENCE: 13

Met Asp Gly Ser Ser Asp Asp Asn Arg Lys Arg Pro His Pro Ala Ser
1 5 10 15

Asn Ala Asn Asp Val Ala Ser Ser Glu Val Ala Ala Gly Asp Asn Lys
20 25 30

Arg Val Lys Ile Glu Asp Val Gly Gln Ala Ala Ala Ala Val Glu Thr
35 40 45

Gln Asp Val Pro Gln Thr Gln Ala Ser Val Asp Ala Val Ala Ser Ser
50 55 60

Ile Val Pro Thr Thr Gln Pro Gln Pro Leu Thr Gln Glu Ala Val Pro
65 70 75 80

-continued

```
Ala Ala Val Ser Ser Thr Thr Thr Thr Ala Val Val Ser Ser Ser Thr
                85                  90                  95

Gln Ile Ser Ala Gly Glu Ala Ala Ala Leu Thr Ala Ser Lys Thr Ala
            100                 105                 110

Thr Ala Lys Pro Ala Ala Asp Gly Asp Leu Met Pro Ala Ala Leu Leu
        115                 120                 125

Thr Ser Ser Ser Ser Thr Gln Ala Val Ala Pro Ala Thr Gln Ala Gln
    130                 135                 140

Ser Val Thr Pro Ala Val Val Gln Ser Thr Thr Gln His Val Pro Ala
145                 150                 155                 160

Ala Ser Thr Ser Ala Gln Pro Pro Ala Lys Lys Glu Val Lys Pro Ala
                165                 170                 175

Ser Thr Pro Ser Thr Thr Val Val Gln Pro Gln Arg Pro Gln Lys Gln
            180                 185                 190

Arg Ala Pro Ser Pro Pro Pro Pro Leu Lys Ala Leu Thr Phe His His
        195                 200                 205

Leu His Lys Lys Tyr Gly Pro Glu Leu Asp Tyr Met Leu Val Glu Phe
    210                 215                 220

Arg Lys Leu Glu Arg Gln Leu Leu Gly Ala Pro Ile His Ala Ala Ala
225                 230                 235                 240

Ala Ala Ser Ala Ala Pro Lys Ala Gly Gly Ala Ala Ala Ala Glu Val
                245                 250                 255

Lys Pro Lys Val Glu Pro Lys Gly Ser Arg Glu Arg Arg Glu Lys Leu
            260                 265                 270

His Gly Phe Ile Leu His Leu Glu Asp Thr Ile Arg Gln Val Glu Glu
        275                 280                 285

Gly Cys Ala Val Glu Arg Ser Glu Arg Asn Leu Lys Cys Glu Asn Asn
    290                 295                 300

Gly Ser Gly Gly Gly Asn Leu Lys Ser Glu Glu Cys Ala Ala Ser His
305                 310                 315                 320

His Gln Gln Gln Pro Lys Gln Gln Pro Phe Glu Glu Glu Lys Lys Ser
                325                 330                 335

Ser Asp Ala Ser Leu Gln Pro Gln Pro Asn Thr Ala Ser Ala Ala Ser
            340                 345                 350

Ser Ala Ala Thr Ile Ile Ser Thr Pro Asn Asn Asn Thr Gly Glu Ala
        355                 360                 365

Pro Lys Phe Thr Ala Ala Asp Ala Ser Leu Ser Gln Leu Pro Pro Glu
    370                 375                 380

Lys Glu Arg Glu Glu Ser Val Gln Arg Leu Glu Glu His Ile Leu Ala
385                 390                 395                 400

Asn Leu Leu Pro Val Lys Ile Arg Leu Thr Arg Gln Leu Ala Ala Gln
                405                 410                 415

Lys Gly Ala Thr Lys Asn Pro Ile Thr Ala Pro Leu Arg Ala Gly Ser
            420                 425                 430

Val Ala Thr Ala Gly Val Gln Lys Ala Gly Val Ser Ile Ala Glu Ala
        435                 440                 445

Val Glu Ala Lys Arg Lys Ala Gln Glu Glu Arg Leu Leu Gln Gln Gln
    450                 455                 460

Leu Val Gln Lys Ser Ser Val Pro Val Ser Lys Asp Ile Pro Ser Gln
465                 470                 475                 480

Phe Gly Lys Pro Ile Gly His Gly Ser Ser Ser Leu Thr Ala Arg Leu
                485                 490                 495

His Gly Gly Val Leu Gly Ala Ser Gly Ser Gly Ala Ala Ala Ala Ser
```

```
            500                 505                 510

Pro Ala Asn Ala Ala Ser Gly Ala Ala Ala Ser Gly Ala Ala Thr Pro
        515                 520                 525

Ser Lys Arg Arg Ile Leu Tyr Ala Gly Val Ala Pro Gly Ser Thr Gln
    530                 535                 540

Val Pro Ser Ser Val His Ala Val Ser Gly Val His Pro Gly Met Val
545                 550                 555                 560

Gly Ala Asp Ala Ala Lys Ala Val Val Val Ala Glu Glu Glu Arg Lys
                565                 570                 575

Arg Leu Lys Tyr Leu Glu Glu Ser Ala Ala Arg Val Ala Gly Val Ala
            580                 585                 590

Pro Ala Gly Gly Gly Ala Leu Asp Arg Lys Pro Ala Ser Arg Pro Thr
        595                 600                 605

Ala Ile Glu Ala Ala Ala Pro Lys Pro Pro Glu Gly Pro Ala Thr Met
    610                 615                 620

Ala Ala Arg Ala Arg Ala Ile Ala Leu Ala Ala Thr Asn Asn Asn Thr
625                 630                 635                 640

Gly Pro Ser Ala Ala Ser Lys Val Ser Arg Pro Asn Gln Gln Ile Pro
                645                 650                 655

Gly Ile Thr Ala Lys Gln Leu Gln Gln Gln His Leu Lys Lys Val Ser
            660                 665                 670

Pro Leu Ala Ala Ala Thr Ala Ala Asn Gln Met Ala His Leu Gly Met
        675                 680                 685

Lys Pro Val Lys Pro Lys Lys Pro His Leu Ala Pro Asp Phe Asn Asp
    690                 695                 700

Pro Ala Leu Thr Ala Thr Gln Gln Asn Glu Leu Arg Leu Lys Glu Ala
705                 710                 715                 720

Arg Trp Arg Gln Arg Lys Arg Arg Lys Glu Arg Arg Arg Lys Arg Ser
                725                 730                 735

Gly Val Val Val Asp His Ala Ala Met Val Thr Gln His Ala Gln Ser
            740                 745                 750

Met Gln Glu Pro Asn Val His Ala Ser Ser Ser Asn Asp Ala Val Pro
        755                 760                 765

Ala Gln Pro Met Val Leu Arg Val Asn Lys Asn Gly Ala Tyr Gly Pro
    770                 775                 780

Arg Thr Val Glu Tyr Val Cys Ala Val Cys Asn Glu Gly Tyr Val Ser
785                 790                 795                 800

Thr Cys Glu Met Asn Pro Trp Trp Ala Leu Ile Asn His Glu Cys Pro
                805                 810                 815

Lys Cys Gly Lys Asn Gln Ile Pro Arg Leu Asp Ile Ser Ala Pro Asn
            820                 825                 830

Asn Val Ile Glu Tyr His Pro Ala Leu Leu Val Gln Glu Asp Gly Lys
        835                 840                 845

Pro Val Ser Ala Pro Val Ser Asn Gly Gly Asp Ser Ser Ser Val Gln
    850                 855                 860

Met Gln Tyr Leu Pro Arg His Leu Ala Lys Lys Ser Ser Leu Ser Asp
865                 870                 875                 880

Ser Glu Val Ser Gln Thr Asp Glu Ser Asp Gly Glu Gly Gly Thr Glu
                885                 890                 895

Glu Tyr Phe Asp Glu Ser Ser Asp Asp Glu Glu Ser Val Asn Lys Asn
            900                 905                 910

Ala Leu Asp Ser Phe Ala Lys Glu Glu Arg Ala Glu Arg Glu Asp Tyr
        915                 920                 925
```

```
Gly Phe Glu Phe Lys Gly Glu Thr Leu Ser Asp Asp Gln Ala Lys Arg
    930                 935                 940

Leu Leu Ile Leu Ile Glu His Ala Ser Ile Cys Pro Gly Arg His Arg
945                 950                 955                 960

Ser Ala Lys His Arg Asn Val Cys His Ser Thr Lys Tyr Leu Met Leu
                965                 970                 975

His Val Arg Asp Cys Pro Gly Leu Leu Ser Asn Gly Asp Val Cys Pro
            980                 985                 990

Phe Pro Trp Cys Arg Lys Thr Lys  His Leu Leu Tyr His  Leu Val Ser
        995                 1000                 1005

Cys Glu  Lys Ser Asn Asp Gly  Lys Glu Cys Gly Ile  Cys Cys Pro
    1010                 1015                 1020

Lys Asn  Leu Ser Ser Asn Leu  Ser Glu Leu Val Gly  Leu Asn Lys
    1025                 1030                 1035

His Arg  Arg Lys Gln Phe Val  Asp Arg Thr Lys Ala  Ile Val Ala
    1040                 1045                 1050

Ala Ala  Lys Arg Gln Gln Leu  Ala Ala Ala Arg Ala  Lys Ala Val
    1055                 1060                 1065

Ala Pro  Arg Ala Ala Val Gln  His Gln Tyr Arg Gly  Pro Val Val
    1070                 1075                 1080

Arg Lys  Gly Pro Ile Pro Ala  Ala Thr Thr Tyr Ala  Ala Pro Pro
    1085                 1090                 1095

Pro Ser  Ala Ser Thr Val Ser  Tyr Ala Thr Thr Ser  Arg Gly Thr
    1100                 1105                 1110

His Met  Pro Ser Thr Asn Asn  Pro Ile Ile Gln Ser  Pro Pro Asp
    1115                 1120                 1125

Ala Lys  Thr Ser Asn Gln Phe
    1130                 1135


<210> SEQ ID NO 14
<211> LENGTH: 1148
<212> TYPE: PRT
<213> ORGANISM: Phaeodactylum tricornutum

<400> SEQUENCE: 14

Val Gly Arg Leu Ala Leu Thr Leu Arg Arg Arg Leu Ala Gly Ile Ser
1               5                   10                  15

Ala Ala Glu Pro Leu Ser Ser Val Thr Thr Val Val Phe Gly Leu Ala
            20                  25                  30

Lys Thr Ala Gln Gly Asp Ala Arg Ser Phe Leu Phe Trp Ala Gly Lys
        35                  40                  45

Ala Ala Glu Ile Val Lys Lys Ala Pro Cys Asp Thr Glu Asn Glu Glu
    50                  55                  60

Thr Thr Val Gly Ala Lys Thr Glu Arg Ile Ala Gln His Arg Thr Asp
65                  70                  75                  80

Arg Arg Gln Arg His Val Leu Met Val Thr Met Ala Ile Pro Thr Asn
                85                  90                  95

Val Cys Leu Leu Leu Ser Glu Ile Phe Arg Phe Leu Met Met Glu Met
            100                 105                 110

Glu Glu His Asp Leu Ala Gln Gln Lys Asp Pro Gly Lys Val Ser Ser
        115                 120                 125

Cys Ser Asp Ser Lys Gly Glu Gly His Ala Leu Glu Val Gln Leu Val
    130                 135                 140

Tyr Val Ser Ser Ala Val Gly Phe Arg Val Ser Trp Arg Ser Ala Ser
```

-continued

```
145                 150                 155                 160

Ser Leu Leu Ser Ser Arg Gly Arg Gly Tyr Pro Ile Leu Ser Asp Gly
                165                 170                 175

Cys Gly Ala Arg Ser Gln Ser Thr Asn Glu Ala Val Ser Arg Thr Thr
            180                 185                 190

Asp Ser Ser Asn His Thr Leu Leu Gln Asn Ser Asn Leu Ser Gln Gln
        195                 200                 205

Pro Pro Leu Pro Leu Leu Leu Pro Ala Thr Asp Ser Leu Arg His Pro
    210                 215                 220

Ala Asn Pro Leu Tyr Ser Arg Asn Arg Ser His Asp Thr Asn Ser Ala
225                 230                 235                 240

Ile Gly Val Ser Asp Pro Ala Thr His Thr Ser Arg Ala Met Ser Ser
                245                 250                 255

His Thr Ser Leu Gln Tyr Ser Ser Ser Gly Gly Ile Ala Asn Ile Ser
            260                 265                 270

Thr Thr Thr Asp Pro Pro His Lys Arg Leu Lys Leu Asp His Ala Met
        275                 280                 285

Ser His Thr Ser Leu Gly Asn Pro Ser Leu Ser Tyr His Asp Phe Ala
    290                 295                 300

Ala His Tyr Asp Ser Arg Ser Thr Leu His Thr Ser Ser Thr Met Asp
305                 310                 315                 320

Leu Gly Val Leu Arg Lys Glu Asp Ser Leu Gly Met Met Arg Lys Asp
                325                 330                 335

Gly Asp Asp Glu Asp Asp Glu Asn Asp Gln Asn Asp Pro Ile Ser Ser
            340                 345                 350

Thr Ala Val Arg Gln Ala Thr Val Gln Pro Thr Ala Leu Pro Asn Glu
        355                 360                 365

Ser Ala Lys Pro Thr His Pro Thr Thr Ala Asn Val Ala Thr Thr Asn
    370                 375                 380

Ser Val Ser Ser Ser Asp Ser Leu Arg Asp Leu Ser Ala His Arg Pro
385                 390                 395                 400

Gln His Pro Gln Asn Thr Thr Arg Leu Pro Val Ser Ser Ser Thr Thr
                405                 410                 415

Thr Val Thr Ser Gly Ser Asn Ser Pro Leu Ser Ala Gly Pro Val Ser
            420                 425                 430

Ala Gln Ala Pro Pro Ser Pro Leu Leu Pro Leu Lys Ala Thr Lys Met
        435                 440                 445

Ser His Leu Arg Gln Lys Tyr Met Gln Glu Leu Glu Tyr Met Leu Cys
    450                 455                 460

Glu Phe Gln Lys Leu Glu Arg Gln Leu Leu Gly Ala Lys Ala Thr Thr
465                 470                 475                 480

Ala Glu Ser Ala Gly Ser Arg Glu Arg Arg Glu Lys Leu His Ser Phe
                485                 490                 495

Ile Thr His Leu Ser Asp Thr Ile Gln Asn Ile Gln Thr Gly Cys Gln
            500                 505                 510

Leu Glu Ser Glu Gly Lys Ser Thr Val Gly Glu Ala Ser Lys Gln Asp
        515                 520                 525

Ile Ala Gln Glu Ala Ala Leu Ala Asp Leu Thr Cys Glu Lys Gly Glu
    530                 535                 540

Glu Glu Asn Val Gln Lys Leu Glu Glu His Ile Leu Ala Asn Leu Leu
545                 550                 555                 560

Pro Val Lys Val Arg Leu Lys Lys Gln Leu Ala Ala Gln Gln Gly Ala
                565                 570                 575
```

```
Lys His Asn Pro Ala Gly Met Pro Val Ala Gln Arg Gly Leu Val Ala
            580                 585                 590

Pro Ser Glu Gly Gly Lys Gly Thr Phe Ala Ala Ala Ala Glu Glu Arg
        595                 600                 605

Arg Lys Gln Leu Ala Asp Ala Ala Ala Ala Ala Gln Gly Phe Asp His
    610                 615                 620

Thr His Val Pro Ala Glu Pro Val His Pro Asp Gln Thr Gln Phe Gly
625                 630                 635                 640

Lys Pro Leu Gln Gly Asn Gly Ser Ser Leu Thr Arg Asn Leu His Gly
                645                 650                 655

Ser Thr Leu Gly Ser Ala Ile Lys Val Gly Thr Asp Lys Ser Lys Ile
            660                 665                 670

Leu Phe Ala Gly Leu Ala Ile Gly Ser Ser Gln Val Lys Ser Ser Val
        675                 680                 685

Asn Ala Ala Ser Ser Val His Gln Leu Val Ile Lys Asp Pro Ala Leu
    690                 695                 700

Leu Glu Leu Ala Arg Gln Gln Ser Ala Ser Lys Gln Gln Glu Asp Leu
705                 710                 715                 720

Pro Pro Gln Thr Gln Gln Glu Asp Ser Pro Thr Gln Ser Lys Pro Asn
                725                 730                 735

Ser Leu Leu Pro Pro Ser Ser Ser Glu Pro Asn Asp Ser Pro Glu Asp
            740                 745                 750

Thr Asn Arg Lys Ala Ile Ser Leu Lys Val Ser Pro Ala Val Ala Ser
        755                 760                 765

Ala Ala Ala Leu Ala Ala Ser Glu Gln Pro Asp Ala Val Leu Ser Lys
    770                 775                 780

Ala Pro Pro Ser Arg Leu Asp Asp Val Asp Ala Thr Tyr Pro Asp Met
785                 790                 795                 800

Pro Ser Ala Ala Leu Thr Asp Glu Glu Arg Arg Thr Leu Arg Arg Leu
                805                 810                 815

Lys Arg Arg Lys Lys Arg Arg Lys Arg Lys Ala Glu Ala Thr Pro Val
            820                 825                 830

Thr Ala Ala Ala Thr Ala Ala Pro Val Ile Asn Arg His His Lys Pro
        835                 840                 845

Thr Thr Lys Lys Arg Gly Pro Arg Thr Val Glu Tyr Met Cys Ala Leu
    850                 855                 860

Cys Asn Glu Val Tyr Asn Ser Thr Cys Asp Tyr Asn Pro Trp Trp Ala
865                 870                 875                 880

Leu Ala Gln His Asp Cys Pro Lys Cys Arg Lys Asn Gln Ile Pro Arg
                885                 890                 895

Val Asp Ile Ser Ala Pro Ala Asn Thr Ile Glu Tyr His Pro Ala Leu
            900                 905                 910

Leu Ala His Ala Asp Glu Asn Gly Gly Ser Thr Pro Thr Pro Pro Ala
        915                 920                 925

Ala Ile Val Lys Pro Val Thr Thr Val Ser Ala Pro Val Thr Ser Val
    930                 935                 940

Pro Lys Cys Gly Asn Asp Ser Asp Ser Phe Gly Ser Asp Leu Ser Asp
945                 950                 955                 960

Asp Asp Leu Asp Gly Leu Leu Ser Asp Thr Asp Ser Glu Gly Ser Gly
                965                 970                 975

Glu Ile Gly Met Glu Arg Ile Asp Ala Leu Ser Pro Ala Glu Gln Ala
            980                 985                 990
```

```
Glu Asn Glu Tyr Phe Gly Val Glu  Tyr Lys Gly Pro Lys  Leu Lys Asp
        995                 1000                 1005

Ser Glu  Ala Ala Arg Leu Leu  Ile Leu Met Gly His  Ala Ser Thr
    1010                 1015                 1020

Cys Pro  Cys Lys His Gln Ser  Ile Lys His Arg Glu  Thr Cys Arg
    1025                 1030                 1035

Asn Thr  Lys Trp Met Met Leu  His Val Arg Asp Cys  Pro Gly Thr
    1040                 1045                 1050

Thr Ser  Ser Phe Asp Val Cys  Pro Phe Pro Trp Cys  Arg Lys Val
    1055                 1060                 1065

Lys His  Leu Leu Tyr His Leu  Val Ser Cys Arg Asp  Ala Lys His
    1070                 1075                 1080

Cys Glu  Ile Cys Ser Pro Thr  Lys Leu Asn Gln Asn  Met Ile Leu
    1085                 1090                 1095

Leu Lys  Gly Leu Asn Gln His  Arg Phe Met Gln Tyr  Arg Glu Arg
    1100                 1105                 1110

Leu Ile  Gly Arg Gly Lys Ala  Leu Thr Lys Val Ser  Asn Ser Ala
    1115                 1120                 1125

Pro Lys  Asn Thr Pro Ala Gln  Ala Gln His Lys Thr  Phe Ile Asp
    1130                 1135                 1140

Val Ser  Gln Met Leu
    1145
```

<210> SEQ ID NO 15
<211> LENGTH: 948
<212> TYPE: PRT
<213> ORGANISM: Cyclotella cryptica

<400> SEQUENCE: 15

```
Met Leu Val Glu Phe Lys Lys Leu Glu Arg Gln Leu Leu Gly Ala Pro
1               5                   10                  15

Ile His Gln Gln Gln Asn Pro Pro Lys Ala Glu Pro Lys Gly Ser Arg
            20                  25                  30

Glu Arg Arg Glu Lys Leu His Gly Phe Ile Leu His Leu Glu Asp Thr
        35                  40                  45

Ile Arg Gln Val Glu Glu Gly Cys Ala Leu Glu Lys Arg Glu Glu Gly
    50                  55                  60

Ser Ile Asp Gln Val Val His Gly Ala Ser Gly Ser Leu Ala Asn Asn
65                  70                  75                  80

Gln Gln Glu Glu Val Glu Glu Glu Glu Lys Lys Ser Ser Asp Ala Ser
                85                  90                  95

Leu Gln Gln Pro Gln His Thr Ala Gln Thr Asn Thr Ala Ser Asn Leu
            100                 105                 110

Asn Asn Leu Asn Lys Thr Thr Ser Asn Met Glu Gly Pro Pro Lys Lys
        115                 120                 125

Phe Thr Ala Ala Glu Ala Ala Leu Ser Ser Leu Pro Pro Glu Lys Glu
    130                 135                 140

Arg Glu Glu Ser Val Gln Arg Leu Glu Glu His Ile Leu Ala Asn Leu
145                 150                 155                 160

Leu Pro Val Lys Val Arg Leu Thr Lys Gln Leu Ala Ala Gln Lys Gly
                165                 170                 175

Ala Thr Arg Asn Pro Val Thr Ala Pro Val Arg Ala Gly Ala Ala Asn
            180                 185                 190

Thr Val Ala Gly Gly Thr Ile Ala Glu Ala Val Glu Ala Lys Arg Arg
        195                 200                 205
```

```
Ala Gln Glu Glu Glu Leu Leu Lys Lys Gln Leu Gln Gln Arg Gln Ile
    210                 215                 220

Thr Thr Ser Gln Tyr Gly Lys Pro Ile Gly Gly Ala Gly Ser Ser Leu
225                 230                 235                 240

Thr Ala Arg Leu His Gly Gly Val Leu Gly Ser Asn Ala Pro Ala Ala
                245                 250                 255

Gly Ala Ser Gly Ser Glu Thr Thr Lys Arg Pro Ile Leu Tyr Ala Gly
            260                 265                 270

Val Ala Pro Gly Ser Ser Gln Val Pro Ser Thr Ile Lys Thr Val Ser
        275                 280                 285

Gly Ala His Pro Gly Leu Ile Gly Lys Asp Ala Thr Lys Ala Val Ala
    290                 295                 300

Leu Ala Glu Glu Glu Arg Arg Arg Leu Lys Asn Leu Glu Glu Asn Ala
305                 310                 315                 320

Thr Arg Val Ala Leu Gly Val Ala Ala Lys Pro Ser Pro Ala Ala Ser
                325                 330                 335

Ala Leu Asp Pro Arg Lys Pro Ala Ala Leu Pro Thr Leu Asn Ala Ser
            340                 345                 350

Ala Leu Pro Lys Gln Pro Glu Gly Pro Ala Thr Leu Ala Ala Arg Ala
        355                 360                 365

Arg Ala Val Ala Leu Ala Ala Ala Ser Ser Gly Gly Ala Thr Ser Lys
    370                 375                 380

Ile Ser Arg Pro Asn Gln Gln Phe Pro Thr Arg Ser Leu Gln Gln His
385                 390                 395                 400

His Val Lys Lys Gly Pro Pro Val Met Ala Ala Pro Ala Ala Thr Met
                405                 410                 415

Ala Ala Pro Ala Ala Thr Ile Ala Ala Pro Arg Ala Pro His Ile Asn
            420                 425                 430

Gln Tyr Thr Lys Pro Ser Ala Ala Val Pro Tyr His Ser Val Pro Thr
        435                 440                 445

Pro Pro Met Thr Ala Lys Ser Lys Lys Pro His Ile Ala Pro Asn Phe
    450                 455                 460

Asn Asp Pro Ser Leu Thr Pro Glu Gln Arg Phe Glu Leu Arg Leu Lys
465                 470                 475                 480

Glu Ala Arg Trp Arg Gln Arg Lys Arg Arg Arg Glu Arg Arg Arg Lys
                485                 490                 495

Arg Leu Glu Gly Tyr Leu His Ala Ala Gly Ala Tyr His Ile Val Pro
            500                 505                 510

Leu Ala Val Gln Gln Gln Pro Ser Leu Ser Leu Ser Ser Gln Pro His
        515                 520                 525

Leu Gln Glu Thr Gln Pro Glu Arg Val Ala Ser Thr Val Val Thr Pro
    530                 535                 540

Asn Ala Pro Ala Pro Pro Pro Pro Val Asn Thr Pro Pro Pro Pro Val
545                 550                 555                 560

Thr Ser Ala Ser Arg Pro Lys Lys Asn Gly Ala Tyr Gly Pro Arg Thr
                565                 570                 575

Val Glu Tyr Val Cys Ala Val Cys Asn Glu Thr Tyr Ile Ser Thr Cys
            580                 585                 590

Glu Phe Asn Pro Trp Trp Ala Leu Thr Ser His Asp Cys Pro Lys Cys
        595                 600                 605

Gly Lys Pro Gln Ile Pro Lys Leu Asp Ile Ser Thr Pro Ala Asn Glu
    610                 615                 620
```

Ile Asp Tyr His Pro Ala Leu Leu Ser Gln Glu Asp Asn Ala Lys Pro
625 630 635 640

Gln Ser Ser Ser Val Ser Ala Ser Ala Asn Ala Ser Asn Pro Ala Val
645 650 655

Ala Ala Pro Gln Val Ala Gln Pro Val Gln Tyr Met Pro Lys Pro Pro
660 665 670

Ala His Met Lys Lys Asn Phe Leu Leu Ser Asp Ser Glu Val Ser Leu
675 680 685

Thr Asp Glu Ser Asp Gly Glu Gly Gly Gly Gly Lys Tyr Asp Glu Ser
690 695 700

Ser Glu Glu Glu Asp Thr Ser Tyr Asp Asn Asp Met Asp Ser Val Thr
705 710 715 720

Arg Glu Glu Arg Val Glu Lys Glu Glu Phe Gly Phe Asp Tyr Lys Gly
725 730 735

Glu Val Leu Ser Glu Asp Gln Ala Arg Arg Leu Leu Val Leu Ile Glu
740 745 750

His Ala Ser Ile Cys Pro Gly Arg His Arg Ser Ala Lys His Arg Asn
755 760 765

Val Cys His Ser Thr Lys Tyr Met Met Leu His Val Arg Asp Cys Cys
770 775 780

Gly Leu Leu Ser Asn Gly Asp Val Cys Pro Phe Pro Trp Cys Arg Lys
785 790 795 800

Thr Lys His Leu Leu Tyr His Leu Val Thr Cys Thr Lys Asn Asp Asp
805 810 815

Gly Ser Lys Cys Ser Ile Cys Cys Pro Glu Asn Leu Ser Ser Asn Leu
820 825 830

Met Asp Leu Val Gly Leu Asn Ser Tyr Arg Arg Lys Ile Phe Val Glu
835 840 845

Arg Ala Lys Ala Val Ala Ala Ala Ala Ala Ala Thr Arg His Gln Met
850 855 860

Ala Ile Ala Lys Ala Lys Ala Ala Ala Gln Ser Ser Thr Gln Pro His
865 870 875 880

Val Leu Thr Ser Ser Gln Ile Leu Thr Ala Pro Ser Thr Asn His Asn
885 890 895

Tyr Glu Ser Gln Thr Lys Pro Phe Ala Thr Ala Ser Thr His Val Ala
900 905 910

Thr His Ala Thr Gln Pro Leu Gly Asn Ala Arg Arg Gly Ser Ser Val
915 920 925

Gln Asp Ala Thr Ile Ala Ser Asn Asn Thr Gly Pro His Leu Asp Ser
930 935 940

Glu Val Val Leu
945

<210> SEQ ID NO 16
<211> LENGTH: 549
<212> TYPE: PRT
<213> ORGANISM: Ectocarpus siliculosus

<400> SEQUENCE: 16

Met Val Met Ala Ala Thr Ala Asp Gly Gly Val Cys Glu Ile Lys Met
1 5 10 15

Asp Asp Ser Gly Arg Leu Thr His Ile Trp Trp Gln Thr Arg Glu Gln
20 25 30

Ala Arg Gln Arg Ser Ser Asp Asp Asp Ala Pro Thr Lys Gly Gly Val
35 40 45

-continued

```
Ala Leu Gly Gly Val Gln Ala Ser Pro Asp Ser Glu Val Ser Arg Arg
    50                  55                  60

Leu Asp Leu Leu Met Asp Lys Ser Phe Gly Asp Leu Gln Phe Leu Ser
65                  70                  75                  80

Asp Glu Phe Ala Lys Leu Glu Val Val Val Ala Pro Ala Val Gln Glu
                85                  90                  95

Arg Asp Asp Ser Gly Lys Ala Gly Thr Asp Ser Lys Leu Gly Arg Leu
            100                 105                 110

Arg Phe Phe Thr Thr His Val Arg Arg Thr Met Ala Arg Met Arg Asp
        115                 120                 125

Ala Arg Ser Gly Arg Asp Pro Met Ser Met Ser Gln Leu Ala Leu Leu
    130                 135                 140

Glu Glu His Ile Ala Thr Ser Ile Ala Pro Gly Gly Gly Gly Gly Val
145                 150                 155                 160

Ser Ser Ser Arg Ser Ser Ser Val Ser Ser Ser Met Gly Gly Arg Ala
                165                 170                 175

Gly Ala Glu Glu Leu Val Gly Ala Gly Arg Glu Glu Glu Glu Glu Trp
            180                 185                 190

Ser Val Gly Leu Glu Leu His Asp Glu Ala Phe Gly Ser Gly Gly Ser
        195                 200                 205

Val Ser Leu Gly Leu Val Ser Pro Ala Pro Ala Ser Val Pro Asp Arg
    210                 215                 220

Gly Ala Asp Gly Gly Ile Tyr Asp Pro His Ala Cys Ser Ala Arg Leu
225                 230                 235                 240

Thr Pro Ala Ser Ser Ser Ser Ser Leu Ser Arg Leu Cys Trp Gly Ser
                245                 250                 255

Gly Gly Gly Thr Gly Gly Ser Ala Gly Gly Gly Gly Arg Asp Val Ala
            260                 265                 270

Arg Gly Gly Arg Pro His Arg His Thr Arg Arg Asp His Val Asp Met
        275                 280                 285

Leu Ser Gln Leu Glu Ala Glu Gly Val Phe Ala Ala Asp Asp Ser Tyr
    290                 295                 300

Ser Pro Cys Gly Gly Gly Gly Gly Ser Arg Gly Gly Gly Gly Met Gly
305                 310                 315                 320

Gly Val Ala Phe Ser Pro Glu Pro Arg Glu Val Arg Tyr Gln Cys Gly
                325                 330                 335

Ala Cys Ala Ala Ser Tyr Ala Ala Thr Val Ser Gly Asn Pro Trp Trp
            340                 345                 350

Leu Leu Val Arg Gln Glu Cys Pro Ile Cys His Lys Met Gln Ile Pro
        355                 360                 365

Arg Val Asp Ile Leu Asn Pro Thr Asn Asn Val Glu Ser His Ile Ala
    370                 375                 380

Phe Leu Thr Glu Asn Ala Ser Asp Gly Asp Gly Ser Cys Met Asp Trp
385                 390                 395                 400

Asp Gly Glu Thr Ser Asp Glu Asn Ser Gly Asp Glu Tyr Ser Gly Asp
                405                 410                 415

Glu Arg Gln Gly Leu Ser Ala Gly Gly Ser Met Ser Gly Gly Asp Gly
            420                 425                 430

Ser Gly Leu Gly Pro Thr Leu Asp Ser Asp Gln Ala Ala Lys Leu Leu
        435                 440                 445

Val Leu Met Cys His Ala Arg His Cys Pro Gly Asn His Arg Ser Ala
    450                 455                 460
```

-continued

```
Arg Leu Ala Glu Val Cys Arg Ser Val Lys Phe Leu Met Leu His Leu
465                 470                 475                 480

Arg Asp Cys Asp Gly Lys Thr Arg Asn Gly Asp Pro Cys Pro Met Pro
                485                 490                 495

Trp Cys Glu Pro Cys Met Ser Leu Leu His His Leu Ile Gln Cys Pro
            500                 505                 510

Glu Ser Thr Gly Cys Lys Gly His Glu His Lys Asn Arg Gly Asp Leu
        515                 520                 525

Pro Ser Gln Thr Pro Ser Gly Phe Gly Arg Leu Arg Thr Leu Arg Phe
    530                 535                 540

Ala Ala Val Phe Ser
545


<210> SEQ ID NO 17
<211> LENGTH: 746
<212> TYPE: PRT
<213> ORGANISM: Navicula sp. WT0229

<400> SEQUENCE: 17

Met Glu Glu Pro Leu Val Val Thr Val Lys Arg Glu Asn Ile Asn Val
1               5                   10                  15

Ser Pro Glu Pro Leu Lys Asn Asp Gly Val Val Ser His Asp Glu Ala
            20                  25                  30

Thr Ser Thr Thr Ala Asp Ser Leu Val Ser Glu Ala Ala Pro Leu Lys
        35                  40                  45

Ala Thr Thr Phe Arg His Leu Asn Leu Lys Tyr Leu Ala Glu Leu Glu
    50                  55                  60

Tyr Met Leu Cys Glu Phe Gln Lys Leu Glu Arg Gln Leu Leu Gly Ala
65                  70                  75                  80

Arg Asn Leu Gln Ala Ser Glu Ser Asp Gly Ser Arg Glu Arg Arg Glu
                85                  90                  95

Lys Leu His Ser Phe Ile Leu His Leu Glu Asp Thr Ile Gln Gln Ile
            100                 105                 110

His Ala Gly Cys Glu Thr Glu Gly Lys Ser Thr Glu Thr Thr Gly Leu
        115                 120                 125

Val Lys Pro Ser Asn Glu Lys Lys Glu Glu Glu Ala Val Gln Lys Leu
    130                 135                 140

Glu Glu His Ile Leu Ala Asn Leu Leu Pro Val Lys Val Arg Leu Thr
145                 150                 155                 160

Lys Gln Leu Ala Ala Gln Gln Gly Ala Lys His Asn Pro Ala Ala Met
                165                 170                 175

Pro Val Arg Gly Val Val Ser Glu Ser Ser Lys Glu Thr Asp Thr Ser
            180                 185                 190

Gln Phe Gly Lys Pro Leu Glu Gly Gly Gly Ser Ser Leu Thr Gln Lys
        195                 200                 205

Leu His Gly Arg Thr Leu Gly Ala Glu Gly Arg Ala His Gly His Gly
    210                 215                 220

Val Gly Thr Val His Ser Lys Arg Ala Glu Ala Lys Val Leu Tyr Ala
225                 230                 235                 240

Gly Met Ala Ile Gly Ser Asp Lys His Gln Met Arg Ser Ser Leu Ser
                245                 250                 255

Ala Ala Ser Ser Ala His Arg Leu Leu Leu Gln Gly Lys Asp Val Thr
            260                 265                 270

Asp Lys Ser Arg Thr Arg Pro Arg Glu Glu Lys Met Ile Glu Arg Arg
        275                 280                 285
```

-continued

```
Gly Ala Thr Asn Lys Asp Gly Gly Ile Pro Pro Ser Asp Asp Leu Pro
    290                 295                 300

Pro Gln Thr Asp Ala Ser Phe Ala His Ala Gly Arg Pro Asp Ala Asp
305                 310                 315                 320

Ser Val Asn Ser Leu Leu Ser Ala Glu Arg Arg Arg Leu Gln Arg Lys
                325                 330                 335

Arg Arg His Lys Arg Lys Arg Ile Leu Leu Gln Asp Pro Gln Gln Gln
            340                 345                 350

Ala Ala Leu Ala Lys Arg Lys Lys Gly Thr Ser Ser Ser Lys Lys Arg
        355                 360                 365

Gly Pro Arg Asn Val Glu Tyr Met Cys Ala Leu Cys Asn Glu Val Tyr
    370                 375                 380

Asn Ser Thr Cys Asp Tyr Asn Pro Trp Trp Ala Leu Thr Gln Glu Glu
385                 390                 395                 400

Cys Pro Lys Cys Gln Lys Thr Gln Ile Pro Arg Ile Asp Ile Gly Ala
                405                 410                 415

Pro Ala Asn Ala Ile Glu Tyr His Pro Ala Leu Leu Ala His Ala Asp
            420                 425                 430

Glu Ser Ala Gly Ala Ala Glu Pro Ser Ala Val Leu Glu Pro Gln Asp
        435                 440                 445

Leu Pro Val Pro Ser Thr Thr Gly Asp Asp Met Glu Tyr Ser Asp Val
    450                 455                 460

Asp Asp Ser Asp Leu Ser Asp Glu Asp Gly Leu Leu Ser Asp Ala Ser
465                 470                 475                 480

Leu Asp Leu Asp Ser Asp Asp Ser Glu Ile Ala Asp Ser Glu Asn Met
                485                 490                 495

Ser Pro Ala Glu Gln Ala Glu Ser Glu Lys Phe Gly Ala Glu Tyr Asp
            500                 505                 510

Gly Pro Lys Phe Ser Asp Ala Glu Ala Ala Arg Leu Leu Asn Leu Met
        515                 520                 525

Leu His Ala Ser Thr Cys Pro Cys Arg His Lys Ser Ser Glu His Tyr
    530                 535                 540

Asp Val Cys Arg Ser Val Lys Trp Met Met Leu His Val Arg Asp Cys
545                 550                 555                 560

Pro Gly Thr Thr Ser Thr Phe Asp Val Cys Pro Phe Pro Trp Cys Arg
                565                 570                 575

Lys Ala Lys His Leu Leu Tyr His Leu Leu Ser Cys Glu Asn Pro Gln
            580                 585                 590

Ser Cys Pro Ile Cys Ser Pro Val His Leu Asn Ala Ser Met Lys Ser
        595                 600                 605

Leu Arg Gly Leu Asn His Tyr Arg Leu Lys Lys Gln Gln Gln Cys Val
    610                 615                 620

Ile Gly Ala Ser Gln Ser Pro Gly Lys Pro Ser Ala Ala Arg Gly Gly
625                 630                 635                 640

His Ser Ser Pro Lys Lys Ser Asn Glu Ser Thr Gln Asp Glu Val Asp
                645                 650                 655

Thr Cys Arg Asp Thr Leu Asp Ala Phe Val Val Gly Thr Lys Glu Pro
            660                 665                 670

Thr Glu Ile Ser Ser Ser Ser Val Pro Ser Asn Ser Thr Ala Ala Val
        675                 680                 685

Asp Gln Pro Ala His Glu Asp Glu Val Lys Thr Gln Leu Tyr Glu Phe
    690                 695                 700
```

```
Val Asp Gln Trp Glu Asp Pro Glu His Pro Ala Ala Leu Lys Asp Asp
705                 710                 715                 720

Gly Leu Asn Asn Ser Gln Leu Thr Val Gly His Cys Asp Asn Asp Val
                725                 730                 735

Leu Ile Lys Gln Glu Asp Asp Asn Ser Gln
            740                 745


<210> SEQ ID NO 18
<211> LENGTH: 327
<212> TYPE: PRT
<213> ORGANISM: Aureococcus anopagefferens

<400> SEQUENCE: 18

Met Arg Arg Ala Ala Ala Glu Ala Lys Ala Met Glu Pro Leu Arg Ala
1               5                   10                  15

Leu Ala Phe Ala Gln Ser Val Lys Tyr Tyr Cys Ser Val Cys Glu His
            20                  25                  30

Ala Tyr Glu Thr Thr Ser Asp Ala Asn Pro Leu Trp Thr Leu Ala Arg
        35                  40                  45

His Ser Cys Pro Gln Cys Gly Ala Leu Gln Tyr Pro Glu Ile Glu Ile
    50                  55                  60

Asp Asp Ile Ser Leu Pro Thr Ala Glu Ala Arg Ala Pro Asp Asp Ala
65                  70                  75                  80

Ser Thr Leu Ser His Ala Gln Gly Asp Gly Ala Arg Ser Pro Pro Arg
                85                  90                  95

Pro Ala Ala Leu Gly Arg Ala Ala Ala Ala Asp Asp Gly Glu Val Leu
            100                 105                 110

Leu Arg Ala Asp Ala Pro Arg Lys Arg Ser Ala Pro Asp Asp Asp Ala
        115                 120                 125

Ser Thr Met Ser His Ala Gln Gly Ala Ala Leu Leu Glu Leu Phe Asp
    130                 135                 140

His Val Arg Ser Cys Pro Gly Arg His Gln Ser Ala Ala His Ala Arg
145                 150                 155                 160

Val Cys Ala Gly Ala Lys Phe Val Met Leu His Ala Arg Asp Cys Asp
                165                 170                 175

Ala Ala Pro Gly Thr Cys Gly Val Glu Trp Cys Gly Ala Val Lys Gly
            180                 185                 190

Leu Leu Ser Arg Val Val Cys Gly Gln Gln Gly Asp Lys Cys Val Val
        195                 200                 205

Cys Ala Glu Pro Ser Glu Ala Met Asp Val Gly Asp Ala Ser Pro Pro
    210                 215                 220

Thr Val Ser Pro Asp Ala Met Asp Val Asp Asp Ala Ser Pro Pro Arg
225                 230                 235                 240

Ala Ser Ser Asp Ala Pro Met Ala Asp Ala Pro Pro Ala Glu Pro Arg
                245                 250                 255

Val Gly Ala Ala Ala Pro Ser Pro Pro Gln Ser Thr Asp Arg Ala Phe
            260                 265                 270

Glu Ala Pro Thr Ala Val Pro Ser Pro Val Arg Ala Ser Pro Ser Arg
        275                 280                 285

Gly Gly Ala Pro Ser Ser Arg Arg Leu Ala Asp Ile Thr Met Ser Glu
    290                 295                 300

Asn Val Glu Met Asp Phe Pro Arg Asp Phe Cys Phe Ala Asp Glu Leu
305                 310                 315                 320

Arg Arg Arg Gly Asp Ala Ala
                325
```

<210> SEQ ID NO 19
<211> LENGTH: 30
<212> TYPE: PRT
<213> ORGANISM: Nannochloropsis gaditana

<400> SEQUENCE: 19

Ala Lys Gln Gln Gln Leu Leu Lys Asp Ser Leu Thr Ala Asp Leu Lys
1 5 10 15

Leu Leu Leu His Glu Phe Glu Arg Phe Gln Gln Ala Thr Ala
20 25 30

<210> SEQ ID NO 20
<211> LENGTH: 1797
<212> TYPE: DNA
<213> ORGANISM: Artificial Sequence
<220> FEATURE:
<223> OTHER INFORMATION: Nannochloropsis oceanica

<400> SEQUENCE: 20
atgcctatgg tcaccctctc ccaggatgca actactaccg cggccggcag catgatgctt 60
cccctccttc cctccatccc tgcttccgct accagcgcct cttttaccgc tccctcagcg 120
tcctccacga ccaccaaatc tcccaaaggt acttcctcca tgactcagct tggagagaca 180
gggcgagaga atactggccg atggacttgt gaagagcatg tgctgtttct taaaggccta 240
gaaatgcacg gcaagggttg gaagaaaatc gcaaagctaa tcaagacccg aacggtggtc 300
caaatccgca cgcacgcgca aaagtacttc cagaaattgg caaaagccaa gaagaacggg 360
caccatggtg atatgctcgg aatggaaggc tcacactttg gggaaaaacg tgtcaaattt 420
accggaaagc gacgtgggct tgtctataat tcgtatttag taggtgccga ggccacctct 480
gcggctatct ccccggcgtt gcagacgttt atgccggcga acttggggat ggagggcgag 540
cgtgtaggcc ttatgacgga taaggaggag gatgcagcaa tcgagaaggg actttatcgt 600
ttcctctccc ccgtagtgct ggatcccgcc acgcgtaatc tggacgcctc cgctcctgag 660
atcttgccct taccacccag cactccagcg atgggcgtgc accataccag tagcagaggt 720
agcagcagag gggggttgga tggagagaca acgggagagg aggacggcgg aagcgattcg 780
attgtaatgg gggatggagg gagcgatcaa gatgcagagt cgtcgttggg cgagcccttg 840
ccaactttgg cgcgggtgac accggagatg tacacacggt gtggagttcc ggaatggttt 900
aagaaagggg gggacattga cgaattgctc attgatgcag ccggactcga ttggagaagt 960
gactcgggtg gggacgcacg gaaggtggtg gatcaaggga caagtatttt gaatgcgaat 1020
attaatggta gtaattgtgc gactgtggcc ccggcagtgg tgcggaaggg ctgtggtagc 1080
aacactaata agatgaactc agcggcgcct gtgctgaaca tgacagggtt ggctggggct 1140
ggagggcttt cagggtggaa gggcaagggt agcgacacta gcgaaggtag cagcagcaac 1200
ggcagcagca agaacatggc tttgacggca aatgcgtcgg cgggatgtgg acaagggagc 1260
tggggagtgc gggggggggc acagaaaaag cagcagcagc agcaacatga ggtaccaacg 1320
cagcagcagc aggtaccaac gcagcagcag caggttcacg gcattcacgt gaaggaggaa 1380
gggatggagc tcctgagagt catggcggat agagggactg ttcacggtca cgtccatgag 1440
gaggatggct ttgcggcgtt tgacccccat catgtcgagc tgaaggagga gcactcccac 1500
catgatttgt tgctggaaga gctgccccac gacagcaacc acgatgacgc cctggcccat 1560
attgtgttct cagtgaatgg agagtcggat cttcattcct tgccgagggg tgcaggaggg 1620

```
gggggagcgc atgtgcatgc gccgccggtt gtggtggggg ggagacagca tcactatcat   1680

cataatgaca atgatatcca tttgcatgcg tacgacgcgt atttggaaga ggaaggggcg   1740

gatggcgggc atgggttgtt gttgttggag gatttggatg ggggaatcga gttttag      1797


<210> SEQ ID NO 21
<211> LENGTH: 598
<212> TYPE: PRT
<213> ORGANISM: Nannochloropsis oceanica

<400> SEQUENCE: 21

Met Pro Met Val Thr Leu Ser Gln Asp Ala Thr Thr Thr Ala Ala Gly
1               5                   10                  15

Ser Met Met Leu Pro Leu Leu Pro Ser Ile Pro Ala Ser Ala Thr Ser
            20                  25                  30

Ala Ser Phe Thr Ala Pro Ser Ala Ser Ser Thr Thr Thr Lys Ser Pro
        35                  40                  45

Lys Gly Thr Ser Ser Met Thr Gln Leu Gly Glu Thr Gly Arg Glu Asn
    50                  55                  60

Thr Gly Arg Trp Thr Cys Glu Glu His Val Leu Phe Leu Lys Gly Leu
65                  70                  75                  80

Glu Met His Gly Lys Gly Trp Lys Lys Ile Ala Lys Leu Ile Lys Thr
                85                  90                  95

Arg Thr Val Val Gln Ile Arg Thr His Ala Gln Lys Tyr Phe Gln Lys
            100                 105                 110

Leu Ala Lys Ala Lys Lys Asn Gly His His Gly Asp Met Leu Gly Met
        115                 120                 125

Glu Gly Ser His Phe Gly Gly Lys Arg Val Lys Phe Thr Gly Lys Arg
    130                 135                 140

Arg Gly Leu Val Tyr Asn Ser Tyr Leu Val Gly Ala Glu Ala Thr Ser
145                 150                 155                 160

Ala Ala Ile Ser Pro Ala Leu Gln Thr Phe Met Pro Ala Asn Leu Gly
                165                 170                 175

Met Glu Gly Glu Arg Val Gly Leu Met Thr Asp Lys Glu Glu Asp Ala
            180                 185                 190

Ala Ile Glu Lys Gly Leu Tyr Arg Phe Leu Ser Pro Val Val Leu Asp
        195                 200                 205

Pro Ala Thr Arg Asn Leu Asp Ala Ser Ala Pro Glu Ile Leu Pro Leu
    210                 215                 220

Pro Pro Ser Thr Pro Ala Met Gly Val His His Thr Ser Ser Arg Gly
225                 230                 235                 240

Ser Ser Arg Gly Gly Leu Asp Gly Glu Thr Thr Gly Glu Glu Asp Gly
                245                 250                 255

Gly Ser Asp Ser Ile Val Met Gly Asp Gly Gly Ser Asp Gln Asp Ala
            260                 265                 270

Glu Ser Ser Leu Gly Glu Pro Leu Pro Thr Leu Ala Arg Val Thr Pro
        275                 280                 285

Glu Met Tyr Thr Arg Cys Gly Val Pro Glu Trp Phe Lys Lys Gly Gly
    290                 295                 300

Asp Ile Asp Glu Leu Leu Ile Asp Ala Ala Gly Leu Asp Trp Arg Ser
305                 310                 315                 320

Asp Ser Gly Gly Asp Ala Arg Lys Val Val Asp Gln Gly Thr Ser Ile
                325                 330                 335

Leu Asn Ala Asn Ile Asn Gly Ser Asn Cys Ala Thr Val Ala Pro Ala
            340                 345                 350
```

```
Val Val Arg Lys Gly Cys Gly Ser Asn Thr Asn Lys Met Asn Ser Ala
        355                 360                 365

Ala Pro Val Leu Asn Met Thr Gly Leu Ala Gly Ala Gly Gly Leu Ser
    370                 375                 380

Gly Trp Lys Gly Lys Gly Ser Asp Thr Ser Glu Gly Ser Ser Ser Asn
385                 390                 395                 400

Gly Ser Ser Lys Asn Met Ala Leu Thr Ala Asn Ala Ser Ala Gly Cys
                405                 410                 415

Gly Gln Gly Ser Trp Gly Val Arg Gly Gly Ala Gln Lys Lys Gln Gln
            420                 425                 430

Gln Gln Gln His Glu Val Pro Thr Gln Gln Gln Gln Val Pro Thr Gln
        435                 440                 445

Gln Gln Gln Val His Gly Ile His Val Lys Glu Glu Gly Met Glu Leu
    450                 455                 460

Leu Arg Val Met Ala Asp Arg Gly Thr Val His Gly His Val His Glu
465                 470                 475                 480

Glu Asp Gly Phe Ala Ala Phe Asp Pro His His Val Glu Leu Lys Glu
                485                 490                 495

Glu His Ser His His Asp Leu Leu Leu Glu Glu Leu Pro His Asp Ser
            500                 505                 510

Asn His Asp Asp Ala Leu Ala His Ile Val Phe Ser Val Asn Gly Glu
        515                 520                 525

Ser Asp Leu His Ser Leu Pro Arg Gly Ala Gly Gly Gly Gly Ala His
    530                 535                 540

Val His Ala Pro Pro Val Val Val Gly Gly Arg Gln His His Tyr His
545                 550                 555                 560

His Asn Asp Asn Asp Ile His Leu His Ala Tyr Asp Ala Tyr Leu Glu
                565                 570                 575

Glu Glu Gly Ala Asp Gly Gly His Gly Leu Leu Leu Leu Glu Asp Leu
            580                 585                 590

Asp Gly Gly Ile Glu Phe
        595


<210> SEQ ID NO 22
<211> LENGTH: 281
<212> TYPE: PRT
<213> ORGANISM: Nannochloropsis oceanica

<400> SEQUENCE: 22

Ser Ala Pro Ala Ala Ser Pro Thr Thr Ser Lys Leu His Lys Gly Thr
1               5                   10                  15

Ser Ser Met Thr Gln Leu Gly Glu Thr Gly Arg Glu Asn Thr Gly Arg
            20                  25                  30

Trp Thr Cys Glu Glu His Val Leu Phe Leu Lys Gly Leu Glu Met His
        35                  40                  45

Gly Lys Gly Trp Lys Lys Ile Ala Lys Leu Ile Lys Thr Arg Thr Val
    50                  55                  60

Val Gln Ile Arg Thr His Ala Gln Lys Tyr Phe Gln Lys Leu Ala Lys
65                  70                  75                  80

Ala Lys Lys Asn Gly His His Gly Asp Met Leu Gly Met Glu Gly Thr
                85                  90                  95

Arg Phe Gly Gly Lys Arg Val Lys Phe Thr Gly Lys Arg Arg Gly Leu
            100                 105                 110

Val Tyr Gly Ser Tyr Leu Val Gly Ala Glu Ala Thr Ser Ala Ala Ile
```

```
        115                 120                 125

Ser Pro Ala Leu Gln Ser Tyr Met Pro Gly Ser Trp Ala Gly Arg Glu
    130                 135                 140

Glu Gly Glu Ala Leu Ser Asp Lys Glu Glu Asp Ala Ala Ile Glu Lys
145                 150                 155                 160

Gly Leu Tyr Arg Phe Leu Ser Pro Val Val Leu Asp Ala Ala Ala Ser
                165                 170                 175

Asn Leu Asp Ala Thr Ala Pro Glu Val Leu Pro Pro Ser Thr Pro Gly
            180                 185                 190

Thr Gly Val His Ala Asn Gly Val Val Gly Ala Asp Gly Glu Thr Thr
        195                 200                 205

Glu Glu Asp Gly Ser Ser Gly Gly Asp Asn Val Asp Val Ser Glu Thr
    210                 215                 220

Ile Asp Asp Ala Asp Ser Ser Ser Gly Glu Pro Leu Pro Arg Leu Ala
225                 230                 235                 240

Arg Val Thr Asn Asp Met Tyr Glu Arg Cys Ser Val Pro Thr Trp Phe
                245                 250                 255

Met Lys Gly Gly Asp Ile Glu Glu Leu Leu Ala Asp Ala Ala Ala Ile
            260                 265                 270

Asp Trp Arg Glu Asp Ser Gly Gly Asp
        275                 280


<210> SEQ ID NO 23
<211> LENGTH: 290
<212> TYPE: PRT
<213> ORGANISM: Nannochloropsis oceanica

<400> SEQUENCE: 23

Thr Ala Pro Ser Ala Ser Ser Thr Thr Thr Lys Ser Pro Lys Gly Thr
1               5                   10                  15

Ser Ser Met Thr Gln Leu Gly Glu Thr Gly Arg Glu Asn Thr Gly Arg
            20                  25                  30

Trp Thr Cys Glu Glu His Val Leu Phe Leu Lys Gly Leu Glu Met His
        35                  40                  45

Gly Lys Gly Trp Lys Lys Ile Ala Lys Leu Ile Lys Thr Arg Thr Val
    50                  55                  60

Val Gln Ile Arg Thr His Ala Gln Lys Tyr Phe Gln Lys Leu Ala Lys
65                  70                  75                  80

Ala Lys Lys Asn Gly His His Gly Asp Met Leu Gly Met Glu Gly Ser
                85                  90                  95

His Phe Gly Gly Lys Arg Val Lys Phe Thr Gly Lys Arg Arg Gly Leu
            100                 105                 110

Val Tyr Asn Ser Tyr Leu Val Gly Ala Glu Ala Thr Ser Ala Ala Ile
        115                 120                 125

Ser Pro Ala Leu Gln Thr Phe Met Pro Ala Asn Leu Gly Met Glu Gly
    130                 135                 140

Glu Arg Val Gly Leu Met Thr Asp Lys Glu Glu Asp Ala Ala Ile Glu
145                 150                 155                 160

Lys Gly Leu Tyr Arg Phe Leu Ser Pro Val Val Leu Asp Pro Ala Thr
                165                 170                 175

Arg Asn Leu Asp Ala Ser Ala Pro Glu Ile Leu Pro Leu Pro Pro Ser
            180                 185                 190

Thr Pro Ala Met Gly Val His His Thr Ser Ser Arg Gly Ser Ser Arg
        195                 200                 205
```

```
Gly Gly Leu Asp Gly Glu Thr Thr Gly Glu Glu Asp Gly Gly Ser Asp
    210                 215                 220

Ser Ile Val Met Gly Asp Gly Gly Ser Asp Gln Asp Ala Glu Ser Ser
225                 230                 235                 240

Leu Gly Glu Pro Leu Pro Thr Leu Ala Arg Val Thr Pro Glu Met Tyr
                245                 250                 255

Thr Arg Cys Gly Val Pro Glu Trp Phe Lys Lys Gly Gly Asp Ile Asp
            260                 265                 270

Glu Leu Leu Ile Asp Ala Ala Gly Leu Asp Trp Arg Ser Asp Ser Gly
        275                 280                 285

Gly Asp
    290


<210> SEQ ID NO 24
<211> LENGTH: 6
<212> TYPE: PRT
<213> ORGANISM: Artificial Sequence
<220> FEATURE:
<223> OTHER INFORMATION: Protein

<400> SEQUENCE: 24

Ser His Ala Gln Lys Tyr
1               5


<210> SEQ ID NO 25
<211> LENGTH: 6
<212> TYPE: PRT
<213> ORGANISM: Artificial Sequence
<220> FEATURE:
<223> OTHER INFORMATION: Protein

<400> SEQUENCE: 25

Thr His Ala Gln Lys Tyr
1               5


<210> SEQ ID NO 26
<211> LENGTH: 598
<212> TYPE: PRT
<213> ORGANISM: Nannochloropsis oceanica CCMP1779

<400> SEQUENCE: 26

Met Pro Met Val Thr Leu Ser Gln Asp Ala Thr Thr Thr Ala Ala Gly
1               5                   10                  15

Ser Met Met Leu Pro Leu Leu Pro Ser Ile Pro Ala Ser Ala Thr Ser
            20                  25                  30

Ala Ser Phe Thr Ala Pro Ser Ala Ser Ser Thr Thr Thr Lys Ser Pro
        35                  40                  45

Lys Gly Thr Ser Ser Met Thr Gln Leu Gly Glu Thr Gly Arg Glu Asn
    50                  55                  60

Thr Gly Arg Trp Thr Cys Glu Glu His Val Leu Phe Leu Lys Gly Leu
65                  70                  75                  80

Glu Met His Gly Lys Gly Trp Lys Lys Ile Ala Lys Leu Ile Lys Thr
                85                  90                  95

Arg Thr Val Val Gln Ile Arg Thr His Ala Gln Lys Tyr Phe Gln Lys
            100                 105                 110

Leu Ala Lys Ala Lys Lys Asn Gly His His Gly Asp Met Leu Gly Met
        115                 120                 125

Glu Gly Ser His Phe Gly Gly Lys Arg Val Lys Phe Thr Gly Lys Arg
    130                 135                 140
```

-continued

```
Arg Gly Leu Val Tyr Asn Ser Tyr Leu Val Gly Ala Glu Ala Thr Ser
145                 150                 155                 160

Ala Ala Ile Ser Pro Ala Leu Gln Thr Phe Met Pro Ala Asn Leu Gly
                165                 170                 175

Met Glu Gly Glu Arg Val Gly Leu Met Thr Asp Lys Glu Glu Asp Ala
            180                 185                 190

Ala Ile Glu Lys Gly Leu Tyr Arg Phe Leu Ser Pro Val Val Leu Asp
        195                 200                 205

Pro Ala Thr Arg Asn Leu Asp Ala Ser Ala Pro Glu Ile Leu Pro Leu
    210                 215                 220

Pro Pro Ser Thr Pro Ala Met Gly Val His His Thr Ser Ser Arg Gly
225                 230                 235                 240

Ser Ser Arg Gly Gly Leu Asp Gly Glu Thr Thr Gly Glu Glu Asp Gly
                245                 250                 255

Gly Ser Asp Ser Ile Val Met Gly Asp Gly Gly Ser Asp Gln Asp Ala
            260                 265                 270

Glu Ser Ser Leu Gly Glu Pro Leu Pro Thr Leu Ala Arg Val Thr Pro
        275                 280                 285

Glu Met Tyr Thr Arg Cys Gly Val Pro Glu Trp Phe Lys Lys Gly Gly
    290                 295                 300

Asp Ile Asp Glu Leu Leu Ile Asp Ala Ala Gly Leu Asp Trp Arg Ser
305                 310                 315                 320

Asp Ser Gly Gly Asp Ala Arg Lys Val Val Asp Gln Gly Thr Ser Ile
                325                 330                 335

Leu Asn Ala Asn Ile Asn Gly Ser Asn Cys Ala Thr Val Ala Pro Ala
            340                 345                 350

Val Val Arg Lys Gly Cys Gly Ser Asn Thr Asn Lys Met Asn Ser Ala
        355                 360                 365

Ala Pro Val Leu Asn Met Thr Gly Leu Ala Gly Ala Gly Gly Leu Ser
    370                 375                 380

Gly Trp Lys Gly Lys Gly Ser Asp Thr Ser Glu Gly Ser Ser Ser Asn
385                 390                 395                 400

Gly Ser Ser Lys Asn Met Ala Leu Thr Ala Asn Ala Ser Ala Gly Cys
                405                 410                 415

Gly Gln Gly Ser Trp Gly Val Arg Gly Gly Ala Gln Lys Lys Gln Gln
            420                 425                 430

Gln Gln Gln His Glu Val Pro Thr Gln Gln Gln Gln Val Pro Thr Gln
        435                 440                 445

Gln Gln Gln Val His Gly Ile His Val Lys Glu Glu Gly Met Glu Leu
    450                 455                 460

Leu Arg Val Met Ala Asp Arg Gly Thr Val His Gly His Val His Glu
465                 470                 475                 480

Glu Asp Gly Phe Ala Ala Phe Asp Pro His His Val Glu Leu Lys Glu
                485                 490                 495

Glu His Ser His His Asp Leu Leu Leu Glu Glu Leu Pro His Asp Ser
            500                 505                 510

Asn His Asp Asp Ala Leu Ala His Ile Val Phe Ser Val Asn Gly Glu
        515                 520                 525

Ser Asp Leu His Ser Leu Pro Arg Gly Ala Gly Gly Gly Gly Ala His
    530                 535                 540

Val His Ala Pro Pro Val Val Val Gly Gly Arg Gln His His Tyr His
545                 550                 555                 560

His Asn Asp Asn Asp Ile His Leu His Ala Tyr Asp Ala Tyr Leu Glu
```

```
                565                 570                 575

Glu Glu Gly Ala Asp Gly Gly His Gly Leu Leu Leu Leu Glu Asp Leu
            580                 585                 590

Asp Gly Gly Ile Glu Phe
        595


<210> SEQ ID NO 27
<211> LENGTH: 676
<212> TYPE: PRT
<213> ORGANISM: Ectocarpus siliculosus

<400> SEQUENCE: 27

Met Ser Ser Gln Leu Gln Val Asp Asp Gly Ala Ala Ser Ser Ser Asp
1               5                   10                  15

Asn Leu Asp Asn Glu Gly Val Cys Gln Pro Gly Asn Glu Asn Thr Gly
            20                  25                  30

Arg Trp Thr Ser Asp Glu His Arg Leu Phe Leu Arg Gly Leu Glu Leu
        35                  40                  45

His Gly Lys Gly Trp Lys Gln Ile Ala Thr Leu Ile Gln Thr Arg Thr
    50                  55                  60

Val Val Gln Ile Arg Thr His Ala Gln Lys Tyr Phe Gln Lys Leu Ser
65                  70                  75                  80

Lys Ala Gln Ala Ser Gly Thr Ser His Leu Asp Pro Ala Thr Leu Met
                85                  90                  95

Ser Thr Met Asp Ala Gly Lys Pro Arg Pro Ala Ser Val Ser Arg Asn
            100                 105                 110

Leu Arg Ser Ser Thr Met Ala Asn Ser Pro Ala Glu Ser Glu Gly Arg
        115                 120                 125

Leu Met Ser Leu Arg Lys Arg Arg Asn Arg Gly Arg His Pro Arg His
    130                 135                 140

Asp Asp Asp Gln Asp Tyr Asp Thr Asn Ser Glu Glu Ser Tyr Asp Tyr
145                 150                 155                 160

Ala Arg Ser Ser Ala Thr Thr Arg Thr Arg Arg Arg Arg Arg Ser Val
                165                 170                 175

Ser Ser Gly Ser Ser Gly Gly Gly Gly Gly Gly Ser Ser Glu Ser Glu
            180                 185                 190

Glu Glu Asp Gly Glu Gly Gly Gly Arg Gly His Arg Gly Val Tyr Arg
        195                 200                 205

Glu Thr Ala Leu Gly Ala Thr Thr Thr Thr Thr Met Met Met Met Val
    210                 215                 220

Arg Gln Ala Glu Glu Ala Pro Ala Phe Thr Val Gly Gly Gly Asn Ser
225                 230                 235                 240

Gly Ala His Gly Ala Glu Phe Asp Glu Glu Glu Ala Glu Glu Glu Leu
                245                 250                 255

Asp Glu Ser Val Asp Val Glu Gly His Asn Ser Asn Asn Lys Asn Val
            260                 265                 270

Gly Ile Ser Ser Ser Leu Leu His Gly Gly Thr Ala Gly Thr Trp Ser
        275                 280                 285

Lys Arg Arg Pro Ala Lys Ser His Arg Pro Ser Pro Thr Lys Ala Ser
    290                 295                 300

Lys Ala Ala Ala Ile Ala Ala Ala Gly Gly Ala Ala Asp Ala Arg Ala
305                 310                 315                 320

Leu Ala Trp Glu Ala Ala Ala Ala Lys Ala Ala Ala Gly Glu Glu Gly
                325                 330                 335
```

-continued

```
Glu Glu Ala Ala Ala Asp Gly Val Val Gly Gly Gly Ser Gly Thr Lys
            340                 345                 350

Arg His Arg Ser Glu Ser Val Ser Ser Ser Ser Asn Asp Ala Ser Leu
        355                 360                 365

Gly Lys Thr Ile Lys Ser Leu Lys Arg Thr Gly Gly Ser Ser Gln Thr
    370                 375                 380

Thr Arg Ile Ser Pro Thr Ser Val Ala Asp Val Asn Ser Phe Met Ser
385                 390                 395                 400

Phe Pro Val Pro Gln Thr Glu Arg Ser Asp Met Ala Met His His Leu
                405                 410                 415

Pro Gln Gln Leu Ala Pro Ser Trp Cys Thr Lys Pro Gln Asp Thr Trp
            420                 425                 430

Met Ala Gly Ala Gly Leu Asp Met Gly Gly Leu Glu Ala Asp Asp Ala
        435                 440                 445

Gly Pro Phe Arg Trp Phe Ile Asp Glu Arg Ser Leu Ser Ala Pro Gly
    450                 455                 460

Ala Phe Phe Gln Pro Pro Val Glu Thr Trp Ser Gly Ser Asp Thr Thr
465                 470                 475                 480

Asp Val Ser Thr Ser Ala Gly Ser Asp His Gln His His Arg Thr Val
                485                 490                 495

Val Pro Glu His Leu Pro Ser Asn Thr Asn Lys Val Asp Met Ser Pro
            500                 505                 510

Gly Gly Val Leu Thr Ser Asp Asn Thr His Asn Gln Glu Asp Val Ser
        515                 520                 525

Ile Ala Lys His Arg Gly Met Met Glu Pro Ile Val Pro Ile Ser Asp
    530                 535                 540

Ala Ala Met Ala Ser Glu Val Ser Arg His Val Glu Ala Asp Ser Ala
545                 550                 555                 560

Thr Ala Cys Ala Ala Ala Gly Cys Ala Gly Gly Ala Ser Ala Ser Ala
                565                 570                 575

Gly Gly Ala Gly Asp Gly Gly His Ser Leu Asp Ile Thr Ser Gly Leu
            580                 585                 590

Trp Leu Asp His Pro Gln Glu Ala His Glu Ala Val Ala Ser Pro Leu
        595                 600                 605

Met Tyr Gly Leu Gly Leu Ser Ala Pro Ala Asn Thr Gly Gly Ala Gly
    610                 615                 620

Gly Gly Gly Gly Ala Gly Gly Leu Gly Gly Gly Leu Ser Leu Pro Ser
625                 630                 635                 640

Leu Asp Glu Glu Glu Val Leu Gly Phe Leu Ala Cys Ala Glu Glu Asn
                645                 650                 655

Ser Arg Gln Ala Ala Ala Ala Ala Ala Gly Gly Asp Ala Asp Glu Asn
            660                 665                 670

Asp Leu Leu Val
        675
```

<210> SEQ ID NO 28
<211> LENGTH: 453
<212> TYPE: PRT
<213> ORGANISM: Navicula sp. WT0229

<400> SEQUENCE: 28

```
Met Lys Val Glu Ala Thr His Gln His Ala Ser Gly Ala Asp His Ser
1               5                   10                  15

Ser Thr Leu Asp Ala Pro Ala Pro Val Leu Ser His Ser Gly Pro Ala
            20                  25                  30
```

```
Ala Ser Asn Ala Ser Asn Asn Ala Pro Lys Ser Lys Lys Lys Lys Gly
        35                  40                  45

Gln Pro Ala Ile Thr Ile Ala Ala Ala Pro Ser Gln Ala Val Ala Pro
    50                  55                  60

Leu Ala Pro Gly Glu Asn Thr Gly Arg Trp Thr Ala Glu Glu His Arg
65                  70                  75                  80

Leu Phe Leu Gln Gly Leu Glu Gln His Gly Lys Gly Trp Lys Lys Ile
                85                  90                  95

Ala Ser Leu Ile Lys Ser Arg Thr Val Val Gln Ile Arg Thr His Ala
            100                 105                 110

Gln Lys Tyr Phe Gln Lys Leu Ala Lys Ala Arg Gln Asn Gly Glu Glu
        115                 120                 125

Gly Asp Ile Thr Met Glu Gly Arg Gly Gly Thr Ala Ser Ile Thr Ser
    130                 135                 140

Ser Thr Thr Ala Thr Ala Ala Leu Thr Asn Lys Arg Arg Arg His Ile
145                 150                 155                 160

Thr Gly Thr Lys Arg Lys Val Ile Gln Ser Ile Val Ala Ser Ala Gln
                165                 170                 175

Arg Gln Ala Lys Lys Ala His Leu Pro Glu Ile Gly Asp Ala Lys Lys
            180                 185                 190

Ser Pro Val Val Pro Gly Val Ala Pro Ala Leu Ala Tyr Tyr Val Thr
        195                 200                 205

Pro Ser Gln Ser Ser Ser Val Ser Ala Gly Ser Asp Val Phe Thr Glu
    210                 215                 220

Gly Asn Leu Ser Gly Pro Val Leu Glu Asp Ser Leu Phe Arg Phe Leu
225                 230                 235                 240

Thr Pro Val Pro Ile Ala Ser Asp Asp Val Asn Glu Val Ala Arg Gln
                245                 250                 255

Ala Gly Ala Asn Pro Ile Thr Leu Pro Ser Ser Asn Ser His Ala Leu
            260                 265                 270

Ser Ser Val Pro Gly Ser Ser Pro Thr Gly Val Gln Glu Leu Ser Ile
        275                 280                 285

Tyr Pro Ser Trp Thr Asp Ala Lys Asp Pro Pro Ser Trp Tyr Ala Lys
    290                 295                 300

Gly Ala Asp Val Asp Ala Leu Leu Asp Val Ser Asp Thr Leu Asp Trp
305                 310                 315                 320

Leu Ala Asp Thr Gly Asp Leu Asp Glu Glu Tyr Gln Pro Gln Ser Asn
                325                 330                 335

Asp Ile Asp Thr Cys Ser Phe Gly Gly Gln Gly Glu His His Glu Met
            340                 345                 350

Gly Ile Ser Asn Val His Asn Asn Thr Ser Val Ser Ser Leu Thr His
        355                 360                 365

Val Asp Pro Asn Met Val Ser Val Val Pro Pro Leu Pro Ser Leu Phe
    370                 375                 380

Glu Gly Asn Pro Asp Val Val Glu Ala Glu Leu Thr Val Gly Lys Asp
385                 390                 395                 400

Val Asn Val Ala Ile Gly Asn Ala Ser Leu Leu Ile Ala Pro Ser Asp
                405                 410                 415

Pro Asn Ala Glu Thr Leu Gln Val Phe Asp Ser Pro Met Glu Glu Gln
            420                 425                 430

Glu Phe Val Ser Thr Leu Leu Glu Thr Thr Ala Glu Ser Ser Asp Asn
        435                 440                 445
```

```
Leu Ala Val Leu Ser
    450


<210> SEQ ID NO 29
<211> LENGTH: 512
<212> TYPE: PRT
<213> ORGANISM: Phaeodactylum tricornutum

<400> SEQUENCE: 29

Met Thr Thr Ala Pro Leu Thr Ala Ala Gln Ser Ser Pro Leu Thr Ile
1               5                   10                  15

Ala Asn Thr Thr Thr Thr Thr Ile Asn Ser Lys Pro Leu Val Asp Ser
            20                  25                  30

Leu Thr Asn Thr Val Pro Glu Thr Val Gln Phe Ser Gly Arg Asp Gly
        35                  40                  45

Asn Ser Ser Asn Ser Glu Thr Asn Lys Ser Asn Ser Asn Arg Thr Pro
    50                  55                  60

Thr Lys Phe Pro Ala Leu Ser Glu Val Ser His Arg Arg Ser Ala Ser
65                  70                  75                  80

Val Ser Thr Ala His Ser Val Thr Ser Lys Ser Lys Gln Asn Ser Thr
                85                  90                  95

Pro Pro Val Asp Met Ala Thr Ala Ser Gly Ser Ala Ser Gln Gly Ser
            100                 105                 110

His Gly Glu Asn Thr Gly Arg Trp Thr Ala Glu Glu His Arg Leu Phe
        115                 120                 125

Leu Gln Gly Leu Glu Gln His Gly Lys Gly Trp Lys Lys Ile Ala Ser
    130                 135                 140

Leu Ile Lys Ser Arg Thr Val Val Gln Ile Arg Thr His Ala Gln Lys
145                 150                 155                 160

Tyr Phe Gln Lys Leu Ala Lys Ala Arg Gln Asn Gly Glu Glu Gly Asp
                165                 170                 175

Val Ala Met Glu Gly Arg Gly Gly Val Ala Ser Ile Thr Ser Val Ser
            180                 185                 190

Thr Thr Ala Val Leu Pro Lys Arg Arg Arg Gln Thr Thr Gly Thr Lys
        195                 200                 205

Arg Lys Ala Ile Gln Ser Val Val Ala Ser Ala Gln Arg Gln Gly Lys
    210                 215                 220

Lys Leu Ala Ala Ala Lys Thr Asn Pro Thr Arg His His Pro Leu Pro
225                 230                 235                 240

Pro Pro Leu Pro Thr Val Ala Pro Ala Leu Ala His Tyr Thr Leu Pro
                245                 250                 255

Ser Thr Ala Met Met Ala Lys Asn Gly Thr Ala Val Lys Glu Glu Tyr
            260                 265                 270

Val Ser Pro Thr Asn Leu Ser Gly Pro Ala Leu Glu Asp Ser Leu Phe
        275                 280                 285

Arg Phe Leu Thr Pro Leu Pro Val Ser Glu Pro Pro Leu Asn Glu Val
    290                 295                 300

Ala Arg Gln Ala Gly Ala Asn Pro Ile Ser Leu Pro Thr Asp Asn Pro
305                 310                 315                 320

Ser Ser Ile Pro Thr Val Gly Ala Gly Glu Ile Ser Pro Thr Gly Val
                325                 330                 335

Ser Asp Leu Met Leu Tyr Pro Ser Trp Thr Asp Ser Lys Glu Pro Pro
            340                 345                 350

Ser Trp Tyr Ser Lys Gly Ala Asp Ile Asp Ala Leu Leu Asp Met Gly
        355                 360                 365
```

```
Asp Ser Leu Asp Trp Leu Asp Asp Thr Gly Asp Leu Asn Glu Ser Tyr
    370                 375                 380

Val Pro Pro Val Val Asp Thr Ala Met Ala Ala Pro Glu Pro His Thr
385                 390                 395                 400

Thr Phe His Arg Tyr Ser Asp Leu Gly His Ser Lys Gly Leu His Ser
                405                 410                 415

Thr Ser Val Thr Ser Leu Pro His Val Asp Ser Asn Ala Asn Val Glu
            420                 425                 430

Ser Val Val Pro Pro Leu Pro Ser Ile Phe Asp Gly Ala Pro Asp Ser
        435                 440                 445

Gly Glu His Leu Glu Thr Thr Glu Gly Met Val Pro Ser Asn Ser Thr
    450                 455                 460

Ser His Leu Ala Asp Glu Ile Asp Asp Ser Glu Gly Ile His Glu His
465                 470                 475                 480

Leu Gln Val Phe Asp Ser Pro Leu Glu Glu Asn Asp Phe Val Ser Ala
                485                 490                 495

Ile Leu Glu Glu Asp Thr Ile Asp Val Thr Ala Ala Leu Ala Ala Ser
            500                 505                 510


<210> SEQ ID NO 30
<211> LENGTH: 1633
<212> TYPE: PRT
<213> ORGANISM: Phaeodactylum tricornutum

<400> SEQUENCE: 30

Met Thr Thr Ala Pro Leu Thr Ala Ala Gln Ser Ser Pro Leu Thr Ile
1               5                   10                  15

Ala Asn Thr Thr Thr Thr Thr Ile Asn Ser Lys Pro Leu Val Asp Ser
            20                  25                  30

Leu Thr Asn Thr Val Pro Glu Thr Val Gln Ser Ser Gly Arg Asp Gly
        35                  40                  45

Asn Ser Ser Asn Ser Glu Thr Asn Lys Ser Asn Ser Asn Arg Thr Pro
    50                  55                  60

Thr Lys Phe Ala Ala Leu Ser Glu Val Pro His Arg Arg Ser Ala Leu
65                  70                  75                  80

Val Ser Thr Ala His Ser Val Thr Ser Lys Ser Lys Gln Asn Ser Thr
                85                  90                  95

Pro Pro Val Asp Met Ala Thr Ala Ser Gly Ser Ala Ser Gln Gly Ser
            100                 105                 110

His Gly Glu Asn Thr Gly Arg Trp Thr Ala Glu Glu His Arg Leu Phe
        115                 120                 125

Leu Gln Gly Leu Glu Gln His Gly Lys Gly Trp Lys Lys Ile Ala Ser
    130                 135                 140

Leu Ile Lys Ser Arg Thr Val Val Gln Ile Arg Thr His Ala Gln Lys
145                 150                 155                 160

Tyr Phe Gln Lys Leu Ala Lys Ala Arg Gln Asn Gly Glu Glu Gly Asp
                165                 170                 175

Val Ala Met Glu Gly Arg Gly Gly Val Ala Ser Ile Thr Ser Val Ser
            180                 185                 190

Thr Thr Ala Val Leu Pro Lys Arg Arg Arg Gln Thr Thr Gly Thr Lys
        195                 200                 205

Arg Lys Ala Ile Gln Ser Val Val Ala Ser Ala Gln Arg Gln Gly Lys
    210                 215                 220

Lys Leu Ala Ala Ala Lys Thr Asn Pro Thr Arg His His Pro Leu Pro
```

-continued

```
225                 230                 235                 240

Pro Pro Leu Pro Thr Val Ala Pro Ala Leu Ala His Tyr Thr Leu Pro
                245                 250                 255

Ser Thr Ala Met Met Ala Lys Asn Gly Thr Ala Val Lys Glu Glu Phe
            260                 265                 270

Val Ser Pro Thr Asn Leu Ser Gly Pro Ala Leu Glu Asp Ser Leu Phe
        275                 280                 285

Arg Phe Leu Thr Pro Val Pro Val Ser Glu Pro Pro Leu Asn Glu Val
    290                 295                 300

Ala Arg Gln Ala Gly Ala Asn Pro Ile Ser Leu Pro Thr Asp Asn Pro
305                 310                 315                 320

Ser Ser Ile Pro Thr Val Gly Ala Gly Glu Ile Ser Pro Thr Gly Val
                325                 330                 335

Ser Asp Leu Met Leu Tyr Pro Ser Trp Thr Asp Ser Lys Glu Pro Pro
            340                 345                 350

Ser Trp Tyr Ser Lys Gly Ala Asp Ile Asp Ala Leu Leu Asp Met Gly
        355                 360                 365

Asp Ser Leu Asp Trp Leu Asp Asp Thr Gly Asp Leu Asn Glu Ser Tyr
    370                 375                 380

Val Pro Pro Val Val Asp Thr Ala Met Ala Ala Pro Glu Pro His Thr
385                 390                 395                 400

Thr Phe His Arg Tyr Ser Asp Leu Gly His Ser Lys Gly Leu His Ser
                405                 410                 415

Thr Ser Val Thr Ser Leu Pro His Val Asp Ser Asn Ala Asn Val Glu
            420                 425                 430

Ser Val Val Pro Pro Leu Pro Ser Ile Phe Asp Gly Ala Pro Asp Ser
        435                 440                 445

Gly Glu His Leu Glu Thr Thr Glu Gly Met Lys Ala Gln Ala Ser Asp
    450                 455                 460

Leu Ser His Lys His Thr His Ser Phe Thr Ala Cys Pro Leu Arg Leu
465                 470                 475                 480

Thr Met Gly Thr Ile Val Ser Thr Val Gly Arg Ser Ala Glu Thr Asp
                485                 490                 495

Phe Phe Val Thr Glu Ser Leu Gln Phe Leu Leu Ser Trp Asn Glu Gly
            500                 505                 510

Pro Arg Arg Gln Thr Arg Arg Ile His Asp Pro Thr Leu Leu Asp Gly
        515                 520                 525

Ile Asp Ser Asn Glu Asn Ile Leu Asp Thr Thr Val Ala Pro Ile Thr
    530                 535                 540

Met Pro Thr Thr Asn Ser Pro Val Glu Ser Arg Thr Leu Ser Trp Thr
545                 550                 555                 560

Asp Leu Gly Leu Asp Thr Asp Glu Asp His Pro Arg Arg Leu Leu Arg
                565                 570                 575

Val Arg Asp Asp Val Ile Ala Tyr Gly Gly Asp Glu Gly Thr Leu Val
            580                 585                 590

Arg Leu Pro Phe Val Thr Thr Ser Asn Ala Gln Asn Ala Asp Thr Gly
        595                 600                 605

Ser Thr Arg Pro Leu Ala Val Arg Arg Phe Asp Glu Asp Ala Ile Arg
    610                 615                 620

Ala Val Ala Val Ser Asp Asp Gly Thr Arg Val Ala Val Gly Thr Asp
625                 630                 635                 640

Ser Gly Ala Thr Leu Phe Tyr Arg Tyr Glu Leu Asp Gly His Val Val
                645                 650                 655
```

```
Asp Ala Pro Gly Lys Gly Leu Val Ser Arg His Gly Phe Val Thr His
            660                 665                 670

Asp Ser Asp Asp Asn Asn Asn Asn Asn Asn Asn Ser His Gln Lys Pro
        675                 680                 685

Ser Ala Asp Leu Phe Gly Ser Gln Pro Asp Ala Leu Ala Phe Val Pro
    690                 695                 700

Gln Gln Arg Pro Gly Glu Val Val Arg His Gly Pro Val Phe Asp Ala
705                 710                 715                 720

Pro Val Arg Gln Leu Leu Phe Leu Pro Asp Ser His Phe Leu Ala Ile
                725                 730                 735

Ala Thr Glu Ala Gly Leu Ala Val Val Ser Thr Asp Thr Asp Ser Gly
            740                 745                 750

Ile Gly Gly Gly Ser Leu Asp Thr Asn His Asn Glu Asn Val Asn His
        755                 760                 765

His Asn Val Lys Tyr Leu His Arg Glu Ala Gln Thr Ala His Asp Glu
    770                 775                 780

Ser Gly Ile Arg Gly Leu Ala Leu Trp Gln Ala Lys Asp Cys Arg Ile
785                 790                 795                 800

Leu Ser Ser Leu Ala Met Asp Gly Arg Leu Cys His Trp Asp Val Ser
                805                 810                 815

Ala Pro Thr Pro Thr Leu Trp Lys Leu Leu His Arg Glu Thr Val Pro
            820                 825                 830

Thr Val Thr Lys Pro Asp Leu Gly Glu Met Leu Gly Ala Asp Ala Trp
        835                 840                 845

Asp Arg Ser Thr Ile Pro Val Ala His Ser His Glu Ser Ile Leu Phe
    850                 855                 860

Leu Pro Gly Glu Thr Tyr Val Gln Ala Arg Arg Tyr Arg Asn His Thr
865                 870                 875                 880

Trp Glu Leu Leu Gln Ser Pro Thr Gly Ala Thr Asn Thr Thr Asp Lys
                885                 890                 895

Val Gln Gly His Ile Glu Ala Ile Val Ala Met Ala Pro Ala Pro Asn
            900                 905                 910

Pro Arg Asp Pro Tyr Leu Val Thr Ser Gly Arg Asp Gly Arg Val Val
        915                 920                 925

Leu Trp Lys Leu Gln Tyr Ser His His Asp Asn Asn Asn Asn Asp Asn
    930                 935                 940

Asn Pro Asn Asp Asn Gly Asp Gly His Ile Val Phe Gln Lys Gln Ile
945                 950                 955                 960

Leu Gln Thr Asp Ser Ala Pro Thr His Leu Leu Trp Thr Leu Asp Gln
                965                 970                 975

Pro Thr Gln Thr Glu Arg Leu Asp Met Val Thr Ala Asp Gly His Trp
            980                 985                 990

Thr Thr Leu Val Gly Arg Asp Gln  Ile Ala Pro Ala Cys  Pro Thr Thr
        995                 1000                1005

Ala Val  Thr Gln Glu Ile Ser  Leu Pro His Arg Gln  Ser Ala Asp
    1010                1015                1020

Ser Val  Arg Glu Lys Glu Lys  Glu His Asp Ala Asp  Ser Asp Asp
    1025                1030                1035

Ser Val  Asp Asp Phe Ser Ser  Asn Lys Pro Ser Thr  His Gln Lys
    1040                1045                1050

Asn Pro  Phe Val Asp Asp Glu  Ala Glu Asp Asp Asn  Asp Asp Asp
    1055                1060                1065
```

```
Thr Leu  Asp Thr Ala Ser Arg  Gly Lys Leu Glu Thr  Thr Ser Pro
    1070                 1075                 1080

Thr Asp  Lys Arg Ala Ser Asn  Leu Asn Ser Ser Ala  Leu Glu Glu
    1085                 1090                 1095

His His  Asn Asp Leu Asp Asp  Asp Ser Ile Gly Asp  Asp Asp Asp
    1100                 1105                 1110

Ser Phe  His Asn Ile Pro Thr  Leu Thr Thr Arg His  Ser Asp Ser
    1115                 1120                 1125

Ile Gln  Trp Pro Glu Pro Gln  Pro Ala Phe Gly Pro  Ser Ser Thr
    1130                 1135                 1140

Ser Leu  Glu Leu Thr Arg Arg  Phe Leu Cys Trp Asn  His Ile Gly
    1145                 1150                 1155

Ser Val  Thr Phe Leu Arg Gly  Gln Ala Gly Ile Asn  Arg Ser Thr
    1160                 1165                 1170

Ile Asp  Ile His Phe Thr Asp  Ser Ala Phe Arg Arg  Pro Val Ser
    1175                 1180                 1185

Phe Thr  Asp Asn Met Gly Phe  Ile Leu Gly Ser Leu  Gly Glu Asp
    1190                 1195                 1200

Gly Gly  Ile Phe Ala Thr Asp  Leu Ala Glu Asp Glu  Asp Ile Asp
    1205                 1210                 1215

Glu Glu  Asp Asp Asp Met Asp  Gly Leu Asn Val Ser  Ala Ala Thr
    1220                 1225                 1230

Lys Ala  Ala Val Lys Arg Ser  Arg Lys Gly Pro Ser  Asn Lys Pro
    1235                 1240                 1245

Thr Gly  Ser Ser Ile Tyr Phe  His Arg Phe Glu Thr  Phe Gly Ser
    1250                 1255                 1260

Leu Arg  Asp Lys Asp Trp Tyr  Leu Thr Leu Pro Asp  Gly Glu Arg
    1265                 1270                 1275

Ala Leu  Gly Cys Ala Ser Gly  Glu Gly Trp Ala Ala  Val Val Thr
    1280                 1285                 1290

Ser Arg  Arg Phe Leu Arg Leu  Phe Ser Ser Gly Gly  Asn Gln Gly
    1295                 1300                 1305

Glu Val  Leu Trp Leu Asn Gly  His Pro Val Thr Met  Ala Gly Arg
    1310                 1315                 1320

Gly Arg  Phe Val Ala Val Val  Tyr His Glu Ser Thr  Pro Leu Pro
    1325                 1330                 1335

Asp Gly  Thr Gln Lys Leu Gly  Tyr Leu Val Leu Asp  Ala Met Ala
    1340                 1345                 1350

Asn Arg  Val Val Ala Lys Gly  Pro Val Ser Cys Ile  Ser Gly Ala
    1355                 1360                 1365

Ser Thr  Leu Ser Trp Leu Gly  Phe Ser Asn Asp Gly  Ser Leu Leu
    1370                 1375                 1380

Ala Met  Asp Ser Asp Gly Met  Leu Ser Met Leu Val  Cys Ala Ser
    1385                 1390                 1395

Ser Leu  Asp Ala Glu Gly Pro  Thr Glu Lys His Trp  Glu Trp Met
    1400                 1405                 1410

Pro Met  Leu Asp Thr Val Gly  Leu Arg Lys Ser Arg  Asp Asp Ser
    1415                 1420                 1425

Phe Trp  Pro Val Thr Val Tyr  Asp Gly Lys Leu Val  Cys Val Pro
    1430                 1435                 1440

Leu Lys  Gly Gly Met Lys His  Pro Asp Ala Val Arg  Arg Pro Val
    1445                 1450                 1455

Thr Ala  Ala Leu Gly Phe Arg  Leu Pro Leu Ala Arg  Gly Pro Leu
```

```
    1460                1465                1470

Thr Lys  Thr His Thr Leu Glu  Glu Leu Ala Val Arg  Ala Ala Ile
    1475                1480                1485

Ala Leu  Gly Gln Lys Lys Ala  Ile His Glu Ile Ser  Arg Glu Gly
    1490                1495                1500

Asp Glu  Asp Asp Glu Asp Phe  Glu Lys Glu Tyr Arg  Ser Leu Ser
    1505                1510                1515

Ala Gln  Val Asp Lys Val Thr  Leu Lys Met Phe Ala  Ala Ile Ala
    1520                1525                1530

Glu Ala  Gly Lys Leu Glu Arg  Ala Leu Asp Leu Val  Glu Arg Leu
    1535                1540                1545

His Leu  Glu Lys Ser Tyr Asp  Leu Ala Met Thr Ile  Gly Asp Arg
    1550                1555                1560

His Arg  Lys Leu Val Asp Leu  Ile Glu Glu Ala Lys  Asp Arg Lys
    1565                1570                1575

Phe Gly  Asp Pro Gly Ser His  Gln Ala Glu Phe Thr  Thr Lys Ala
    1580                1585                1590

Glu Ser  Pro Asn Tyr Gln Arg  Pro Arg Ile Ser Pro  Asp Ser Ala
    1595                1600                1605

Gly Ala  Lys Arg Ser Leu Asp  Asp Glu Asp Glu Asp  Val Arg Ser
    1610                1615                1620

Arg Leu  Val Arg Arg Lys Pro  Thr Phe Ala
    1625                1630


<210> SEQ ID NO 31
<211> LENGTH: 991
<212> TYPE: PRT
<213> ORGANISM: Thalassiosira pseudonana

<400> SEQUENCE: 31

Met Ser Thr Thr Leu Ser Ala Val Gln Phe His Phe Gln Glu Thr Thr
1               5                   10                  15

Thr Thr Ala Ala Ala Asn Glu Asn Gly Ser Gly Asp Glu Lys Ile Ile
            20                  25                  30

Ser Thr Ala Ala Thr Thr Thr Thr Thr Thr Thr Glu Gly Ser Leu Ala
        35                  40                  45

Ala Glu Glu Gly Ala Ile Gln Ser Pro Arg Lys Ile Ser Glu Gly Asp
    50                  55                  60

Tyr Thr Leu Gly Ala Leu Leu Thr Ser Ser Gly Gly Ala Ser Val Ser
65                  70                  75                  80

Arg Val Val Thr Lys Glu Ser Leu Leu Gly Asn Asn Asn Asn Gly Ser
                85                  90                  95

Glu Gln Thr Thr Ala Thr Gly Pro Lys Ala Phe Ser Val Pro Ser Pro
            100                 105                 110

Leu Asp His Asn Asp Gly Gly Ser Phe Ser Phe Ser Ala Pro Glu Thr
        115                 120                 125

Thr Phe Gln Ser Ala Pro Leu Asn Ser Gly Gly Ser Ser Ser Ala Ser
    130                 135                 140

Arg Cys Gly Glu Gln Glu Val Asp Gln Ala Phe Ala Ala Glu Ile Ala
145                 150                 155                 160

Lys Ile Asp Phe Ser Val Pro Cys Pro Leu Asn Ser Phe His Gln Val
                165                 170                 175

Asp Tyr Ser Thr Thr Asn Asp Gly Lys Thr Thr Pro Val Glu Glu Glu
            180                 185                 190
```

-continued

```
Thr Leu Tyr Leu Pro Pro Glu Asp Ser Asn Asn Asn Asn Ala Val Val
        195                 200                 205

Ser Ala Tyr Asn Ser Pro Ile Pro Pro Leu Phe Ser Ser Ser Ser Ala
    210                 215                 220

Pro Ile Thr Ile Asn Asp Pro Leu Ile Ser Leu Arg Ser Ser Ser Pro
225                 230                 235                 240

Leu Leu Tyr Ala Ala Ser Phe Asn Thr Pro Gln Glu Glu Asn Thr Ser
                245                 250                 255

Trp Ala Ala Val Gly Gly Ala Thr Ser Ile Val Ser Thr Gly Leu Ser
            260                 265                 270

Val Gln Val Pro Val Glu Val Ala Ala Val Ser Thr Ala Ala Val Val
        275                 280                 285

Ala Ser Asn Ser Ala Val Val Val Thr Pro Pro Thr Thr Leu Glu Glu
    290                 295                 300

Asp Gly Ser Ser Ile Ser Ile Ala Lys Lys Lys Lys Ser Lys Ala Pro
305                 310                 315                 320

Lys Thr Gln Lys Ser Arg Thr Lys Ser Lys Gln Pro Thr Ala Thr Ser
                325                 330                 335

Gly Val Val Ala Pro Ile Ala Arg His Ser Ala Thr Thr Asn Thr Thr
            340                 345                 350

Met Asp Arg His Asn Met Gly Ser Ala Pro Ser Pro Leu Gly Thr Thr
        355                 360                 365

Ala Ser Thr Met Ser Ile Ser Ile Pro His His Thr Tyr Gln His Gln
    370                 375                 380

Gln Gly Ala Val Asp Glu Pro Glu Thr Pro Ser Ser Ser Gly Ser Pro
385                 390                 395                 400

Ser Gly Asn Thr Val Ser Thr Leu Asn Pro Asn Thr Asn Ala Val Glu
                405                 410                 415

Asn Thr Gly Arg Trp Thr Ala Glu Glu His Arg Leu Phe Leu Gln Gly
            420                 425                 430

Leu Glu Gln His Gly Lys Gly Trp Lys Lys Ile Ala Gly Leu Ile Lys
        435                 440                 445

Ser Arg Thr Val Val Gln Ile Arg Thr His Ala Gln Lys Tyr Phe Gln
    450                 455                 460

Lys Leu Ala Lys Ala Arg Ala Gly Asp Gly Ser Gly Ile Pro Met Ile
465                 470                 475                 480

Gly Gly Gly Ala Gly Glu Asp Ser Pro Glu Leu Gly Pro Gln Ala Ala
                485                 490                 495

Val Ala Val Ser Asn Thr Met Asn Ser Ser Gly Gly Gly Lys Ala Gly
            500                 505                 510

Gly Gly Leu Gln Met Leu Pro Pro Ala Asn Thr Val Thr Met Arg Thr
        515                 520                 525

Val Asn Gln Gln His His Gly Asn His Gly Asn Met Ser Leu Gly Thr
    530                 535                 540

Asp Ser Val Ser Met Ala Ala Ala Ala Gly Gln Ile Asp Ile Ala Ser
545                 550                 555                 560

Gly Val Ser Thr Ser Ser Gly Gly Ala Ser Ser Arg Asn Thr Thr Thr
                565                 570                 575

Thr Ser Gly Gly Leu Lys Arg Arg Thr Asn Ala Lys Ser Ala Gly Gly
            580                 585                 590

Gly Gly Gly Thr Lys Arg Arg Ala Ile Gly Ser Val Val Arg Ser Ala
        595                 600                 605

Val Arg Glu Gly Arg Asn Val Lys Arg Gln Lys Ile Ala Glu Ala Arg
```

```
    610                 615                 620

Arg Asn Gly Gly Ala Thr Ala Ala Thr Ser Gly Gly Asp Gly Gly Val
625                 630                 635                 640

Pro Asn Pro Leu Pro Ala Ile Ser Asn Ile Leu Asp Pro Tyr Val Pro
                645                 650                 655

Ser Val Ala Ser Ala Ala Ala Val Ala Gly Thr Lys Lys Gly Arg Gly
            660                 665                 670

Arg Gln Gln Ile Val Gln Thr Ala Thr His Gly Ser Leu Pro Met Ala
        675                 680                 685

Ala Leu Glu Asp Ala Val Phe Arg Leu Leu Thr Pro Ala Pro Gly Ala
    690                 695                 700

Pro Leu Ser His Pro Ser Ala Ser Ser Gln Pro Ile Ser Asp Pro Leu
705                 710                 715                 720

Ala Pro Asn Gln Val Lys Met Pro Val Ala His Ala His Tyr Leu Gln
                725                 730                 735

Gln Gln Ala Ala Gln Asn Pro Ser Pro Thr Gly Val Thr Glu Met Thr
            740                 745                 750

Phe Pro Ser Trp Val Asp Pro Asn Asn Pro Pro Gln Trp Tyr Asn Glu
        755                 760                 765

Gly Gly Asp Ile Asp Asn Leu Leu Asp Glu Ala Glu Ala Leu Asp Trp
    770                 775                 780

Leu Thr Asp Thr Gly Asp Ile Asn Glu Thr Tyr Pro Pro Ala Val Ala
785                 790                 795                 800

Ala Thr Gln Ala Ala Val Ala Asn Asp Pro Ser Asp Tyr Glu Pro Thr
                805                 810                 815

Pro Val Asn Asn Tyr Ser Tyr His Val Asp Asn Ser Gly Ala Thr Thr
            820                 825                 830

Pro Ser Leu Ala Ser Val Asp Pro Thr Ala Val Lys Met Glu Asp His
        835                 840                 845

Thr Met Val His Asp Pro Thr Gly Met Met His Pro Ser Ala Asp Ser
    850                 855                 860

Leu Ser Phe Leu Val Asp Pro Pro Glu Glu Gly Val Thr Ser Ala Glu
865                 870                 875                 880

Leu Pro Ala Phe Leu Asn Asp Asp Ser Pro Gln His Gly Val Ala Ser
                885                 890                 895

Met Pro Phe Ser Ser Ala Thr Glu Ala Val Glu Ser His Thr Phe Glu
            900                 905                 910

Asn Lys Ile Asn Thr Ala Val Ser Asp Gly Asn Leu Met Gly Phe Pro
        915                 920                 925

Asp Leu Asp Met Gly Asp Glu Gln Ala Phe Val Ser Ala Leu Leu Asp
    930                 935                 940

Asn Ser Gly Gln Ser Thr Leu Ser Phe Pro Lys Leu Asn Ser Glu Leu
945                 950                 955                 960

His Ile Gly Ser Leu Ser Gly Ile Gly Leu Ser Gly Val Gly Val Ser
                965                 970                 975

Ser Asp Ala Leu Gly Glu Pro Leu Glu Asp Asp His Leu Asp Asp
            980                 985                 990
```

<210> SEQ ID NO 32
<211> LENGTH: 408
<212> TYPE: PRT
<213> ORGANISM: Ectocarpus siliculosus

<400> SEQUENCE: 32

-continued

Met Thr Pro Lys Asn Thr Gly Arg Trp Thr Tyr Asp Glu His Arg Leu
1               5                   10                  15

Phe Leu Arg Gly Leu Glu Leu His Gly Lys Gly Trp Lys Lys Ile Ala
            20                  25                  30

Ser Leu Ile Lys Thr Arg Thr Val Val Gln Ile Arg Thr His Ala Gln
        35                  40                  45

Lys Tyr Phe Gln Lys Ile Ala Lys Ala Lys Gln Asn Gly Glu His Gly
    50                  55                  60

Asp Val Ala Met Asp Ser Lys Gly His Gly Ser Arg Arg Lys Ser Arg
65                  70                  75                  80

Gly Arg Arg Arg Met Glu Asp Leu Leu Arg Gly Ser Thr Ala Val Ala
                85                  90                  95

Pro Ser Leu Gln Pro Tyr Val Ala Gly Ala Gly Ala Val Glu Thr Gly
            100                 105                 110

Leu Tyr Arg Phe Leu Ser Pro Ile Thr Ile Gln Asp Leu Glu Arg Pro
        115                 120                 125

Pro Ala Ala Ala Gly Gln Gly Gly Thr Ala Gly Gly Val Gly Gly Gly
    130                 135                 140

Ala Ala Gly Leu Gly Gly Asn Gly Gly Ala Ser Leu Gln Ser Gln Leu
145                 150                 155                 160

Ala Gly His Ala Thr Ser Ser Ala Gly Ala Ser Pro Thr Thr Thr Thr
                165                 170                 175

Ala Gly Ala Ala Met Ala Ala Ala Ala Ala Val Leu Pro Pro Asn Trp
            180                 185                 190

Tyr Arg Ala Gly Arg Gly Val Asp Asp Leu Leu Thr Glu Ala Glu Gly
        195                 200                 205

Leu Asp Trp Leu Ala Asp Ser Gly Gly Ala Val Ala Val Thr Ser Val
    210                 215                 220

Ser Ala Val Asn Pro Ala Ala Ala Ala Ala Ala Ser Pro Ala Pro Ala
225                 230                 235                 240

Ala Val Ala Gly Ala His Ala Gly Val Ala Arg Val Ala Ser Ser Ser
                245                 250                 255

Glu Leu Ser Ser Gln Pro Leu Leu Lys Lys Val Arg Ser Thr Thr Val
            260                 265                 270

Asp Ser Ser Ala Pro Leu Ala Thr Ala Thr Thr Met Asn Thr Ser Ser
        275                 280                 285

Thr Ala Ala Ala Ala Met Gly Gly Ile Ala Arg Pro Ser Ala Ser Ala
    290                 295                 300

Ala Ala Met Thr Pro Ser Ser Trp Ser Leu Pro Pro Pro Arg Pro Val
305                 310                 315                 320

Ala Cys Pro Pro Pro Ala Ala Pro Pro Thr Ala Gly Val Ala Val Asp
                325                 330                 335

Glu Leu Thr Pro Ser Gly Leu Gln Gly Ser Asp Ala Glu Glu Gly His
            340                 345                 350

Leu Ser Gly Leu Ser Asp Leu Glu Ser Leu Met Glu Asp Gln Glu Leu
        355                 360                 365

Pro Gly Ser Gln Pro Phe Gly Pro Val Ser Thr Ala Ala Glu Val Ala
    370                 375                 380

Gly Ala Gly Gly Asp Gly Met Asp Asp Gly Met Val Asp Glu Asp Ala
385                 390                 395                 400

Phe Val Asn Ala Leu Leu Asp Ala
                405

<210> SEQ ID NO 33
<211> LENGTH: 2016
<212> TYPE: DNA
<213> ORGANISM: Nannochloropsis CCMP 1179

<400> SEQUENCE: 33
atggatgaag ttaaatatgc cgctggcggg ctgatcaagc ccgggacgca aggcctgggc 60
agcatgctct ctacaccctt gacgccctcg gcttctctta ttgcatcgtc ggtggtagag 120
gccgatgcaa agcaacaaca actgctgaag gattccctca ccgccgacct caaattgctc 180
ctgcacgaat tcgaacgctt ccagcaggcc actgcagcag cagcgggaac aggaggcgtg 240
ggcgaggagg aggcagctga gcgatcgacg aaagtggagt tctttttggg atacattgag 300
cgagttctcc acgatttggc aggggctgac gcatcgaaac tgcaggatct cgaggtgcgg 360
atcaagacaa gtctactacc actcaagggc caggtggtta gccagcttgc ggcgcaaaat 420
aataactccc ctcctcccca taaggagcag cagtcatctt ggttccatcc ttcttccacc 480
tgctcctccc tctcctcctc ttcttccgtc tccagcgtgc acacaactcc tcctggatct 540
cccttggcaa gggaggagac ggtgatgagc acctacggtc cctttaccca ctcccgcgtc 600
gcagcagcag acgcagtctt tctctcctct tcctctgctg cttctcggct gatgccgcct 660
gtgagtttcc ggagggatca gagtgacata agtgggatta cgtcgtgctc gtcatcatcg 720
tcgtcatgcg ggggggaagg aggtgcgggg catatggacg atttagattt ggagtgtttt 780
agcttgataa tggacgaggc tgccgctact gctcctttta ctactgcagg taatggtggg 840
aaggatctgc cggccaatgg ctcatgtgtt gatgatgaca tgacggatgc tggctctcta 900
acttcagagg aaagcagcgt gtttgtgtcc tccccccggg agtcctcctc ttcgctcagc 960
actgttagta cgggcttgga cccaacaagc agcaacagtg gaaataagcg gaccttgccc 1020
ttagaatttc ccagcagcag cagcagcagc agcagcagca gcagtctttc tctggccaca 1080
gcgtcctccg tatctacaga cactctgcag cagccgctca agcgcgcccg cagcgtcatc 1140
ctacccacca gcagcagcag cagcagcagt tgtgctacgc atgcacctcc ctgcctcgcc 1200
tcctcctcca cctcctcctc ttcttctttc tcttcccctt tctcttcctc ttcggtggcg 1260
acagtggcag cagcagatgt cagcaagcct ctccttcgtc aggttgagta tcagtgcggt 1320
gcttgcgccg acacctacac cgctgcctcc tccctcaatc cctggtgggc cctcgagcga 1380
caggagtgtc ccaagtgcaa gaaggttcaa gttccacgca ttgacattaa cctgcctgcc 1440
aacaccatgg aataccaccc ggctttgctc gcggaggaag gcgatgatga cgatgatgat 1500
gaggtgggag gcgggaggga gggagggatg atgatgatgc cggggggagg ggatggacat 1560
ggacatgtgg aggaaagaga ggagggagag acgagtgaga aagggagcgg tggaagtagc 1620
gtactagagg aggacgagga agcagtgttg agccctatgc aagcttcaca gctgttgagt 1680
ttgttggagc atgcgcggac atgcccgggc aatcatgctg ccgagaaaca ccaggctgtg 1740
tgtacgagtg ccaagtatct catgttgcat gtgagggatt gtgatggcag gacgttagat 1800
ggggaggctt gtggattctc gtggtgcagg ccttgcaaac acttgctcgg gcacctggtc 1860
cggtgttacg aagccgagaa gtgtcagatc tgctgtttct cacaccaaga agaggaggag 1920
aaagtggaaa agaaggtgat gatgagtgtg gaggagatga ttgaggagaa aggaatgagg 1980
gtcgacacct acaggagctt gacgagcttg agctga 2016

<210> SEQ ID NO 34
<211> LENGTH: 2364
<212> TYPE: DNA

<213> ORGANISM: Ectocarpus siliculosus

<400> SEQUENCE: 34
atgctggcgc aactggcgca gcagcagcag cagtcctccc cctccaccgc cgcaacggct 60
acgccgtcta ccgaaaccat cggcaccgac gccggcggca acacgcctcc cccccccagc 120
ggaagcctct tcctcggggg cgtcggcggc ggcaaggacg gcgccaccgc ggtcagcgac 180
ggctgggtgg ttgggtcgcc ctcccctact ctccccccgt cgtcctccaa cgagagcggc 240
ggcggcggcg gcggcggcgg ccgcgtgaac atttccacgt gcgattccgg cgggcagttg 300
tctgggacga cgtcttcggc gtcgctgccg agagcgtgct cttcgctgtc cttcgcggac 360
ctgggcgacc tgtgcgggga tcaggaggga ggagacgttt ttctagtcgg gggggaggac 420
tgcgacgacg atgcccacgg gtcggggatc ggtcttgacc tgtacgacct gggacagggg 480
ggcaaagacc cttttcttcc cgaggggcag caacgcgccg gtcggtggag ctccatctcc 540
actaggtcgt cgtcttcgac ggcatccacg gacggggaag aactctcgga cgattcgctc 600
tccgtcgatg cggactgcag cggcagcagc agcacgccgt gcagcccgtc tgcggtcagc 660
tccggcgagc cgtccttgct ggcggcggcg gcggcggcaa cgagagccgc caaagcaatc 720
aagaccgagg cccggcccga cggcagcgct ggtctagaag cgggcgcggt acagcagggg 780
gttgccgctg gggcgcttc tgccaccaag agcggcatcg accaggagat gggagagctg 840
tcggagctgt tcgctcccga tgccttcctg atgagtaccg tcctggacac cgagatggag 900
gccggcggcg gcggtgcggc gcgagcagga gcgtcgggca tcgaggtttc gatcgagccc 960
accgccactg agcccagcaa ggcctcgcag catgctgctg ctgcggtcgg ccctaggcct 1020
acgacggcag caggggctag tgctgtcgcc gtcactgcgc cggccgcggt ggtcaagatg 1080
gagttcctgc ctgccgcggg agcgtccgct ccttctccgg catcaccacc cgctcccact 1140
gctgccgctg ccgcctccgt tttgccggca ccggcagcgg tagctccgaa acaggagtgc 1200
cgctgcggac aggcggcgtg tccgtcgctg atcacggccg cccgaaagcg accggtggcg 1260
gagctctcgc cttcgttgtc gggggcggac ggccccgcgc cgctgtccat ggtcacgggc 1320
ctgcccttcc accagtcctc gcggcagcgg aagcggcagc ggagcctcgc cccggtgctc 1380
tcggcgccgc gcaccgtgag ctacgagtgc tcgctctgca aggagagcta cccgtccgag 1440
atcgcgtcca acccgtggtg gtcgctgttc ctgcacgagt gcccacggtg ccaccggatg 1500
cagatacctc gagtcgacgc gacgagcgcg gccgtgagcg tggactacat ccacgccgtg 1560
tgcgcggagg aaggggaggg ctgcgacagc gacgggtacg gcagcgagtc gtgctccgac 1620
agcgacgacg acgttaccga tgacggcagg gagagggaag ggatagccgc cttcgacacg 1680
gacatcatcg cgggggactc gcaggccggc tgcaaggagg gccgcctgtc gaccttccag 1740
gcgtcccgcc tgctggtgct catgtcccac gccaggacgt gccccgggca ccacgccaac 1800
cccaagcacg ccgaggtctg ccggtcgacc aagttcctca tgctgcacat gcgcgactgc 1860
acgggtcaca ccgctaacgg ggatccgtgc gagcaccggt ggtgccggcc gtgcaagagc 1920
ctcctgagcc acctcgtccg gtgcccggac ccgaacacct gccggatctg cacgccgctc 1980
gacctaccgg gcccgctgcg acagctgcgg gatcttaacg tcgcccaggc gcggcatgcc 2040
tccgccgcgg ccgccgccgc cgctgccgct actacttcta ctaccgctcc ttcttctgct 2100
gccgtggcgg tgcccggcgt gggcggtgtt ccctcttcgc ttgcggcggc ggcggcgccg 2160
gctgctgctg ccagggtgcc gtcgatgccg gctcctgcga cggcggtaga cgccgctacc 2220
gtgaagtctg aggagatgtg ccgccccgcc ggggccgcta cggcgatggg gctggcggtt 2280
tctgcgacga cgacgacgtc gctgcggcaa cagctgcagc agcgggtggt tgggggtgcg 2340
ggaggggtag tcacgactcg ttga 2364

<210> SEQ ID NO 35
<211> LENGTH: 3408
<212> TYPE: DNA
<213> ORGANISM: Thalasiossira pseudonana

<400> SEQUENCE: 35
atggacggtt catccgacga caaccgtaag cggccgcacc ctgcatccaa tgccaacgat 60
gtggcttcgt cagaggttgc tgcgggagat aacaaacgag taaaaatcga agatgtagga 120
caggcagcag cggcggtgga gacacaagat gtgccacaga ctcaggcgtc ggtggatgct 180
gttgcttcat ctattgtacc gacgacgcaa ccgcagcctc tgacacagga agctgttcca 240
gcagccgtat cgtccacaac aactaccgct gttgtatcct cttcgacaca aatatctgcg 300
ggggaagcgg cggctctgac tgcttcgaaa actgcaacag ctaagccagc agcagacggt 360
gacttaatgc ctgctgccct cctcacatcg tcgtcgtcaa ctcaagctgt tgctccagca 420
actcaagctc agagtgtgac accagcagtt gtccaaagta caactcagca tgttcctgct 480
gctagcacat cagcacagcc tccagcaaaa aaagaggtca agccagcatc aacaccatcc 540
accaccgtcg tccaaccgca acgaccacaa aaacaacgag caccatctcc acccccaccc 600
ctaaaagcac ttactttcca ccacctccac aaaaaatatg gccccgagtt agactacatg 660
ctcgttgaat ttcgtaaact ggaacgacaa ctgttgggtg ctcccattca tgctgccgct 720
gctgcatctg ctgctcccaa agcaggagga gcagcagctg ccgaggtgaa gccaaaggtg 780
gaaccgaagg ggtcgagaga acgaagggag aagttgcatg ggtttatatt gcatttggag 840
gatacgatac ggcaggtaga ggagggttgt gccgttgaac ggagtgaaag gaatttgaag 900
tgcgagaaca atggtagtgg cggcgggaac ttgaagagtg aagagtgcgc tgctagtcat 960
catcaacaac aaccgaaaca acaaccgttt gaggaggaga agaagtcatc tgatgcttca 1020
ttgcagccgc agcccaatac agcatcagct gcttcatctg ccgcaacaat aatatcaact 1080
ccaaacaaca acactggcga agcacccaaa ttcacagcag cagacgcatc actttcccaa 1140
ctccccccag aaaaagaacg ggaagaatca gtccagcgcc tcgaagagca catccttgcc 1200
aacctccttc cagtaaagat acgtctgacg agacaattgg cagcacaaaa gggagctaca 1260
aagaatccaa tcacagctcc actacgtgct ggctcggtgg cgaccgcggg cgttcaaaag 1320
gcaggcgtga gtattgcaga ggctgtggag gcaaaaagaa aggcacaaga agagaggttg 1380
ttgcaacaac aattggtgca aaagtcttct gttcctgtga gcaaagacat tccttctcag 1440
tttgggaaac cgattggtca tggcagttca tcgttgacag ctcggttgca tggaggagtc 1500
ctgggtgctt cggggtctgg agctgctgct gctagtcctg ccaatgctgc gtcaggtgct 1560
gcagcgagtg gtgcagcaac tccatcgaaa cgacgaattc tgtatgcagg tgtagctcct 1620
ggatcgacac aggttccatc gtcagtccat gcagtctctg gagttcatcc tggaatggtc 1680
ggagctgatg ctgccaaggc ggtagttgtg gcagaggagg aacgaaagcg actcaagtac 1740
ttggaagaga gtgcagctcg tgtagcgggc gtggctcctg cgggaggagg agccttggac 1800
agaaagcctg catctcgtcc aacagcaatt gaagcggcag cgccgaaacc gccagaaggt 1860
ccagcgacaa tggccgcacg tgctcgggca attgcattgg ctgcgacaaa caacaatact 1920
gggccttctg cagcgagtaa agtatcccgt ccaaatcagc agatacctgg tatcactgcc 1980
aaacagctac aacaacaaca tttgaagaag gtgtctcccc tggcagctgc aacggctgcc 2040
aatcaaatgg cacatttagg gatgaaacca gtcaaaccaa agaaaccaca tcttgcacca 2100
gatttcaacg atccggcatt gacagccaca caacaaaatg agttacgcct caaagaggca 2160
cgttggaggc aacggaagcg tcgaaaggaa cgtcgtcgta aacggtcggg cgttgttgtt 2220
gatcatgcgg cgatggttac tcagcatgct cagtcaatgc aagagcccaa tgttcacgca 2280
tcttcctcca atgacgcagt tccggcgcag ccaatggttt tgagggtgaa caagaatgga 2340
gcgtatggac cccgcactgt ggaatacgtg tgcgctgtct gtaacgaggg atatgtttct 2400
acttgcgaga tgaatccttg gtgggcctta atcaatcatg aatgtccaaa gtgtggaaag 2460
aatcagattc cacgcctcga tatctctgca ccaaacaacg taatagaata ccatcctgca 2520
ttgctggttc aagaagatgg caaaccagtt tcagcgccag tgtccaacgg tggcgactct 2580
tcaagcgtgc aaatgcaata tctcccacgg catcttgcta aaaagtcgtc tttgtctgat 2640
tcggaagtaa gtcaaaccga cgagagcgac ggagaaggtg gtaccgaaga atactttgat 2700
gaaagcagcg atgacgagga atcagtaaac aagaatgcgc tcgattcctt tgctaaagag 2760
gagagagcgg aacgcgagga ctatggcttt gagttcaaag gagagacatt aagtgatgat 2820
caagcaaagc ggttgcttat attgattgag catgcatcca tttgtcctgg aagacaccga 2880
tctgcaaagc acagaaatgt ctgtcacagc acaaaatact tgatgcttca cgtgcgagat 2940
tgtcccggct tgctatccaa cggagacgtc tgtccatttc cttggtgccg aaagacaaaa 3000
caccttcttt accatcttgt ctcatgcgag aaaagtaacg acggtaaaga gtgcggtatt 3060
tgttgcccaa agaatctatc ttccaacctt tcggagttag ttggtcttaa caaacaccgt 3120
cggaagcaat ttgtggatcg gacaaaggcg attgtggcag ctgcgaaacg tcagcaactt 3180
gctgcagcca gagcaaaagc cgtcgctccc agagctgccg tccaacatca gtatcgtggt 3240
ccggtggtac gaaagggtcc gattccagct gcaacaactt atgctgctcc acctccatca 3300
gcatctacgg tttcttatgc aactacttct cgcggaaccc atatgccatc gacgaacaat 3360
ccgatcatcc aatctcctcc agatgcaaaa acatccaacc aattttga 3408

<210> SEQ ID NO 36
<211> LENGTH: 3447
<212> TYPE: DNA
<213> ORGANISM: Phaeodactylum tricornicum

<400> SEQUENCE: 36
gtcggtcgct tggcgttgac tttgcgccgc agattggccg gtatttctgc agcggaaccg 60
ctgtcgtcag tcacaactgt cgttttcggt ttggcgaaaa cagcccaggg cgatgcgcga 120
tccttccttt tctgggcagg aaaggccgcg gaaattgtca aaaaggctcc atgtgacacc 180
gagaacgaag aaacaactgt cggtgccaaa acagaaagaa tcgcgcaaca ccgtaccgat 240
cgacgacaac ggcatgtcct catggtaacg atggcaattc ctacgaatgt ttgcttgctt 300
ctctcagaaa tattccgttt cttaatgatg gagatggagg agcacgattt ggcgcaacaa 360
aaagaccccg gtaaagtctc gagctgttct gacagtaagg gagaaggaca cgcgctcgaa 420
gtgcaactcg tttacgtttc ttccgcggtg gggttccgtg tttcttggcg tagtgcgtcg 480
tcgttgttgt cctcacgggg gcgggggtat ccaatcttgt cggatggttg tggtgcccgt 540
tcgcagtcca caaacgaggc agtttccagg actaccgaca gttcgaacca cactttgcta 600
cagaattcga atctctcgca gcagcctccc ctccctcttc tgcttcctgc cactgattct 660
ttgcggcatc ccgcaaaccc tctctacagc aggaatcgat cacacgacac gaatagcgct 720

-continued

```
ataggcgttt ccgaccccgc tacgcatacg agccgtgcca tgagcagtca cacgtcgctg    780
caatactcga gttccggagg catcgcgaac atctctacca caaccgatcc tccacacaaa    840
cgactcaagt tggaccatgc catgagccac acatcgctcg gcaacccatc cttgagctat    900
cacgattttg ccgcacatta cgacagtcgc agtaccttac acactagtag caccatggat    960
ctaggcgttt tgcggaaaga agattccttg ggcatgatgc gcaaggacgg cgacgacgag   1020
gacgacgaaa atgatcagaa cgacccgata tcctccacag ctgtacgaca agcgacggtc   1080
caacctactg ctcttccgaa tgaaagtgcg aaacccacac accccactac agcgaacgta   1140
gccaccacaa attccgtttc gtcctccgac agtctgcgcg atctatccgc acaccgtcca   1200
caacatccac agaatactac tcgtcttccc gtttcttcgt caacgactac ggtaacatcg   1260
ggttcgaatt ctccgctctc tgcggggccg gtatcagccc aagctcctcc ctcgcctctg   1320
ttacctctca aggctaccaa aatgtcacac ctccgccaaa aatacatgca agaactagag   1380
tacatgctgt gtgagttcca aaagctggaa cgtcagctac taggtgccaa ggcgacgaca   1440
gccgaatccg ctggcagccg cgaacgtcga gaaaaactgc attcgttcat cacgcacctg   1500
agcgatacga tccagaacat acagaccgga tgtcagctag agtcggaggg aaaatcaacc   1560
gtcggagaag cttccaagca agatatagcc caggaggccg cgctggcaga tttgacgtgc   1620
gaaaaggggg aagaggaaaa cgtgcaaaag ctggaagagc acattctagc caatctgttg   1680
cccgtcaaag tccggctcaa gaaacaactg gcggcccagc aaggtgccaa gcataacccg   1740
gcggggatgc cggttgcgca aaggggacta gtggcaccga gcgaaggtgg taaaggcacg   1800
tttgcggcag cggccgaaga gcgcagaaag caattggcgg acgcggccgc cgcggcacaa   1860
ggcttcgatc atacacacgt accggcggaa ccggttcatc cagaccagac acaatttggt   1920
aaaccactac aaggaaacgg ctcctcgttg acgcgaaatt tgcatggatc cactttggga   1980
tccgcgatta aagtgggaac ggataagtcc aaaattttgt tcgctggttt ggcgatcgga   2040
tcgtcgcaag taaagtcgtc ggtcaacgca gcttcgtcgg tacatcagct cgtaattaag   2100
gatcccgctt tgttggagtt ggctcgccaa cagagcgcgt caaaacaaca agaggacctt   2160
ccaccgcaaa cacaacaaga agactctcca acgcaaagca aacccaattc gctgctgcct   2220
ccttcctcgt ccgagccgaa tgactctcca gaggatacaa accgtaaggc tatatcacta   2280
aaagtttcgc ctgctgttgc ttctgcagca gctttggccg cgtctgagca accagacgca   2340
gtcttgtcaa aggctccacc aagcagatta gatgatgttg atgccaccta ccccgacatg   2400
ccatcggcag ctttaaccga tgaagaacgg cgaaccctcc gtcgtctcaa acgccgaaaa   2460
aagagacgaa aacgcaaggc cgaagcaact ccagtcacgg cagcggccac ggcagcacca   2520
gtgatcaatc gccatcacaa gccgacgaca aaaaaacggg gacctcggac ggtggaatac   2580
atgtgtgctt tgtgtaacga agtctacaat tctacctgtg attataatcc ttggtgggct   2640
ctggctcaac atgattgtcc aaaatgtcga aaaaatcaga taccgcgggt agatattagc   2700
gcacctgcca atacgatcga atatcatccg gcgttgctag ctcacgcaga cgaaaatggc   2760
ggtagtactc cgacaccgcc tgcagcaata gtgaagccag tcacaactgt gtcggctcct   2820
gtcactagtg tgccaaaatg tggtaatgat tccgattcgt tcggatctga cttgtcagac   2880
gatgatcttg acggcctgtt gtcagacact gactcggagg gctcgggaga aataggtatg   2940
gaaagaatag atgcgctatc gcctgcggaa caagcagaga atgaatattt tggggtggaa   3000
tacaaggggc caaaattgaa agacagtgaa gctgctcggc tactgattct catggggcat   3060
```

-continued

```
gcgtcgacct gtccttgcaa gcatcaatcg atcaaacatc gtgaaacctg cagaaatacg   3120
aaatggatga tgttgcatgt tcgggattgt ccaggaacta catcttcgtt tgatgtctgc   3180
ccatttccat ggtgccgcaa agtcaagcat ttgttgtatc atcttgtctc gtgtcgcgat   3240
gccaagcact gtgagatctg ctcaccgacc aagctcaacc aaaatatgat cctgttaaag   3300
gggttgaatc agcaccgctt catgcaatat agggagcggc tgatcggccg tggaaaggcg   3360
ttgacaaagg tgtcaaatag tgcgccgaaa aatactccag ctcaggcgca gcacaaaact   3420
ttcatcgacg tttcgcaaat gctgtaa                                       3447
```

<210> SEQ ID NO 37
<211> LENGTH: 2847
<212> TYPE: DNA
<213> ORGANISM: Cyclotella cryptica

<400> SEQUENCE: 37

```
atgctcgtcg aattcaaaaa actcgaacgt caacttctcg gggcacctat ccatcagcaa     60
caaaaccctc cgaaggccga accaaaggga agccgtgaac gcagggaaaa gttgcacggc    120
ttcattttgc atctcgagga tacaatacgc caggttgaag agggatgtgc tttggaaaag    180
cgtgaggagg gatcgataga ccaagttgtt catggtgctt cgggatcact ggcgaataac    240
caacaggaag aagtggaaga ggaagagaag aaatcatccg atgcgtcact tcaacaaccc    300
caacacacgg cacaaaccaa caccgccagc aatctcaaca atctcaataa aaccacgagt    360
aatatggaag gtccaccgaa aaagttcaca gccgccgaag ccgccctctc ctccctcccg    420
cccgaaaaag aacgcgaaga atctgtccaa cgactcgaag aacacatact cgccaaccta    480
ttgccagtca aagttcgatt gaccaaacaa ctcgccgcac aaaaaggtgc gacacgtaat    540
cctgtcacag cccccgtccg agctggcgca gcaaatacag tggcaggggg gaccatcgct    600
gaagcggtcg aagctaaacg aagggctcag gaggaggaat tgttgaagaa acaactgcaa    660
caaaggcaga ttacgactag tcaatatggt aaacccattg gtggggcggg atcttcgttg    720
actgctagat tgcatggagg tgttcttggt tcgaatgccc ctgctgcagg tgcaagtgga    780
tctgagacga cgaagcgtcc tatactctac gcgggggtgg cgcctggatc gtctcaagtt    840
ccgtcaacta tcaaaaccgt atcgggagct catcccggcc taattggaaa agatgccacc    900
aaagctgtgg ctttggccga ggaagaacga agacgcttga aaaatcttga agagaatgcc    960
acccgtgtcg cattgggagt tgccgcgaaa ccatctccag ctgcatcagc attggatccc   1020
agaaaaccag cggcgctgcc cacgttgaat gcatcagcat tgccaaagca gccggaaggt   1080
cccgccacgc ttgcggcccg ggcacgagcc gtggcattgg cggctgccag cagcggaggc   1140
gcgacgtcga aaatttcgcg acccaatcaa caattcccga ccaggtcatt gcagcaacat   1200
catgtgaaga aaggccctcc tgtgatggct gctccagctg cgacgatggc tgctccagct   1260
gcgacgattg ctgctcccag agctcctcat atcaatcagt ataccaagcc atccgcggcc   1320
gtgccttatc attctgtccc gacccctccc atgacggcaa aatcgaagaa accccacata   1380
gcgcccaatt tcaacgaccc atctctcact cccgagcaac gattcgagtt acgtttaaag   1440
gaagcacggt ggaggcagcg taaacgacgg agagaacggc gacgcaaacg tttggagggg   1500
tatttacatg ctgctggagc gtatcatata gttcccttag ccgtccaaca gcaaccatct   1560
ctgtctctgt cgtcgcaacc gcatttgcaa gaaacacagc cggaacgagt tgcatccact   1620
gtcgttaccc ctaatgctcc agcgcctccg cctccagtaa acactccgcc accaccagtc   1680
acctcggcct cgcgacccaa aaagaatgga gcttacgggc ctcgaacagt agagtatgtc   1740
```

-continued tgtgcggttt gtaatgagac atacatatca acttgtgaat tcaacccttg gtgggcactg 1800
acaagtcacg attgtcccaa atgcggcaaa ccgcaaatcc caaagcttga catttctacc 1860
cctgcaaatg aaatcgacta tcatcctgct ctattgagtc aagaagataa cgctaaacct 1920
cagagttctt ctgtgtcggc ttcggcgaat gcaagcaacc ctgcagtagc tgccccacag 1980
gttgcacaac cagtccaata catgcccaag ccgcccgctc acatgaagaa gaacttcttg 2040
ctctcagatt ccgaagtcag tttgacagac gagagtgatg gcgaaggtgg cggtggaaag 2100
tacgacgaga gcagcgaaga agaagacacg agttacgaca atgacatgga ttcggtgacg 2160
cgcgaagaac gggtagagaa ggaagagttt ggatttgact acaagggaga ggtattgagt 2220
gaagaccaag cgaggaggtt gttggtgctg atcgaacacg cctccatttg ccctggaaga 2280
caccgatcag caaaacatcg caacgtatgc catagcacaa aatacatgat gcttcatgtc 2340
agagattgct gcggtctatt atccaacggt gatgtgtgcc cattcccttg gtgccgaaaa 2400
acaaaacacc ttctctatca ccttgtcact tgcacaaaga acgacgacgg cagcaaatgt 2460
tcaatatgct gtccggaaaa cctttcgtca aatctcatgg atttggttgg cttgaattca 2520
tatcgccgga agatttttgt agagcgagcg aaggctgtag cggctgcagc cgcggcgaca 2580
cgtcatcaaa tggcgatagc aaaagcaaaa gctgccgcgc aatcatcaac acaaccgcat 2640
gtcttaacaa gctctcagat tctgactgca ccttcaacta accataatta cgagtcgcag 2700
accaaacctt tcgctactgc atcgacccat gttgcaactc atgctacaca accattagga 2760
aatgctagga ggggctcttc cgttcaagat gctacgatag catcgaacaa tacaggaccc 2820
caccttgatt cggaagttgt tttatag 2847

<210> SEQ ID NO 38
<211> LENGTH: 1650
<212> TYPE: DNA
<213> ORGANISM: Ectocarpus silicosis

<400> SEQUENCE: 38
atggtcatgg ccgcgacggc cgacggcgga gtgtgcgaga tcaagatgga tgacagcggc 60
cgcctgacgc acatctggtg gcaaacgaga gagcaggcgc gacagcgctc gagcgatgac 120
gatgctccga cgaagggtgg cgttgcgttg ggcggtgtgc aagccagccc cgactcggag 180
gtgtcaagac ggctggatct actcatggac aagtccttcg gagatcttca gttcctctcg 240
gacgaatttg cgaagctgga ggtcgtggtg gcgccggcag tgcaggagcg ggacgacagc 300
ggcaaggcgg gcacagactc gaagctgggg aggctccgct tcttcaccac acacgtccgt 360
cggacgatgg cccggatgcg ggacgcgagg agcgggcgcg accccatgtc catgtcccag 420
ctggctctgc tagaggagca catcgcgacg tccattgctc cgggggggggg gggaggggta 480 tccagttcgc ggagctcgtc ggtgtcgagc agcatgggcg gtagagccgg cgcggaggag 540
ctggtcggag ccgggcggga ggaggaggag gagtggtcgg tgggcctgga gctgcacgac 600
gaggcgttcg gcagcggcgg gagcgtttct ctgggcctgg tgtcgcccgc cccggcgtcg 660
gtccccgaca gaggagcgga cggaggtatc tacgaccccc acgcctgctc cgcgcgcttg 720
acgcctgcaa gtagcagttc ttccctctcg cgcctctgct ggggcagcgg cggcggaacc 780
ggcggtagcg cgggcggcgg gggaagagat gttgcccggg gggggaggcc acaccgtcac 840
acgcggcgag atcacgtgga catgctgagc cagctcgagg cggagggggt gttcgccgcg 900
gacgacagct actcgccctg cggcggtggt ggcggcagcc gcggaggcgg tggcatgggc 960

```
ggggtcgcgt tttcgccaga gccccgggag gtgaggtacc agtgcggggc gtgcgcggcg   1020
agctacgcgg cgacggtgtc gggaaaccca tggtggctgc tggtgaggca ggagtgcccg   1080
atatgccaca agatgcaaat acctcgcgtg gacatcttga atcccaccaa caacgtcgag   1140
agtcacatcg cgtttctgac ggagaatgct tctgacggcg atggcagctg catggactgg   1200
gacggggaaa cgagcgatga aaactccggc gacgagtact cgggggacga gcggcaaggg   1260
ttgtccgcgg gaggaagcat gtcgggcggc gacggcagcg ggcttggacc taccctggac   1320
tccgaccagg ccgccaagct gctggtgctt atgtgccacg cccggcactg cccggggaat   1380
caccgctccg ctaggctggc agaggtgtgc cgaagcgtca agtttctgat gctgcacttg   1440
cgagactgcg acgggaagac caggaacgga gacccttgtc cgatgccgtg gtgcgagcct   1500
tgcatgtccc tcctgcatca cctcatccag tgtccggagt cgacgggatg caaggggcac   1560
gagcacaaga acaggggtga tctgcctagc caaacaccgt caggtttcgg acgcctgaga   1620
acgcttcggt ttgcggccgt tttttcttga                                     1650
```

<210> SEQ ID NO 39
<211> LENGTH: 2241
<212> TYPE: DNA
<213> ORGANISM: Navicula sp. WT0229

<400> SEQUENCE: 39

```
atggaagaac cgctggtggt gactgtgaaa cgagaaaaca taaatgtatc acccgaacca     60
ctcaagaatg atggggtcgt cagtcacgat gaggctactt cgacgacggc agattccctc    120
gtctccgaag ccgctccact caaagcgacc acctttcgac acctgaatct aaagtatttg    180
gcggaactcg agtacatgct ctgtgaattc cagaaactcg aacgacaatt gttgggagct    240
cggaacttgc aagcgagcga gtcggatggg tcgagagagc gaagagaaaa gctacattcc    300
tttattctgc atctagaaga tacgattcag cagattcacg caggatgcga aacagaaggg    360
aaatcaacgg agactaccgg attggtcaag ccatcgaacg aaaagaaaga ggaagaagcc    420
gtacagaagc tggaagaaca catcctggcc aacttgttgc cggtcaaagt cagactaaca    480
aaacaactcg cggcgcagca gggcgccaaa cacaacccgg ctgccatgcc ggtgcgcggg    540
gtggtctcgg aatcgtccaa agaaacggat acttcccaat ttggaaagcc gttagagggc    600
ggcgggtcca gcttgacaca aaaactccac ggaagaacat tgggcgcgga agggagggca    660
cacggacacg gcgtgggtac cgtccacagc aaacgggccg aagccaaggt tttatatgct    720
ggaatggcga ttggtagtga taaacatcaa atgagaagtt cactgagtgc ggcgagttcc    780
gcgcatcgac tgttgttgca aggaaaggac gtcacggaca agagtcgcac gcggccgcga    840
gaagaaaaaa tgatcgagag aagaggcgcg acaaacaaag acggtggtat tcctccaagt    900
gatgacctac caccacagac cgacgcatcc tttgctcatg ccggcagacc ggacgccgac    960
tcggtcaact cattgctatc tgccgagcga cgacgcttgc agagaaaacg acgccacaaa   1020
cgaaaacgaa ttcttttgca agatccgcaa cagcaagccg ctcttgcaaa aagaaaaaag   1080
ggaaccagca gcagtaagaa acggggaccg cgaaatgtgg aatacatgtg tgctctttgc   1140
aatgaagtgt ataactcgac atgcgattac aatccctggt gggcgctgac gcaggaagaa   1200
tgtcccaagt gtcaaaaaac tcagattccc cgaatcgaca ttggtgcccc cgccaatgcc   1260
atcgaatacc atcccgcctt gctagcacac gcggacgaat ctgccggcgc agcagaacca   1320
agtgctgtcc ttgaaccaca agacttgcct gtcccttcga caacaggaga tgatatggaa   1380
tatagcgacg tggacgactc ggatttatca gatgaagatg gactgctaag tgatgcgagt   1440
```

```
cttgacttgg attcggacga ctccgaaatt gccgattcgg agaatatgtc tcctgccgag   1500

caggccgagt cggaaaagtt tggtgctgaa tacgacggtc ccaaattttc cgacgcggaa   1560

gcggctcgtc ttttaaattt gatgctacac gcttcgacat gtccttgcag acacaagtca   1620

tcggaacatt acgacgtgtg tcggagtgta aagtggatga tgttacatgt tcgagactgc   1680

cctggaacaa cgtcaacttt tgacgtttgt ccctttccct ggtgtagaaa ggcaaagcac   1740

ctgctctacc atcttttatc ttgcgaaaac ccccaaagtt gtcccatttg ctcacctgta   1800

cacttgaatg cgagcatgaa atcgcttcgt gggctgaatc actatagact gaaaaagcaa   1860

caacagtgtg taataggtgc aagtcagtca ccagggaaac catccgcagc gaggggcggc   1920

cattcatctc cgaaaaagtc caacgagtca actcaggatg aagtggacac atgcagagac   1980

acgctagacg cgtttgtagt tggaacgaag gagccgacgg agatttcgtc atcgtcggta   2040

ccctcaaact ctacagccgc cgtcgatcag ccagctcatg aagatgaagt gaaaacccaa   2100

ttgtatgaat ttgtagatca atgggaagat cccgaacatc ctgccgctct gaaagatgat   2160

ggattgaaca attcacagtt gacggttggt cattgcgaca atgatgtatt gataaagcag   2220

gaggacgaca attcgcagta a                                              2241
```

<210> SEQ ID NO 40
<211> LENGTH: 984
<212> TYPE: DNA
<213> ORGANISM: Aureococcus anopagefferens

<400> SEQUENCE: 40

```
atgcggcgcg cggcggcgga ggcgaaagcg atggaaccgc tgcgtgcgct ggcgttcgct     60

cagtcggtca agtactactg ctccgtgtgc gagcacgcct acgagacgac gtcggacgcg    120

aacccgttat ggacgctcgc gcgccacagc tgcccccagt gcggcgcgct ccagtacccg    180

gagatcgaga tcgacgacat ctcgctgccg acggccgagg cgcgcgcgcc cgacgacgcg    240

tcgacgctgt cccatgccca gggcgacggc gcgcggtcgc cgccgcggcc cgcggcgctc    300

ggccgcgcgg ccgccgccga cgacggcgag gtgctcctcc gcgccgacgc gccgcggaag    360

cgcagcgcgc ccgacgacga cgcgtcgacg atgtcccacg cccagggcgc ggcgctcctc    420

gagctcttcg accacgtgcg gagctgcccc ggccgccacc agtccgcggc ccacgcgcgc    480

gtctgcgcgg gcgccaagtt cgtcatgctc cacgcgcgcg actgcgacgc cgcgccgggc    540

acctgcggcg tcgagtggtg cggcgcggtc aagggcctcc tctcgcgcgt cgtctgcggc    600

cagcagggcg acaagtgcgt cgtctgcgcg gagccgtccg aggcgatgga cgtgggcgac    660

gcgtcgccgc ccacggtgtc gccggacgcc atggacgtgg acgacgcgtc gccgcccagg    720

gcgtcgtcgg acgcgccgat ggccgacgcg ccgccggcgg agccgcgcgt cggtgcggcc    780

gcgccgtcgc cgccccagtc gacggaccgg gcgttcgagg cgcccacggc cgtgccgtcg    840

ccggtccgcg cgtcgccgtc gcggggcggc gcgccgtcgt cgcggcgcct cgcggacatc    900

acgatgtcgg agaacgtcga gatggacttc ccgcgtgact tctgcttcgc cgacgagctg    960

cggcggcggg gcgacgccgc gtga                                           984
```

<210> SEQ ID NO 41
<211> LENGTH: 1797
<212> TYPE: DNA
<213> ORGANISM: Nannochloropsis oceanica CCMP1779

<400> SEQUENCE: 41

```
atgcctatgg tcaccctctc ccaggatgca actactaccg cggccggcag catgatgctt     60
cccctccttc cctccatccc tgcttccgct accagcgcct cttttaccgc tccctcagcg    120
tcctccacga ccaccaaatc tcccaaaggt acttcctcca tgactcagct tggagagaca    180
gggcgagaga atactggccg atggacttgt gaagagcatg tgctgtttct taaaggccta    240
gaaatgcacg gcaagggttg gaagaaaatc gcaaagctaa tcaagacccg aacggtggtc    300
caaatccgca cgcacgcgca aaagtacttc cagaaattgg caaaagccaa gaagaacggg    360
caccatggtg atatgctcgg aatggaaggc tcacactttg ggggaaaacg tgtcaaattt    420
accggaaagc gacgtgggct tgtctataat tcgtatttag taggtgccga ggccacctct    480
gcggctatct ccccggcgtt gcagacgttt atgccggcga acttggggat ggagggcgag    540
cgtgtaggcc ttatgacgga taaggaggag gatgcagcaa tcgagaaggg actttatcgt    600
ttcctctccc ccgtagtgct ggatcccgcc acgcgtaatc tggacgcctc cgctcctgag    660
atcttgccct taccacccag cactccagcg atgggcgtgc accataccag tagcagaggt    720
agcagcagag gggggttgga tggagagaca acgggagagg aggacggcgg aagcgattcg    780
attgtaatgg gggatggagg gagcgatcaa gatgcagagt cgtcgttggg cgagcccttg    840
ccaactttgg cgcgggtgac accggagatg tacacacggt gtggagttcc ggaatggttt    900
aagaaagggg gggacattga cgaattgctc attgatgcag ccggactcga ttggagaagt    960
gactcgggtg gggacgcacg gaaggtggtg gatcaaggga caagtatttt gaatgcgaat   1020
attaatggta gtaattgtgc gactgtggcc ccggcagtgg tgcggaaggg ctgtggtagc   1080
aacactaata agatgaactc agcggcgcct gtgctgaaca tgacagggtt ggctggggct   1140
ggagggcttt cagggtggaa gggcaagggt agcgacacta gcgaaggtag cagcagcaac   1200
ggcagcagca agaacatggc tttgacggca aatgcgtcgg cgggatgtgg acaagggagc   1260
tggggagtgc ggggggggc acagaaaaag cagcagcagc agcaacatga ggtaccaacg   1320
cagcagcagc aggtaccaac gcagcagcag caggttcacg gcattcacgt gaaggaggaa   1380
gggatggagc tcctgagagt catggcggat agagggactg ttcacggtca cgtccatgag   1440
gaggatggct ttgcggcgtt tgacccccat catgtcgagc tgaaggagga gcactcccac   1500
catgatttgt tgctggaaga gctgccccac gacagcaacc acgatgacgc cctggcccat   1560
attgtgttct cagtgaatgg agagtcggat cttcattcct tgccgagggg tgcaggaggg   1620
gggggagcgc atgtgcatgc gccgccggtt gtggtggggg ggagacagca tcactatcat   1680
cataatgaca atgatatcca tttgcatgcg tacgacgcgt atttggaaga ggaaggggcg   1740
gatggcgggc atgggttgtt gttgttggag gatttggatg ggggaatcga gttttag      1797
```

<210> SEQ ID NO 42
<211> LENGTH: 2031
<212> TYPE: DNA
<213> ORGANISM: Ectocarpus silicosis

<400> SEQUENCE: 42

```
atgtcgtctc aactccaggt agacgacggc gcagccagca gcagcgataa cttggacaac     60
gagggtgtgt gccagccggg caacgaaaac acagggcggt ggacttcgga cgagcaccgg    120
ctgtttttga ggggcctcga gcttcacggc aaggggtgga agcagatcgc caccctcatc    180
cagacgagga ccgtcgttca aattcgcact catgcccaga agtatttcca gaagctgtcc    240
aaggcgcagg ctagtggcac gtcacacctg gaccccgcaa ccctcatgag caccatggac    300
gctggaaagc ctcgccccgc ctctgtgtca cggaacttgc gaagcagcac aatggcgaac    360
```

```
agcccggcgg agtcggaagg gaggctcatg agcctgagga agcgccgcaa tcgtggccgc    420
cacccgagac acgacgatga ccaagactac gacaccaaca gcgaggagag ctacgactac    480
gcccgcagca gcgccaccac gcgcacccgc cgacgcaggc ggagcgtcag cagcggcagc    540
agcggcggcg gcggcggcgg atcgagcgaa agcgaagagg aggacgggga aggtggtggc    600
aggggtcacc gcggtgtgta ccgcgagacg gcgctgggcg cgacgacgac gacgacgatg    660
atgatgatgg tgaggcaggc agaagaagcg cctgcgttta cggtcggtgg cggcaacagt    720
ggtgcgcacg gcgcggagtt tgatgaggag gaggcggagg aggagttgga cgagagcgtg    780
gatgtcgagg gacacaacag caacaacaaa aacgtcggta tttcgtcgtc gctcctgcac    840
ggcggcaccg ccggtacgtg gagcaagcgg cggccggcca aaagccaccg gccttccccg    900
acgaaggcgt ccaaggccgc cgccattgcc gccgccggcg gcgcggccga cgcccgcgcg    960
ctcgcgtggg aggccgcggc ggcgaaggct gccgcgggag aggagggcga ggaggctgct   1020
gctgatggtg tagtgggcgg tgggtccggg acgaagcgtc accggagcga gagcgttagc   1080
agcagcagca acgacgcgtc gctcggcaag accatcaaga gcctcaagcg cacgggcggg   1140
tcgtctcaga ccacacggat tagtcctact tcagtggcgg atgtcaacag cttcatgtcg   1200
ttcccggtgc cgcaaacgga gcgctcggac atggcgatgc accacctacc gcagcagttg   1260
gccccctcct ggtgcaccaa gccccaggac acctggatgg ccggggcagg gctggacatg   1320
gggggtctcg aggcggacga cgcggggccc ttccggtggt tcatcgacga gcgttcgctt   1380
tccgcaccag gcgcgttttt ccagccgccg gtggagacct ggagcggttc cgacacgacc   1440
gacgtctcca cgtccgcggg cagcgaccac cagcaccacc ggaccgtcgt acccgagcat   1500
cttccctcca acacgaacaa ggtcgacatg tccccggggg gcgttttgac tagcgacaac   1560
acgcataatc aagaggacgt ttccatcgcc aagcaccggg gcatgatgga gccaatcgtc   1620
cccatttccg acgcggcaat ggccagcgag gtcagccgtc acgtcgaggc cgacagcgcc   1680
accgcctgtg ctgccgcggg ctgcgccggc ggcgcaagcg cgagcgccgg cggcgccggc   1740
gacggcggcc actcgctcga catcacctcg ggcctctggc tcgaccaccc gcaggaggcc   1800
cacgaggccg tcgcgtcgcc cctgatgtac ggcctcggcc tgtccgctcc cgccaacacc   1860
gggggcgccg gcggcggggg cggggcgggg gggctcggcg ggggcctgtc tctgccttcc   1920
ctcgacgagg aggaggtcct ggggttcttg gcctgcgcgg aggagaacag caggcaggcc   1980
gccgccgccg ccgccggggg cgacgcggat gagaacgatt tgctagtctg a            2031
```

<210> SEQ ID NO 43
<211> LENGTH: 1362
<212> TYPE: DNA
<213> ORGANISM: Navicula sp. WT0229

<400> SEQUENCE: 43

```
atgaaagtcg aggcaactca tcaacacgcg tcgggggctg atcattcttc aacgctggac     60
gcccccgctc cagttctctc tcattctggt ccagcggcgt ctaatgcatc gaataatgca    120
cccaaatcga aaaagaaaaa aggccaaccg gcgataacga ttgctgctgc ccctagccaa    180
gctgttgctc ctttggctcc gggggagaat acaggtcggt ggactgctga agaacatcgc    240
ttgttcttgc aaggcctcga acagcacggg aaaggatgga aaaagatcgc ttctctgata    300
aaatcacgaa cagtggtgca gatccgaacc catgctcaaa aatacttcca gaagttggca    360
aaggcacgcc agaatggaga ggaaggtgat attacaatgg aagggcgcgg aggaactgct    420
```

-continued

```
tccatcactt cgagcacgac tgcaacagct gcgctgacaa acaagcgtcg tcgccatatc    480
acaggaacaa agcgcaaggt gatacaatcc attgtagcat cagcgcaacg gcaagcaaag    540
aaagcgcatt tgcctgaaat cggagatgca aagaagagtc cggttgttcc aggggttgca    600
cccgctttag cgtactatgt cacgccaagt cagtcgtcct cagtaagcgc tggttccgac    660
gtgtttacgg aaggaaatct atctggcccc gttctcgaag actctttgtt caggtttttg    720
accccagttc cgattgcctc tgatgatgtg aatgaggtag cacgccaggc gggcgcgaac    780
ccgattactt tgccctcttc gaatagtcat gcattatcat ctgttccagg aagctcgcct    840
actggagtcc aggagttgtc aatttaccca tcgtggactg acgcgaaaga tccccccttct    900
tggtacgcca agggagcaga tgtggatgcc ctcctggatg tatcggacac tcttgattgg    960
ttagcagata cgggtgatct tgacgaagaa taccaaccgc agtcaaatga catcgacact   1020
tgttcattcg gtggccaagg cgagcaccat gagatgggaa tatccaatgt gcacaacaac   1080
actagcgtga gttcgcttac tcacgtcgac ccaaatatgg tctcggttgt ccctcctcta   1140
ccctctctct ttgaaggtaa tcctgatgta gtagaagcgg agctaactgt agggaaagat   1200
gtaaacgtcg ccatcggaaa cgcctccctt cttatcgcgc caagcgatcc taatgcggag   1260
acccttcagg tgtttgatag ccccatggaa gagcaagagt tcgtgtctac cttactggaa   1320
acaactgccg aaagtagcga caacctggcc gtcttaagtt ag                        1362
```

<210> SEQ ID NO 44
<211> LENGTH: 1539
<212> TYPE: DNA
<213> ORGANISM: Phaeodactylum tricornutum

<400> SEQUENCE: 44

```
atgaccacgg cgccactcac tgcagctcaa tcttctccct tgactattgc caatacgacg     60
acaacgacaa tcaatagcaa gcctctcgtg gattctctta ccaatacagt tccagagaca    120
gtccaattct ctggacgaga cggtaattcc tcaaacagtg agaccaacaa aagcaacagc    180
aacaggactc ccactaaatt tcctgcgttg tccgaagtgt cgcatcgacg ctcggcatcg    240
gtgtctacgg ctcactccgt cacgtcgaaa tccaaacaga attctactcc accggtagac    300
atggcaacgg cgtccggatc agccagtcaa ggctcgcacg gcgaaaacac gggacgctgg    360
accgcggaag aacaccgctt gttcttacag ggttggaac agcatggcaa gggatggaag    420
aaaatcgcgt cgctcatcaa gtcgcgaacc gtcgtacaga ttcggacgca cgcccagaag    480
tactttcaga aattggccaa ggctcgccaa aatggggaag aaggcgatgt cgccatggaa    540
ggtcgcggtg gcgtggcttc cattacctcc gtctcgacaa ctgctgtttt acccaagcga    600
cgtcgccaga caaccggaac aaaacgcaag gccattcaat ccgtcgtggc ttccgcccag    660
cggcaaggca agaaacttgc cgccgcaaag acgaatccta ctcgacacca tcccttgccg    720
ccgcccctac caacggtcgc ccccgcactc gcgcattaca ctctccccag tactgcgatg    780
atggccaaaa acggcaccgc agtgaaggaa gaatacgtct cgcccaccaa tctttcagga    840
ccggccctag aagattcatt attccgcttc ttaaccccgc ttccggtatc ggaaccaccg    900
ctcaacgaag tagctcgtca agccggtgcc aaccccattt ctctccccac cgacaaccca    960
agctctattc caacggtggg tgcaggagaa atctcgccca cgggagtttc ggatttgatg   1020
ctttacccct cgtggacaga ctcaaaagag ccaccttctt ggtacagcaa gggcgccgac   1080
attgacgcat tgctcgatat gggggattcg ttggactggt tggacgacac gggggatttg   1140
aacgagtcat atgtaccacc cgtcgtggac acagcaatgg ccgctccaga accgcacacg   1200
```

```
acctttcaca ggtactccga tctgggacat tcaaagggac ttcacagtac cagtgtgacg   1260

tctctgccac atgtcgattc caacgcaaat gtggaatccg ttgtgccgcc acttccctcc   1320

atattcgatg gagcccccga ctcgggagag catcttgaga ccacggaagg gatggtacct   1380

tccaacagta cttctcactt ggcggatgaa atcgacgaca gtgaaggcat acacgaacac   1440

ctacaagtat ttgacagtcc tttggaggag aacgacttcg tatcggccat cctcgaagaa   1500

gacacgattg atgttacagc agctctagca gcgagctaa                          1539
```

<210> SEQ ID NO 45
<211> LENGTH: 4902
<212> TYPE: DNA
<213> ORGANISM: Phaeodactylum tricornutum

<400> SEQUENCE: 45

```
atgaccacgg cgccgctcac tgcagctcaa tcttctccct tgactatagc caatacgacg     60

acaacgacaa tcaatagcaa gcctctcgtg gattctctta ccaatactgt tccagagaca    120

gtccaatcct ctggacgaga cggtaattcc tcaaacagtg agaccaacaa aagcaacagc    180

aacaggactc ccactaaatt tgctgcgttg tccgaagtgc cgcatcgacg ctcggcattg    240

gtgtctacgg ctcactccgt cacgtcgaaa tccaaacaga attctactcc accggtagac    300

atggcaacgg cgtccggatc agccagtcaa ggctcgcacg gcgaaaacac gggacgctgg    360

accgcggaag aacaccgctt gttcttacag gggttggaac agcatggcaa gggatggaag    420

aaaatcgcgt cgctcatcaa gtcgcgaacc gtcgtacaga ttcggacgca cgcccagaag    480

tactttcaga aattggccaa ggctcgccaa aatggggaag aaggcgatgt cgccatggaa    540

ggtcgcggtg gcgtggcttc cattacctcc gtctcgacaa ctgctgtttt acccaagcga    600

cgtcgccaga caaccggaac aaaaacgcaag gccattcaat ccgtcgtggc ttccgcccag    660

cggcaaggca agaaacttgc cgccgcaaag acgaatccta ctcgacacca tcccttgccg    720

ccgcccctac caacggtcgc ccccgcactc gcgcattaca ctctccccag tactgcgatg    780

atggccaaaa acggcaccgc agtgaaggaa gaattcgtct cgcccaccaa tctttcagga    840

ccggccctag aagattcatt attccgcttc ttaaccccgg ttccggtatc ggaaccaccg    900

ctcaacgaag tagctcgtca agccggtgcc aacccgattt ctctccccac cgacaaccca    960

agctctattc caacggtggg tgcaggagaa atctcgccca cgggagtttc agatttgatg   1020

ctttacccct cgtggacaga ctcaaaagag ccaccttctt ggtacagcaa gggcgccgac   1080

attgacgcat tgctcgatat gggggattcg ttggactggt tggacgacac gggggatttg   1140

aacgagtcat atgtaccacc cgtcgtggac acagcaatgg ccgctccaga accgcacacg   1200

acctttcaca ggtactccga tctgggacat tcaaagggac ttcacagtac cagtgtgacg   1260

tctctgccac atgtcgattc caacgcaaat gtggaatccg ttgtgccgcc acttccctcc   1320

atattcgatg gagcccccga ctcgggagag catcttgaga ccacggaagg gatgaaagcc   1380

caagcatcgg atctctcgca caaacacacg cactcgttta cggcctgtcc gcttcgactc   1440

accatgggca cgatagtatc tacagtgggt cggagcgcag agacagattt tttcgtcacc   1500

gagtctctac agttcctact gtcttggaac gagggaccaa gacggcaaac gcggcggatc   1560

catgatccaa cactccttga cggaattgac agtaacgaga atattctcga cacgacagtc   1620

gcccccatca caatgccaac gaccaattcg ccagtcgaaa gccgaacgtt gtcgtggacg   1680

gatctcgggt tggacacgga cgaagatcac ccgcgtcgtt tgttgcgtgt gcgggacgac   1740
```

-continued

```
gtgattgcct acggcggcga cgaaggcaca ctggtacgct tacctttcgt cacaacgagc   1800
aacgcccaaa atgccgacac ggggtccacg cgacccttgg ccgtgcgtcg ctttgatgaa   1860
gacgccatac gtgccgtcgc agtctcggac gacggaaccc gcgttgccgt cggaacggat   1920
agcggtgcca ctcttttcta ccgttacgag ttggatggac acgtagtaga cgcacctgga   1980
aaggggctcg tctcccgaca cggatttgtc acgcacgaca gtgacgacaa caacaacaac   2040
aacaacaact cccaccagaa accctcggca gacttgtttg gatcgcagcc cgacgccctc   2100
gcctttgtcc cacagcaacg tcccggggaa gtcgtccgtc acggacccgt ctttgacgct   2160
cctgtacggc aactcctctt tctccccgac tcgcatttcc tcgccattgc cacggaagcc   2220
ggattggccg ttgtttccac cgataccgac agcggcattg gtggtggcag tctggacact   2280
aaccacaacg agaacgtcaa ccaccacaac gtcaaatacc tccaccggga agcccaaacg   2340
gcacacgacg aatccggcat acgcggactc gccctctggc aagcaaagga ctgtcgtata   2400
ctctcctcac tcgccatgga cgggcgtctc tgtcactggg atgtctctgc tcccactccc   2460
acactctgga aactactgca ccgcgagaca gtaccgaccg ttaccaagcc cgacctgggc   2520
gaaatgctcg gtgccgatgc ctgggatcga tccaccatcc ccgtcgccca ttcccacgaa   2580
agcatactct ttttgcccgg agaaacctac gtacaggcgc gtcgctaccg caaccacacc   2640
tgggaactcc tacagtcccc taccggggcc accaatacta ccgacaaagt acagggacac   2700
attgaagcca ttgtcgccat ggccccggca cccaaccctc gagatccgta cctcgtcacc   2760
agtggacgcg acggacgagt cgtcctctgg aaactacagt actctcatca cgacaacaac   2820
aacaacgaca acaatccaaa cgacaatggt gacgggcaca ttgtctttca aaaacaaatc   2880
ctccagacgg attccgcccc aactcatttg ttgtggacac tggaccaacc gacgcaaacg   2940
gaacgtctcg acatggtgac cgccgacgga cactggacta ctctggtagg acgcgaccag   3000
attgctccgg cctgtccaac cactgcagtg acccaagaga tctccctccc acaccgccaa   3060
tcagccgatt ccgtgcggga aaaagagaag gaacatgacg cagactcgga cgacagcgtt   3120
gatgactttt cttcgaacaa accttccaca caccaaaaga atccgtttgt ggacgacgag   3180
gcggaggacg acaacgatga cgatacgctc gatacggcct cgcgtggaaa actggagacg   3240
acctcaccaa cggacaagcg cgcctccaat cttaacagca gcgctctcga agaacaccac   3300
aatgatctag acgacgactc catcggtgac gatgacgact ccttccacaa cattccgact   3360
ctcaccacgc gacattccga ttcgatccag tggcctgaac cacaacccgc ctttggtcct   3420
tcttccacat cgcttgaatt gactcgccgc tttttgtgct ggaatcacat tgggtccgtt   3480
acgtttcttc gaggacaggc cggcatcaac cgcagcacga tcgacattca ctttacggac   3540
tcggcatttc gtcggcccgt ttccttcacc gataatatgg gcttcattct ggggtccctg   3600
ggggaagacg gcggaatatt cgccaccgac ttggcggaag acgaggatat tgatgaggag   3660
gacgacgata tggacggctt gaacgtgtcg gctgctacca aggccgccgt caaacgttcg   3720
cgcaagggtc cttcgaacaa accgaccggg tcgagcattt actttcatcg cttcgaaacg   3780
ttcggatcct tacgcgacaa ggattggtac ttgacgctcc cagatgggga gcgggctttg   3840
gggtgtgcgt ccggtgaagg atgggccgcc gtcgtaacga gtcgccgttt cttgcggctc   3900
ttttcttcgg gcggcaatca aggagaggtg ctttggctga acggccaccc cgtcaccatg   3960
gctggacggg gacggttcgt cgcggtggta tatcacgaaa gtacaccgtt accagatgga   4020
acacaaaaac tcggatactt ggtgttggat gcgatggcga atcgcgtagt tgccaagggg   4080
ccagtgtcat gtattagcgg tgcatcgact ctttcatggt tggggttcag caatgatgga   4140
```

tctctgctgg ccatggattc ggatggtatg ctgtcaatgt tggtttgcgc atcatccttg 4200
gatgcggagg gaccgacgga aaaacactgg gaatggatgc caatgctgga cacggtgggg 4260
ttacgtaaat cccgggacga ttccttctgg ccggtcacag tttatgacgg aaagttggtg 4320
tgcgtcccgc tcaagggtgg gatgaagcat cctgatgcgg tgcgccgtcc cgtcacggcc 4380
gctctcggct ttcgtcttcc cctggcccgg ggtcctttga ccaagacgca cacgttggaa 4440
gagcttgcgg tgcgcgccgc gattgcgcta gggcagaaaa aggcaattca cgagattagc 4500
cgggaaggcg acgaggacga cgaggacttt gaaaaagaat accgttccct ttcggcccaa 4560
gtggacaagg tcacgctaaa aatgtttgca gcaatcgcgg aagccggtaa attggagcgc 4620
gctttggatt tggtggagcg tttgcatttg gaaaagagct acgacttggc catgacgatt 4680
ggcgaccggc accgcaaact tgtcgatttg atcgaagagg ccaaggatcg caagtttgga 4740
gatccgggat cgcaccaagc cgagtttacg accaaagcgg aatccccgaa ctatcaacgc 4800
ccccgcatct ctccagattc ggctggggca aaacgcagtc ttgacgatga ggacgaggac 4860
gtccgaagcc gtctcgtgcg tcgcaaacca acgtttgcct aa 4902

<210> SEQ ID NO 46
<211> LENGTH: 2976
<212> TYPE: DNA
<213> ORGANISM: Phaeodactylum tricornutum

<400> SEQUENCE: 46
atgtcaacaa cactctccgc cgttcaattt cacttccaag aaacgacaac aacagcagca 60
gccaacgaga acggcagcgg tgacgagaag ataatatcaa cggcagcaac gacgacgacg 120
acgacgacgg agggatcatt agcagcggag gaaggagcaa tccagtctcc tagaaagatt 180
agcgagggag actacacact cggcgccctc ctgaccagca gcggcggtgc ctccgtctcc 240
agagtggtga cgaaggaatc tctcctcggc aacaacaaca acggcagcga acaaaccacc 300
gctactggcc ccaaagcctt ctccgtccct tctcccctcg atcacaacga cgggggatcg 360
ttttcgttct ctgctcccga gaccaccttc cagtcggccc cgctcaacag cggtggtagt 420
agcagcgcca gtcgctgtgg cgaacaagaa gtcgatcaag cgtttgctgc cgagatcgca 480
aagattgact tttcggtgcc ttgtcctttg aactcgtttc atcaagtcga ttacagtact 540
accaacgacg gaaagacaac tccggtagaa gaagagacac tctaccttcc tcctgaagat 600
tccaacaaca acaacgcagt agtatcagcc tacaactctc ccatcccccc actcttttca 660
tcttcatcag ctccaattac aatcaacgat ccactcattt cattaagatc ttccagtcca 720
ttactctacg ctgcttcttt caatacacca caagaggaaa acaccagttg ggctgctgtt 780
ggtggtgcta catccattgt ttcaacgggt ctttcggttc aagttccggt agaagtagcc 840
gcagtgtcca cggcagcagt tgttgcaagt aatagtgctg ttgttgtaac tccaccaact 900
actttggagg aggacggtag tagtattagt attgccaaga agaaaaagag taaggctccc 960
aaaacacaaa agtcaaggac caagtctaag caaccaacag caacgtcggg agttgtagca 1020
ccaatcgcaa ggcactcggc aactacgaat actacaatgg atcgacacaa catgggatct 1080
gcaccatccc cattgggaac aacagccagc acaatgtcca tctccattcc ccaccacacc 1140
taccaacacc aacaaggagc ggtagacgaa cccgaaacac cctcctcctc cggctctccc 1200
tccggcaaca ccgtatccac cctcaacccc aacaccaacg ccgtcgaaaa caccggccgt 1260
tggacagcag aagaacatcg tctcttcctc caagggttgg aacaacacgg gaaaggatgg 1320
aaaaagattg ccggtcttat taaatcacgt actgtggttc agattcgtac tcatgctcaa 1380
aagtactttc aaaagttagc gaaggctcgt gccggggatg ggagtggtat tccaatgatt 1440
ggtggtggtg cgggggagga tagtccggag ttgggtcctc aagcagcagt ggcggtgagt 1500
aataccatga atagtagtgg gggaggaaaa gcaggagggg ggttgcagat gttgcctcct 1560
gcgaatacgg tgacgatgcg tactgtgaat caacagcatc atggaaatca cggtaacatg 1620
tccttgggga cggattctgt gagtatggcc gcggcagctg gtcagattga cattgcgtcg 1680
ggagtttcca caagcagtgg gggagcttct tcgaggaata ccaccaccac ttccggggga 1740
ttgaagcgtc gtaccaatgc caagtcagcc ggaggggggg gagggacgaa acgtcgtgcc 1800
attggatcag tggtgaggag tgcagtgagg gaggggagga atgtcaagcg ccaaaagatt 1860
gccgaggcta ggcgcaatgg aggtgctaca gctgcgacaa gtggaggaga tggaggggtg 1920
cccaatccac tcccagccat ttccaacatt ttggatccgt atgtcccatc ggtggcatcg 1980
gctgcggctg ttgctgggac gaagaaggga cggggaagac agcagattgt gcagacggcg 2040
actcatggtt ctttgcccat ggctgctttg gaggatgcag tgtttcgtct cctaacacca 2100
gcaccaggag ctccactctc ccatccttcg gcatcgtcac aaccaatcag tgatcccctt 2160
gcacccaacc aggtcaagat gcccgtagct cacgctcact acctccaaca gcaggcagct 2220
caaaacccaa gccccacggg tgtgaccgag atgacctttc cttcgtgggt ggatcccaac 2280
aatcctcctc agtggtataa cgaagggggt gacattgaca atctcctcga cgaagcggag 2340
gctttagatt ggcttacgga tacgggcgac atcaacgaga cgtatccacc agcggttgct 2400
gccactcaag ctgccgtggc gaatgatccc tctgattatg agccaacacc cgtcaataac 2460
tattcttacc acgttgacaa ctcaggtgcc accactccat cactggcatc tgtcgatccc 2520
accgccgtca aaatggaaga tcacaccatg gttcacgatc ctaccggaat gatgcatcca 2580
tctgctgact cgctgtcctt cttggttgat cctcccgagg agggagttac ctcagctgaa 2640
ttgccagcgt tccttaacga tgactccccc cagcacgggg tcgcctccat gccctttttct 2700 tcggcgactg aagcagtgga gtctcatact tttgaaaaca aaattaacac tgccgtttct 2760
gacggaaatc tcatgggttt ccccgatcta gacatgggag acgaacaggc atttgtctcg 2820
gcgctattgg acaactctgg gcagagcact ttgtcgtttc ccaagttgaa ttcagagttg 2880
cacatcggga gtctgtcagg gattggattg agtggcgttg gtgttagtag cgatgccttg 2940
ggagagcctt tggaggatga tcaccttgat gattga 2976

<210> SEQ ID NO 47
<211> LENGTH: 1227
<212> TYPE: DNA
<213> ORGANISM: Ectocarpus siliculosus

<400> SEQUENCE: 47
atgacgccga agaacacggg gcgatggacg tacgacgagc acaggctctt cctgcggggg 60
ctggagctgc acggcaaggg ttggaagaag atcgcgtcgc tcatcaagac gaggacggtg 120
gtgcagatcc ggacccacgc gcagaagtac ttccagaaga tcgccaaggc caagcagaac 180
ggggagcacg gggacgtggc gatggactcg aaggggcacg ggtctcgaag aaaaagcaga 240
gggcggagaa gaatggaaga cctgctgagg gggtcgacgg cagtggcccc ttccctgcag 300
ccctacgtgg ccggggcagg ggcggtggag accgggctct accgcttcct gtccccgata 360
acaatacagg acctggagcg gccaccagct gcggcgggac aggggggcac agcaggcggg 420
gtgggcgggg gggcggctgg actcggcggg aacggcgggg cttcgcttca gtcccagctg 480
gccgggcacg caacgtcgtc ggcaggagcg tcgccgacaa cgacaacggc gggagcggca 540
atggcggcgg cagcggcggt ccttcctccg aactggtacc gagcaggccg tggcgtggac 600
gacctgctca ccgaggctga ggggctagac tggctggccg acagcggggg tgcggtggcc 660
gtcacgtcgg tgtcggcggt taacccggcc gccgccgccg ccgcctcccc cgcccccgcc 720
gccgttgccg gtgcccacgc cggcgtcgcc agggtcgcgt cgtcgtcgga gctgtcgagc 780
cagcctttgc tcaagaaggt ccggtccacc accgtggact cgtcggcccc gctggccacg 840
gcgacgacga tgaacacctc ctcgaccgct gccgctgcca tgggcggcat cgcgcggccc 900
tcggccagcg ctgccgcgat gacgccgtcg tcttggtcgt tgccgccgcc ccggccggtg 960
gcgtgcccgc cgcctgccgc acctccaacc gctggagtgg ctgtggacga gctgaccccg 1020
tccggcttgc agggctcgga tgccgaggag gggcaccttt cgggcttgtc ggacctggaa 1080
agcctcatgg aggaccaaga gctcccgggc tctcagccgt ttggaccagt gtcgaccgct 1140
gccgaagtgg ccggcgcggg cggtgatggc atggacgacg gcatggttga cgaagacgca 1200
ttcgtcaacg cgcttctaga cgcctag 1227

<210> SEQ ID NO 48
<211> LENGTH: 5414
<212> TYPE: DNA
<213> ORGANISM: Artificial Sequence
<220> FEATURE:
<223> OTHER INFORMATION: LAR1 knockout construct

<400> SEQUENCE: 48
caacgtcttt ctctcggtaa cgtcggcgcg aggacaggtt gtgcccaacg cctgcaggat 60
gcgaaccatc tggatgtcgt gacgtcgccc tcttctcgaa agtgctcggt ttccgtagtc 120
gcgttgctgc acagtatatt tcacagcact tcaccaacca cgctagaaaa atggtgtcgc 180
ctggtctttc tatcagtgtc caaagaaagc accctgtttc gtctttgaac gtgtatcatg 240
caagatactt gatcgaggtc gcgatagaga cggccatctg ggtccgggtt cttgcgccat 300
tcggaaccgc aaaaccgtaa ttatgagggg agcaagtggt tctctccccg gcgggcttgt 360
tggacggact gctttgatct tcgtaaagcg cccatttttc gcacgcgctt tctacttgct 420
agccttctta agtcaaggga gagtgcaggt gacgcggcga ggctgtgagt gcaggggctc 480
ggacatcatc aagcagcaac ttccgagcaa caaggtcaag atagaaacag aaggcgagca 540
gctgaagaag ggtatatagt gcttttgtgg ctatgtgcac ccatccaagc tttgctaacc 600
ctgtgccaag caacctccgt cacaagctct tctcaaatgc ccttacttta tttcccacac 660
aggagcgcgg gggcgtcttg ttttgcatcc atttcttggg aagcgaatca ggaaccaaag 720
gtacacgaga acgctctcca gtacacagga gacctaattt gtccgattta ggcaaacctc 780
tcttttggca cgtgggcacc atcttgtgct cgtgtacgaa ggtgttcccg tagtttcaga 840
gtgtgtactt gtggtcgtgt cgtgtgaatt gcccgtcctc tcccaccttc taagaaacaa 900
gatcgcctcg tctgcagtac gggcattgtt tcacttcttc cttcggtggc gagactcgac 960
ggacaacagt cacacacaca caacacacac agtgtttttc actgcttttt cattgaattc 1020
tgcgtgtttt tagtgcgtgt gcgggtgtct caagggctca ggtgactggc gcttctccac 1080
cccctacact ttttgaacga gaacgaggag tgctgcgtct tcagacaaac caagcaccat 1140
gtcctccccc aagaacattc tggcccccgc aagcttgtcc ctaaacaatt acaataaacc 1200
cagccacgat ctcggcagcc caaagacgca acaccatcac catggcctgc atcatcagca 1260

-continued

```
ccagcacaag cagcagtacc agcaccaaca gcaactgcag cacgcccatg ttctcggtgg   1320
caaatcagta gccggttcca acaagatcct tcctttcacc tcatctatgg atgaagttaa   1380
atatgccgct ggcgggctga tcaagcccgg gacgcaaggc ctgggcagca tgctctctac   1440
acccttgacg ccctcggctt ctcttattgc atcgtcggtg gtagaggccg atgcaaagca   1500
acaacaactg ctgaaggatt ccctcaccgc cgacctcaaa ttgctcctgc acgaattcga   1560
acgcttccag caggccactg cagcagcagc gggaacagga ggcgtgggcg aggaggaggc   1620
agctgagcga tcgacgaaag tggagttctt tttgggatac attgagcgag ttctccacga   1680
tttggcaggg gctgacgcat cgaaactgca ggatctcgag gtgcggatca agacaagtct   1740
actaccactc aagggccagg tggttagcca gcttgcggcg caaaataata actcccctcc   1800
tccccataag gagcagcagt catcttggtt ccatccttct tccacctgct cctccctctc   1860
ctcctcttct tccgtctcca gcgtgcacac aactcctcct ggatctccct tggcaaggga   1920
ggagacggtg atgagcacct acggtccctt tacccactcc cgcgtcgcag cacgtgcagg   1980
tgtacagatt gaaggaaaca atggagatat ctttggcagt tgaaaaccgt gttcgaatca   2040
tgcttttcta ctctccaact gagacgaaat ttatagcgcc atgtcgcttc tgactaccag   2100
gcttaggaag gcctcatcac aagctggatc ggttcgaatt aagcaggcac tgaagccaag   2160
cttgcaagac agccaccttt taattccctc aaaacacttt ctcaattcag cccggtaaat   2220
atgccgattc acagcggcca agatagaggg gaggttagca agaatgttgc gatccctccc   2280
cagtcgttgc ctcgcacaca acctaggcct tcacctttcc atggaaaatt gagaagtgaa   2340
tattggtttt cttacggcat atcagatgaa atcatgaccc ctaaacatga agagctgcag   2400
gcaaaacacc tgctctggac gagcacgatg aaatctcgag aacccgccgt acttcagttg   2460
atcccgcatg atgacggccg ccattgaaat aagccacctc actttattct agcaccgatt   2520
tccaccgttg tgagggccga acgaggacaa tttcgtgcga aacaagcacg aacacgcaca   2580
cgattagtag tacagacgag cagatcgatg gcatgcggca cggtctcgcg ttctcggcga   2640
ccaggacaac ggagcagagg gaggcctgcc gagttccgag ggcatttta gtccaaaatt   2700
gtgttgacac gtgaacaagt ggcttgaaaa gaggaaggaa atgcctgggt ttcccttcga   2760
gagcgggaac tcgcttgtgc gtcatcctag ctacccatgg tccctttgtg ggggaggctg   2820
tttcgtccta ccgaatgtgt ggcgctccat gcatcttctg cctcccaaac caccaacatg   2880
agcacgcgaa ggaaggagaa aaaagtggcc gcaacgttct cttctcatat ttattgtctc   2940
atcacaaaca taggtacata atacaacaat catggatccc cgggtaccga gctcgatggc   3000
caagccttta tcccaagagg aatccacgct gatcgaacgt gcaactgcga ccatcaacag   3060
catacctatt agcgaggact actcggtggc cagtgcagcc ctctcgtccg acggtcggat   3120
ctttaccggc gtgaatgtat atcatttcac cggagggcca tgcgcggagc tcgtggtcct   3180
cggaacggcc gctgcggctg ctgccggaaa tctgacgtgc atagtggcca tcgggaacga   3240
aaaccgcggc attctgtctc cgtgcgggcg atgtcggcag gtgctgcttg acttgcaccc   3300
ggggatcaag gcaattgtca aagattccga tgggcagccc acagcggttg gcatcaggga   3360
gttgcttccc tctggctacg tctgggaggg ttgacagcag cagttgtgct acgcatgcac   3420
ctccctgcct cgcctcctcc tccacctcct cctcttcttc tttctcttcc cctttctctt   3480
cctcttcggt ggcgacagtg gcagcagcag atgtcagcaa gcctctcctt cgtcaggttg   3540
agtatcagtg cggtgcttgc gccgacacct acaccgctgc ctcctccctc aatccctggt   3600
gggccctcga gcgacaggag tgtcccaagt gcaagaaggt tcaagttcca cgcattgaca   3660
```

taaacctgcc tgccaacacc atggaatacc acccggcttt gctcgcggag gaaggcgatg 3720
atgacgatga tgatgaggtg ggaggcggga gggagggagg gatgatgatg atgccggggg 3780
gaggggatgg acatggacat ttggaggaaa gagaggaggg agagacgagt gagaaaggga 3840
gcggtggaag tagcgtacta gaggaggacg aggaagcagt gttgagccct atgcaagctt 3900
cacagctgtt gagtttgttg gagcatgcgc ggacatgccc gggcaatcat gctgccgaga 3960
aacaccaggc tgtgtgtacg agtgccaagt atctcatgtt gcatgtgagg gattgtgatg 4020
gcaggacgtt agatggggag gcttgtggat tctcgtggtg caggccttgc aaacacttgc 4080
tcgggcacct ggtccggtgt tacgaagccg agaagtgtca gatctgctgt ttctcacacc 4140
aagaagagga ggagaaagtg gaaaagaagg tgatgatgag tgtggaggag atgattgagg 4200
agaaaggaat gagggtcgac acctacagga gcttgacgag cttgagctga gacaaggtgt 4260
gatgagaaga ggaggggaag aagggaggga catatctgta tggccgcatg tattgtggta 4320
agaaatgtgc gtgtcttgat gtgatatatt taaatgtctg agtgagtgaa tgtccgagtg 4380
agtgaatgtc cgagtgagtg aatgtccgcg cttgtgtgta tcggtaggta cgagcgaggg 4440
aaaagagtga tctaatgtcc ctgcctgtcc atcagtctga tgacaactga gaaaaaacat 4500
cgattgggag agtgaaagta gaaatgatgt atgaaaccaa ccaggagtga cggcaacgat 4560
gctggcgctg catgtgcaaa cgagcgcatg attaatcgaa cgagtacatg gacaagaaga 4620
cacgtgtatg agagagagga aatgagatag agagagggag agagaatgag agagtaaaag 4680
atgatttatt tatttatatc gaaaatctat tgcccgccca tctatgattt agatctatta 4740
cccacctatc tacatagcga tcgagtgacg aataaataag gcatctacat atatgataaa 4800
tttctacgct tgattcgtgc tttcgattct atatgccatt ggtagataga gaccaatagt 4860
cagcggcagc atcagcgcga gaacgatgaa gcctgtcttt ctgatgtacg agtagtgtga 4920
aggaagagat caaagagggg atgacgtatc aggacaagta ggaagaggcg ttcgtttggg 4980
aacgggaaat atgacgaatg agcatgcacg tggcactcat cgcgtgaagc agagggtgct 5040
gggggaaacc ctcgaagcaa gaagacgacg acaagaacga tgatcatgcc tatcaataca 5100
ctgagaagaa atacacaagt aacagatgta gttccatagg acaacaaaaa cagaatcaga 5160
ggtcgatatg aaaacccaaa aaaaaaacca ataagattca atttagaaac acccaaaaat 5220
cagcgagcag aagttagcac gtaccacggt aacaacagag aagagcaatc gacgaccata 5280
actaaaaata gaaaacaaaa aataaaaaag atagagaaaa cccacgccag tccgcccccc 5340
agaaattcga gggctacggt gcctgcagca atacagcgag ttttccttga gaagggtaat 5400
aacacacaag aaac 5414

<210> SEQ ID NO 49
<211> LENGTH: 3415
<212> TYPE: DNA
<213> ORGANISM: Artificial Sequence
<220> FEATURE:
<223> OTHER INFORMATION: LAR2 knockout construct

<400> SEQUENCE: 49
ctgtatgctc gtcgtcgatc cagttaaagc gcgatgctta ccagaccccc tcatctagta 60
aattgtgcct ggatctgagc catccccccg agtacattgc tttgacccgt cgctgtttaa 120
tctgacagat tgctataata gcaccaatga acaatcattt ttattttcac acgcaatctc 180
acaacatcct ctccttcccc tcaaaagcag gatgcaacta ctaccgcggc cggcagcatg 240

-continued

```
atgcttcccc tccttccctc catccctgct tccgctacca gcgcctcttt taccgctccc    300
tcagcgtcct ccacgaccac caaatctccc aaaggtactt cctccatgac tcagcttgga    360
gagacagggc gagagaatac tggccgatgg acttgtgaag agcatgtgct gtttcttaaa    420
ggcctagaaa tgcacggcaa gggttggaag aaaatcgcaa agctaatcaa gacccgaacg    480
gtggtccaaa tccgcacgca cgcgcaaaag tacttccaga aattggcaaa agccaagaag    540
aacgggcacc atggtgatat gctcggaatg gaaggctcac actttggggg aaaacgtgtc    600
aaatttaccg gaaagcgacg tgggcttgtc tataattcgt atttagtagg tgccgaggcc    660
acctctgcgg ctatctcccc ggcgttgcag acgtttatgc cggcgaactt ggggatggag    720
ggcgagcgtg taggccttat gacggataag gaggaggatg cagcaatcga gaagggactt    780
tatcgtttcc tctcccccgt agtgctggat cccgccacgc gtaatctgga cgcctccgct    840
cctgagatct tgcccttacc acccagcact ccagcgatgg gcgtgcacca taccagtagc    900
agaggtagca gcagaggggg gttggatgga gagacaacgg gagaggagga cggcggaagc    960
gattcgattg taatggggga tggagggagc gatcaagatg cagagtcgtg caggtgtaca   1020
gattgaagga aacaatggag atatctttgg cagttgaaaa ccgtgttcga atcatgcttt   1080
tctactctcc aactgagacg aaatttatag cgccatgtcg cttctgacta ccagtcttag   1140
gaaggcctca tcacaagctg gatcggttcg aattaagcag gcactgaagc caagcttgca   1200
agacagccac cttttaattc cctcaaaaca ctttctcaat tcagcccggt aaatatgccg   1260
attcacagcg gccaagatag aggggaggtt agcaagaatg ttgcgatccc tccccagtcg   1320
ttgcctcgca cacaacctag gccttcacct ttccatggaa aattgagaag tgaatattgg   1380
ttttcttacg gcatatcaga tgaaatcatg accccctaaac atgaagagct gcaggcaaaa   1440
cacctgctct ggacgagcac gatgaaatct cgagaacccg ccgtacttca gttgatcccg   1500
catgatgacg gccgccattg aaataagcca cctcacttta ttctagcacc gatttccacc   1560
gttgtgaggg ccgaacgagg acaatttcgt gcgaaacaag cacgaacacg cacacgatta   1620
gtagtacaga cgagcagatc gatggcatgc ggcacggtct cgcgttctcg gcgaccagga   1680
caacggagca gagggaggcc tgccgagttc cgaggggcat tttagtccaa aattgtgttg   1740
acacgtgaac aagtggcttg aaaagaggaa ggaaatgcct gggtttccct tcgagagcgg   1800
gaactcgctt gtgcgtcatc ctagctaccc atggtccctt tgtgggggag gctgtttcgt   1860
cctaccgaat gtgtggcgct ccatgcatct tctgcctccc aaaccaccaa catgagcacg   1920
cgaaggaagg agaaaaaagt ggccgcaacg ttctcttctc atatttattg tctcatcaca   1980
aacataggta cataatacaa caatcatgga tccccgggta ccgagctcga tggccaagcc   2040
tttatcccaa gaggaatcca cgctgatcga acgtgcaact gcgaccatca acagcatacc   2100
tattagcgag gactactcgg tggccagtgc agccctctcg tccgacggtc ggatctttac   2160
cggcgtgaat gtatatcatt tcaccggagg gccatgcgcg gagctcgtgg tcctcggaac   2220
ggccgctgcg gctgctgccg gaaatctgac gtgcatagtg gccatcggga acgaaaaccg   2280
cggcattctg tctccgtgcg ggcgatgtcg gcaggtgctg cttgacttgc acccggggat   2340
caaggcaatt gtcaaagatt ccgatgggca gcccacagcg gttggcatca gggagttgct   2400
tccctctggc tacgtctggg agggttgagt ggtagcaaca ctaataagat gaactcagcg   2460
gcgcctgtgc tgaacatgac agggttggct ggggctggag ggctttcagg gtggaagggc   2520
aagggtagcg acactagcga aggtagcagc agcaacggca gcagcaagaa catggctttg   2580
acggcaaatg cgtcggcggg atgtggacaa gggagctggg gagtgcgggg gggggcacag   2640
```

aaaaagcagc agcagcagca acatgaggta ccaacgcagc agcagcaggt accaacgcag 2700
cagcagcagg ttcacggcat tcacgtgaag gaggaaggga tggagctcct gagagtcatg 2760
gcggatagag ggactgttca cggtcacgtc catgaggagg atggctttgc ggcgtttgac 2820
ccccatcatg tcgagctgaa ggaggagcac tcccaccatg atttgttgct ggaagagctg 2880
ccccacgaca gcaaccacga tgacgccctg gcccatattg tgttctcagt gaatggagag 2940
tcggatcttc attccttgcc gaggggtgca ggaggggggg gagcgcatgt gcatgcgccg 3000
ccggttgtgg tggggggagag acagcatcac tatcatcata atgacaatga tatccatttg 3060
catgcgtacg acgcgtattt ggaagaggaa ggggcggatg gcgggcatgg gttgttgttg 3120
ttggaggatt tggatggggg aatcgagttt tagagatgga gagggagaag ggaagtgtgc 3180
atgtgtaaga aaagaaagga ggaaattcaa ggaagagctg gaagggagag aaaaagatgc 3240
ggctataatg gtgttcatga aggcacattg ccacaaaaat aaacgaacgg ggagaagagg 3300
cgtttggaaa gaggagagag atgtgaaagg acctgaggta gagtgttggt tgaattacac 3360
taaacgccaa ccttgtgtcc ttgtgtcgcg cgtgcacgaa cgatccagac gaagg 3415

<210> SEQ ID NO 50
<211> LENGTH: 4553
<212> TYPE: DNA
<213> ORGANISM: Artificial Sequence
<220> FEATURE:
<223> OTHER INFORMATION: LAR1 RNAi construct

<400> SEQUENCE: 50
caggtgtcca ctcccaggtt caatacagct cttaagcggc cgcaagcttg ccgccaacat 60
gtcactcaga ggtacgtcgg tcgcaactgc gtgcacttcg tggccgagga gcaggactaa 120
agatcttcta gagtcggggc ggccggccgc ttcgagcaga catgataaga tacattgatg 180
agtttggaca aaccacaact agaatgcagt gaaaaaaatg ctttatttgt gaaatttgtg 240
atgctattgc tttatttgta accattataa gctgcaataa acaagttaac aacaacaatt 300
gcattcattt tatgtttcag gttcaggggg aggtgtggga ggttttttaa agcaagtaaa 360
acctctacaa atgtggtaaa atcgataagg atctgaacga tggagcggag aatgggcgga 420
actgggcgga gttaggggcg ggatgggcgg agttaggggc gggactatgg ttgctgacta 480
attgagatgc atgctttgca tacttctgcc tgctggggag cctggggact ttccacacct 540
ggttgctgac taattgagat gcatgctttg catacttctg cctgctgggg agcctgggga 600
ctttccacac cctaactgac acacattcca cagccatatg cacgtgaagg gcgaattcgt 660
ttaaacctgc aggactagtc gtcatgataa taatggtttc ttagacgtca ggtggcactt 720
ttcggggaaa tgtgcgcgga acccctattt gtttattttt ctaaatacat tcaaatatgt 780
atccgctcat gagacaataa ccctgataaa tgcttcaata atattgaaaa aggaagagta 840
tgagtattca acatttccgt gtcgccctta ttcccttttt tgcggcattt tgccttcctg 900
tttttgctca cccagaaacg ctggtgaaag taaaagatgc tgaagatcag ttgggtgcac 960
gagtgggtta catcgaactg gatctcaaca gcggtaagat ccttgagagt tttcgccccg 1020
aagaacgttt tccaatgatg agcactttta aagttctgct atgtggcgcg gtattatccc 1080
gtattgacgc cgggcaagag caactcggtc gccgcataca ctattctcag aatgacttgg 1140
ttgagtactc accagtcaca gaaaagcatc ttacggatgg catgacagta agagaattat 1200
gcagtgctgc cataaccatg agtgataaca ctgcggccaa cttacttctg acaacgatcg 1260

-continued

```
gaggaccgaa ggagctaacc gctttttttgc acaacatggg ggatcatgta actcgccttg   1320
atcgttggga accggagctg aatgaagcca taccaaacga cgagcgtgac accacgatgc   1380
ctgtagcaat ggcaacaacg ttgcgcaaac tattaactgg cgaactactt actctagctt   1440
cccggcaaca attaatagac tggatggagg cggataaagt tgcaggacca cttctgcgct   1500
cggcccttcc ggctggctgg tttattgctg ataaatctgg agccggtgag cgtgggtctc   1560
gcggtatcat tgcagcactg gggccagatg gtaagccctc ccgtatcgta gttatctaca   1620
cgacggggag tcaggcaact atggatgaac gaaatagaca gatcgctgag ataggtgcct   1680
cactgattaa gcattggtaa ctgtcagacc aagtttactc atatatactt tagattgatt   1740
taaaacttca tttttaattt aaaaggatct aggtgaagat cctttttgat aatctcatga   1800
ccaaaatccc ttaacgtgag ttttcgttcc actgagcgtc agaccccgta gaaaagatca   1860
aaggatcttc ttgagatcct ttttttctgc gcgtaatctg ctgcttgcaa acaaaaaaac   1920
caccgctacc agcggtggtt tgtttgccgg atcaagagct accaactctt tttccgaagg   1980
taactggctt cagcagagcg cagataccaa atactgttct tctagtgtag ccgtagttag   2040
gccaccactt caagaactct gtagcaccgc ctacatacct cgctctgcta atcctgttac   2100
cagtggctgc tgccagtggc gataagtcgt gtcttaccgg gttggactca agacgatagt   2160
taccggataa ggcgcagcgg tcgggctgaa cggggggttc gtgcacacag cccagcttgg   2220
agcgaacgac ctacaccgaa ctgagatacc tacagcgtga gctatgagaa agcgccacgc   2280
ttcccgaagg gagaaaggcg gacaggtatc cggtaagcgg cagggtcgga acaggagagc   2340
gcacgaggga gcttccaggg ggaaacgcct ggtatcttta tagtcctgtc gggtttcgcc   2400
acctctgact tgagcgtcga tttttgtgat gctcgtcagg ggggcggagc ctatggaaaa   2460
acgccagcaa cgcggccttt ttacggttcc tggccttttg ctggcctttt gctctacgta   2520
tcctgcaggt cgactctaga gaggattgat ttccgagtca aagattcgta tagctgcaaa   2580
tgcactcatt gatgagatac ctgaagagga ggatgacaaa cagtacttgg caagtgaatc   2640
ttttcgggaa ttcatacggt attttgatgg actggatgca ctaatggagt cggcttcacg   2700
gccgttcggt ggaggagaag atccaaggat gaatgcattg actttgttgg gagaggtgga   2760
ggaatcattg aggatgtttg tcaagattgc gaagtgatga ttgcatgcat cgcgctgatg   2820
aaagaaatgt gctcaatgtc gacgaaccat aggcattgat actggagaga atgaagacat   2880
agtaacgcag gagacgtcaa ctgaatccaa aactcgatgg atttccaata caaattatgt   2940
aaacttatca ttctttatcc cagccaaggc agcctaaact cgtacccccca aagtagtggc   3000
gccaacagcg cgacagagtg aggatcttca accctcccag acgtagccag agggaagcaa   3060
ctccctgatg ccaaccgctg tgggctgccc atcggaatct ttgacaattg ccttgatccc   3120
cgggtgcaag tcaagcagca cctgccgaca tcgcccgcac ggagacagaa tgccgcggtt   3180
ttcgttcccg atggccacta tgcacgtcag atttccggca gcagccgcag cggccgttcc   3240
gaggaccacg agctccgcgc atggccctcc ggtgaaatga tatacattca cgccggtaaa   3300
gatccgaccg tcggacgaga gggctgcact ggccaccgag tagtcctcgc taataggtat   3360
gctgttgatg gtcgcagttg cacgttcgat cagcgtggat tcctcttggg acaaaggctt   3420
ggccatggca tgattgttgt attatgtacc tatgtttgtg atgagacaat aaatatgaga   3480
agagaacgtt gcggccactt ttttctcctt ccttcgcgtg ctcatgttgg tggtttggga   3540
ggcagaagat gcatggagcg ccacacattc ggtaggacga aacagcctcc cccacaaagg   3600
gaccatgggt agctaggatg acgcacaagc gagttcccgc tctcgaaggg aaacccaggc   3660
```

```
atttccttcc tcttttcaag ccacttgttc acgtgtcaac acaattttgg actaaaatgc   3720

ccctcggaac tcggcaggcc tccctctgct ccgttgtcct ggtcgccgag aacgcgagac   3780

cgtgccgcat gccatcgatc tgctcgtctg tactactaat cgtgtgcgtg ttcgtgcttg   3840

tttcgcacga aattgtcctc gttcggccct cacaacggtg gaaatcggtg ctagaataaa   3900

gtgaggtggc ttatttcaat ggcggccgtc atcatgcggg atcaactgaa gtacggcggg   3960

ttctcgagat ttcatcgtgc tcgtccagag caggtgtttt gcctgcagct cttcatgttt   4020

aggggtcatg atttcatctg atatgccgta agaaaaccaa tattcacttc tcaattttcc   4080

atggaaaggt gaaggcctag gttgtgtgcg aggcaacgac tggggaggga tcgcaacatt   4140

cttgctaacc tcccctctat cttggccgct gtgaatcggc atatttaccg ggctgaattg   4200

agaaagtgtt ttgagggaat taaaaggtgg ctgtcttgca agcttggctt cagtgcctgc   4260

ttaattcgaa ccgatccagc ttgtgatgag gccttcctaa gcctggtagt cagaagcgac   4320

atggcgctat aaatttcgtc tcagttggag agtagaaaag catgattcga acacggtttt   4380

caactgccaa agatatctcc attgtttcct tcaatctgta cacctgcacg ggtaccgagc   4440

tcgcttccat tcaggtcgag gtggcccggc tccatgcacc gcgacgcaac gcggggaggc   4500

agacaaggta tagggcggcg cctcataatc aaagatgagc cagccacgaa gct          4553
```

```
<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51

gtgaaaccag cactcaatct ctc                                             23


<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52

agttcgaata tcctgcaatc gt                                              22


<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53

gggaggctga gatcaagcac                                                 20


<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54

caggagccct accgtcatgt                                                 20
```

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
tacttgcagg aggccgagat 20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
agggagctaa cagcgtggac 20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tgccccgaag aagctagatg 20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
cacgacccag cctaggaaac 20

<210> SEQ ID NO 59
<211> LENGTH: 399
<212> TYPE: DNA
<213> ORGANISM: Artificial Sequence
<220> FEATURE:
<223> OTHER INFORMATION: Synthetic

<400> SEQUENCE: 59
atggccaagc ctttgtccca agaggaatcc acgctgatcg aacgtgcaac tgcgaccatc 60
aacagcatac ctattagcga ggactactcg gtggccagtg cagccctctc gtccgacggt 120
cggatcttta ccggcgtgaa tgtatatcat ttcaccggag ggccatgcgc ggagctcgtg 180
gtcctcggaa cggccgctgc ggctgctgcc ggaaatctga cgtgcatagt ggccatcggg 240
aacgaaaacc gcggcattct gtctccgtgc gggcgatgtc ggcaggtgct gcttgacttg 300
cacccgggga tcaaggcaat tgtcaaagat tccgatgggc agcccacagc ggttggcatc 360
agggagttgc ttccctctgg ctacgtctgg gagggttga 399

<210> SEQ ID NO 60
<211> LENGTH: 1602
<212> TYPE: DNA
<213> ORGANISM: Nannochloropsis gaditana

<400> SEQUENCE: 60

```
gtgtggtgaa gcagggaagt gggagaaggt cctggagctc ttggcggaga tgccttcaat     60
gggcgtgtca cccaacgtgg tggcatacac ggctgctgtc gctgcgtgtg gacgaggagg    120
gcagccagag cgggctttgg ggttgctgcg ggaaatgaaa agcgagggga tcagtccgaa    180
tgtacaatgc tacaatactt tgctttgggc actggctaaa ggtggggact ggcagcagtg    240
tctggcgtta ttggaggaga tgaaggaaga gggcaagacg gatgctcaca gttatcgtat    300
tgtgatgggc gttgtaaaaa gtaagcaagg gcaagagcat gttatggagg ctcttcaggc    360
ggatatggag gggtcgagga ccgaggcggc gaatgacagc tttggatgcc ggtaaataat    420
ttttaagatt acggaaagtg tagcttgtaa ttagcaattt gtgagtgtgc atagacctga    480
tagaaacgat agaaaataaa gttgaacaaa gtatcaattg tgaattcaat tcacggatat    540
ataaatagaa tctcgcccag gtgtcaaagt aagttctctc tgctattccc cgtccatggt    600
ttcgatctgt actttcctcc atctcccggc caccaaaaag ttagcacaac gtttacggaa    660
ccagaaggca ataacagtat ttagggtaat cattttagac gtgctaagtt ccacataccg    720
aaataaatgt atttacaaaa ggtttcactc gtcgccttga ccagctcaca cgaccccgaa    780
gcagaagtct tcttttcctt caaaccatgc accgcacagc attgctaaga gagggagtgt    840
cactctgttg cttctctcga tgcacgaaaa ggtgctcctc cgagggctcc caacttatct    900
cagtggcagg gatgtctctc atcacatttc tgctcattcg acaacgtcat gagaagatct    960
ggtgtctttc tgcggattgc gccctcgaca acactattgt tcctgggagc gctctttcgg   1020
cctgacacaa atgcccgtgc cttcaaggcg tgggtatttt cctagtgtct ttcacgtaaa   1080
gcgtgcgcac gtctggccac tatttggtac tcgactgtgc ctccatttgt ccttttttatg  1140
gtgatgctct tttctttgtc cacttagata caccttggcg tgccggtggc ccgtgtttaa   1200
gcctacccca agcaggcttc cttgctacca atagcttgcc ggtaaaaatg ctcacatcgt   1260
cttattcgcc ctctccattc tgtaaccgtt ccctcccctc cctcggacag tcccggcctc   1320
ccatctcgtc ggcaccatag cgaagggtca gtccaccacc agcgcgcgag tctcgtcccg   1380
agcgcggccc gtggcttgga tcaattgctt ttggaagccg acagcaagca cggaaatgcg   1440
ccgtagctgg ccacaaaatt cctcgactaa cgacacctag ttagccaacc acgtcgacgt   1500
ccattcacca cggtcggaca gggcgagcta ggcgacaggt tctttcccgc acctggccag   1560
accccacccg gccaccagac gataatgggg atgcctagca ac                      1602
```

```
<210> SEQ ID NO 61
<211> LENGTH: 1134
<212> TYPE: DNA
<213> ORGANISM: Nannochloropsis gaditana

<400> SEQUENCE: 61
```

```
aattcaagtc ggggttgttg ccattgacgg atggtacgac attgaggaca tttttgagta     60
agctgcttaa ttgtgatcct atgaggataa gcaaaaaatt tgtgggtcag aattgcatcg    120
gaaagcaagt gtttcgtcgg cggcagcaag cagagatgga caggttgtcc cctgaagaga    180
ttgaacggag tcgacaagaa cttgccgaac tagagagacg atttttggag cgcgtggctc    240
agacaaatcg atgtaagaat tctgctgtgg ggacgaagca tgggaaagac tcggcgtcgg    300
gtcaggtggc gccggaggtg ttgcgacgac agcaagagta cctgggccca ggtgggcagg    360
tggtgggtaa tcccctcctc cccccctgga tgctccctcc caccgcggat gcatcgatgg    420
agggagggga gggcattcaa ggtggagatg gtcattcgaa ttcctcgcca gagaggggggg   480
```

```
ggatggggat gaccggtcgc ggtggtggtg gtagttcttt tcgtttgatg ggtggaggaa    540

cgggagcagg gagcaagcag cagcagcagc agagccagca gcagcagcag ccgccttttt    600

cggatttgcc ctgcgcacac cagttgcacc atcctcagtc acatctccat catccacgac    660

gtatcccctc ctcatcgtcg tccaccctag gagggctgaa cacgggtagt ctctccgcga    720

tcgcgtcggc gaatatgtca cgcaccgatt ctcaggatag cctaacagcg ttaggtggca    780

caatgtcggc agacgctctt ggacatttgg cggactttcc gcgtgtgacc agcctaggag    840

atcttgccgg actcaacatg tttacctcca gccctttccc ctccacggac aatctcctca    900

gccttcacca gcagcaacac gcccaaagtg ctcaaattgt tccggccact gctgcttctc    960

ttgccgcgca tagcaccacc agcttagcag cagcggcagc agcagcagca gtggctccgt   1020

cgagcacacc gatcagtcgt agcaccagtg gcaacggtaa tggcgggagc agcagcagca   1080

gcagcagcag cagcagcagc agcaatgcga atggtcttcc accactagcc aatg         1134
```

```
<210> SEQ ID NO 62
<211> LENGTH: 2526
<212> TYPE: DNA
<213> ORGANISM: Nannochloropsis gaditana

<400> SEQUENCE: 62

atgatggaga tgccaaccaa ccgcagcggc cctgggacgg actcgggaga gaagtgccca     60

aatcctccca cggttggtgc acttgtcacg actacgcttt cgcccaaaag tgaatctcct    120

aagagagttg ctgttcccac gttaggagcg cccgtggcgg ctccaccggc gtccgccgtg    180

gccgtggcag caagggggca cggatcctcc ctgcagaatg ggctcccagc ccgcaacggg    240

gacggtggca gctctttgac gccaacttct ggcccaagag aatttcttca agtggcgagt    300

aaaccgcctg gcacggagat gcctgctcta gacgcgtcaa caagtggatt gatacataag    360

ccggcgagta gcgacgccgc cacggctctc tcacagcacc acgatgcgtt gatacagcga    420

gagctgaatg cgatcattgg tcaaaagcgg gaacacaggg accgcagtga agagtcgact    480

gtgcttcttc cgtccacctc tccgatctcg gttcccgtac caagacacca agcgagcgca    540

cgacccgggc caggccccgc ctcgcatgcc ctcccgcct cgcccccgc acaagcaggc    600

tcaaacgcca gaggaagcgg gcagacggtc tcgaataggt cgcctccatc cgcgaacgcg    660

caagccctta tgcctcctac gcgtcactcg acaagggggg ccaccgccgc agcggcggct    720

ggtattagca agtccatcga agaggcctgc catgccgccg ccctagagga cggcgtgttg    780

agctcgaagg ggggaggcgc gctgaatgct ggatacggga atgctaagca aggtagcgtg    840

gttagcccgg gcgagacaag cgcgctgaca agcgctaata aagctggcaa ggtcaagaac    900

ggtctgcgac gagggaagtg gacgccggag gaagaggctt acgcgaaccg tttgattgtc    960

gagttcaaat ctggattgtt accgctcact gatggaacaa cgctacggac atttctgtca   1020

aaacttttga attgcgatcc catgcgtatc tccaagaaat tcgtggggca aaattgtatc   1080

gggaagcaag tttttcgacg ccggcagcag gcggacttgg atcgcctatc cacggacgag   1140

attgagcgca gtcgacaaga gctagcggag ctggagcgcc gttttttaga gcgcgttgct   1200

caaacaaacc gttgcaaaaa ttcggttgca ggctccaagc acggtaaaga cagcgccgcg   1260

gggcaagtgg ctcctgaggt gccacgtcgg caacaggagt accttggtcc tgacggccgg   1320

attgttggga accccgtcct tccgccttgg atgctgccac cagctgcaca ggctgcgaac   1380

gaaggggagc ctgcgtcagc ctcaacaacg ccgcgctcaa actgttcgag cggtatcaac   1440

agcggcttcc ggggagccgc aggccccaat tcgaccaagg gaacaagcag gcatcatcag   1500
```

-continued

```
aatattgccc ctgaacacac aggcgctact cttcatcaca tcagccacct tcatcagcct   1560

tcgggccttc ggcgcggtcc tggcggatct gacactggga ttttgtcggt aactgcagcg   1620

acaaacatgc ctcgaacgga ctcacaggac agtctgtcgg tgctagggcg caccatctcg   1680

gcagatgcac tcggccacct cacggacttc ccccatacca ccagtttggg tgaccttgcc   1740

ggcctgaata tgttcacatc cagccctttt ccctccaccg acaatctttt gagcctgcac   1800

cagcatcagc accaacagac ggtagcggcg gcacccagag gccatactac tctctcagcg   1860

cataacgcaa caagcgtggc ggcagcggcg gcagcagcag ccgtcgcccc ttcgagcacg   1920

tccatcagtc gcaacacagg ggacagtgcc ccccgcggcc ccaacgtgag tggacacggg   1980

tctcagctgc caatgagcac tacccgtggc actgtggcaa cggtcacaca aaatcctgtc   2040

ataacagcaa ccgcgaggaa tgccggtggt gcaaacactg ctggatcggt ttcatcaacg   2100

acgacgaccc aaaagcggat tccgcgtgtg gattcggcca caggcttgtc ctccctgcgt   2160

gtcatgagcg ggctgcctcg aaacacctcc gttgaggact ttctgtcgct ggtggattac   2220

ggagatattc ctgcaccaga caaggacctc ctctcgaagt gcgttttccc tcagaacagc   2280

gctgcacgcg ctgcccagac cgctgcctca cagcaggctg ccgtggcgtt cacaggcatt   2340

gggaagcctt cagtcatcct cgctggcggt gtgaaggtgg aaggcggcgc acccacagga   2400

ccaatacccg gggctcaca cgatgttgcg ggaggaaaac gtgatcgagg tgatacctta   2460

cctacgatat cgacaggaag ttcagcgatg ggtgccaggt tgaagcaacc gaaaattgaa   2520

agataa                                                              2526
```

```
<210> SEQ ID NO 63
<211> LENGTH: 841
<212> TYPE: PRT
<213> ORGANISM: Nannochloropsis gaditana

<400> SEQUENCE: 63

Met Met Glu Met Pro Thr Asn Arg Ser Gly Pro Gly Thr Asp Ser Gly
1               5                   10                  15

Glu Lys Cys Pro Asn Pro Pro Thr Val Gly Ala Leu Val Thr Thr Thr
            20                  25                  30

Leu Ser Pro Lys Ser Glu Ser Pro Lys Arg Val Ala Val Pro Thr Leu
        35                  40                  45

Gly Ala Pro Val Ala Ala Pro Pro Ala Ser Ala Val Ala Val Ala Ala
    50                  55                  60

Arg Gly His Gly Ser Ser Leu Gln Asn Gly Leu Pro Ala Arg Asn Gly
65                  70                  75                  80

Asp Gly Gly Ser Ser Leu Thr Pro Thr Ser Gly Pro Arg Glu Phe Leu
                85                  90                  95

Gln Val Ala Ser Lys Pro Pro Gly Thr Glu Met Pro Ala Leu Asp Ala
            100                 105                 110

Ser Thr Ser Gly Leu Ile His Lys Pro Ala Ser Ser Asp Ala Ala Thr
        115                 120                 125

Ala Leu Ser Gln His His Asp Ala Leu Ile Gln Arg Glu Leu Asn Ala
    130                 135                 140

Ile Ile Gly Gln Lys Arg Glu His Arg Asp Arg Ser Glu Glu Ser Thr
145                 150                 155                 160

Val Leu Leu Pro Ser Thr Ser Pro Ile Ser Val Pro Val Pro Arg His
                165                 170                 175

Gln Ala Ser Ala Arg Pro Gly Pro Gly Pro Ala Ser His Ala Leu Pro
```

-continued

```
            180                 185                 190

Ala Ser Pro Pro Ala Gln Ala Gly Ser Asn Ala Arg Gly Ser Gly Gln
        195                 200                 205

Thr Val Ser Asn Arg Ser Pro Pro Ser Ala Asn Ala Gln Ala Leu Met
    210                 215                 220

Pro Pro Thr Arg His Ser Thr Arg Gly Ala Thr Ala Ala Ala Ala Ala
225                 230                 235                 240

Gly Ile Ser Lys Ser Ile Glu Glu Ala Cys His Ala Ala Ala Leu Glu
                245                 250                 255

Asp Gly Val Leu Ser Ser Lys Gly Gly Gly Ala Leu Asn Ala Gly Tyr
            260                 265                 270

Gly Asn Ala Lys Gln Gly Ser Val Val Ser Pro Gly Glu Thr Ser Ala
        275                 280                 285

Leu Thr Ser Ala Asn Lys Ala Gly Lys Val Lys Asn Gly Leu Arg Arg
    290                 295                 300

Gly Lys Trp Thr Pro Glu Glu Glu Ala Tyr Ala Asn Arg Leu Ile Val
305                 310                 315                 320

Glu Phe Lys Ser Gly Leu Leu Pro Leu Thr Asp Gly Thr Thr Leu Arg
                325                 330                 335

Thr Phe Leu Ser Lys Leu Leu Asn Cys Asp Pro Met Arg Ile Ser Lys
            340                 345                 350

Lys Phe Val Gly Gln Asn Cys Ile Gly Lys Gln Val Phe Arg Arg Arg
        355                 360                 365

Gln Gln Ala Asp Leu Asp Arg Leu Ser Thr Asp Glu Ile Glu Arg Ser
    370                 375                 380

Arg Gln Glu Leu Ala Glu Leu Glu Arg Arg Phe Leu Glu Arg Val Ala
385                 390                 395                 400

Gln Thr Asn Arg Cys Lys Asn Ser Val Ala Gly Ser Lys His Gly Lys
                405                 410                 415

Asp Ser Ala Ala Gly Gln Val Ala Pro Glu Val Pro Arg Arg Gln Gln
            420                 425                 430

Glu Tyr Leu Gly Pro Asp Gly Arg Ile Val Gly Asn Pro Val Leu Pro
        435                 440                 445

Pro Trp Met Leu Pro Pro Ala Ala Gln Ala Ala Asn Glu Gly Glu Pro
    450                 455                 460

Ala Ser Ala Ser Thr Thr Pro Arg Ser Asn Cys Ser Ser Gly Ile Asn
465                 470                 475                 480

Ser Gly Phe Arg Gly Ala Ala Gly Pro Asn Ser Thr Lys Gly Thr Ser
                485                 490                 495

Arg His His Gln Asn Ile Ala Pro Glu His Thr Gly Ala Thr Leu His
            500                 505                 510

His Ile Ser His Leu His Gln Pro Ser Gly Leu Arg Arg Gly Pro Gly
        515                 520                 525

Gly Ser Asp Thr Gly Ile Leu Ser Val Thr Ala Ala Thr Asn Met Pro
    530                 535                 540

Arg Thr Asp Ser Gln Asp Ser Leu Ser Val Leu Gly Arg Thr Ile Ser
545                 550                 555                 560

Ala Asp Ala Leu Gly His Leu Thr Asp Phe Pro His Thr Thr Ser Leu
                565                 570                 575

Gly Asp Leu Ala Gly Leu Asn Met Phe Thr Ser Ser Pro Phe Pro Ser
            580                 585                 590

Thr Asp Asn Leu Leu Ser Leu His Gln His Gln His Gln Gln Thr Val
        595                 600                 605
```

```
Ala Ala Ala Pro Arg Gly His Thr Thr Leu Ser Ala His Asn Ala Thr
    610                 615                 620

Ser Val Ala Ala Ala Ala Ala Ala Ala Ala Val Ala Pro Ser Ser Thr
625                 630                 635                 640

Ser Ile Ser Arg Asn Thr Gly Asp Ser Ala Pro Arg Gly Pro Asn Val
                645                 650                 655

Ser Gly His Gly Ser Gln Leu Pro Met Ser Thr Thr Arg Gly Thr Val
            660                 665                 670

Ala Thr Val Thr Gln Asn Pro Val Ile Thr Ala Thr Ala Arg Asn Ala
        675                 680                 685

Gly Gly Ala Asn Thr Ala Gly Ser Val Ser Ser Thr Thr Thr Thr Gln
    690                 695                 700

Lys Arg Ile Pro Arg Val Asp Ser Ala Thr Gly Leu Ser Ser Leu Arg
705                 710                 715                 720

Val Met Ser Gly Leu Pro Arg Asn Thr Ser Val Glu Asp Phe Leu Ser
                725                 730                 735

Leu Val Asp Tyr Gly Asp Ile Pro Ala Pro Asp Lys Asp Leu Leu Ser
            740                 745                 750

Lys Cys Val Phe Pro Gln Asn Ser Ala Ala Arg Ala Ala Gln Thr Ala
        755                 760                 765

Ala Ser Gln Gln Ala Ala Val Ala Phe Thr Gly Ile Gly Lys Pro Ser
    770                 775                 780

Val Ile Leu Ala Gly Gly Val Lys Val Glu Gly Gly Ala Pro Thr Gly
785                 790                 795                 800

Pro Ile Pro Gly Gly Ser His Asp Val Ala Gly Gly Lys Arg Asp Arg
                805                 810                 815

Gly Asp Thr Leu Pro Thr Ile Ser Thr Gly Ser Ser Ala Met Gly Ala
            820                 825                 830

Arg Leu Lys Gln Pro Lys Ile Glu Arg
        835                 840


<210> SEQ ID NO 64
<211> LENGTH: 103
<212> TYPE: PRT
<213> ORGANISM: Nannochloropsis gaditana

<400> SEQUENCE: 64

Leu Arg Arg Gly Lys Trp Thr Pro Glu Glu Glu Ala Tyr Ala Asn Arg
1               5                   10                  15

Leu Ile Val Glu Phe Lys Ser Gly Leu Leu Pro Leu Thr Asp Gly Thr
            20                  25                  30

Thr Leu Arg Thr Phe Leu Ser Lys Leu Leu Asn Cys Asp Pro Met Arg
        35                  40                  45

Ile Ser Lys Lys Phe Val Gly Gln Asn Cys Ile Gly Lys Gln Val Phe
    50                  55                  60

Arg Arg Arg Gln Gln Ala Asp Leu Asp Arg Leu Ser Thr Asp Glu Ile
65                  70                  75                  80

Glu Arg Ser Arg Gln Glu Leu Ala Glu Leu Glu Arg Arg Phe Leu Glu
                85                  90                  95

Arg Val Ala Gln Thr Asn Arg
            100


<210> SEQ ID NO 65
<211> LENGTH: 2697
<212> TYPE: DNA
```

<213> ORGANISM: Nannochloropsis oceanica
<220> FEATURE:
<221> NAME/KEY: misc_feature
<222> LOCATION: (2524)..(2558)
<223> OTHER INFORMATION: n is a, c, g, or t

<400> SEQUENCE: 65
atgtcagcca ctccatcggg gccgtccttt aaggtggaca ccaacaagac cgctgccggg 60
gccgcactgg ggcccccacc ggcctcggtc aacacggcca cagcgggcgc agcaggttgt 120
gcatcctcca cccttaatgg catcagcagc catggtaacg gcaacagcag cagcaacaca 180
catcacaggt ccgccaagct gcacgatggg gcagcccgca ttgccaatac gacgacgacc 240
accactagca aaataaaagt ggaggaacca accaacggtg gtggaagcat ggaggccgca 300
tcagcggcgg tcgatggcaa ggacgctctc attcagcatg aactcaatgc gctactcagc 360
caaaagcgtg acgccgctgc tgatggccgt agccaagatt cctcccctgc ctcatccact 420
tcctccaccc caacgaccgc cccatccatg atgcctacga ccatgaacgc ccctctcttc 480
aaaccttctc ctactgctgc tgcttctttg tcttcgtcac cagcagtgcc aaccaccgga 540
ggaggagcag ggaaagggct tatgcaagtc gctgcctcca gacccctccc tacctcatcg 600
tcgtcgtccg caacagcgca ggccccccctg gccgccacgc ggcattcgac gagaggcgca 660
acggcggcgg cagcagcagc ggggatcagc aagtccattg aggaggcctg tcatgccgct 720
gccctagaag atggtgtgct tggatccaaa ggaggggggg gcgggggagc ggtaggagga 780
ggtggtggag gaggggcagg acatggccat gccaagcaag gtgggggagg aattggtaat 840
ggaggcgtat cgtcgtcaac ggcagctagt aatggcagtg ggaaaccggg gaaggctaag 900
aatggattga ggagagggaa atggacgccg gaggaggagg cgtatgcaaa tcgattaatc 960
gtggaattca agtcggggtt gttgccattg acggatggta cgacattgag gacatttttg 1020
agtaagctgc ttaattgtga tcctatgagg ataagcaaaa aatttgtggg tcagaattgc 1080
atcggaaagc aagtgtttcg tcggcggcag caagcagaga tggacaggtt gtcccctgaa 1140
gagattgaac ggagtcgaca agaacttgcc gaactagaga gacgattttt ggagcgcgtg 1200
gctcagacaa atcgatgtaa gaattctgct gtggggacga agcatgggaa agactcggcg 1260
tcgggtcagg tggcgccgga ggtgttgcga cgacagcaag agtacctggg cccaggtggg 1320
caggtggtgg gtaatcccct cctccccccc tggatgctcc ctcccaccgc ggatgcatcg 1380
atggagggag gggagggcat tcaaggtgga gatggtcatt cgaattcctc gccagagagg 1440
ggggggatgg ggatgaccgg tcgcggtggt ggtggtagtt cttttcgttt gatgggtgga 1500
ggaacgggag cagggagcaa gcagcagcag cagcagagcc agcagcagca gcagccgcct 1560
ttttcggatt tgccctgcgc acaccagttg caccatcctc agtcacatct ccatcatcca 1620
cgacgtatcc cctcctcatc gtcgtccacc ctaggagggc tgaacacggg tagtctctcc 1680
gcgatcgcgt cggcgaatat gtcacgcacc gattctcagg atagcctaac agcgttaggt 1740
ggcacaatgt cggcagacgc tcttggacat ttggcggact ttccgcgtgt gaccagccta 1800
ggagatcttg ccggactcaa catgtttacc tccagccctt tcccctccac ggacaatctc 1860
ctcagccttc accagcagca acacgcccaa agtgctcaaa ttgttccggc cactgctgct 1920
tctcttgccg cgcatagcac caccagctta gcagcagcgg cagcagcagc agcagtggct 1980
ccgtcgagca caccgatcag tcgtagcacc agtggcaacg gtaatggcgg gagcagcagc 2040
agcagcagca gcagcagcag cagcagcaat gcgaatggtc ttccaccact agccaatgcc 2100
agcagcacgg tgatagtcgc tggcggcggt cggttggcga caggaaagag caacaacggc 2160

-continued

```
aacataacta atagtggagg gacgagcagt agcactaccg cagcaggagg acggcgtatg   2220

ccccgcgtgg actcggccac aggcttatcc tccttacggg tgatgagcgg attacctcgg   2280

aatacatccg tggaagactt tctatccttg gtcgattacg gtgacatccc ggcgccagac   2340

caagacctgc tctccaagtg cgtctttcct caagccatca aggcgcctgt gacccagcag   2400

tctgccgtgg cctttaccgg aatcggaagg agttccgcgg tgccggctgg aggaggtggt   2460

ggaggagtgg ggggagattc ggatgatgtg gctcatacaa gaggaggagg aggaggagga   2520

ggannnnnnn nnnnnnnnnn nnnnnnnnnn nnnnnnnnag cagcagcagc agcagcagca   2580

acagcggctt tgttaacatc aggggtaaag gggactggtg ggaagagggg tcgggcagac   2640

ttgccgtcgg cggcagtggt gggacaaaag ccgaaacaag ccaaggtgga tgggtaa      2697
```

<210> SEQ ID NO 66
<211> LENGTH: 898
<212> TYPE: PRT
<213> ORGANISM: Nannochloropsis oceanica
<220> FEATURE:
<221> NAME/KEY: misc_feature
<222> LOCATION: (842)..(853)
<223> OTHER INFORMATION: Xaa can be any naturally occurring amino acid

<400> SEQUENCE: 66

```
Met Ser Ala Thr Pro Ser Gly Pro Ser Phe Lys Val Asp Thr Asn Lys
1               5                   10                  15

Thr Ala Ala Gly Ala Ala Leu Gly Pro Pro Pro Ala Ser Val Asn Thr
            20                  25                  30

Ala Thr Ala Gly Ala Ala Gly Cys Ala Ser Ser Thr Leu Asn Gly Ile
        35                  40                  45

Ser Ser His Gly Asn Gly Asn Ser Ser Ser Asn Thr His His Arg Ser
    50                  55                  60

Ala Lys Leu His Asp Gly Ala Ala Arg Ile Ala Asn Thr Thr Thr Thr
65                  70                  75                  80

Thr Thr Ser Lys Ile Lys Val Glu Glu Pro Thr Asn Gly Gly Gly Ser
                85                  90                  95

Met Glu Ala Ala Ser Ala Ala Val Asp Gly Lys Asp Ala Leu Ile Gln
            100                 105                 110

His Glu Leu Asn Ala Leu Leu Ser Gln Lys Arg Asp Ala Ala Ala Asp
        115                 120                 125

Gly Arg Ser Gln Asp Ser Ser Pro Ala Ser Ser Thr Ser Ser Thr Pro
    130                 135                 140

Thr Thr Ala Pro Ser Met Met Pro Thr Thr Met Asn Ala Pro Leu Phe
145                 150                 155                 160

Lys Pro Ser Pro Thr Ala Ala Ala Ser Leu Ser Ser Ser Pro Ala Val
                165                 170                 175

Pro Thr Thr Gly Gly Gly Ala Gly Lys Gly Leu Met Gln Val Ala Ala
            180                 185                 190

Ser Arg Pro Leu Pro Thr Ser Ser Ser Ser Ser Ala Thr Ala Gln Ala
        195                 200                 205

Pro Leu Ala Ala Thr Arg His Ser Thr Arg Gly Ala Thr Ala Ala Ala
    210                 215                 220

Ala Ala Ala Gly Ile Ser Lys Ser Ile Glu Glu Ala Cys His Ala Ala
225                 230                 235                 240

Ala Leu Glu Asp Gly Val Leu Gly Ser Lys Gly Gly Gly Gly Gly Gly
                245                 250                 255
```

-continued

```
Ala Val Gly Gly Gly Gly Gly Gly Gly Ala Gly His Gly His Ala Lys
            260                 265                 270

Gln Gly Gly Gly Gly Ile Gly Asn Gly Gly Val Ser Ser Ser Thr Ala
        275                 280                 285

Ala Ser Asn Gly Ser Gly Lys Pro Gly Lys Ala Lys Asn Gly Leu Arg
    290                 295                 300

Arg Gly Lys Trp Thr Pro Glu Glu Glu Ala Tyr Ala Asn Arg Leu Ile
305                 310                 315                 320

Val Glu Phe Lys Ser Gly Leu Leu Pro Leu Thr Asp Gly Thr Thr Leu
                325                 330                 335

Arg Thr Phe Leu Ser Lys Leu Leu Asn Cys Asp Pro Met Arg Ile Ser
            340                 345                 350

Lys Lys Phe Val Gly Gln Asn Cys Ile Gly Lys Gln Val Phe Arg Arg
        355                 360                 365

Arg Gln Gln Ala Glu Met Asp Arg Leu Ser Pro Glu Glu Ile Glu Arg
    370                 375                 380

Ser Arg Gln Glu Leu Ala Glu Leu Glu Arg Arg Phe Leu Glu Arg Val
385                 390                 395                 400

Ala Gln Thr Asn Arg Cys Lys Asn Ser Ala Val Gly Thr Lys His Gly
                405                 410                 415

Lys Asp Ser Ala Ser Gly Gln Val Ala Pro Glu Val Leu Arg Arg Gln
            420                 425                 430

Gln Glu Tyr Leu Gly Pro Gly Gly Gln Val Val Gly Asn Pro Leu Leu
        435                 440                 445

Pro Pro Trp Met Leu Pro Pro Thr Ala Asp Ala Ser Met Glu Gly Gly
    450                 455                 460

Glu Gly Ile Gln Gly Gly Asp Gly His Ser Asn Ser Ser Pro Glu Arg
465                 470                 475                 480

Gly Gly Met Gly Met Thr Gly Arg Gly Gly Gly Gly Ser Ser Phe Arg
                485                 490                 495

Leu Met Gly Gly Gly Thr Gly Ala Gly Ser Lys Gln Gln Gln Gln Gln
            500                 505                 510

Ser Gln Gln Gln Gln Gln Pro Pro Phe Ser Asp Leu Pro Cys Ala His
        515                 520                 525

Gln Leu His His Pro Gln Ser His Leu His His Pro Arg Arg Ile Pro
    530                 535                 540

Ser Ser Ser Ser Ser Thr Leu Gly Gly Leu Asn Thr Gly Ser Leu Ser
545                 550                 555                 560

Ala Ile Ala Ser Ala Asn Met Ser Arg Thr Asp Ser Gln Asp Ser Leu
                565                 570                 575

Thr Ala Leu Gly Gly Thr Met Ser Ala Asp Ala Leu Gly His Leu Ala
            580                 585                 590

Asp Phe Pro Arg Val Thr Ser Leu Gly Asp Leu Ala Gly Leu Asn Met
        595                 600                 605

Phe Thr Ser Ser Pro Phe Pro Ser Thr Asp Asn Leu Leu Ser Leu His
    610                 615                 620

Gln Gln Gln His Ala Gln Ser Ala Gln Ile Val Pro Ala Thr Ala Ala
625                 630                 635                 640

Ser Leu Ala Ala His Ser Thr Thr Ser Leu Ala Ala Ala Ala Ala Ala
                645                 650                 655

Ala Ala Val Ala Pro Ser Ser Thr Pro Ile Ser Arg Ser Thr Ser Gly
            660                 665                 670

Asn Gly Asn Gly Gly Ser Ser Ser Ser Ser Ser Ser Ser Ser Ser Ser
```

-continued

```
        675                 680                 685

Ser Asn Ala Asn Gly Leu Pro Pro Leu Ala Asn Ala Ser Ser Thr Val
    690                 695                 700

Ile Val Ala Gly Gly Gly Arg Leu Ala Thr Gly Lys Ser Asn Asn Gly
705                 710                 715                 720

Asn Ile Thr Asn Ser Gly Gly Thr Ser Ser Ser Thr Thr Ala Ala Gly
                725                 730                 735

Gly Arg Arg Met Pro Arg Val Asp Ser Ala Thr Gly Leu Ser Ser Leu
            740                 745                 750

Arg Val Met Ser Gly Leu Pro Arg Asn Thr Ser Val Glu Asp Phe Leu
        755                 760                 765

Ser Leu Val Asp Tyr Gly Asp Ile Pro Ala Pro Asp Gln Asp Leu Leu
    770                 775                 780

Ser Lys Cys Val Phe Pro Gln Ala Ile Lys Ala Pro Val Thr Gln Gln
785                 790                 795                 800

Ser Ala Val Ala Phe Thr Gly Ile Gly Arg Ser Ser Ala Val Pro Ala
                805                 810                 815

Gly Gly Gly Gly Gly Gly Val Gly Gly Asp Ser Asp Asp Val Ala His
            820                 825                 830

Thr Arg Gly Gly Gly Gly Gly Gly Gly Xaa Xaa Xaa Xaa Xaa Xaa Xaa
        835                 840                 845

Xaa Xaa Xaa Xaa Xaa Ala Ala Ala Ala Ala Ala Ala Thr Ala Ala Leu
    850                 855                 860

Leu Thr Ser Gly Val Lys Gly Thr Gly Gly Lys Arg Gly Arg Ala Asp
865                 870                 875                 880

Leu Pro Ser Ala Ala Val Val Gly Gln Lys Pro Lys Gln Ala Lys Val
                885                 890                 895

Asp Gly
```

<210> SEQ ID NO 67
<211> LENGTH: 2343
<212> TYPE: DNA
<213> ORGANISM: Phytophthora ramorum

<400> SEQUENCE: 67

```
atgggaacgg gagaagcgct gcacattcct cgcgcggacc cgagctccat gagcgcgtac      60

ctgcctccgc agccttacaa ctcgtcgggg gtgcgacccg acggaccccc gtacctgccg     120

cccgggtcgt gtctcgtgtg ctacaacccg caggtggacg tgctgctgga gccgtgccac     180

caccagttcc acgcgtcctg tatcgagcgc tggctcagca aggacaaggt ctgccccacc     240

tgctggacgc ccatccaggc gccgcgccgc ctcgtcccgc agcagtacgc acagccgcaa     300

cagcaggacg gcggcggata ccccgcagac agcaaagcgc acgtgttgga ggccgcggag     360

ccgcccaccc cagccgccag cgcggacgcc agcgcgcagc cacccgcggc tatgcggaag     420

ggcaagtgga cggccgagga gagcgcgtac tgcgaccggt tgatcgagga gttcaagaag     480

ggaaacctgc cgctggctga gggcacgacg ctgcgcacgt ttctgagcaa actgctgaac     540

tgcgacccca tgcgcatctc gaagaagtac acgggcgacc agtgcatcgg caagatcatt     600

ttccgccgga gagaggacga cgtgtccaag gacgacatgg agagcatccg caaggacctg     660

gccgagctcg agaagacgta cctggagagg gagcagtaca accagcggcg gcgcgagaag     720

cggctcgagt cggagctctc gagggacaag agtcgctttg cggccaccag gtccattgga     780

tacgcagcgg caggcaattc ggcgccgatg cggccgcccc accctcagca gcagcaacaa     840
```

-continued

```
cagggaggtt acccgcaggc tgcagtccag cccatgacaa agcaggagcc gcgacctgga     900

ccgggtcctg tgcagcagcc caactatgga gctccaggtc gaggtggtat gcctgtccag     960

cctcctctac accccccaca gcagagcaat aacgtgccct cgcacctatt taatggcgac    1020

cacagcaatg tatcgatgct tggcattgct ggcgcgcaga cacagggtca aggtcaggtt    1080

ccgaaccagg acaacaagcc ggctagcagc tccgctatgg acggcgggga cgggtttccg    1140

cgcgtgtcgt ccatcgacag cttttcttgt ctgttccctc gcgtggccag tattgaaaac    1200

ttccagcacg cgacgtcatc tggttttggc ggcatgaact ctgtcggttc gtacccgtcg    1260

acggagactc aaaacacgat gaccagcagt ggattcgacg cccagccttc cggtttgccc    1320

aaaccattgt cgattggcga aggccttaac gcctacttcc ctcgtatcca gtcgctagaa    1380

cagctttcaa acctactgca agaccacgga ccgaacagtc cacgtggagg agcaacatcg    1440

tcgtcgactc agaacagtcg ggataccatg gagaattcaa gcgacagcaa acaacagatt    1500

aaggacaatt ttacatccgg aggtcatcgg aggaggctgg gcgagaatgg tattaaggaa    1560

gagcagccgc gggaagcaga tttcaacgca cagacagggc ccagcagcag caataacagc    1620

agcaacagtt ctagcagcag cgacagcagt gccgtttcca cttcgatgag cgtgacgacc    1680

ggttccacta gcactggact gacaaagcgc ctcagcccca gtcacaatgc atcggcctct    1740

tcaggttcag gcaaccagat ccagattccc aagccgctga acaagatgcc gcgaagctcg    1800

tcgggcatct tcccgcgcgt gccgtccatg gacaagatgc ctcgtgtgcc ttcgctcgac    1860

aagatgcctc gcgttgcatc tctcgacaag ctgccgcgca tcccgtctat ggacaagctc    1920

cacacggtgg gcggcggcga gcaacgcatc ccgagggtgc cgtccatgga caagatggcg    1980

cgtgtgccga gctcggacat gctgtctcgc tttggctcca gcgaccacct tagcagcttc    2040

ccgtcgttct ctaacctaag cacgttgtct tcaagcgcct cgtacgacaa gctgagctcg    2100

ctgggtgggt ttaagtcggg cttcccgcgc aattcgtcca ttgaggacat tttgtctctc    2160

gtggcctcgt ccgagtcgac tggtcttccg tcaaatggct cgacgttgca gctgagtgca    2220

ctggccgcag ttgcgggcga ggagtcctcc catattgcca acgagcggaa gcggcggctg    2280

gaaagctccc agcaggacgc atcgttggca tcagataaca agaagagcaa attatcggcg    2340

tga                                                                  2343
```

<210> SEQ ID NO 68
<211> LENGTH: 780
<212> TYPE: PRT
<213> ORGANISM: Phytophthora ramorum

<400> SEQUENCE: 68

```
Met Gly Thr Gly Glu Ala Leu His Ile Pro Arg Ala Asp Pro Ser Ser
1               5                   10                  15

Met Ser Ala Tyr Leu Pro Pro Gln Pro Tyr Asn Ser Ser Gly Val Arg
            20                  25                  30

Pro Asp Gly Pro Pro Tyr Leu Pro Pro Gly Ser Cys Leu Val Cys Tyr
        35                  40                  45

Asn Pro Gln Val Asp Val Leu Leu Glu Pro Cys His His Gln Phe His
    50                  55                  60

Ala Ser Cys Ile Glu Arg Trp Leu Ser Lys Asp Lys Val Cys Pro Thr
65                  70                  75                  80

Cys Trp Thr Pro Ile Gln Ala Pro Arg Arg Leu Val Pro Gln Gln Tyr
                85                  90                  95

Ala Gln Pro Gln Gln Gln Asp Gly Gly Gly Tyr Pro Ala Asp Ser Lys
```

-continued

```
            100                 105                 110

Ala His Val Leu Glu Ala Ala Glu Pro Pro Thr Pro Ala Ala Ser Ala
        115                 120                 125

Asp Ala Ser Ala Gln Pro Pro Ala Ala Met Arg Lys Gly Lys Trp Thr
    130                 135                 140

Ala Glu Glu Ser Ala Tyr Cys Asp Arg Leu Ile Glu Glu Phe Lys Lys
145                 150                 155                 160

Gly Asn Leu Pro Leu Ala Glu Gly Thr Thr Leu Arg Thr Phe Leu Ser
                165                 170                 175

Lys Leu Leu Asn Cys Asp Pro Met Arg Ile Ser Lys Lys Tyr Thr Gly
            180                 185                 190

Asp Gln Cys Ile Gly Lys Ile Ile Phe Arg Arg Arg Glu Asp Asp Val
        195                 200                 205

Ser Lys Asp Asp Met Glu Ser Ile Arg Lys Asp Leu Ala Glu Leu Glu
    210                 215                 220

Lys Thr Tyr Leu Glu Arg Glu Gln Tyr Asn Gln Arg Arg Arg Glu Lys
225                 230                 235                 240

Arg Leu Glu Ser Glu Leu Ser Arg Asp Lys Ser Arg Phe Ala Ala Thr
                245                 250                 255

Arg Ser Ile Gly Tyr Ala Ala Ala Gly Asn Ser Ala Pro Met Arg Pro
            260                 265                 270

Pro His Pro Gln Gln Gln Gln Gln Gln Gly Gly Tyr Pro Gln Ala Ala
        275                 280                 285

Val Gln Pro Met Thr Lys Gln Glu Pro Arg Pro Gly Pro Gly Pro Val
    290                 295                 300

Gln Gln Pro Asn Tyr Gly Ala Pro Gly Arg Gly Gly Met Pro Val Gln
305                 310                 315                 320

Pro Pro Leu His Pro Pro Gln Gln Ser Asn Asn Val Pro Ser His Leu
                325                 330                 335

Phe Asn Gly Asp His Ser Asn Val Ser Met Leu Gly Ile Ala Gly Ala
            340                 345                 350

Gln Thr Gln Gly Gln Gly Gln Val Pro Asn Gln Asp Asn Lys Pro Ala
        355                 360                 365

Ser Ser Ser Ala Met Asp Gly Gly Asp Gly Phe Pro Arg Val Ser Ser
    370                 375                 380

Ile Asp Ser Phe Ser Cys Leu Phe Pro Arg Val Ala Ser Ile Glu Asn
385                 390                 395                 400

Phe Gln His Ala Thr Ser Ser Gly Phe Gly Gly Met Asn Ser Val Gly
                405                 410                 415

Ser Tyr Pro Ser Thr Glu Thr Gln Asn Thr Met Thr Ser Ser Gly Phe
            420                 425                 430

Asp Ala Gln Pro Ser Gly Leu Pro Lys Pro Leu Ser Ile Gly Glu Gly
        435                 440                 445

Leu Asn Ala Tyr Phe Pro Arg Ile Gln Ser Leu Glu Gln Leu Ser Asn
    450                 455                 460

Leu Leu Gln Asp His Gly Pro Asn Ser Pro Arg Gly Gly Ala Thr Ser
465                 470                 475                 480

Ser Ser Thr Gln Asn Ser Arg Asp Thr Met Glu Asn Ser Ser Asp Ser
                485                 490                 495

Lys Gln Gln Ile Lys Asp Asn Phe Thr Ser Gly Gly His Arg Arg Arg
            500                 505                 510

Leu Gly Glu Asn Gly Ile Lys Glu Glu Gln Pro Arg Glu Ala Asp Phe
        515                 520                 525
```

```
Asn Ala Gln Thr Gly Pro Ser Ser Ser Asn Asn Ser Ser Asn Ser Ser
    530                 535                 540

Ser Ser Ser Asp Ser Ser Ala Val Ser Thr Ser Met Ser Val Thr Thr
545                 550                 555                 560

Gly Ser Thr Ser Thr Gly Leu Thr Lys Arg Leu Ser Pro Ser His Asn
                565                 570                 575

Ala Ser Ala Ser Ser Gly Ser Gly Asn Gln Ile Gln Ile Pro Lys Pro
            580                 585                 590

Leu Asn Lys Met Pro Arg Ser Ser Ser Gly Ile Phe Pro Arg Val Pro
        595                 600                 605

Ser Met Asp Lys Met Pro Arg Val Pro Ser Leu Asp Lys Met Pro Arg
    610                 615                 620

Val Ala Ser Leu Asp Lys Leu Pro Arg Ile Pro Ser Met Asp Lys Leu
625                 630                 635                 640

His Thr Val Gly Gly Gly Glu Gln Arg Ile Pro Arg Val Pro Ser Met
                645                 650                 655

Asp Lys Met Ala Arg Val Pro Ser Ser Asp Met Leu Ser Arg Phe Gly
            660                 665                 670

Ser Ser Asp His Leu Ser Ser Phe Pro Ser Phe Ser Asn Leu Ser Thr
        675                 680                 685

Leu Ser Ser Ser Ala Ser Tyr Asp Lys Leu Ser Ser Leu Gly Gly Phe
    690                 695                 700

Lys Ser Gly Phe Pro Arg Asn Ser Ser Ile Glu Asp Ile Leu Ser Leu
705                 710                 715                 720

Val Ala Ser Ser Glu Ser Thr Gly Leu Pro Ser Asn Gly Ser Thr Leu
                725                 730                 735

Gln Leu Ser Ala Leu Ala Ala Val Ala Gly Glu Glu Ser Ser His Ile
            740                 745                 750

Ala Asn Glu Arg Lys Arg Arg Leu Glu Ser Ser Gln Gln Asp Ala Ser
        755                 760                 765

Leu Ala Ser Asp Asn Lys Lys Ser Lys Leu Ser Ala
    770                 775                 780
```

<210> SEQ ID NO 69
<211> LENGTH: 2799
<212> TYPE: DNA
<213> ORGANISM: Ectocarpus siliculosus

<400> SEQUENCE: 69

```
atgcagcctg ggatttcccc cagagttacg ccgggagtgg cggtggcgac ggtggcggga     60

gggggggggg ggagagagac gtgcaggagc actagcggta cgattgcgat cgaggcggct    120

ggcagagcgg ctgcggttgc tgatggggtg attgcgaggc cagcagtctc tcaacaacaa    180

ccgcagctgc agcgcgcagc caccaaggcc cccgtgccgg tagcggcggc tccgaccccg    240

gcccaggccg ccgcctacgc gaaagcggtg gcgacggcgc agcagcaaca gcgggcccac    300

gccgccgcga cggcggcggc ggcggcggcg agggtagcga gatcgaacgc gatcgccact    360

tcgtacacaa gcaacgccgc cgccgccgca gcagcagcag cagcggcggc agccgcggcc    420

gccccctcgg ctgccggtgc gtcgccggcg acgcatcggc aacagcagca ccccggtgtc    480

gtcgtcgccg cccggcccac cgtggtggcc ccgggccaca gcaacggcca catctacaac    540

gcggcccagc ggcagcagca gcagcagcac gcggccgctt ttggggcgat gggggcagcg    600

gcggcggcgg cggcggcggg gggtcaccat caccaccatc acttgcagca gtttcagcag    660
```

-continued

```
ggcgggggca gtgggttcct ggggctgcag gggggcgcta gcgcgatggg ggcggcggcg    720
gcagcggcgg cagcggcagc ggcggcggcg gcggcggtgc aggcgaaagc gaagaagccg    780
aacgggttga ggagagggaa gtggacgtcc gaggaggagg actacgcgaa ccgccttatc    840
caggagttca agagcgggtt gttgccgctg acggacggaa cgacgctcag aacgttcctg    900
agcaagctgc tcaactgcga ccccatgcgc atctccaaga agttcgtggg tagcaactgc    960
atcgggaagc aggtgttccg caggaggcag gccgacatgg accggttaca gcccgccgac   1020
atcgagagga gccgctctca gcttgcagat ctagagagga ggttcttgga gcgggtagcc   1080
atgacgaacc gatgcaagac cggcggggag ataggctcga aagaaggcgg cagcagcttc   1140
gacctcctgc gcccgaatca gccacctccg gctacccagc cgtggatgct gccgccgtcg   1200
ccccctgcgg ttactctcgc ggggacgctg tcgcccgcgg cggcgacgca gagggcgaac   1260
gtggcggggg ctcctgcaga tgaagccaca gggggcgtgc tcgctgagac aacagcggta   1320
gcagcggagg cggcagggca ccagcgaaat agcaccacac cgccacctcg accaccatca   1380
tcggcagcag caacagcacc agggtcggcg gaggtagcgc catcgccgtc atcagcagcg   1440
ttgccgtcta gttccgtttt gggcgcgagc catgccgggc caggggggagt cgcgaaagca   1500
ccgaacgggc tggtgcttgg tggcccaccc gaaaaggagt ctcaacacag gcccctcacg   1560
tcgcagcagc aaccgaatgc tcaaggtacg agcaccactg ctctggcccc tgccccggct   1620
accccagctg agataaacga tgttggggtc aaggcggggt cggccgcggg tatcgctaac   1680
ggcaaccacc tggcagcaac aacgtcagcg gcgtcagcag tggcagcaac accgcctgct   1740
tcgtcagggt ccggtgtatc ggctgctgcg acaagggcta atggtgcgcc tgcatcgacc   1800
agtgcggctg cggccacgcc ggcgtcgttc ctagacgcgg gaggcgcgct gccgtcgttg   1860
cccgggactg gggacgggag ggtagcttcc gcgatccccg gaagtaccgc tgcagttgtt   1920
cccaagcagg aactcacggc cagtgggaca ggcttgggtg tccgcacatc gaggtcgggg   1980
gcaagcaacg gcttcaacac cagctccggc ctgggtggaa gcggcatcga ccggaccaca   2040
tctctcgagg ccctctcgct gctggagctg ccacacatcc aaggtatgac caaccttgct   2100
gtgctggggc tgtggcctgg cgcctttccc ccttcgggat cttcgacagg gacaacgact   2160
gggactcctc tcaaggcgat gaacggcggt ttgaagagaa cgccttcatg ggcgaggatc   2220
agctcgtacg aacacctgca gagcctcgat gaaggggctc ccctgtatcc gacgacaaac   2280
ggcaacggag caggcagtgt gagcagcaac atcgcgagca gtagcagcag caacagccat   2340
tccgcatctg gactaggagg aggcaattct agcggtggca gcggcactag caccatgacg   2400
tcatcatcat cgccatcgcc atcctcagcc gccgcacctt cgcccttcat gccgagaaac   2460
acctcggtcg aggacttcct cagccttgtc gagtccggag acattccgcc tccagagggt   2520
gccgccgggt tcacggtgcc catgtggatc tacagcggag actcgagcaa caccacgaac   2580
ggcaacccca acggacacgc tcctaatggg agttcgaatg gtgcttcaac tcctgctgcc   2640
agcgagcgtc cagcggggca ctctaaaccg tcctcaaaat ctaagaacaa gggctcgggt   2700
agcggttctg ctcgcggggc ttctggaatg tcatcactcg agaagtccaa gtcgaaacgg   2760
ctgaagtcga cgcaggctaa ggccgaggcc aagagttga                          2799
```

<210> SEQ ID NO 70
<211> LENGTH: 932
<212> TYPE: PRT
<213> ORGANISM: Ectocarpus siliculosus

<400> SEQUENCE: 70

```
Met Gln Pro Gly Ile Ser Pro Arg Val Thr Pro Gly Val Ala Val Ala
1               5                   10                  15

Thr Val Ala Gly Gly Gly Gly Gly Arg Glu Thr Cys Arg Ser Thr Ser
            20                  25                  30

Gly Thr Ile Ala Ile Glu Ala Ala Gly Arg Ala Ala Ala Val Ala Asp
        35                  40                  45

Gly Val Ile Ala Arg Pro Ala Val Ser Gln Gln Gln Pro Gln Leu Gln
    50                  55                  60

Arg Ala Ala Thr Lys Ala Pro Val Pro Val Ala Ala Ala Pro Thr Pro
65                  70                  75                  80

Ala Gln Ala Ala Ala Tyr Ala Lys Ala Val Ala Thr Ala Gln Gln Gln
                85                  90                  95

Gln Arg Ala His Ala Ala Ala Thr Ala Ala Ala Ala Ala Ala Arg Val
            100                 105                 110

Ala Arg Ser Asn Ala Ile Ala Thr Ser Tyr Thr Ser Asn Ala Ala Ala
        115                 120                 125

Ala Ala Ala Ala Ala Ala Ala Ala Ala Ala Ala Ala Ala Pro Ser Ala
    130                 135                 140

Ala Gly Ala Ser Pro Ala Thr His Arg Gln Gln Gln His Pro Gly Val
145                 150                 155                 160

Val Val Ala Ala Arg Pro Thr Val Val Ala Pro Gly His Ser Asn Gly
                165                 170                 175

His Ile Tyr Asn Ala Ala Gln Arg Gln Gln Gln Gln Gln His Ala Ala
            180                 185                 190

Ala Phe Gly Ala Met Gly Ala Ala Ala Ala Ala Ala Ala Ala Gly Gly
        195                 200                 205

His His His His His His Leu Gln Gln Phe Gln Gln Gly Gly Gly Ser
    210                 215                 220

Gly Phe Leu Gly Leu Gln Gly Gly Ala Ser Ala Met Gly Ala Ala Ala
225                 230                 235                 240

Ala Ala Ala Ala Ala Ala Ala Ala Ala Ala Ala Ala Val Gln Ala Lys
                245                 250                 255

Ala Lys Lys Pro Asn Gly Leu Arg Arg Gly Lys Trp Thr Ser Glu Glu
            260                 265                 270

Glu Asp Tyr Ala Asn Arg Leu Ile Gln Glu Phe Lys Ser Gly Leu Leu
        275                 280                 285

Pro Leu Thr Asp Gly Thr Thr Leu Arg Thr Phe Leu Ser Lys Leu Leu
    290                 295                 300

Asn Cys Asp Pro Met Arg Ile Ser Lys Lys Phe Val Gly Ser Asn Cys
305                 310                 315                 320

Ile Gly Lys Gln Val Phe Arg Arg Arg Gln Ala Asp Met Asp Arg Leu
                325                 330                 335

Gln Pro Ala Asp Ile Glu Arg Ser Arg Ser Gln Leu Ala Asp Leu Glu
            340                 345                 350

Arg Arg Phe Leu Glu Arg Val Ala Met Thr Asn Arg Cys Lys Thr Gly
        355                 360                 365

Gly Glu Ile Gly Ser Lys Glu Gly Gly Ser Ser Phe Asp Leu Leu Arg
    370                 375                 380

Pro Asn Gln Pro Pro Pro Ala Thr Gln Pro Trp Met Leu Pro Pro Ser
385                 390                 395                 400

Pro Pro Ala Val Thr Leu Ala Gly Thr Leu Ser Pro Ala Ala Ala Thr
                405                 410                 415
```

```
Gln Arg Ala Asn Val Ala Gly Ala Pro Ala Asp Glu Ala Thr Gly Gly
            420                 425                 430

Val Leu Ala Glu Thr Thr Ala Val Ala Ala Glu Ala Ala Gly His Gln
        435                 440                 445

Arg Asn Ser Thr Thr Pro Pro Pro Arg Pro Pro Ser Ser Ala Ala Ala
    450                 455                 460

Thr Ala Pro Gly Ser Ala Glu Val Ala Pro Ser Pro Ser Ser Ala Ala
465                 470                 475                 480

Leu Pro Ser Ser Ser Val Leu Gly Ala Ser His Ala Gly Pro Gly Gly
                485                 490                 495

Val Ala Lys Ala Pro Asn Gly Leu Val Leu Gly Gly Pro Pro Glu Lys
            500                 505                 510

Glu Ser Gln His Arg Pro Leu Thr Ser Gln Gln Gln Pro Asn Ala Gln
        515                 520                 525

Gly Thr Ser Thr Thr Ala Leu Ala Pro Ala Pro Ala Thr Pro Ala Glu
    530                 535                 540

Ile Asn Asp Val Gly Val Lys Ala Gly Ser Ala Ala Gly Ile Ala Asn
545                 550                 555                 560

Gly Asn His Leu Ala Ala Thr Thr Ser Ala Ala Ser Ala Val Ala Ala
                565                 570                 575

Thr Pro Pro Ala Ser Ser Gly Ser Gly Val Ser Ala Ala Ala Thr Arg
            580                 585                 590

Ala Asn Gly Ala Pro Ala Ser Thr Ser Ala Ala Ala Ala Thr Pro Ala
        595                 600                 605

Ser Phe Leu Asp Ala Gly Gly Ala Leu Pro Ser Leu Pro Gly Thr Gly
    610                 615                 620

Asp Gly Arg Val Ala Ser Ala Ile Pro Gly Ser Thr Ala Ala Val Val
625                 630                 635                 640

Pro Lys Gln Glu Leu Thr Ala Ser Gly Thr Gly Leu Gly Val Arg Thr
                645                 650                 655

Ser Arg Ser Gly Ala Ser Asn Gly Phe Asn Thr Ser Ser Gly Leu Gly
            660                 665                 670

Gly Ser Gly Ile Asp Arg Thr Thr Ser Leu Glu Ala Leu Ser Leu Leu
        675                 680                 685

Glu Leu Pro His Ile Gln Gly Met Thr Asn Leu Ala Val Leu Gly Leu
    690                 695                 700

Trp Pro Gly Ala Phe Pro Pro Ser Gly Ser Ser Thr Gly Thr Thr Thr
705                 710                 715                 720

Gly Thr Pro Leu Lys Ala Met Asn Gly Gly Leu Lys Arg Thr Pro Ser
                725                 730                 735

Trp Ala Arg Ile Ser Ser Tyr Glu His Leu Gln Ser Leu Asp Glu Gly
            740                 745                 750

Ala Pro Leu Tyr Pro Thr Thr Asn Gly Asn Gly Ala Gly Ser Val Ser
        755                 760                 765

Ser Asn Ile Ala Ser Ser Ser Ser Ser Asn Ser His Ser Ala Ser Gly
    770                 775                 780

Leu Gly Gly Gly Asn Ser Ser Gly Gly Ser Gly Thr Ser Thr Met Thr
785                 790                 795                 800

Ser Ser Ser Ser Pro Ser Pro Ser Ser Ala Ala Ala Pro Ser Pro Phe
                805                 810                 815

Met Pro Arg Asn Thr Ser Val Glu Asp Phe Leu Ser Leu Val Glu Ser
            820                 825                 830

Gly Asp Ile Pro Pro Pro Glu Gly Ala Ala Gly Phe Thr Val Pro Met
```

```
        835                 840                 845

Trp Ile Tyr Ser Gly Asp Ser Ser Asn Thr Thr Asn Gly Asn Pro Asn
    850                 855                 860

Gly His Ala Pro Asn Gly Ser Ser Asn Gly Ala Ser Thr Pro Ala Ala
865                 870                 875                 880

Ser Glu Arg Pro Ala Gly His Ser Lys Pro Ser Ser Lys Ser Lys Asn
                885                 890                 895

Lys Gly Ser Gly Ser Gly Ser Ala Arg Gly Ala Ser Gly Met Ser Ser
            900                 905                 910

Leu Glu Lys Ser Lys Ser Lys Arg Leu Lys Ser Thr Gln Ala Lys Ala
        915                 920                 925

Glu Ala Lys Ser
    930


<210> SEQ ID NO 71
<211> LENGTH: 3288
<212> TYPE: DNA
<213> ORGANISM: Aureococcus anophagefferens

<400> SEQUENCE: 71

atgaagcagc gcaaggcgcc ggcgaaagcc actgcgccgg atgcggacga cgagcccaag     60

gatcgcacgt cgctctacgg ctcgctgctg cgccgctttc cgctggccat gaacgccgtc    120

caggccggcg cgctgagcgc ggcgtcccag ctgctgtcgc agcggctcaa gggcgcggcg    180

gcgctcgact tcgcgccggc gctgcggttc gcgctcatca gcgctttcgt ggtgacgccc    240

gtgagcacgg tcttcttttc catcgtcggc aagttccggc tccggacgcc cgcgtcgctg    300

gcgctcgact tcttcgtcgg cgggccgttc ctcaactgcg ccttcatcgc cgcgctccac    360

ggcctccagg gccaggacct ggccttcatc ctcggcgtgc tgcggtcgcg ggccttctgg    420

gtcgacatgg tcctcggctc gaacaaggtg tggctgcccg cgaaggtcgc catgtactcg    480

ctcgtgccgc cggagtactg ggggctctgg tgctcctgcg tctccttcgg ctggggcatc    540

gtcctcgcga cgatcgcctc gaagaagaag aaggcgagtg acacgaattg ggccgcggtc    600

ggcggcggct cggccgcctt cgtcgtcgtt tggtgcgcgg gcgcgtacat aaattacggg    660

cggatgaacg agaagctgga gaagcagagc aagatcgtcc cgctcgtcca gtccggactc    720

gagaccccgc tgccgctcga cccgtcgacg caggccgtcg ggaccccgct gccgctcgac    780

ccgtcgacgc gggccgtcgg cgcgcgggcg ttgccggtgg cccaggtcgt cgccgcgata    840

ccggggccga agacccagct cgtcgtcgcg gcgtcccccg gcccgctcgg agtccatttc    900

aaggcgggga cggcggcggt cgcggagctt tccccggcct cgcagctcgc gggcgaggtc    960

gagatcggcg acgtcctcga gtccgtcaac ggacgcccgg ctaccgccgc gtccctcgcg   1020

gccaggcgcg gcatcctcga ggagaacgac gacggcgaaa cgccgcggac cctcgtcttc   1080

gcgcggcccg accggaggtt cgccgtccac gcggcgccgg gctccctcgg cgtcgtcttc   1140

gcccccggca cgacgcgcgt cggacgcgct cccgaacgag gaagcgttct ggggccggcg   1200

cgatcgcagc tcttcggctt cgtcgacgag ggcgacgcgc tcctctccgt gaacggccgc   1260

ccggccgccg ccgcgagccc ggccgagggg ggcgtcctcg acgaggagga cgacggcgcg   1320

cgcgcgcgac tcctcgtctt cgagcgcggc cccaagcagc gaaacgagct ctcgcccaac   1380

gtcgagttcg tcatacgagc gaagcccggg ccgctcggcg tcgtcttcaa gaaccggcca   1440

atcttcggga acgggcggcg cccgcagcgt ctcccacacg ctcccgaatc gttctcgcga   1500

aagagcatcg cgcgccgcgg cgaccaatcg ctgtttctcg gcgcgccgaa accgatccct   1560
```

-continued

```
gtttctcgcg gcgaggacgc gaccatggcc gcgacggagg acgccgccgc cctgacgacg   1620

aacgtcgacg ccctggaggc cgcggccgcc gcgccgctgc ccgacgagtc gcagatcgag   1680

gcgtccgcgg agaagtcgcc gccgcggagc ccgcggtcgc gcaaggcgga cggcgacaag   1740

cccgcgccga agccgcggcg cgagaacggc ctgcggcgcg gcaagtggac cgtcgaggag   1800

gaggcctacg cgaaccggct gatccacgag ttcaagctcg gcctgctgcc gctcaccgac   1860

ggcacgacgc tccggacgtt cctgtcgaag ctgctcaact gcgaccccat gcgcatctcg   1920

aagaagttcg tgggctcgaa ctgcatcggc aagcaggtct tccgccggcg ccaggcggac   1980

atggaccggc tcacgcccga cgacatcaag cggagccgct acgagctcgc ggaactggag   2040

cgccggttcc tcacgcgcgt cgcgcagagc caccggtccg ccaagtcggg cggcgcgggc   2100

gccaagggcg tcaagggcgg cgacggcaag gccctgggcg gcgggctcat gcaggcccag   2160

cagcggccca tgctcgcgcc gtggctcctg ccgccgcacg cggccgcggg cgcgccgacg   2220

gtccgcgcgg gcgcgggcgc cgtcgccatc gccgcgccct acggcctgcc gtcctacgcg   2280

gcgccgccgc ccgccgcggc gccgccgccg ccgccgccgc cgaagcccga cgcggacgcg   2340

gcggccgcgg agaaggcgaa gcgcgcggcg ctcgagggcc tgcacctgcc gtcgctccag   2400

tccgacgcgt cgctccagtc gctgggcctc acggcgcgcg agccgtcctt cgcgtccctc   2460

ggcgccgcct ggccgtcggc gccgaacctc gcccagggct ggcagagctc gaactcgctc   2520

gcgggcgacg cggccgcggc cggccggccg cgcgcgccga gcggcgacgc gggcctgagc   2580

tcctggccgt ccttctccca cctcgtcacg acggccgacg actcgccgcg gctcccgccc   2640

gcggcgccgc ccaaggccgc ggcgccgccg ctcgacatcg cggccgctgc caagcccgcg   2700

gaggcgccgc cgctcgcgcg gcccgcgccg cccgcgccgc ccgcgccgcc ggcggccgcc   2760

gcgccgccgc cgccgccgcc cgccgccgcg gccccgcccg cggccgccgc cgccgtcgcc   2820

gcgctcgcgt ccccgcacgg ccgcacgcgc gagctgacgc ccgagcccga ggagccgacg   2880

gcgaagcggc ggtcggagcc ttccgcgaag cgcgagcggc cgccccacgt gtcgagctcc   2940

gacgaggact ccaacggcgg cgccggcgcg gccgaggacc tcgacccgac gacgctcgag   3000

cagcagcgca aggacgtgcg ccgcgagcgc aaccggcagc acgcgcgcgt ctcgcgagag   3060

cgcaagcgcc agaagctcga gcacctccag gaggagaacg acgcgctccg ccgccaggag   3120

gccgccctga tggaccagcg cgaccgcatc aacgcgcgcc tcctgcgcgt cgagtacgag   3180

aaccgcgcgc tccgcgcctg gatccagaac cacgcgggcg acggcgcgcc gccgccgccg   3240

ccggccgccg acgacgacga ggcgagccgg cccgtgcccg accactga                3288
```

<210> SEQ ID NO 72
<211> LENGTH: 1095
<212> TYPE: PRT
<213> ORGANISM: Aureococcus anophagefferens

<400> SEQUENCE: 72

```
Met Lys Gln Arg Lys Ala Pro Ala Lys Ala Thr Ala Pro Asp Ala Asp
1               5                   10                  15

Asp Glu Pro Lys Asp Arg Thr Ser Leu Tyr Gly Ser Leu Leu Arg Arg
            20                  25                  30

Phe Pro Leu Ala Met Asn Ala Val Gln Ala Gly Ala Leu Ser Ala Ala
        35                  40                  45

Ser Gln Leu Leu Ser Gln Arg Leu Lys Gly Ala Ala Ala Leu Asp Phe
    50                  55                  60
```

-continued

```
Ala Pro Ala Leu Arg Phe Ala Leu Ile Ser Ala Phe Val Val Thr Pro
65                  70                  75                  80

Val Ser Thr Val Phe Phe Ser Ile Val Gly Lys Phe Arg Leu Arg Thr
                85                  90                  95

Pro Ala Ser Leu Ala Leu Asp Phe Phe Val Gly Gly Pro Phe Leu Asn
            100                 105                 110

Cys Ala Phe Ile Ala Ala Leu His Gly Leu Gln Gly Gln Asp Leu Ala
        115                 120                 125

Phe Ile Leu Gly Val Leu Arg Ser Arg Ala Phe Trp Val Asp Met Val
    130                 135                 140

Leu Gly Ser Asn Lys Val Trp Leu Pro Ala Lys Val Ala Met Tyr Ser
145                 150                 155                 160

Leu Val Pro Pro Glu Tyr Trp Gly Leu Trp Cys Ser Cys Val Ser Phe
                165                 170                 175

Gly Trp Gly Ile Val Leu Ala Thr Ile Ala Ser Lys Lys Lys Lys Ala
            180                 185                 190

Ser Asp Thr Asn Trp Ala Ala Val Gly Gly Gly Ser Ala Ala Phe Val
        195                 200                 205

Val Val Trp Cys Ala Gly Ala Tyr Ile Asn Tyr Gly Arg Met Asn Glu
    210                 215                 220

Lys Leu Glu Lys Gln Ser Lys Ile Val Pro Leu Val Gln Ser Gly Leu
225                 230                 235                 240

Glu Thr Pro Leu Pro Leu Asp Pro Ser Thr Gln Ala Val Gly Thr Pro
                245                 250                 255

Leu Pro Leu Asp Pro Ser Thr Arg Ala Val Gly Ala Arg Ala Leu Pro
            260                 265                 270

Val Ala Gln Val Val Ala Ala Ile Pro Gly Pro Lys Thr Gln Leu Val
        275                 280                 285

Val Ala Ala Ser Pro Gly Pro Leu Gly Val His Phe Lys Ala Gly Thr
    290                 295                 300

Ala Ala Val Ala Glu Leu Ser Pro Gly Ser Gln Leu Ala Gly Glu Val
305                 310                 315                 320

Glu Ile Gly Asp Val Leu Glu Ser Val Asn Gly Arg Pro Ala Thr Ala
                325                 330                 335

Ala Ser Leu Ala Ala Arg Arg Gly Ile Leu Glu Glu Asn Asp Asp Gly
            340                 345                 350

Glu Thr Pro Arg Thr Leu Val Phe Ala Arg Pro Asp Arg Arg Phe Ala
        355                 360                 365

Val His Ala Ala Pro Gly Ser Leu Gly Val Val Phe Ala Pro Gly Thr
    370                 375                 380

Thr Arg Val Gly Arg Ala Pro Glu Arg Gly Ser Val Leu Gly Pro Ala
385                 390                 395                 400

Arg Ser Gln Leu Phe Gly Phe Val Asp Glu Gly Asp Ala Leu Leu Ser
                405                 410                 415

Val Asn Gly Arg Pro Ala Ala Ala Ala Ser Pro Ala Glu Gly Gly Val
            420                 425                 430

Leu Asp Glu Glu Asp Asp Gly Ala Arg Ala Arg Leu Leu Val Phe Glu
        435                 440                 445

Arg Gly Pro Lys Gln Arg Asn Glu Leu Ser Pro Asn Val Glu Phe Val
    450                 455                 460

Ile Arg Ala Lys Pro Gly Pro Leu Gly Val Val Phe Lys Asn Arg Pro
465                 470                 475                 480

Ile Phe Gly Asn Gly Arg Arg Pro Gln Arg Leu Pro His Ala Pro Glu
```

-continued

```
                485                 490                 495

Ser Phe Ser Arg Lys Ser Ile Ala Arg Arg Gly Asp Gln Ser Leu Phe
            500                 505                 510

Leu Gly Ala Pro Lys Pro Ile Pro Val Ser Arg Gly Glu Asp Ala Thr
        515                 520                 525

Met Ala Ala Thr Glu Asp Ala Ala Ala Leu Thr Thr Asn Val Asp Ala
    530                 535                 540

Leu Glu Ala Ala Ala Ala Ala Pro Leu Pro Asp Glu Ser Gln Ile Glu
545                 550                 555                 560

Ala Ser Ala Glu Lys Ser Pro Pro Arg Ser Pro Arg Ser Arg Lys Ala
                565                 570                 575

Asp Gly Asp Lys Pro Ala Pro Lys Pro Arg Arg Glu Asn Gly Leu Arg
            580                 585                 590

Arg Gly Lys Trp Thr Val Glu Glu Glu Ala Tyr Ala Asn Arg Leu Ile
        595                 600                 605

His Glu Phe Lys Leu Gly Leu Leu Pro Leu Thr Asp Gly Thr Thr Leu
    610                 615                 620

Arg Thr Phe Leu Ser Lys Leu Leu Asn Cys Asp Pro Met Arg Ile Ser
625                 630                 635                 640

Lys Lys Phe Val Gly Ser Asn Cys Ile Gly Lys Gln Val Phe Arg Arg
                645                 650                 655

Arg Gln Ala Asp Met Asp Arg Leu Thr Pro Asp Asp Ile Lys Arg Ser
            660                 665                 670

Arg Tyr Glu Leu Ala Glu Leu Glu Arg Arg Phe Leu Thr Arg Val Ala
        675                 680                 685

Gln Ser His Arg Ser Ala Lys Ser Gly Gly Ala Gly Ala Lys Gly Val
    690                 695                 700

Lys Gly Gly Asp Gly Lys Ala Leu Gly Gly Gly Leu Met Gln Ala Gln
705                 710                 715                 720

Gln Arg Pro Met Leu Ala Pro Trp Leu Leu Pro Pro His Ala Ala Ala
                725                 730                 735

Gly Ala Pro Thr Val Arg Ala Gly Ala Gly Ala Val Ala Ile Ala Ala
            740                 745                 750

Pro Tyr Gly Leu Pro Ser Tyr Ala Ala Pro Pro Pro Ala Ala Ala Pro
        755                 760                 765

Pro Pro Pro Pro Pro Pro Lys Pro Asp Ala Asp Ala Ala Ala Ala Glu
    770                 775                 780

Lys Ala Lys Arg Ala Ala Leu Glu Gly Leu His Leu Pro Ser Leu Gln
785                 790                 795                 800

Ser Asp Ala Ser Leu Gln Ser Leu Gly Leu Thr Ala Arg Glu Pro Ser
                805                 810                 815

Phe Ala Ser Leu Gly Ala Ala Trp Pro Ser Ala Pro Asn Leu Ala Gln
            820                 825                 830

Gly Trp Gln Ser Ser Asn Ser Leu Ala Gly Asp Ala Ala Ala Ala Gly
        835                 840                 845

Arg Pro Arg Ala Pro Ser Gly Asp Ala Gly Leu Ser Ser Trp Pro Ser
    850                 855                 860

Phe Ser His Leu Val Thr Thr Ala Asp Asp Ser Pro Arg Leu Pro Pro
865                 870                 875                 880

Ala Ala Pro Pro Lys Ala Ala Ala Pro Pro Leu Asp Ile Ala Ala Ala
                885                 890                 895

Ala Lys Pro Ala Glu Ala Pro Pro Leu Ala Arg Pro Ala Pro Pro Ala
            900                 905                 910
```

```
Pro Pro Ala Pro Pro Ala Ala Ala Ala Pro Pro Pro Pro Pro Pro Ala
        915                 920                 925

Ala Ala Ala Pro Pro Ala Ala Ala Ala Ala Val Ala Ala Leu Ala Ser
    930                 935                 940

Pro His Gly Arg Thr Arg Glu Leu Thr Pro Glu Pro Glu Glu Pro Thr
945                 950                 955                 960

Ala Lys Arg Arg Ser Glu Pro Ser Ala Lys Arg Glu Arg Pro Pro His
                965                 970                 975

Val Ser Ser Ser Asp Glu Asp Ser Asn Gly Gly Ala Gly Ala Ala Glu
            980                 985                 990

Asp Leu Asp Pro Thr Thr Leu Glu  Gln Gln Arg Lys Asp  Val Arg Arg
        995                 1000                1005

Glu Arg  Asn Arg Gln His Ala  Arg Val Ser Arg Glu  Arg Lys Arg
    1010                1015                1020

Gln Lys  Leu Glu His Leu Gln  Glu Glu Asn Asp Ala  Leu Arg Arg
    1025                1030                1035

Gln Glu  Ala Ala Leu Met Asp  Gln Arg Asp Arg Ile  Asn Ala Arg
    1040                1045                1050

Leu Leu  Arg Val Glu Tyr Glu  Asn Arg Ala Leu Arg  Ala Trp Ile
    1055                1060                1065

Gln Asn  His Ala Gly Asp Gly  Ala Pro Pro Pro Pro  Pro Ala Ala
    1070                1075                1080

Asp Asp  Asp Glu Ala Ser Arg  Pro Val Pro Asp His
    1085                1090                1095


<210> SEQ ID NO 73
<211> LENGTH: 2013
<212> TYPE: DNA
<213> ORGANISM: Thalassiosira pseudonana

<400> SEQUENCE: 73

atgcaagctg cccgatcggc agcgaaggca gatggagtag cccaaccaaa taatgatgta      60

gcaaaagcat ctgattctca agagaaggcg aatgcaaagt ctgatgaaga ggagaaaagt     120

ggaaacgatg atgccgtccc aaatggagat gaaaaagatg ccgaagacgc agccgctccg     180

gcttcgtccc aaaacggatc ggctctcaac cagatgctga gtgccatcaa ccgaccaccc     240

aatcaagtga cttccaccaa ccttgtagga tcagtagatg atccgtctgc tctatctgaa     300

tctcccggcg aaccggacag tgccgccgat cgtcgtcggg ctccccttcg tcgtgggaaa     360

tggactgcgg aggaagaagc ctacgctagt cgtctcattc aagagttcaa agctggtttg     420

ctccccctca ccgatggcac aactctccgt accttcttga gtaagctctt gaactgtgat     480

cctatgcgta tctccaagaa gtttgttggg agcaactgta tcggcaaaca agtctttcgt     540

cgacggggag ctgatgttaa caacttgact ccagcacaaa tccagcaaac tcgtctcgaa     600

ctatccgagt tggagaagag gttcttggat cgcgtctcgc agaacaagaa atctggtggt     660

tcccccaaga gtgaacggcc ggccagcaag ccccagtctg gaaatgatgg tggtctctct     720

ggcgtgtctg ggatgtcggg aataggcaac atgaacaagt ctgctgcggc ggctggtcgt     780

gcactgctcc aaggaaacaa gggcggtgga aatggagata gtggtcctac agggttgctt     840

gctcagcttc aagccagtca accaggaatg tttgatgcga atactgcaat ggcttacaat     900

tccaatgctt caggtggcgg gcaggcagtc atgggagtca acagtgcttc cattaacaac     960

ctcatgcttc aaaccggcat gacggccgag caaatctccc aactcactca gacaaagggc    1020
```

-continued

```
attaactcct cggcatccct tgctaatttg cttggaaaga agcgaagctt tgatggtctc   1080

atgtccttgg actttcagag tatgcagagt attgataatt tggccaactt gattcagcaa   1140

ggaataccta gtcaatctct ccacaagaat caaatgaaga atttcgactg gaacagtggt   1200

gccggcgctc aaggaagcga cgcaggggct ccttcatctg gcactaaggg atctcttgag   1260

aatcttgttc tcagtctatc tggaaacaac acccagcaga ttgataacaa taatgccact   1320

gcttcaatga gcaatcaagc aaacgtaaac tatggcaatc ttcttcagag tatgcaaggg   1380

aacgcacaaa atggaaacat caatgaccta cttcagagta tgcaccagtc tgctaacaac   1440

aacaacaaca tgaatcagaa tcagaacttt gggaatctcc ttcaaggcat gggcaattca   1500

ttccttcaga atcccatgat gggtaatgat tttttaaaca taatgaatgg tggtggcgga   1560

gacttgtctc agcagaatat gatgcatttc aataatacat ttgcaatgca gcagaatccc   1620

atgatggcgg ctgcaattgc gcaacaacag cttcttgctc aagcgggagg aaaccccgcc   1680

attgctaatg tcttagctca acaaggtatt atgggcggca tgacgaacat ggctaacaac   1740

tttggcaaca actttggcaa tcaaaacaca aacgacttgc ttcagcagtt aattgcccag   1800

caacaaggag aaagtggata caataaccaa ctacaacagc agcaacatca taatcatcat   1860

cagcaacatc agcagcagca gcagcagcag caacaacagg ggcaagcaca ggaggggaac   1920

aagcgtaact tcgacaaaat gaagcaaggt ggagggattg accaaggtgg agacgatgga   1980

caggctgcaa agaaacaaca atgcgacgtt tga                                2013


<210> SEQ ID NO 74
<211> LENGTH: 670
<212> TYPE: PRT
<213> ORGANISM: Thalassiosira pseudonana

<400> SEQUENCE: 74

Met Gln Ala Ala Arg Ser Ala Ala Lys Ala Asp Gly Val Ala Gln Pro
1               5                   10                  15

Asn Asn Asp Val Ala Lys Ala Ser Asp Ser Gln Glu Lys Ala Asn Ala
            20                  25                  30

Lys Ser Asp Glu Glu Glu Lys Ser Gly Asn Asp Asp Ala Val Pro Asn
        35                  40                  45

Gly Asp Glu Lys Asp Ala Glu Asp Ala Ala Ala Pro Ala Ser Ser Gln
    50                  55                  60

Asn Gly Ser Ala Leu Asn Gln Met Leu Ser Ala Ile Asn Arg Pro Pro
65                  70                  75                  80

Asn Gln Val Thr Ser Thr Asn Leu Val Gly Ser Val Asp Asp Pro Ser
                85                  90                  95

Ala Leu Ser Glu Ser Pro Gly Glu Pro Asp Ser Ala Ala Asp Arg Arg
            100                 105                 110

Arg Ala Pro Leu Arg Arg Gly Lys Trp Thr Ala Glu Glu Glu Ala Tyr
        115                 120                 125

Ala Ser Arg Leu Ile Gln Glu Phe Lys Ala Gly Leu Leu Pro Leu Thr
    130                 135                 140

Asp Gly Thr Thr Leu Arg Thr Phe Leu Ser Lys Leu Leu Asn Cys Asp
145                 150                 155                 160

Pro Met Arg Ile Ser Lys Lys Phe Val Gly Ser Asn Cys Ile Gly Lys
                165                 170                 175

Gln Val Phe Arg Arg Arg Gly Ala Asp Val Asn Asn Leu Thr Pro Ala
            180                 185                 190

Gln Ile Gln Gln Thr Arg Leu Glu Leu Ser Glu Leu Glu Lys Arg Phe
```

-continued

```
        195                 200                 205

Leu Asp Arg Val Ser Gln Asn Lys Lys Ser Gly Gly Ser Pro Lys Ser
    210                 215                 220

Glu Arg Pro Ala Ser Lys Pro Gln Ser Gly Asn Asp Gly Gly Leu Ser
225                 230                 235                 240

Gly Val Ser Gly Met Ser Gly Ile Gly Asn Met Asn Lys Ser Ala Ala
                245                 250                 255

Ala Ala Gly Arg Ala Leu Leu Gln Gly Asn Lys Gly Gly Gly Asn Gly
            260                 265                 270

Asp Ser Gly Pro Thr Gly Leu Leu Ala Gln Leu Gln Ala Ser Gln Pro
        275                 280                 285

Gly Met Phe Asp Ala Asn Thr Ala Met Ala Tyr Asn Ser Asn Ala Ser
    290                 295                 300

Gly Gly Gly Gln Ala Val Met Gly Val Asn Ser Ala Ser Ile Asn Asn
305                 310                 315                 320

Leu Met Leu Gln Thr Gly Met Thr Ala Glu Gln Ile Ser Gln Leu Thr
                325                 330                 335

Gln Thr Lys Gly Ile Asn Ser Ser Ala Ser Leu Ala Asn Leu Leu Gly
            340                 345                 350

Lys Lys Arg Ser Phe Asp Gly Leu Met Ser Leu Asp Phe Gln Ser Met
        355                 360                 365

Gln Ser Ile Asp Asn Leu Ala Asn Leu Ile Gln Gln Gly Ile Pro Ser
    370                 375                 380

Gln Ser Leu His Lys Asn Gln Met Lys Asn Phe Asp Trp Asn Ser Gly
385                 390                 395                 400

Ala Gly Ala Gln Gly Ser Asp Ala Gly Ala Pro Ser Ser Gly Thr Lys
                405                 410                 415

Gly Ser Leu Glu Asn Leu Val Leu Ser Leu Ser Gly Asn Asn Thr Gln
            420                 425                 430

Gln Ile Asp Asn Asn Asn Ala Thr Ala Ser Met Ser Asn Gln Ala Asn
        435                 440                 445

Val Asn Tyr Gly Asn Leu Leu Gln Ser Met Gln Gly Asn Ala Gln Asn
    450                 455                 460

Gly Asn Ile Asn Asp Leu Leu Gln Ser Met His Gln Ser Ala Asn Asn
465                 470                 475                 480

Asn Asn Asn Met Asn Gln Asn Gln Asn Phe Gly Asn Leu Leu Gln Gly
                485                 490                 495

Met Gly Asn Ser Phe Leu Gln Asn Pro Met Met Gly Asn Asp Phe Leu
            500                 505                 510

Asn Ile Met Asn Gly Gly Gly Gly Asp Leu Ser Gln Gln Asn Met Met
        515                 520                 525

His Phe Asn Asn Thr Phe Ala Met Gln Gln Asn Pro Met Met Ala Ala
    530                 535                 540

Ala Ile Ala Gln Gln Gln Leu Leu Ala Gln Ala Gly Gly Asn Pro Ala
545                 550                 555                 560

Ile Ala Asn Val Leu Ala Gln Gln Gly Ile Met Gly Gly Met Thr Asn
                565                 570                 575

Met Ala Asn Asn Phe Gly Asn Asn Phe Gly Asn Gln Asn Thr Asn Asp
            580                 585                 590

Leu Leu Gln Gln Leu Ile Ala Gln Gln Gln Gly Glu Ser Gly Tyr Asn
        595                 600                 605

Asn Gln Leu Gln Gln Gln Gln His His Asn His His Gln Gln His Gln
    610                 615                 620
```

```
Gln Gln Gln Gln Gln Gln Gln Gln Gln Gly Gln Ala Gln Glu Gly Asn
625                 630                 635                 640

Lys Arg Asn Phe Asp Lys Met Lys Gln Gly Gly Gly Ile Asp Gln Gly
                645                 650                 655

Gly Asp Asp Gly Gln Ala Ala Lys Lys Gln Gln Cys Asp Val
            660                 665                 670


<210> SEQ ID NO 75
<211> LENGTH: 1902
<212> TYPE: PRT
<213> ORGANISM: Phaeodactylum tricornutum

<400> SEQUENCE: 75

Ala Thr Gly Thr Cys Ala Ala Gly Thr Cys Thr Ala Thr Thr Gly Ala
1               5                   10                  15

Thr Ala Cys Ala Thr Gly Cys Cys Gly Cys Cys Cys Ala Ala Ala Gly
            20                  25                  30

Cys Gly Cys Gly Gly Cys Gly Cys Ala Gly Gly Cys Cys Gly Ala Cys
        35                  40                  45

Gly Gly Thr Cys Thr Cys Thr Cys Thr Gly Thr Gly Cys Cys Thr Gly
    50                  55                  60

Gly Gly Cys Ala Thr Cys Gly Cys Thr Thr Gly Gly Ala Gly Gly Cys
65                  70                  75                  80

Gly Gly Cys Gly Cys Ala Cys Thr Cys Cys Ala Thr Gly Gly Cys Gly
                85                  90                  95

Gly Cys Gly Cys Cys Ala Cys Cys Gly Cys Ala Gly Cys Ala Gly Cys
            100                 105                 110

Cys Thr Cys Ala Cys Cys Cys Thr Gly Cys Thr Cys Thr Gly Gly Ala
        115                 120                 125

Thr Gly Thr Ala Ala Thr Thr Cys Cys Cys Ala Ala Cys Ala Ala Thr
    130                 135                 140

Ala Ala Gly Ala Ala Ala Ala Ala Ala Gly Gly Cys Cys Cys Gly Cys
145                 150                 155                 160

Cys Cys Cys Thr Thr Cys Gly Thr Cys Gly Ala Gly Gly Gly Ala Ala
                165                 170                 175

Ala Thr Gly Gly Ala Cys Thr Cys Cys Ala Gly Ala Gly Gly Ala Gly
            180                 185                 190

Gly Ala Ala Gly Cys Gly Thr Ala Cys Gly Cys Gly Ala Ala Thr Cys
        195                 200                 205

Gly Cys Thr Thr Gly Ala Thr Thr Cys Thr Ala Gly Ala Ala Thr Thr
    210                 215                 220

Cys Ala Ala Ala Thr Cys Thr Gly Gly Cys Cys Thr Thr Thr Thr Gly
225                 230                 235                 240

Cys Cys Cys Cys Thr Gly Ala Cys Gly Gly Ala Thr Gly Gly Gly Ala
                245                 250                 255

Cys Thr Ala Cys Ala Thr Thr Gly Cys Gly Thr Ala Cys Cys Thr Thr
            260                 265                 270

Cys Thr Thr Gly Thr Cys Cys Ala Ala Ala Thr Thr Gly Cys Thr Cys
        275                 280                 285

Ala Ala Cys Thr Gly Cys Gly Ala Thr Cys Cys Cys Ala Thr Gly Cys
    290                 295                 300

Gly Thr Ala Thr Thr Thr Cys Cys Ala Ala Ala Ala Ala Gly Thr Thr
305                 310                 315                 320

Cys Gly Thr Gly Gly Gly Ala Ala Gly Cys Ala Ala Cys Thr Gly Cys
```

```
                325                 330                 335

Ala Thr Cys Gly Gly Cys Ala Ala Gly Cys Ala Ala Gly Thr Cys Thr
            340                 345                 350

Thr Cys Cys Gly Ala Ala Gly Ala Cys Gly Cys Ala Cys Gly Gly Cys
        355                 360                 365

Ala Gly Ala Thr Cys Thr Cys Ala Ala Cys Ala Gly Gly Cys Thr Ala
    370                 375                 380

Ala Cys Ala Cys Cys Gly Gly Ala Gly Cys Ala Gly Ala Thr Thr Cys
385                 390                 395                 400

Ala Gly Cys Ala Ala Ala Gly Thr Cys Gly Cys Gly Cys Cys Gly Ala
                405                 410                 415

Ala Cys Thr Gly Ala Gly Cys Gly Ala Ala Cys Thr Cys Gly Ala Ala
            420                 425                 430

Cys Gly Cys Cys Gly Ala Thr Thr Thr Thr Thr Gly Gly Ala Gly Cys
        435                 440                 445

Gly Thr Gly Thr Thr Gly Cys Gly Cys Ala Ala Ala Cys Cys Ala Ala
    450                 455                 460

Thr Cys Gly Gly Gly Thr Cys Ala Ala Gly Thr Cys Gly Thr Cys Cys
465                 470                 475                 480

Gly Gly Thr Gly Thr Thr Gly Gly Cys Gly Gly Gly Gly Cys Gly Gly
                485                 490                 495

Cys Thr Thr Cys Cys Gly Cys Gly Gly Cys Thr Cys Cys Cys Gly Ala
            500                 505                 510

Ala Gly Cys Thr Ala Thr Cys Ala Thr Cys Ala Thr Gly Gly Gly Gly
        515                 520                 525

Ala Gly Ala Cys Cys Cys Ala Ala Ala Ala Thr Ala Gly Ala Ala Cys
    530                 535                 540

Ala Cys Gly Ala Gly Ala Cys Ala Ala Thr Gly Gly Ala Gly Cys Cys
545                 550                 555                 560

Thr Cys Cys Cys Ala Gly Thr Cys Cys Thr Cys Cys Gly Thr Gly Gly
                565                 570                 575

Thr Thr Gly Cys Ala Gly Cys Cys Thr Cys Cys Gly Thr Thr Thr Gly
            580                 585                 590

Gly Gly Thr Ala Cys Ala Ala Ala Cys Ala Ala Gly Gly Cys Gly Cys
        595                 600                 605

Gly Gly Gly Ala Gly Cys Gly Gly Cys Ala Thr Thr Cys Gly Cys Gly
    610                 615                 620

Gly Cys Thr Gly Cys Thr Ala Ala Thr Cys Thr Cys Thr Cys Cys Gly
625                 630                 635                 640

Gly Ala Thr Cys Cys Ala Ala Cys Ala Gly Thr Cys Gly Cys Gly Cys
                645                 650                 655

Cys Gly Cys Cys Gly Cys Cys Gly Cys Thr Gly Gly Ala Cys Gly Cys
            660                 665                 670

Gly Cys Cys Ala Thr Gly Cys Thr Cys Gly Cys Thr Gly Gly Thr Ala
        675                 680                 685

Cys Ala Ala Gly Thr Gly Gly Thr Cys Thr Cys Ala Ala Cys Gly Gly
    690                 695                 700

Ala Gly Ala Thr Cys Gly Cys Cys Gly Gly Gly Cys Gly Ala Gly Thr
705                 710                 715                 720

Gly Gly Gly Ala Thr Gly Ala Gly Thr Thr Cys Ala Cys Ala Gly Gly
                725                 730                 735

Ala Ala Cys Thr Thr Thr Thr Gly Gly Cys Cys Ala Thr Gly Gly Cys
            740                 745                 750
```

```
Cys Gly Ala Ala Thr Thr Thr Cys Ala Ala Cys Gly Thr Cys Ala Ala
        755                 760                 765

Gly Cys Ala Thr Cys Cys Cys Ala Ala Thr Cys Gly Ala Cys Cys Ala
    770                 775                 780

Thr Gly Ala Thr Gly Cys Ala Gly Ala Ala Thr Cys Cys Cys Thr Thr
785                 790                 795                 800

Thr Cys Ala Thr Cys Ala Ala Gly Gly Gly Thr Cys Gly Gly Cys Ala
                805                 810                 815

Ala Cys Cys Ala Ala Cys Thr Thr Gly Cys Thr Cys Gly Cys Thr Gly
            820                 825                 830

Cys Thr Ala Cys Gly Cys Gly Gly Thr Cys Gly Gly Gly Cys Ala Gly
        835                 840                 845

Thr Ala Gly Cys Ala Ala Cys Gly Gly Cys Cys Thr Thr Thr Cys Thr
    850                 855                 860

Ala Gly Cys Gly Cys Ala Gly Cys Gly Thr Thr Cys Thr Cys Gly Cys
865                 870                 875                 880

Ala Ala Thr Thr Ala Gly Cys Gly Cys Ala Ala Ala Gly Cys Gly Thr
                885                 890                 895

Gly Thr Cys Gly Gly Cys Thr Gly Cys Cys Cys Gly Ala Cys Thr Thr
            900                 905                 910

Thr Cys Thr Gly Gly Ala Cys Thr Gly Cys Ala Ala Ala Gly Cys Ala
        915                 920                 925

Ala Cys Ala Ala Thr Gly Cys Ala Thr Cys Cys Ala Thr Gly Ala Ala
    930                 935                 940

Cys Ala Ala Thr Thr Thr Ala Ala Thr Gly Cys Thr Ala Ala Ala Gly
945                 950                 955                 960

Ala Cys Gly Gly Gly Ala Cys Thr Cys Thr Cys Thr Cys Gly Ala Gly
                965                 970                 975

Ala Ala Cys Ala Gly Thr Thr Gly Ala Cys Thr Cys Ala Ala Cys Thr
            980                 985                 990

Ala Gly Cys Ala Ala Gly Ala Gly  Ala Cys Cys Gly Thr  Gly Gly Thr
        995                 1000                1005

Cys Thr  Cys Thr Cys Gly Thr  Cys Ala Gly Ala Thr  Thr Cys Cys
    1010                1015                1020

Cys Thr  Cys Thr Cys Gly Ala  Ala Cys Ala Thr Gly  Ala Thr Cys
    1025                1030                1035

Cys Ala  Gly Cys Gly Ala Cys  Ala Gly Ala Ala Cys  Thr Cys Gly
    1040                1045                1050

Thr Thr  Cys Gly Ala Thr Gly  Cys Thr Cys Thr Thr  Ala Thr Gly
    1055                1060                1065

Thr Cys  Gly Thr Thr Gly Gly  Ala Thr Thr Thr Thr  Cys Ala Ala
    1070                1075                1080

Ala Gly  Thr Cys Thr Thr Cys  Ala Ala Thr Cys Cys  Ala Thr Cys
    1085                1090                1095

Gly Ala  Thr Ala Ala Thr Cys  Thr Thr Gly Cys Cys  Ala Ala Cys
    1100                1105                1110

Thr Thr  Ala Ala Thr Thr Cys  Ala Ala Ala Cys Ala  Gly Gly Gly
    1115                1120                1125

Ala Cys  Cys Gly Cys Ala Gly  Gly Ala Ala Gly Thr  Cys Ala Thr
    1130                1135                1140

Thr Cys  Cys Ala Ala Thr Ala  Thr Ala Cys Cys Gly  Gly Ala Ala
    1145                1150                1155
```

```
Thr Cys  Gly Gly Gly Thr Ala  Thr Gly Ala Ala Gly  Ala Ala Cys
    1160                 1165                 1170

Gly Cys  Gly Gly Ala Cys Thr  Thr Thr Gly Gly Cys  Thr Ala Thr
    1175                 1180                 1185

Thr Cys  Thr Thr Cys Ala Cys  Gly Ala Cys Ala Gly  Ala Ala Cys
    1190                 1195                 1200

Ala Thr  Ala Ala Cys Gly Gly  Gly Ala Gly Cys Thr  Thr Cys Thr
    1205                 1210                 1215

Thr Cys  Thr Gly Gly Ala Gly  Ala Cys Thr Thr Ala  Thr Cys Gly
    1220                 1225                 1230

Ala Ala  Cys Gly Cys Cys Gly  Cys Thr Cys Gly Thr  Cys Gly Cys
    1235                 1240                 1245

Thr Thr  Ala Gly Cys Gly Ala  Gly Cys Gly Cys Gly  Gly Gly Ala
    1250                 1255                 1260

Cys Gly  Ala Ala Thr Gly Gly  Ala Ala Ala Gly Thr  Cys Thr Thr
    1265                 1270                 1275

Cys Thr  Gly Cys Ala Ala Thr  Cys Ala Ala Thr Gly  Thr Cys Cys
    1280                 1285                 1290

Ala Ala  Cys Ala Ala Thr Ala  Ala Thr Thr Thr Thr  Cys Ala Cys
    1295                 1300                 1305

Ala Ala  Cys Ala Ala Thr Gly  Gly Gly Ala Thr Cys  Gly Gly Thr
    1310                 1315                 1320

Gly Gly  Ala Ala Ala Cys Ala  Ala Thr Gly Ala Thr  Ala Cys Gly
    1325                 1330                 1335

Cys Cys  Cys Gly Ala Thr Thr  Cys Thr Ala Ala Cys  Gly Thr Gly
    1340                 1345                 1350

Ala Ala  Thr Cys Thr Thr Ala  Ala Cys Ala Ala Cys  Thr Thr Gly
    1355                 1360                 1365

Cys Thr  Thr Cys Ala Ala Thr  Cys Thr Ala Thr Gly  Cys Ala Thr
    1370                 1375                 1380

Gly Gly  Thr Gly Gly Thr Ala  Gly Cys Ala Thr Gly  Cys Thr Cys
    1385                 1390                 1395

Gly Gly  Thr Ala Thr Gly Gly  Gly Cys Gly Ala Cys  Cys Gly Cys
    1400                 1405                 1410

Ala Gly  Cys Ala Gly Cys Gly  Cys Ala Gly Cys Ala  Thr Cys Thr
    1415                 1420                 1425

Cys Thr  Cys Cys Thr Thr Gly  Gly Thr Thr Cys Cys  Gly Gly Gly
    1430                 1435                 1440

Ala Ala  Cys Gly Gly Ala Cys  Cys Cys Ala Gly Thr  Gly Cys Gly
    1445                 1450                 1455

Gly Thr  Gly Ala Gly Thr Cys  Thr Ala Gly Cys Ala  Ala Ala Thr
    1460                 1465                 1470

Thr Thr  Gly Cys Thr Cys Cys  Gly Cys Cys Ala Ala  Gly Ala Thr
    1475                 1480                 1485

Thr Cys  Thr Thr Cys Cys Ala  Cys Thr Gly Gly Thr  Thr Thr Gly
    1490                 1495                 1500

Ala Cys  Gly Gly Cys Thr Thr  Thr Gly Cys Gly Thr  Ala Thr Gly
    1505                 1510                 1515

Cys Ala  Gly Gly Ala Cys Gly  Gly Thr Thr Thr Ala  Ala Ala Thr
    1520                 1525                 1530

Cys Ala  Ala Cys Gly Cys Ala  Ala Thr Thr Cys Gly  Ala Gly Cys
    1535                 1540                 1545

Gly Thr  Thr Gly Ala Thr Gly  Ala Cys Thr Thr Thr  Thr Thr Gly
```

```
    1550                1555                1560

Ala Gly  Cys Thr Thr Gly Gly  Thr Thr Gly Cys Gly  Gly Cys Cys
    1565                1570                1575

Gly Gly  Ala Gly Ala Thr Ala  Thr Cys Cys Cys Gly  Cys Ala Cys
    1580                1585                1590

Cys Ala  Ala Gly Ala Thr Cys  Cys Ala Thr Cys Ala  Thr Thr Gly
    1595                1600                1605

Cys Thr  Gly Ala Ala Thr Gly  Thr Thr Cys Cys Ala  Thr Thr Gly
    1610                1615                1620

Ala Thr  Gly Cys Ala Thr Cys  Ala Gly Cys Ala Ala  Gly Gly Gly
    1625                1630                1635

Cys Cys  Gly Cys Cys Ala Gly  Gly Ala Thr Cys Ala  Ala Gly Cys
    1640                1645                1650

Gly Ala  Ala Gly Cys Thr Gly  Cys Thr Gly Cys Cys  Ala Ala Gly
    1655                1660                1665

Thr Thr  Ala Ala Thr Gly Gly  Cys Cys Cys Ala Gly  Cys Ala Gly
    1670                1675                1680

Cys Ala  Ala Ala Thr Gly Cys  Thr Ala Cys Ala Ala  Gly Cys Thr
    1685                1690                1695

Thr Cys  Gly Gly Gly Gly Ala  Ala Thr Thr Cys Thr  Gly Cys Ala
    1700                1705                1710

Cys Thr  Gly Gly Cys Gly Ala  Ala Thr Gly Cys Gly  Cys Thr Gly
    1715                1720                1725

Gly Cys  Ala Thr Cys Thr Cys  Gly Thr Thr Cys Thr  Thr Thr Thr
    1730                1735                1740

Gly Gly  Thr Ala Ala Thr Thr  Thr Gly Cys Ala Ala  Ala Ala Cys
    1745                1750                1755

Thr Cys  Cys Cys Ala Thr Cys  Ala Thr Ala Gly Cys  Gly Gly Ala
    1760                1765                1770

Gly Gly  Cys Ala Thr Gly Cys  Ala Thr Thr Cys Gly  Ala Cys Ala
    1775                1780                1785

Ala Cys  Gly Ala Gly Cys Gly  Cys Gly Gly Cys Thr  Gly Cys Thr
    1790                1795                1800

Thr Thr  Gly Gly Cys Gly Ala  Thr Gly Gly Cys Thr  Cys Ala Ala
    1805                1810                1815

Gly Cys  Ala Cys Gly Thr Gly  Cys Gly Gly Cys Thr  Gly Cys Gly
    1820                1825                1830

Ala Ala  Thr Gly Gly Ala Thr  Cys Gly Ala Ala Gly  Cys Gly Ala
    1835                1840                1845

Ala Ala  Thr Cys Thr Thr Gly  Ala Cys Thr Ala Thr  Cys Thr Thr
    1850                1855                1860

Ala Gly  Thr Gly Gly Gly Gly  Gly Thr Thr Ala Cys  Ala Thr Cys
    1865                1870                1875

Gly Gly  Thr Cys Ala Ala Gly  Gly Thr Gly Ala Cys  Thr Cys Cys
    1880                1885                1890

Ala Ala  Gly Cys Gly Gly Thr  Ala Ala
    1895                1900
```

<210> SEQ ID NO 76
<211> LENGTH: 633
<212> TYPE: PRT
<213> ORGANISM: Phaeodactylum tricornutum

<400> SEQUENCE: 76

Met Ser Ser Leu Leu Ile His Ala Ala Gln Ser Ala Ala Gln Ala Asp
1 5 10 15

Gly Leu Ser Val Pro Gly His Arg Leu Glu Ala Ala His Ser Met Ala
20 25 30

Ala Pro Pro Gln Gln Pro His Pro Ala Leu Asp Val Ile Pro Asn Asn
35 40 45

Lys Lys Lys Gly Pro Pro Leu Arg Arg Gly Lys Trp Thr Pro Glu Glu
50 55 60

Glu Ala Tyr Ala Asn Arg Leu Ile Leu Glu Phe Lys Ser Gly Leu Leu
65 70 75 80

Pro Leu Thr Asp Gly Thr Thr Leu Arg Thr Phe Leu Ser Lys Leu Leu
85 90 95

Asn Cys Asp Pro Met Arg Ile Ser Lys Lys Phe Val Gly Ser Asn Cys
100 105 110

Ile Gly Lys Gln Val Phe Arg Arg Arg Thr Ala Asp Leu Asn Arg Leu
115 120 125

Thr Pro Glu Gln Ile Gln Gln Ser Arg Ala Glu Leu Ser Glu Leu Glu
130 135 140

Arg Arg Phe Leu Glu Arg Val Ala Gln Thr Asn Arg Val Lys Ser Ser
145 150 155 160

Gly Val Gly Gly Ala Ala Ser Ala Ala Pro Glu Ala Ile Ile Met Gly
165 170 175

Arg Pro Lys Ile Glu His Glu Thr Met Glu Pro Pro Ser Pro Pro Trp
180 185 190

Leu Gln Pro Pro Phe Gly Tyr Lys Gln Gly Ala Gly Ala Ala Phe Ala
195 200 205

Ala Ala Asn Leu Ser Gly Ser Asn Ser Arg Ala Ala Ala Ala Gly Arg
210 215 220

Ala Met Leu Ala Gly Thr Ser Gly Leu Asn Gly Asp Arg Arg Ala Ser
225 230 235 240

Gly Met Ser Ser Gln Glu Leu Leu Ala Met Ala Glu Phe Gln Arg Gln
245 250 255

Ala Ser Gln Ser Thr Met Met Gln Asn Pro Phe His Gln Gly Ser Ala
260 265 270

Thr Asn Leu Leu Ala Ala Thr Arg Ser Gly Ser Ser Asn Gly Leu Ser
275 280 285

Ser Ala Ala Phe Ser Gln Leu Ala Gln Ser Val Ser Ala Ala Arg Leu
290 295 300

Ser Gly Leu Gln Ser Asn Asn Ala Ser Met Asn Asn Leu Met Leu Lys
305 310 315 320

Thr Gly Leu Ser Arg Glu Gln Leu Thr Gln Leu Ala Arg Asp Arg Gly
325 330 335

Leu Ser Ser Asp Ser Leu Ser Asn Met Ile Gln Arg Gln Asn Ser Phe
340 345 350

Asp Ala Leu Met Ser Leu Asp Phe Gln Ser Leu Gln Ser Ile Asp Asn
355 360 365

Leu Ala Asn Leu Ile Gln Thr Gly Thr Ala Gly Ser His Ser Asn Ile
370 375 380

Pro Glu Ser Gly Met Lys Asn Ala Asp Phe Gly Tyr Ser Ser Arg Gln
385 390 395 400

Asn Ile Thr Gly Ala Ser Ser Gly Asp Leu Ser Asn Ala Ala Arg Arg
405 410 415

Leu Ala Ser Ala Gly Arg Met Glu Ser Leu Leu Gln Ser Met Ser Asn

```
            420                 425                 430

Asn Asn Phe His Asn Asn Gly Ile Gly Gly Asn Asn Asp Thr Pro Asp
        435                 440                 445

Ser Asn Val Asn Leu Asn Asn Leu Leu Gln Ser Met His Gly Gly Ser
    450                 455                 460

Met Leu Gly Met Gly Asp Arg Ser Ser Ala Ala Ser Leu Leu Gly Ser
465                 470                 475                 480

Gly Asn Gly Pro Ser Ala Val Ser Leu Ala Asn Leu Leu Arg Gln Asp
                485                 490                 495

Ser Ser Thr Gly Leu Thr Ala Leu Arg Met Gln Asp Gly Leu Asn Gln
            500                 505                 510

Arg Asn Ser Ser Val Asp Asp Phe Leu Ser Leu Val Ala Ala Gly Asp
        515                 520                 525

Ile Pro His Gln Asp Pro Ser Leu Leu Asn Val Pro Leu Met His Gln
    530                 535                 540

Gln Gly Pro Pro Gly Ser Ser Glu Ala Ala Ala Lys Leu Met Ala Gln
545                 550                 555                 560

Gln Gln Met Leu Gln Ala Ser Gly Asn Ser Ala Leu Ala Asn Ala Leu
                565                 570                 575

Ala Ser Arg Ser Phe Gly Asn Leu Gln Asn Ser His His Ser Gly Gly
            580                 585                 590

Met His Ser Thr Thr Ser Ala Ala Ala Leu Ala Met Ala Gln Ala Arg
        595                 600                 605

Ala Ala Ala Asn Gly Ser Lys Arg Asn Leu Asp Tyr Leu Ser Gly Gly
    610                 615                 620

Tyr Ile Gly Gln Gly Asp Ser Lys Arg
625                 630
```

<210> SEQ ID NO 77
<211> LENGTH: 792
<212> TYPE: DNA
<213> ORGANISM: Phaeodactylum tricornutum

<400> SEQUENCE: 77

```
atgctgccac cacccccggc gaacgctgca tctgtgagca aattgccaat gggaactccg      60

tctccgcttt cggttgaccc aacaagctct tcagttgtca cagtaggcac aggagggacc     120

aacaaggccg gctcgctgag gcaaaacgcg acaccgtatc atcatcacac acggacgact     180

tctgttaatc gatcagcgac tgtctcgtca agggaaatgg ccctgcaaaa taatacagtt     240

gcaactcgcc tgacgaagta cccaacctcg atcagcaccc gggcgaacac ccatgctaag     300

gcgacagcga ccaacatggc atccgccacg gcactgggga gcagtttaag atacgcagca     360

agacccgcaa ctgttccatc cagcggtgtc gtagccgctg catcttccct tgcgcagtcg     420

gcacagacgc cttcatcatt acatcgacct gtagcgggct tgtcgcacta cacaatcccg     480

cccgacgctt catcgatctc taccaaaaag aaaggtggtc aacctctcag aagagggaag     540

tggacgaccg aagaggaggc atatgcggct aggctaatac atgagtttaa atcaggctta     600

ctcccgctca cggatggaac gactctcagg aactttctat cgaagctgtt aaattgcgac     660

ccgatgagga tatcgaagaa atttgtgggc aacaattgta ttggaaagca agtctttcga     720

cggaaggtgg cggacataaa cagtttgacc cctgcgcaga tatcccaaat aagggttgag     780

ttgagcgagt ga                                                         792
```

<210> SEQ ID NO 78

<211> LENGTH: 263
<212> TYPE: PRT
<213> ORGANISM: Thalassiosira oceanica

<400> SEQUENCE: 78

Met Leu Pro Pro Pro Pro Ala Asn Ala Ala Ser Val Ser Lys Leu Pro
1 5 10 15

Met Gly Thr Pro Ser Pro Leu Ser Val Asp Pro Thr Ser Ser Ser Val
20 25 30

Val Thr Val Gly Thr Gly Gly Thr Asn Lys Ala Gly Ser Leu Arg Gln
35 40 45

Asn Ala Thr Pro Tyr His His His Thr Arg Thr Thr Ser Val Asn Arg
50 55 60

Ser Ala Thr Val Ser Ser Arg Glu Met Ala Leu Gln Asn Asn Thr Val
65 70 75 80

Ala Thr Arg Leu Thr Lys Tyr Pro Thr Ser Ile Ser Thr Arg Ala Asn
85 90 95

Thr His Ala Lys Ala Thr Ala Thr Asn Met Ala Ser Ala Thr Ala Leu
100 105 110

Gly Ser Ser Leu Arg Tyr Ala Ala Arg Pro Ala Thr Val Pro Ser Ser
115 120 125

Gly Val Val Ala Ala Ala Ser Ser Leu Ala Gln Ser Ala Gln Thr Pro
130 135 140

Ser Ser Leu His Arg Pro Val Ala Gly Leu Ser His Tyr Thr Ile Pro
145 150 155 160

Pro Asp Ala Ser Ser Ile Ser Thr Lys Lys Lys Gly Gly Gln Pro Leu
165 170 175

Arg Arg Gly Lys Trp Thr Thr Glu Glu Glu Ala Tyr Ala Ala Arg Leu
180 185 190

Ile His Glu Phe Lys Ser Gly Leu Leu Pro Leu Thr Asp Gly Thr Thr
195 200 205

Leu Arg Asn Phe Leu Ser Lys Leu Leu Asn Cys Asp Pro Met Arg Ile
210 215 220

Ser Lys Lys Phe Val Gly Asn Asn Cys Ile Gly Lys Gln Val Phe Arg
225 230 235 240

Arg Lys Val Ala Asp Ile Asn Ser Leu Thr Pro Ala Gln Ile Ser Gln
245 250 255

Ile Arg Val Glu Leu Ser Glu
260

<210> SEQ ID NO 79
<211> LENGTH: 633
<212> TYPE: DNA
<213> ORGANISM: Nannochloropsis gaditana

<400> SEQUENCE: 79
atgaagaccg ccgctctgct caccgtctcc tccctcatgg gcgcctccgc ctttgtggcc 60
cccgccccca agttcagccg cacccgcggt gttgcccgca tgtccttcga ggacgaggcc 120
ggcgtgaccg cccccctggg ctactgggac ccgcttggct tctccgccga tggtgatgtc 180
gagaaattca accgttaccg cgccatcgag atcaagcacg gccgagtggc catgcttgcc 240
atgctccaca ccctggtgac cggcctcggc gtgaagctcc ccggccttgt ggctgccggt 300
gacggcatcc ccgcctccat gcccgcgggc atcaacgcca tcacctccgg cgcttgggcc 360
gcacagggat gggcgcaggt gctcctcttc tgctccgccc tcgaggtcct ggccccccag 420

-continued

```
aaggaggaca agatccccgg ggatgtgcag cccgacacct ctgccttcgc caagctcgag    480

gacaagaccg aggaggaggc gctcgcctac cagaacaagg agatcaacaa cggccgcctg    540

gccatggttg cctggaccgg agccactgtg ggcgccctcc tcaccaacgg cgaggacccc    600

atcaccaccc ttctctccaa gctcggcaac taa                                 633
```

<210> SEQ ID NO 80
<211> LENGTH: 654
<212> TYPE: DNA
<213> ORGANISM: Nannochloropsis gaditana

<400> SEQUENCE: 80

```
atgcgttttt tcgaacaaaa tggaaggacc gccgctctgc tcaccgtctc ctccctcatg     60

ggagcctctg cctttgtggc ccccgccccc aagttcagcc gcacccgcgg tgttgcccgc    120

atgtccttcg agggcgaggc cggcgtgacc gcccccccttg gctactggga ccccccttggc    180

ttctccgccg atggtgatgt cgagaagttc aaccgttacc gcgccatcga gatcaagcac    240

ggccgagtgg ccatgcttgc catgctccac accctggtga ccggcctcgg cgtgaagctc    300

cccggccttg tggctgccgg tgacggcatc cccgcctcca tgcccgcggg catcaacgcc    360

atcacctccg gcgcttgggc cgcacaggga tgggcgcagg tgctcctctt ctgctccgcc    420

ctcgaggtcc tggcccccca gaaggaggac aagatccccg gggatgtgca gcccgacacc    480

tctgccttcg ccaagttcga ggacaagacc gaggaggagg cactcgccta ccagaacaag    540

gagatcaaca acggccgcct ggccatggtt gcctggaccg gagccactgt gggcgccctc    600

ctcaccaacg gcgaggaccc catcaccacc ctcctggcca agctcggcaa ctaa          654
```

<210> SEQ ID NO 81
<211> LENGTH: 672
<212> TYPE: DNA
<213> ORGANISM: Nannochloropsis gaditana

<400> SEQUENCE: 81

```
atgcgctctg ttgccttcat cgtcgccacc acggcagcca tgtctactgc ttttgtcctc     60

ccctctgcgc ccaaggcacc tcagacccag ctggctgcga agagcaaggc cgtccctttc    120

ctggaagccc ccaaggccct ggatggctcc cttcccgcgg acgttggctt cgaccccctg    180

aacttgtcgg acatcgattt tgacttcacc tacttgatgg tgcctaccaa gtgggacgag    240

tctcgcacgg ggctttcggc gctcaagtgg ttccgggagg ctgagatcaa gcacgggcgc    300

tttgccatgc ttgccgtctt gggatgggtg gctgtggaca tgggtctgcg ccttcccgtg    360

gccaagtacg cggggtacaa cgccgtgcag gcccacgacg tgttcgtgaa gagcggagac    420

atgacggtag ggctcctggc catcggcttc ctggaggtgg tgatgggcgc aggcatctac    480

gaaatgagca aggttctgga tcgggcggcc ggcgacttca gcttcgaccc cttgggcctg    540

ggcaaggacc ccgccaagta cgcacgctac caggtgtcgg aaatcaagaa cgggcgcctg    600

gccatgcttg ctttcggcgg catcgctacg caggctgtgc tgaccaacgg aggctttcct    660

tactaccagt aa                                                        672
```

<210> SEQ ID NO 82
<211> LENGTH: 816
<212> TYPE: DNA
<213> ORGANISM: Nannochloropsis gaditana

<400> SEQUENCE: 82

```
atgtgcggca tattatccat tgataccaag tatctgcgtt gtctgaatat gtgtgtatta     60
```

```
gatgtgaata gtgtcagtgg ccttgtaaag gtagccttcc atgctccagg atcccgtcta    120

ccatcggtac gtgctttcct gatctattct aatccgttcc tcacctgcgt ctataacctc    180

acacagattt gttctctaac taaaattatg aagctcttgt ctttcgcttg cctcatcggc    240

gccgctgccg cctttgtgcc ccccatgccc gctacgactc gtgcccgcgg cgctgtctcc    300

atgatggctg agaagtccaa atccatccct tttttgcccc gcccgcctgc gctggacggc    360

actgccccgg gagacgtggg ctttgacccg gtcgggttca caagctggct gcccttggcg    420

tacttgcagg aggccgagat caagcactgc cgcatcgcca tgttggcaac cctcgggtgg    480

attgtcgcgg attttgtcca cctccctggt gatgtccacg ctgttagctc cctggccgcc    540

cacgacgtgg ctgtaaagtc gggcgccctc gcccaaatcc tcatctggac ctccatcgcg    600

gaagcgatct ccgtcgttgc catctctcag atgctcgagg gctctggccg ccagcccggt    660

gacttcaagt tcgatcccct gggctttgcc aaagacgagc agactctgaa gaagctgcag    720

ctgaacgagc tcaagaatgg acgtttggcc atgctcgcct tctctggcat tgtcacccaa    780

gccgccctga ccggccactc cttcccgtac atgtaa                              816


<210> SEQ ID NO 83
<211> LENGTH: 660
<212> TYPE: DNA
<213> ORGANISM: Nannochloropsis gaditana

<400> SEQUENCE: 83

atgcgcacca ccgcttgctt gctcgccggt ctgggcctca cccaggcttt tctggccccc     60

accctcccca gcgcccgctc gttcagccgc accgccgtga ccatgaagtt gggctcctct    120

gcacagggcc tagccggaag cgacatcgag ttccccgagt tcgaccccct gggattcacc    180

aacaacccaa agcccgagac attggactgg taccgtgccg ctgagctcaa gcacgggcgc    240

gttgccatgt tggcggccct gggtcagatc gtgcagcact tctacaccct ccccgacgcg    300

tccggcgtct tctccgcggg agaccggccc atcgaggccc tgaacaaggt ggtggcagag    360

cggcccttgg cagccattca gattggcctg gccatctttg cggtggaggc gctggggcag    420

ttcaaccagg ccaagcccgg gcaggccccc ggggatctgg gctgggaccc tctgaacttg    480

aagagcgacg accccgagat ctacgctaag gtccagaacc gcgagctcaa gaacgggcgc    540

cttgctatga tcgccatcgc cggcatgttg gtgcaggaga acttgacggg cctcggcgtc    600

atcgagcagt gggtcaaggg cgacatcaac ccattcgggg acggacgtgg cttcttctag    660


<210> SEQ ID NO 84
<211> LENGTH: 603
<212> TYPE: DNA
<213> ORGANISM: Nannochloropsis gaditana

<400> SEQUENCE: 84

atgaagttcg cctccctcct gtctttgctt gcggcccccc tcctggcctc tgctttcctt     60

gctccggccc ccaagactac tcgcgcccgc ggtgtggtct ccatggtcca atccaaagct    120

ctgcctttct tggctgcccc gaagaagcta gatggttccc tggtcggcga ctttggcttc    180

gaccccatgg ggatctcgga tcaggtggca aatttgaagt acgtacgcgc ggccgagctt    240

aaacacgggc gggtggccat gcttggtttc ctaggctggg tcgtgacgca attcgtccac    300

ctcccggggg agatctacgc ggaatccaac ccgctgaagg cgatcgccgc cgtgcccctc    360

atcagccacg tgcaaatctt tctcttcatc gctgccatcg agctggcgac cctggatagg    420
```

```
acgtacacgg cggacaagcc ttgggacctg ggcttcgacc ccatgaacat gagcaaggga    480

aagtccgagc aacagatgaa ggatctggag ctcaaggagc tcaagaatgg ccgcctggca    540

atgatcgcca tcatcggact catggcccag accgcctaca cgggcattcc ccttttctct    600

tga                                                                  603
```

<210> SEQ ID NO 85
<211> LENGTH: 1218
<212> TYPE: DNA
<213> ORGANISM: Nannochloropsis gaditana

<400> SEQUENCE: 85

```
atgttctgtg tcgaagcgtc cggggaccgg tccaccccgc atcgtcctcg ggtccttatt     60

tttctccaca accttcagat aaacttgtct atactctcta gtacaatgcg tgtcctactt    120

tctctcttgg cgtgcgcggc cacggcctct gctttccttc tccccactcc taccacgcgt    180

cctgcctcgg cgctctttgc gtccactgtg ggcgccaagg acatcgtcga cacggccgtc    240

gacgcaggat ccttcaagac gcttgccacc gcactcacgg ccgccggcct cgtggagacg    300

ctgaagggac ccggcccttt cacggtgttc gcacccaccg acgaggcctt caacaaactc    360

gaggcagcga ccctgaacgc tctcctggcc gacaaggaga agctcacctc cattcttact    420

taccacgtcg tgtcaggccg cgtgcccgct gccgacgtgc tgaagctgac cagcgccaag    480

actgtgcaag gcggagacgt tgctgtcgct gtctccagca ccggcgtcaa ggtcaacaac    540

gcgaacgtgg tggcgacgga cgtggaggcc tcgaacggca tcatccacat catcgattcc    600

gtcctcatcc ccggtgcggt cgccgccccc gcggctgggt ctaaggaggt ggacaagaag    660

agcctggcct accgcgaggt gatggaggcg ggcgccacgg ctccctttgg cttctttgac    720

cccatcgggc tcagcaccgg gaagaccttt aaggaactga agaagtggcg cgagtccgag    780

gtcaagcacg gtcgggttgc catgctggcc gtcgtcggcg tcctcctcca ggaggttttc    840

gcgcctttct acaaccccga gaccggcagc agcgaccctg gccccgccat tttccacttc    900

caggagctgg aggccctcaa ccctttcctc ttcgttttcc tcattctggg catcgccatc    960

gtcgagtcct tcaccatcag caaaggctgg gagtctccgg aggaaatgcg cgccggcggc   1020

aacacgatcg cgggtctccg agacacgtac gtggccggcg acttggagtt cgacccccctc   1080

ggcctggctc ctacggcgga cgtggacgcg ttcatcaacc agcgttccaa ggagctcaac   1140

aacggtcgct tggccatgat tgcttgggcg ggcatggtcg tccaagagct gatctccaac   1200

tcaaaaatct tctcctaa                                                 1218
```

<210> SEQ ID NO 86
<211> LENGTH: 705
<212> TYPE: DNA
<213> ORGANISM: Nannochloropsis gaditana

<400> SEQUENCE: 86

```
atgaagacgg cagcgatttt ctccctgttg gctgttgccg ccaacgcctt tgtgctccct     60

actcccaaag ctccccagac tgtcgtgaag ggactccct tcgataccgt tgacaaggcg    120

gaaatggcgg tggagaacaa ggccctgtcc ggcatgagcg tctttgagcg cgccatggcc    180

gatttcaacg tccgctaccc cgccgtggcc gcgttgggct tgggcccgag cgtgaaggcc    240

gagcgatgga acggccggca cgccatgttt gggtggatcg ccctgttggc gacggggtac    300

gcccaggcgc acgggctgct cccggagggg ggcatggacg cgaaggagtg gggcacgtgg    360

gtcatcgtca acacggaccc tgccaccggc gcagttacca ccatccctgc cgcccgagcc    420
```

```
gccatcgcca tcgcccacct ccacctgggg gccgtgggtg tctttgctgc ctacagcaag    480

aacagcgtca aggacaggct gctcttggaa ccgggggaga aggacgaggc tcctgccggc    540

ctcttccctg ccctgcgccc cggctgacc aaggacgccg agatcctcaa cgggcgcatc    600

gccatgctgg ggctcattgc ccttgtcgcc gtcgctgccg ccacggggca ggacatcctc    660

tccgtcattg accagggtct gggggggctt cttctcaagg cctga                    705
```

<210> SEQ ID NO 87
<211> LENGTH: 888
<212> TYPE: DNA
<213> ORGANISM: Nannochloropsis gaditana

<400> SEQUENCE: 87

```
atggcatgcc cccatggcct gagaatcgtt aactttttca ctggtgcccc tcaagagcct     60

acacttttgt tcctacgttt cctcgctctt ccctcccgaa aaactcgtgc catgtcctcc    120

gcttcattca caaatgctcc ttgcccttct ccttcccttc agagttcacc taagaagatg    180

accatgttcc gcaagctggc cctggccctt ctctgctcct ccgcggtcgc cttccatgca    240

cccgcacccg taagccgcag ctcagtacgc ctccaggccg agaacaaacc cgccgcaccg    300

cccgctgcag cccctgctgc cgctgctact gcggcggcgg ctgctgctcc cccccccccc    360

gcgaagcccc aacccgtgtt ctcgaagtcg gtgccgttcc tcttgaagcc caagaacttg    420

gatgggatgg tgggcgatgt gggcttcgac cctctgggcc tggctgagta cgtggacatc    480

cgatggctgc gagaggcgga gctgaagaac ggccgcgtcg caatgcttgc cttcttgggc    540

ttcgtggtcc aggaatttat ccgcctccca ggagacctgt actcggagcc caacggggtc    600

aaagccttct tccaagtcgg accccagccc ctcattcaga tcttcctctt ctgtgggttt    660

ttggaattca ccctccacaa ggggaagatg acgcaaatgg acatgtttgc ggacggaaag    720

cgcgagcccg ggaactttgg ctttgatccc ttgggtttcg gcaaggatcc ctccaaacgc    780

gagcgactgg cactggcaga gctcaagaac ggacgtctgg ccatgatcgc gatcggtggt    840

cttatccacc atgccctcgt gacgggccat gccacgttta gcagctaa                 888
```

<210> SEQ ID NO 88
<211> LENGTH: 717
<212> TYPE: DNA
<213> ORGANISM: Nannochloropsis gaditana

<400> SEQUENCE: 88

```
atgaagttcc tcgcagtcct tactggtgtc ctcgccacag cctctgcttt cgtgcctcat     60

gccacgctct ccgctgggcg acgaagcagc agcgctctga ggatgtcggc atcggacatg    120

atcgggattg acgtcgagac gggcggtctg ttcgatcccc tgggcttctc caaggatgaa    180

caatccctgt acaagtaccg gcaagtcgag ctcaagcacg gccgagtggc gatgctcgcc    240

tgcctgggca ccctggtgca gtcctacacc cacctccccg acgacgtttt cagcaatccc    300

cggcccctgg gagcactcgg acagctcctg tccgagcgtc ccttggcaat cctccagatc    360

gtcatagcca tcactttgat cgaggtgacg agcgggaagc aggaccccga gctggcgccc    420

ggtcagttgg gacgcttcgg tgaggccttc aagcccgagg gcgaggccga aatggccgcc    480

gtccagctca aggagcttaa aaatgggcga cttgcgatgg taagacaagg atggagcttg    540

ttgagattta gaatgctgtg ggaaggggtc gccatcatcg gacagtgggt gcaagagctg    600

ttgacgggcc agggccccat tgagcagatc acctccgggc acatctcccc cttcggcgac    660
```

ggacagggtc ttttctgtaa gtgccagtta aacaaccacc aagtcctcat tggttga 717

<210> SEQ ID NO 89
<211> LENGTH: 741
<212> TYPE: DNA
<213> ORGANISM: Nannochloropsis gaditana

<400> SEQUENCE: 89
atgatgcgcg ccgttgtttt gctggggctg ctgtcctctg ccgccgcttt cattcctgcg 60
actttcaaca caggcaagag ctcatacgcc cgcaaaaact tggtggtggc ctccgtttct 120
gacttgatcg gagcggacac ggagacgggc gggatctggg atcctctggg cctgagccag 180
aacgagggtt ccctccgtaa gtaccgcgag tgcgagctca agcacgggcg tgtagccatg 240
gctgccatgc tcggtatctt tgtccaaggt ctctaccacc ttccggatcc cgtctttagc 300
aaccctcgcc ctctggctgc cttgcagcag gtctacgagc aacgtcccga ggccatttgg 360
cagatcatcg taggactggg cgtgatcgag ttcacggggg gccgacaaaa ggaggaccgt 420
gcccctggcg acttgaactt tggttcttct ttcatcccca agagcgagaa ggagttcgag 480
gaattgcagc tgaaggagct gaaaaacggg cgcctggcga tggtggcctc catgggcgcc 540
ctgctccagg aatacctgac aggccagggg ccggtggagc aagtcttggc tggccacttg 600
aatcccttcg gtgacggcca agggttcttc tgtaaaaacc cagccgactt cttggcaccg 660
caaacgggag ggcccatggc gagaacaagc ttgatttttc atttcatcgg gcacacggag 720
aacacttccg gcgtagaata g 741

<210> SEQ ID NO 90
<211> LENGTH: 402
<212> TYPE: DNA
<213> ORGANISM: Nannochloropsis gaditana

<400> SEQUENCE: 90
atgaagttct tggccctcgc caccatcgtg agcactgcct ctgccttcct ggctcctgtt 60
ccgatacaca cccgtaccca gggccgcatg tacatggccg accaggctcc tgtggatgag 120
gaagtgcggt ccatcgcctt gccgttcgct gccaagccgc agaacttgaa tggcgagctt 180
gctggggatg taggctttga tcctttcaag ttctctgaca agggtgatgt ggccaaattc 240
cgcgtggctg agctgaagca tggacgtgtg gccatgcttg cggtagttgg tgtgctcgtg 300
caagaacttt accagtggaa cgaaaacttt ccctccaaga acttcctgga ggccctcaag 360
accgcccccg ccctcggtct gctccagctc ttcgtcttcc tg 402

<210> SEQ ID NO 91
<211> LENGTH: 663
<212> TYPE: DNA
<213> ORGANISM: Nannochloropsis gaditana

<400> SEQUENCE: 91
atgaagacag tatttgctct tgctgccctc ctcccatgcg cggctggttt tgtggctccg 60
gtggccttcc ccacagcctc ctccgcaggg aaagccgtgc gaggccgcac taccatgatg 120
gcggaacgat ccaagtccct tcccttcctg atgaagccca agaacttgga cgggtccatg 180
gcgggtgacg ttggcttcga ccccttgggc ctgtcagaga tcaacgaagt cggcatcgac 240
ctgtactggt tgcgggaggc ggaactcaag cactgccgcc tcgggatgat ggccgcggcc 300
ggcattctct tcgtggaggc tgtgggaccc gcccccggtt tcccctccac caagagccaa 360
atggatgcgt tctggaccgt gtacgccgag aagccttccc tcgtgggggc ggccttggta 420

```
gctattgcga ttttggaagt gatctcgggt gtcgccacca cccagggccg tcaaaacggg    480

gaccgagcgc ccggcgacta caacttcgac cccctgggct ttggaaagga ccccgccaag    540

ttcaaagact tgcagctcaa ggaagtgaag aacggccgcc ttgccatgat tgctgccgca    600

ggcatgattc ttcaaggtgt ctccactcac caaggtgcat tgcaaaactt gaacggaaac    660

tag                                                                  663
```

```
<210> SEQ ID NO 92
<211> LENGTH: 681
<212> TYPE: DNA
<213> ORGANISM: Nannochloropsis gaditana

<400> SEQUENCE: 92

atgtcacaca gcctacttcc tctcttcata cagagcacca tgcgcgtcgc tgctgccctc     60

atcgccaccc tggccaccgc ctccgccttc ctcgcccccg cctcccttcc ctcctcctcc    120

tccttccgcc gcactcaagg ccgtgtctcc atggacatct cgggcatcgt gggctccgac    180

gtggaggtgc cggaattcga ccccctgggc ctggccaaga acaaggacga ggaaacgctg    240

ggctggtacc gcgcggccga actcaagcac gggcgtgtgt gcatgctggc ctcggtcggg    300

tacctcgtcc aggggctgta ccaccttccc gacgggccct tcgaggcctc caagcccatc    360

gacgccctgc tcaaggtctc aagcgaacgc ccgctggccg ccgtgcagat cgccatcgcc    420

atcgccgccc tggaagtgct cggtgcctcc atccagaagt acacggcccc gggagacctg    480

acctttgacc cccttggctt gaagcccgaa gaccctgagg agctcgcgga gctgcagctg    540

aaggagctga agaacgggcg gttggccatg ttggccacgg cgggcttggc cgcccaggaa    600

tacgtgactg gccaggggcc agtggagcag ctgctctcgg gccacatctc cccctttcggt    660

gacggccaag ggcgttctg a                                               681
```

```
<210> SEQ ID NO 93
<211> LENGTH: 915
<212> TYPE: DNA
<213> ORGANISM: Nannochloropsis gaditana

<400> SEQUENCE: 93

atgaagacct cccttgttac cttggcgctg gccacagtcc ccgccactgc cttcatgggc     60

ggcttcatgg gcaagaactt cgccgccccc gctaaggtag cctccaccac caccaccacc    120

atgttcctga acttcggctc caagaaggca gcgcccgccc ccaagaccgc gcccaagacc    180

gcccctgcca agaagggcgg ggtctctatc cccaaacccg cgggcaaagt ggccgccaag    240

cctgcggcca agcccgcttc caagccggtg tccaaagtgg cgcccaagaa agctgccccc    300

gcgcctaaga aagccgcccc cgcgcccaag aaagccgccc cgacaagggc cgcagccaag    360

ctggccgccc ccctatccaa ccctgatttc gccggcggct tgatcggctc ggatgtggag    420

gcgatccgat tcgatccctg gaacctggcc agtgagcgag accccgaagg cctcgcatgg    480

taccgatccg ccgagctcaa gcacggccgc atctgcatgc tcgccgccct gggtctcctc    540

gtgcagtcct cctaccacct ccccgacgag gtcttcagca actccaaggg cctcgacgcg    600

ctcttccagg tctcagcgga gcggcctcag gccatcgccc agatcctcat cgccatcggc    660

gccatcgagg ttgcggggct ggcagccagc gagggcaagg cccccggaga cttcggcttc    720

gaccccctga acctgaagcc caagacggag gaggctttca acgagctgca gctgaaggag    780

atcaagaacg gacggctggc gatggtggga gtggcgggga tgctcattca ggagaccctg    840
```

```
accaaccagg gcgtgctcga gcagatcaac agtggtcact tgagcccttt caacgacggc    900

cagggcgtgt tctag                                                     915


<210> SEQ ID NO 94
<211> LENGTH: 729
<212> TYPE: DNA
<213> ORGANISM: Nannochloropsis gaditana

<400> SEQUENCE: 94

atgcgtgtac tctctttcct tgctattatc ggcactgccg ctgccttcgt caagcccacc     60

ctccctgctg ctgggtctcg cactcgtgcc ggcgctctcc gcatgaacct cgccgagatc    120

gagctggagg cgggcaagac ctctcctttc cccgatggct tcgatcctct cggtctgtcc    180

aaggataagt cattcaagga gctcaagaag tggcgcgagg cggagctcaa gcacggccgc    240

gttgccatgc ttgccgtcct gggcacggcc gtgcaagaga acttccaccc cctgtggggc    300

ttcaacgaga aggagatgga tggtgccatc tttcacttcc aggagatcca aaacgtctac    360

cccctttttct ggaccgccct ccttttcatc atcggcatca ttgaggctcg caccatctcc    420

accggatggg atgagaacat ggccggatct tcccagatcg ccggcgtgaa ggaggactac    480

atctgcggga acctgggcct ggaccccctc aagatcatcg aaaatgacga cgaggaggct    540

ttcctgtcct accgcaacaa gtctcaccgg ttcttgccct acctcatctt tcaggagctc    600

aacaacggcc gtctggctat gatcgcagcc gctgggatca ccgtccagga gaagttcgtc    660

accaacggcc tccccgagtt cgagttccac cgattcgccc tctcggacgt ctacaacttc    720

ttcttctaa                                                            729


<210> SEQ ID NO 95
<211> LENGTH: 903
<212> TYPE: DNA
<213> ORGANISM: Nannochloropsis gaditana

<400> SEQUENCE: 95

atgaagaccg cagtcctctt cctgtcgggt ctggtcggcg cccaggcttt cctcaccccc     60

aacgcccggg tgccagccgc aaccaagatg gaggccatca aggcggggaa gggagccaag    120

gccggtaagg ccgctactgc caacaactac ctcaaggagg tggagcctgg ctcgggccca    180

ctcggaaagt ggtacgtccg ggacgacccg accctctcga ccgcccttcc ctgggtcaca    240

cggcccgaga tcggggacgg ctctctggtg ggggacttcg gtttcgatcc ttttggcctt    300

tccaagatct tcgatgtgaa ttggttgcgc aatgcggagc tcaagcacgg acgattggcc    360

atgttggcca cgctgggtat ggttacgccc gagctggtgc aggcccctgc tggattcgag    420

ggcttcaagt ttgcgcccga gttctcggag ctgaacgcca ttaaggcatt gagcgccgtg    480

cctaccttgg gtttggcgca gatcattctg gccatatctt tcgtggaggt ggcgaccttt    540

agcaaggtgt acaatgagcg cttcacgttc gaagacaacc tgaccccctt ggagcgcaag    600

aaagtcgtcc agggccgctt ctctgacctt tctggcgccg ccaagacaca agccaaagcg    660

ggcgtgaacc cgttcgggaa cgccgtggac gtgggttttc aggatcccga gaagttcgtg    720

cccggggacc tgggcttcga ccccgtcggc ttcacagaca acggcatcaa cccggactac    780

gccctggccg agatcaagca cgcccgcctt gccatgcttg gcgcagccgg catgcttatc    840

caggaattcc tccaacccaa gggtatcctg agccagacgg tcgagtgggc ccagagccag    900

taa                                                                  903
```

<210> SEQ ID NO 96
<211> LENGTH: 714
<212> TYPE: DNA
<213> ORGANISM: Nannochloropsis gaditana

<400> SEQUENCE: 96
atggatagaa agtggaatga gaatgcggcc accaggatgc accacactcc tgtcttcccc 60
tctccgcgtc gagtgacatc cacactgtca aatatgaaga ctgcatttgc cttcctagcc 120
ctcctgggcg tctccactgc cttcatgccc actgctccgc gcatgacccg aggccgcagt 180
gtgcgcatgg ctgtgaacga gatgattggc tcggatgttg agaccaacgg tgtctttgac 240
ccccttggtc ttgccaagga tgaggcctcc ctctaccgtt cccgtttgat tgaactcaag 300
cacggccgcg ttgctatgtt ggcttgcctc ggtacccttg tgcaatcgtt ctaccatctg 360
cccgacgagg tcttctccaa cccccgcccc ctcgccgccc tcgcacaagt gtattctgag 420
cgtcccgtag ccttctggca gatcttcctg gctatcggtg ccatcgagct taccatcggc 480
aagcaggaca ccgccaaccg cgcccccggt gacgtcggct tcggcgctgc tttcatcccg 540
gacgatgcgg aagacttcgc ggctctccag ctcaaggagc ttaagaacgg ccgcttggct 600
atgatggcca tcattggaca gttcgtgcag gagaagctga cgggccaggg accgatcgag 660
cagctgttgg aggggcactt ttctcccttc ggtgatggac agggagcttt ctaa 714

<210> SEQ ID NO 97
<211> LENGTH: 327
<212> TYPE: DNA
<213> ORGANISM: Nannochloropsis gaditana

<400> SEQUENCE: 97
atgaagtgca tcgtatttgc gggcctgctg gcgtctgcca ctgcttttat ggctcctgct 60
ccgcgtgttt cgtctcgctc cgcgttgaga atgggactgg aaggccaggt gggctacgac 120
gtcgagactg gcggcaaacc atgggacccg ctgggcttcg ccgggatctc ggagcgcaac 180
aacttgggca ttaacccgca catcaagtgg ctgcaggagt ccgagatcaa gcacggacgg 240
accgccatgc tggccttcct cggagtgatc gtgcccggat cccttggggt gtatgtgccc 300
acctaccccc agctatggga agagtag 327

<210> SEQ ID NO 98
<211> LENGTH: 879
<212> TYPE: DNA
<213> ORGANISM: Nannochloropsis gaditana

<400> SEQUENCE: 98
atgttgagca gcgctcgttc ttgccaccat cttaccctcg ttcccctcct cttcgacttt 60
acacacgtcg taccatctca cattctctca acacaacatc ttcctccacc agcttttttt 120
tttcctgcgc gttcaagaat gagggtcatt gctcttctct ctctcgcctc gatggcaagt 180
gccttcatcg cccctacacc cttggcccgt cgtgccaccg gcgcggtgcg catggccgcg 240
gatgacgacc tgtctactgc gcttcctttc gacaagcgac cgcccaacct ggacggcagc 300
cttcctgggg atgtgggttt tgacccggtc ggcttctcga acaaccctcc ccgtccttgg 360
ctgatcggag gctcgggccg ctccctgaag tggtaccgtg aagcagagat tgttcacggc 420
cgagtcgcca tgcttgccgc cctcggatgg gtgttcccca acatctatca ccttccgggg 480
aacgaggacg ttggtgtgga tgcgtttgcg aacctgaacc ctttcggggc tttgaccacc 540
gtcccggccg cgggcctctg gcagatcgcc gccacggtgg gcgcgattga gcttttccgc 600

```
gtgaaccgtg tcatccgtgg agacaaggag gcgggtgatc tcggactcgg ccagggagag    660

gggcgatgga accccttcgg attcaactac tccgaggagg agtatgccga gaagcagttg    720

caggagatca agaacggacg tctggcgatg gtgggcatct tgggtcttct tttgcaggcc    780

agtgtgactg ggaagggtat tgtgcagcag ctggggggct ctttcgacgt gcctgaagct    840

gtctccaagg ctggctacta cttccctgac ggcgtctaa                           879


<210> SEQ ID NO 99
<211> LENGTH: 633
<212> TYPE: DNA
<213> ORGANISM: Nannochloropsis gaditana

<400> SEQUENCE: 99

atgaagaccg ccgctctgct caccgtctcc tccctcatgg gcgcctccgc ctttgtggcc     60

cccgccccca agttcagccg cacccgcggt gttgcccgca tgtccttcga ggacgaggcc    120

ggcgtgaccg ccccccctggg ctactgggac ccgcttggct tctccgccga tggtgatgtc    180

gagaaattca accgttaccg cgccatcgag atcaagcacg gccgagtggc catgcttgcc    240

atgctccaca ccctggtgac cggcctcggc gtgaagctcc ccggccttgt ggctgccggg    300

gacggcatcc ccgcctccat gcccgcgggc atcaacgcca tcacctccgg cgcttgggcc    360

gcacagggat gggcgcaggt gctcctcttc tgctccgccc tcgaggtcct ggccccccag    420

aaggaggaca agatccccgg ggatgtgcag cccgacacct ctgccttcgc caagctcgag    480

gacaagaccg aggaggaggc gctcgcctac cagaacaagg agatcaacaa cggccgcctg    540

gccatggttg cctggaccgg agccactgtg ggcgccctcc tcaccaacgg cgaggacccc    600

atcaccaccc ttctctccaa gctcggcaac taa                                 633


<210> SEQ ID NO 100
<211> LENGTH: 726
<212> TYPE: DNA
<213> ORGANISM: Nannochloropsis gaditana

<400> SEQUENCE: 100

atgcttgccc catgtccgac gcgggggcga ccccgcgtgg acgtgcgctt gcagaacgtt     60

tactccctcc tcctagacaa tggaatccac tccccctct tcaaaatgaa gtccgcgatg    120

gtacttgtcg gcagcttggc tgtggcctct gcattcgttc ccgcggcccc taagatgtct    180

cgcactcgtg ggatgacacg catggccgtg aacgacatcc tgggctcaga cgtggagact    240

ggcggcgtgt gggacccccct caatttttcc aaagatgagg gcagcctgta ccgatatcgc    300

gccgtggagc tcaagcacgg ccgattggcg atgcttgccg tgttaggcct gtgggtctct    360

gagttctatc accccctcta cgacggaaag atctcaccgg gcatcaaggc catcggggaa    420

ctgccgggcc cggcctggct gcagatcctt gccactattg gtgtgattga actgaccgtg    480

ggaaagcagg acacggagaa taaggcaccg ggcgacctcg gcttcgggta caacttcaac    540

cccttcaaga acgaccccga gaagttcgcc gagctgcaac tcaaagaact taaaaacggg    600

cgcctggcca tgcttggcgc ggcaggaatt ctgctgcagg agagtatcac cggccagact    660

tgcttcgagc agatcgccgc gcagcatctc agcccgtttg gtgacggaca gggcttttttc    720

tggtga                                                               726


<210> SEQ ID NO 101
<211> LENGTH: 714
<212> TYPE: DNA
<213> ORGANISM: Nannochloropsis gaditana
```

<400> SEQUENCE: 101
atgattgccc agcctgctcg gctcttgttc tgcgtggccc tcccggccct tgccaccgcc 60
ttcctggccc gtgctcccac cacagtacct cacactcact cggtgaggaa agggcgtact 120
gttgttatgg agtctatctc ggagttcctc aagtttgatg cgaaactcgg cgagttggag 180
gtgaccaaag cgggagtctc tgctccattc gggttcttcg atcccttgaa cttttacgga 240
ggcaaaacca ttcgccagaa gaaaaagctg cgcgagtctg aactcaaaca cggtcgcgtt 300
gctatgatgg cggtgctggg cattttcgtc caagaactct ggcatcctct tctggcaggt 360
gatgatttcg aaaccgcgct cagccaatac tacggcgtga cggagtttat tcccgacttc 420
ggcgcggggg ccctctttgt cctttctctt tttgagttca aaagcatcgc tatgggatgg 480
gatcccgtcg aggagactct caaagagcca aaaattgccg gtatgcgtga tgattatgtg 540
gcgggagact tacagtacga tcctctgggc ttctgtcccg acgatgacga agcctttgtg 600
cgcatgcgca ctaaggagct caacaacggg cgtatggcca tgatcgccgc cattggcatc 660
atcggacagg agctggccac gggcgtgcct gttgtcaagt cgctctttgg gtaa 714

<210> SEQ ID NO 102
<211> LENGTH: 1338
<212> TYPE: DNA
<213> ORGANISM: Nannochloropsis gaditana

<400> SEQUENCE: 102
atgttgcgca ctcaatccat ccgttacaat tttcctactc tcatgcattt cgacacgcag 60
gaatcgaggg cacaatttgg ttttctaggc cgccggctca tcaaggagtc catcgctatg 120
gtccgagccc ggtgtcggaa cccttccccc tgtcgatttc accccacttg cctctttaag 180
tggccgtcca ttatctgcct ttcctacatc ctccgagaat tttacgttgt tacggccttt 240
gtcccgccat ttccaccggc ggagaccccc aggaaccttt tttgtccctc cgctgcatcc 300
cttccacctc cgccgcccga gaccgacctc ctctctactc tggcccaaga cggacgcttc 360
acacgcctcc tccacctttt caaagaggta gggctcgacg ccaccctgag tggccctggg 420
ccgtggactg tgcttgcgcc cacggacgcg gctctggacg accaggtagc caacctcacc 480
ctcatcgtgg ctgcacggga gccaaagcgg cacctgacac ccttgctgtc ctaccacatc 540
atcccaggga aagccatggg cctgggagac ctggtggccg ccggtgacgc gaggactcgg 600
gtcaagacgt tggagcgcag cggtttgtcg atcgctgtct atgggggcac ggtcctggtg 660
gacgaaggcc gtatcctgga gtggggcatg gaagcaggca acggagtcgt gcatgtgatg 720
gacagcctcc ttctccctgc cctcccgtcc gacttcgatc ctttcgccgc cccggaggcc 780
gcctccccgg gccccgtcct gggggtgacc gctcccctcg gctgctggga tcctctgggc 840
ttgtggacgg gaaaggacgc cgcaacgcaa gcccgtttgc gtgacgcgga aatcaagcac 900
gcgcgcttgg ccatgctggc tgcaataggg atcctcacgc aggagctggt ggtacccact 960
catccgtacg cgttccagcc tgtattggat gcattgcgtg gcagcacaca catggctccc 1020
gacgtttcat ttctactacc tttgcctccg attgcggcgt tggcagcgat ccttgctccc 1080
ggagtcgcgt gggaagtgtg gtcactgcga agagcctcga aggacaaggc gccgggcagg 1140
ccatccaagg aggaggcact cacccagata ctgaaacgag aatcccccga ctttgaggca 1200
gagagggagg aagagcgtga aaaaatcgat gcggggaata gagaattgaa caacggtaga 1260

-continued

```
ctggctatga tagctgtcgt tggaatgcta gtgcaggaaa tcgtcacggg tcgaagcgtt    1320

ctgagtcctt ggatgtga                                                   1338
```